United States Patent
Kakizuka et al.

(10) Patent No.: US 9,573,887 B2
(45) Date of Patent: Feb. 21, 2017

(54) NAPHTHALENE DERIVATIVE

(75) Inventors: Akira Kakizuka, Kyoto (JP); Seiji Hori, Kyoto (JP); Toshiyuki Shudo, Osaka (JP); Tomohiro Fuchigami, Osaka (JP)

(73) Assignees: Daito Chemix Corporation, Osaka (JP); Kyoto University, Kyoto (JP)

( * ) Notice: Subject to any disclaimer, the term of this patent is extended or adjusted under 35 U.S.C. 154(b) by 0 days.

(21) Appl. No.: 13/813,190

(22) PCT Filed: Jul. 28, 2011

(86) PCT No.: PCT/JP2011/067320
§ 371 (c)(1),
(2), (4) Date: Mar. 18, 2013

(87) PCT Pub. No.: WO2012/014994
PCT Pub. Date: Feb. 2, 2012

(65) Prior Publication Data
US 2013/0184241 A1    Jul. 18, 2013

(30) Foreign Application Priority Data
Jul. 30, 2010   (JP) ................. 2010-172467

(51) Int. Cl.
| | | |
|---|---|---|
| C07D 213/77 | (2006.01) |
| A61K 31/4418 | (2006.01) |
| C07D 213/76 | (2006.01) |
| C07C 245/10 | (2006.01) |
| C07C 309/47 | (2006.01) |
| C07C 323/48 | (2006.01) |
| C07D 215/38 | (2006.01) |
| C07D 217/14 | (2006.01) |
| C07D 333/38 | (2006.01) |
| C07D 401/04 | (2006.01) |
| C07D 401/12 | (2006.01) |
| C07D 405/04 | (2006.01) |
| C07D 405/12 | (2006.01) |
| C07D 409/04 | (2006.01) |
| C07D 409/14 | (2006.01) |
| C07D 413/04 | (2006.01) |
| C07D 213/81 | (2006.01) |
| C07D 213/30 | (2006.01) |
| C07D 213/42 | (2006.01) |
| C07D 401/10 | (2006.01) |
| C07D 405/10 | (2006.01) |
| C07D 409/10 | (2006.01) |

(52) U.S. Cl.
CPC ........ *C07C 245/10* (2013.01); *A61K 31/4418* (2013.01); *C07C 309/47* (2013.01); *C07C 323/48* (2013.01); *C07D 213/30* (2013.01); *C07D 213/42* (2013.01); *C07D 213/76* (2013.01); *C07D 213/77* (2013.01); *C07D 213/81* (2013.01); *C07D 215/38* (2013.01); *C07D 217/14* (2013.01); *C07D 333/38* (2013.01); *C07D 401/04* (2013.01); *C07D 401/10* (2013.01); *C07D 401/12* (2013.01); *C07D 405/04* (2013.01); *C07D 405/10* (2013.01); *C07D 405/12* (2013.01); *C07D 409/04* (2013.01); *C07D 409/10* (2013.01); *C07D 409/14* (2013.01); *C07D 413/04* (2013.01)

(58) Field of Classification Search
CPC . A61K 31/4418; C07D 213/77; C07D 213/76
See application file for complete search history.

(56) References Cited

U.S. PATENT DOCUMENTS

| 2,865,916 A | 12/1958 | Leavitt et al. |
| 7,387,667 B1 | 6/2008 | Lin et al. |

FOREIGN PATENT DOCUMENTS

| CN | 86105522 A | 2/1988 |
| CN | 1746229 A | 3/2006 |
| CN | 101633796 A | 1/2010 |
| DE | 2436257 A1 | 2/1976 |
| DE | 3417237 A1 | 11/1985 |

(Continued)

OTHER PUBLICATIONS

Charrier (CAPLUS Abstract of: Scienze Fisiche, Matematiche e Naturali, Rendiconti (1929), 10, 189-93).*

(Continued)

*Primary Examiner* — Robert Havlin
(74) *Attorney, Agent, or Firm* — Morgan, Lewis & Bockius LLP

(57) ABSTRACT

The present invention provides compounds which can regulate VCP activity. The present invention provides the compound of formula (I)

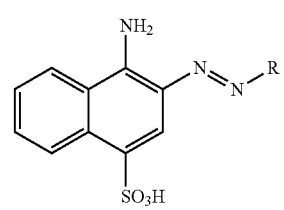

(R is as defined in the description)
or oxides, esters, prodrugs, pharmaceutically acceptable salts or solvates thereof. The compounds can regulate VCP activity, and thus are useful for treating VCP-mediated diseases such as neurodegenerative diseases.

14 Claims, No Drawings

(56) References Cited

FOREIGN PATENT DOCUMENTS

| DE | 10053796 A1 | 5/2002 |
|---|---|---|
| JP | 58-174463 A | 10/1983 |
| JP | 2004-75921 A | 3/2004 |
| WO | 2006/025304 A1 | 3/2006 |

OTHER PUBLICATIONS

Takahashi et al. (CAPLUS Abstract of: Yakugaku Zasshi (1946), 66(No. 7/8A), 28-9).*
Bursavich et al. (Bioorg. Med. Chem. Lett. 20 (2010) 1677-1679).*
Kubinyi (3D QSAR in Drug Design: Ligand-Protein Interactions and Molecular Similarity, vol. 2-3, Springer, 1998, 800 pages). p. 243-244 provided.*
Wermuth, The Practice of Medicinal Chemsitry, 2d ed. (2003), 768 pages. Chs. 9-10 provided.*
Saikachi (CAPLUS Abstract of: Yakugaku Zasshi (1944), 64, 328-30).*
Ueda et al. (CAPLUS Abstract of: Yakugaku Zasshi (1952), 72, 260-4).*
Fisichella et al. (CAPLUS Abstract of: Journal of the Society of Dyers and Colourists (1978), 94(12), 521-3).*
Gordon ("Structure-based design and synthesis of small molecule human immunodeficiency virus type 1 integrase inhibitors", Doctor of Philosophy thesis, Department of Chemistry, University of Wollongong, 2007).*
Extended European Search Report issued in corresponding European Patent Application No. 11812583.0 dated Feb. 18, 2014.
Kakizuka, "Protein precipitation: a common etiology in neurodegenerative disorders?" Trends in Genetics, 14: 396-402 (1998).
Hirabayashi et al., "VCP/p97 in abnormal protein aggregates, cytoplasmic vacuoles, and cell death, phenotypes relevant to neurodegeneration," Cell Death and Differentiation, 8: 977-984 (2001).
Higashiyama et al., "Identification of ter94, Drosophila VCP, as a modulator of polyglutamine-induced neurodegeneration," Cell Death and Differentiation, 9: 264-273 (2002).
Mizuno et al., "Vacuole-creating protein in neurodegenerative diseases in humans," Neuroscience Letters, 343: 77-80 (2003).
Ishigaki et al., "Physical and Functional Interaction between Dorfin and Valosin-containing Protein that are Colocalized in Ubiquitylated Inclusions in Neurodegenerative Disorders," The Journal of Biological Chemistry, 279: 51376-51385 (2004).
Kobayashi et al., "Involvement of valosin-containing protein (VCP)/p97 in the formation and clearance of abnormal protein aggregates," Genes Cells, 12: 889-901 (2007).
Kitami et al., "Dominant-negative effect of mutant valosin-containing protein in aggresome formation," FEBS Letter, 580: 474-478 (2006).
Watts et al., "Inclusion body myopathy associated with Paget disease of bone and frontotemporal dementia is caused by mutant valsin-containing protein," Nature Genetics, 36: 377-381 (2004).
Dai et al., "Involvement of Valosin-containing Protein, an ATPase Co-purified with IkBa and 26 S Proteasome, in Ubiquitin-Proteasome-mediated Degradation of IkBa," The Journal of Biological Chemistry, 273: 3562-3573 (1998).
Kobayashi et al., "Functional ATPase Activity of p97/Valosin-containing Protein (VCP) is Required for the Quality Control of Endoplasmic Reticulum in Neuronally Differentiated Mammalian PC12 Cells," The Journal of Biological Chemistry, 277: 47358-47365 (2002).
Ye et al., "A membrane protein complex mediates retro-translocation from the ER lumen into the cytosol," Nature, 429: 841-847 (2004).
Rabouille et al., "An NSF-like ATPase, p97, and NSF Mediate Cisternal Regrowth from Mitotic Golgi Fragments," Cell, 82: 905-914 (1995).
Wojcik et al., "RNA interference of valosin-containing protein (VCP/p97) reveals multiple cellular roles linked to ubiquitin/proteasome-dependent proteolysis," Journal of Cell Science 117: 281-292 (2004).
Yamamoto et al., "Expression level of valosin-containing protein (VCP) as a prognostic marker for gingival squamous cell carcinoma," Annals of Oncology, 15: 1432-1438 (2004).
Doolman et al., "Ubiquitin is Conjugated by Membrane Ubiquitin Ligase to Three Sites, including the N Terminus, in Transmembrane Region of Mammalian 3-Hydroxy-3-methylglutaryl Coenzyme a Reductase," The Journal of Biological Chemistry, 279: 38184-38193 (2004).
Wang et al., "SPFH1 and SPFH2 mediate the ubiquitination and degradation of inositol 1,4,5-trisphosphate receptors in muscarinic receptro-expressing HeLa cells," Biochimical et Biophysica Acta, 1793: 1710-1718 (2009).
Rudyk et al., "Synthesis and evaluation of analogues of congo red as potential compounds against transmissible spongiform encephalopathies," European Journal of Medicinal Chemistry, 38: 567-579 (2003).
Ueda et al., "Researches on Chemotherapeutic Drugs against Viruses, XI, Synthesis and Antiviral Effects of 3-Alkyl-phenylazo-4-aminonaphthalenesulfonic Acid and its Sulfonamide Derivatives," Pharmaceutical Bulletin, 1: 271-274 (1953).
Hiyama, "Studies on Naphthalene Sulfonic Acid Derivatives, III, Naphthylazobenzene Sulfonamide Derivatives; Synthesis and Tests for their Effects on Bacteria and Viruses," Yakugaku Zasshi, 72: 1374-1377 (1952).
Ueda et al., "Researches on Chemotherapeutic Drugs against Viruses IV. Studies on the Syntheses and Antiviral Effects of 3-Phenylazonaphthionie Acid and its Derivatives," Yakugaku Zasshi, 72: 260-264 (1952).
Sekar et al., "Synthesis of Azo Reactive Dyes Containing Aldehyde Group," Asian Journal of Chemistry, 19: 2565-2573 (2007).
Wang et al., "Structure-properties relationships investigation on the azo dyes derived from benzene sulfonamide intermediates," Dyes and Pigments, 76: 636-645 (2008).
Akerman et al., "Interaction of oxidative bleach containing detergents with dyes. Part 1: Preparation and resistance of 1-amino-2-arylazonaphthalene-4-suphonic acid dyes to hydrogen peroxide and m-chloroperbenzoic acid," Dyes and Pigments, 59: 285-292 (2003).
Stopa et al., "Supramolecular ligands: Monomer structure and protein ligation capability," Biochimie, 80: 963-968 (1998).
Inoue et al., "Ultraviolet and visible absorption spectra of 1-amino-2-(1,3,5-trianzinyl) azonaphthalene-4-sulfonic acids and of their metal complexes," Senryo to Yakuhin, 41: 27-36 (1996).
Watanabe et al., "The Effect of Substituent on Absorption Bands of Sodium 2-(Substituted Phenylazo)-1-Naphthylamine Sulfonates," Tokyo Kogyo Koto Senmon Gakko Kenkyu Hokokusho, 13: 67-70 (1981).
Arcoria et al., "Study on new direct azo dyes. Dyes from 2-(p-aminophenyl)-,2,5-bis (p-aminophenyl)-and 2,5-bis (p-aminostyryl) thiophene: dyeing thermodynamics, metallization, CIE measurement," Chimica e l'Industria, 60: 981-986 (1978).
Barni et al., "Acid dyes for wool and nylon from p-amino-alpha-methylcinnamaldehyde," Tinctoria, 72: 147-151 (1975).
Fisichella et al., "Substantivity of mono- and disazo direct dyes from trans-2-(4-aminostyryl) furan," Tinctoria, 71: 189-191 (1974).
Mikhailova et al., "Effect of the nature of the complex-forming substituent on the stability of chromium-containing azo dyes," Zhurnal Obshchei Khimii, 36: 333-336 (1966).
Budesinsky et al., "Complexes of metallochromic substances. IV, Metallochromic properties of 2-(o-carboxyphenylazo) naphthionic acid amd 2-(0-Arsonophenylazo)-naphthionic acid," Fresenius' Zeitschrift fuer Analytische Chemie, 207: 241-247 (1965).
Pershin et al., "Some regularities in influenza virus control with synthetic drugs," Farmakologiya i Toksikologiya (Moscow), 24: 690-695 (1961).
Harada et al., "Azo dyes. XXI. Azo dyes from dehydrothio-p-toluidine," Hiroshima Daigaku Kogakubu Kenkyu Hokoku, 11:31-36 (1962).

(56) References Cited

OTHER PUBLICATIONS

Roseira et al., "The mechanism of color changes in acid solutions of secondary diazo dyes," Anais da Academia Brasileira de Ciencias, 30: 311-321 (1958).
Holmes et al., "The absorption spectra and the substantivity to cotton of Congo red and related structures," Transactions of the Faraday Society, 54: 1166-1171 (1958).
Tatsuoka et al., "Studies on atimalarials. VIII. Syntheses of antimalarials with azo groups," Ann. Rept. Takeda Research Lab, 10: 16-32 (1951).
Takahashi et al., "Pyridine derivatives containing sulfur. XXI. Synthesis of azopyridinesulfonic acids," Yakugaku Zasshi, 28-29 (1946).
Saikachi et al., "Pyridine derivatives containing sulfur. IX. Synthesis of azopyridines," Yakugaku Zasshi, 64: 328-330 (1944).
Kakizuka, "Feature: Modulating vital functions with a Ubiquitination: VCP involved in an aggregation and extraction of an abnormal protein in neurodegenerating disease," Seitai No Kagaku, 60 (6): 579-584 (2009).
Kakizuka, "Neurodegenerating disease and VCP," Clinical Neuroscience (separate volume), vol. 27, No. 9, 964-965, Sep. 2009.
Ramadan et al., "Cdc48/p97 promotes reformation of the nucleus by extracting the kinase Aurora B from chromatin," Nature, 450: 1258-1262 (2007).
Johnson et al., "Exome Sequencing Reveals VCP Mutations as a Cause of Familial ALS," Neuron. 10: 857-864 (2010).
International Search Report issued in corresponding International Application No. PCT/JP2011/067320 dated Oct. 11, 2011.
International Preliminary Report on Patentability issued in corresponding International Application No. PCT/JP2011/067320 dated Feb. 14, 2013.

\* cited by examiner

NAPHTHALENE DERIVATIVE

TECHNICAL FIELD

The present invention relates to naphthalene derivatives, especially 4-amino-naphthalene-1-sulfonic acid derivatives, and pharmaceutical compositions comprising them and use thereof.

BACKGROUND ART

Valosin-containing protein (VCP) belongs to a subfamily of ATPase, AAA (ATPases Associated with diverse cellular Activities), and is highly conserved among species. ATPases belonging to AAA are characterized in that they possess SRH (Second region of homology) region consisting of a similar amino acid sequence as a common structure in their C-terminal, in addition to Walker A motif (WA) which binds to ATP and Walker B motif (WB) which is involved in hydrolysis by the ATPase. The coordinated activity of WA, WB and SRH regions is thought to hydrolyze ATPs. VCP is mainly consisted of four regions, N-terminal region, D1 ATPase (D1) region, D2 ATPase (D2) region and C-terminal region, and possesses two ATPase regions characteristic of AAA family. Among them, D2 ATPase region is considered to be mainly responsible for the ATPase activity. In the two ATPase regions ATPase domain is followed by α-helix-enriched region, each of them is called D1α and D2α domain, respectively. The N-terminal region is known to have a function binding to and recognizing ubiquitin or degenerated proteins, and to be a binding region with cofactors such as Npl4, Ufd1 and p47 (Non-patent Literature 1).

It has been previously reported that VCP is involved in mechanisms of onset of neurodegenerative diseases. One of the mechanisms of onset of neurodegenerative diseases is an excess biological reaction for accumulation and aggregation of abnormal proteins (feedback mechanism). VCP is implied to be involved in such biological reactions. In particular, VCP recognizes and binds to extended polyglutamine observed in the neurodegenerative diseases such as Machado-Joseph disease (MJD) and Huntington's chorea. In addition, it was observed that VCP is co-localized with intranuclear inclusion bodies of MJD or Huntington's chorea, Lewy bodies of Parkinson's disease and aggregations in motor neurons, and recognize and bind to proteins which are believed to be involved in the pathogenesis of several neurodegenerative diseases. Furthermore, VCP is known to be involved in myopathy called IBMPFD (Inclusion Body Myopathy with Paget disease of bone and Front-temporal Dementia), which is dominantly inherited and associated with inclusion bodies after middle age, osteoporosis of Paget type, and diseases associated with frontotemporal dementia. Therefore, VCP is thought to serve not only as a sensor of abnormal proteins, but as an executioner of neuronal death (Non-patent Literature 2).

CITATION LIST

Non-Patent Literature

Non-patent Literature 1: Seitai No Kagaku 60 (6): 579-584, 2009
Non-patent Literature 2: Clinical Neuroscience (separate volume), Vol. 27, No. 9, 964-965, September 2009

SUMMARY OF INVENTION

Technical Problem to be Solved by the Invention

Based on these findings, new approach for the treatment of diseases is expected in which VCP-mediated diseases such as neurodegenerative diseases are treated by regulating ATPase activity of VCP. However, practical means for executing such approach are not available. For solving the problem, the purpose of the present invention is to provide the compounds useful as VCP regulators and the pharmaceutical compositions comprising them.

Solution to Problem

In one aspect, the present invention relates to the compounds of formula (I)

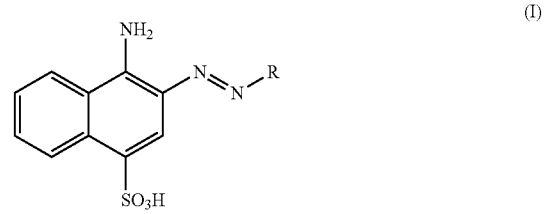

wherein
R refers to aryl or heteroaryl;
the aryl or heteroaryl may independently of one another be substituted by one or more substituent Ra;
Ra is independently of one another selected from the group consisting of halo, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclyl, substituted heterocyclyl, amino; substituted amino selected from —$NR^{21}R^{22}$ in which $R^{21}$ and $R^{22}$ is independently selected from the group consisting of hydrogen, $R^{30}$ and —$SO_2$—$R^{30}$, or $R^{21}$ and $R^{22}$, together with the nitrogen to which they are attached, form heterocyclyl or substituted heterocyclyl, provided that $R^{21}$ and $R^{22}$ are not simultaneously hydrogen; cyano, nitro; acyl selected from H—C(O)—, $R^{30}$—C(O)— and $NR^{27}R^{28}$—$NR^{26}$—C(O)— in which $R^{26}$, $R^{27}$ and $R^{28}$ are independently selected from the group consisting of hydrogen, $R^{30}$, —C(O)O—$R^{30}$ and —$SO_2$—$R^{30}$, or $R^{27}$ and $R^{28}$ may optionally, together with the nitrogen to which they are attached, refer to heterocyclyl or substituted heterocyclyl; acylamino selected from —$NR^{20}C(O)$—$R^{30}$ in which $R^{20}$ is hydrogen, alkyl or substituted alkyl; alkoxy, substituted alkoxy, carboxyl; carboxyl ester selected from —C(O)O—$R^{30}$; thioacyl selected from H—C(S)— and $R^{30}$—C(S)—; thiocyanate, thiol, alkylthio, substituted alkylthio; substituted sulfonyl selected from —$SO_2$—$R^{30}$; aminosulfonyl selected from —$SO_2NR^{23}R^{24}$ in which $R^{23}$ and $R^{24}$ are independently selected from the group consisting of hydrogen, $R^{30}$, hydroxy, alkoxy, substituted alkoxy, amino, the above-defined substituted amino and the above-defined acylamino, or $R^{23}$ and $R^{24}$ may optionally, together with the nitrogen to which they are attached, form heterocyclyl or substituted heterocyclyl; and aminocarbonyl selected from —C(O)$NR^{23}R^{24}$ in which $R^{23}$ and $R^{24}$ is as defined above;
$R^{30}$ is selected from alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclyl and substituted heterocyclyl;

the substituted alkyl, the substituted alkenyl, the substituted alkynyl or the substituted alkoxy independently of one another refer to the respective groups substituted with one or more substituent Rb;

Rb is independently of one another selected from the group consisting of alkoxy, substituted alkoxy, the above-defined acyl, the above-defined acylamino; acyloxy selected from $-C(O)O-R^{30}$; amino, the above-defined substituted amino, the above-defined aminocarbonyl; aminothiocarbonyl selected from $-C(S)NR^{23}R^{24}$ in which $R^{23}$ and $R^{24}$ are as defined above; aminocarbonylamino selected from $-NR^{20}C(O)NR^{23}R^{24}$ in which $R^{20}$, $R^{23}$ and $R^{24}$ are as defined above; aminothiocarbonylamino selected from $-NR^{20}C(S)NR^{23}R^{24}$ in which $R^{20}$, $R^{23}$ and $R^{24}$ are as defined above; aminocarbonyloxy selected from $-O-C(O)NR^{23}R^{24}$ in which $R^{23}$ and $R^{24}$ are as defined above; aminosulfonyl selected from $-SO_2NR^{23}R^{24}$ in which $R^{23}$ and $R^{24}$ are as defined above; aminosulfonyloxy selected from $-O-SO_2NR^{23}R^{24}$ in which $R^{23}$ and $R^{24}$ are as defined above; aminosulfonylamino selected from $-NR^{20}-SO_2NR^{23}R^{24}$ in which $R^{20}$, $R^{23}$ and $R^{24}$ are as defined above; amidino selected from $-C(=NR^{25})NR^{23}R^{24}$ in which $R^{25}$ is independently selected from the group consisting of hydrogen, $R^{30}$, hydroxy, alkoxy, substituted alkoxy, amino, the above-defined substituted amino and the above-defined acylamino, and $R^{23}$ and $R^{24}$ are as defined above; aryl, substituted aryl, aryloxy, substituted aryloxy, arylthio, substituted arylthio, azide, carboxyl, the above-defined carboxyl ester; (carboxyl ester)amino selected from $-NR^{20}-C(O)O-R^{30}$ in which $R^{20}$ is as defined above; (carboxyl ester)oxy selected from $-O-C(O)O-R^{30}$; cyano, cyanate, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino; substituted guanidino selected from $-NR^{29}C(=NR^{29})N(R^{29})_2$ in which $R^{29}$ is independently selected from the group consisting of hydrogen, alkyl, substituted alkyl, aryl, substituted aryl, heteroaryl, substituted heteroaryl, heterocyclyl and substituted heterocyclyl, or two $R^{29}$ attached to the same guanidino nitrogen atom together with the nitrogen to which they are attached optionally form heterocyclyl or substituted heterocyclyl, provided that at least one $R^{29}$ is not hydrogen); halo, hydroxy, hydroxyamino, alkoxyamino, hydrazino; substituted hydrazino selected from $-NR^{26}NR^{27}R^{28}$ in which $R^{26}$, $R^{27}$ and $R^{28}$ are as defined above; heteroaryl, substituted heteroaryl, heteroaryloxy, substituted heteroaryloxy, heteroarylthio, substituted heteroarylthio, heterocyclyl, substituted heterocyclyl, heterocyclyloxy, substituted heterocyclyloxy, heterocyclylthio, substituted heterocyclylthio, nitro, spirocycloalkylidene, $SO_3H$, the above-defined substituted sulfonyl, $-OSO_2-R^{30}$, the above-defined thioacyl, thiocyanate, thiol, alkylthio and substituted alkylthio;

the substituted aryl, the substituted cycloalkyl, the substituted cycloalkenyl, the substituted heteroaryl and the substituted heterocyclyl independently of one another refer to the respective groups substituted with one or more substituent Rc;

Rc is independently of one another selected from the group consisting of oxo, thione, alkyl, substituted alkyl, alkenyl, substituted alkenyl, alkynyl, substituted alkynyl, alkoxy, substituted alkoxy, the above-defined acyl, the above-defined acylamino, the above-defined acyloxy, amino, the above-defined substituted amino, aminocarbonyl, the above-defined aminothiocarbonyl, the above-defined aminocarbonylamino, the above-defined aminothiocarbonylamino, the above-defined aminocarbonyloxy, the above-defined aminosulfonyl, the above-defined aminosulfonyloxy, the above-defined aminosulfonylamino, the above-defined amidino, aryl, substituted aryl, aryloxy, substituted aryloxy, arylthio, substituted arylthio, azide, carboxyl, the above-defined carboxyl ester, the above-defined (carboxyl ester)amino, the above-defined (carboxyl ester)oxy, cyano, cyanate, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, the above-defined substituted guanidino, halo, hydroxy, hydroxyamino, alkoxyamino, hydrazino, the above-defined substituted hydrazino, heteroaryl, substituted heteroaryl, heteroaryloxy, substituted heteroaryloxy, heteroarylthio, substituted heteroarylthio, heterocyclyl, substituted heterocyclyl, heterocyclyloxy, substituted heterocyclyloxy, heterocyclylthio, substituted heterocyclylthio, nitro, $SO_3H$, the above-defined substituted sulfonyl, sulfonyloxy, thioacyl, thiocyanate, thiol, alkylthio and substituted alkylthio;

when the above-defined substituent Rb or Rc has a further substituent, the further substituent is as defined above, provided that the further substitution is up to three times, or oxides, esters, prodrugs, pharmaceutically acceptable salts or solvates thereof, and the compositions involving them and methods for using them.

Effects of Invention

These compounds can regulate ATPase activity of VCP, and therefore be useful for the treatment of VCP-mediated diseases such as IBMPFD, neurodegenerative diseases, muscle diseases, bone diseases, inflammatory diseases, cystic fibrosis, autoimmune diseases, viral infections, tumor diseases, dyslipidemia, hypertension, benign prostatic hyperplasia, chronic obstructive pulmonary disease, urinary frequency, urinary incontinence, irritable bowel syndrome, allergic disease, gastric ulcer, duodenal ulcer, depression, anxiety, schizophrenia, migraine, pain and vomiting.

DESCRIPTION OF EMBODIMENTS

Definition

Unless defined otherwise, the terms used herein have the same meaning as commonly understood to one of ordinary skill in the art in the field of organic chemistry, medicine, pharmacology, molecular biology, microbiology and the like. The definitions of several terms used herein are described below. These definitions herein take precedence over the general understanding.

"Alkyl" refers to monovalent saturated aliphatic hydrocarbyl groups having from 1 to 10 carbon atoms and preferably 1 to 6 carbon atoms. The term "$C_{x-y}$alkyl" refers to alkyl groups having from x to y carbons. This term includes, but not limited to, by way of example, linear and branched hydrocarbyl groups such as methyl($CH_3-$), ethyl($CH_3CH_2-$), n-propyl($CH_3CH_2CH_2-$), isopropyl(($CH_3)_2CH-$), n-butyl($CH_3CH_2CH_2CH_2-$), isobutyl ((CH$_3$)$_2$CHCH$_2$—), sec-butyl((CH$_3$)(CH$_3$CH$_2$)CH—), t-butyl((CH$_3$)$_3$C—), n-pentyl(CH$_3$CH$_2$CH$_2$CH$_2$CH$_2$—), and neopentyl ((CH$_3$)$_3$CCH$_2$—).

The prefix "substituted" for a group means that one or more hydrogen atom of the group is replaced by an indicated substituent. When the substituent is not specifically defined in the context, the prefix is understood based on the following definitions.

"Substituted alkyl" refers to an alkyl group having from 1 to 5, preferably 1 to 3, or more preferably 1 to 2 substituents selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, azide, carboxyl, carboxyl ester, (carboxyl ester)amino, (carboxyl ester)oxy, cyano, cyanate, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, hydroxyamino, alkoxyamino, hydrazino, substituted hydrazino, heteroaryl, substituted heteroaryl, heteroaryloxy, substituted heteroaryloxy, heteroarylthio, substituted heteroarylthio, heterocyclyl, substituted heterocyclyl, heterocyclyloxy, substituted heterocyclyloxy, heterocyclylthio, substituted heterocyclylthio, nitro, spirocycloalkylidene, SO$_3$H, substituted sulfonyl, sulfonyloxy, thioacyl, thiocyanate, thiol, alkylthio and substituted alkylthio, wherein said substituents are as defined herein.

"Alkylidene" or "alkylene" refers to divalent saturated aliphatic hydrocarbyl groups having from 1 to 10 carbon atoms and preferably 1 to 6 carbon atoms. "C$_{x-y}$alkylene" refers to alkylene groups having from x to y carbons. The alkylidene and alkylene groups include branched and straight chain hydrocarbyl groups.

"Substituted alkylidene" or "substituted alkylene" refers to an alkylidene group having from 1 to 5, preferably 1 to 3, or more preferably 1 to 2 substituents selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, azide, carboxyl, carboxyl ester, (carboxyl ester)amino, (carboxyl ester)oxy, cyano, cyanate, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, hydroxyamino, alkoxyamino, hydrazino, substituted hydrazino, heteroaryl, substituted heteroaryl, heteroaryloxy, substituted heteroaryloxy, heteroarylthio, substituted heteroarylthio, heterocyclyl, substituted heterocyclyl, heterocyclyloxy, substituted heterocyclyloxy, heterocyclylthio, substituted heterocyclylthio, nitro, oxo, thione, spirocycloalkylidene, SO$_3$H, substituted sulfonyl, sulfonyloxy, thioacyl, thiocyanate, thiol, alkylthio and substituted alkylthio, wherein said substituents are defined herein.

"Alkoxy" refers to the group —O-alkyl wherein alkyl is defined herein. Alkoxy includes, by way of example, methoxy, ethoxy, n-propoxy, isopropoxy, n-butoxy, t-butoxy, sec-butoxy and n-pentoxy.

"Substituted alkoxy" refers to the group —O— (substituted alkyl) wherein the substituted alkyl is defined herein.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, substituted hydrazino-C(O)—, heteroaryl-C(O)—, substituted heteroaryl-C(O)—, heterocyclyl-C(O)— and substituted heterocyclyl-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, substituted hydrazino, heteroaryl, substituted heteroaryl, heterocyclyl and substituted heterocyclyl are as defined herein. "Acetyl" group refers to the group CH$_3$C(O)—.

"Acylamino" refers to the groups —NR$^{20}$C(O)alkyl, —NR$^{20}$C(O) substituted alkyl, —NR$^{20}$C(O)cycloalkyl, —NR$^{20}$C(O) substituted cycloalkyl, —NR$^{20}$C(O)cycloalkenyl, —NR$^{20}$C(O) substituted cycloalkenyl, —NR$^{20}$C(O) alkenyl, —NR$^{20}$C(O) substituted alkenyl, —NR$^{20}$C(O) alkynyl, —NR$^{20}$C(O) substituted alkynyl, —NR$^{20}$C(O)aryl, —NR$^{20}$C(O) substituted aryl, —NR$^{20}$C(O)heteroaryl, —NR$^{20}$C(O) substituted heteroaryl, —NR$^{20}$C(O)heterocyclyl and —NR$^{20}$C(O) substituted heterocyclyl wherein R$^{20}$ is hydrogen or alkyl, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclyl and substituted heterocyclyl are as defined herein.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O) O—, aryl-C(O)O—, substituted aryl-C(O)O—, cycloalkyl-C(O)O—, substituted cycloalkyl-C(O)O—, cycloalkenyl-C(O)O—, substituted cycloalkenyl-C(O)O—, heteroaryl-C(O)O—, substituted heteroaryl-C(O)O—, heterocyclyl-C(O)O— and substituted heterocyclyl-C(O)O—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclyl and substituted heterocyclyl are as defined herein.

"Amino" refers to the group —NH$_2$.

"Substituted amino" refers to the group —NR$^{21}$R$^{22}$, wherein R$^{21}$ and R$^{22}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclyl, substituted heterocyclyl, —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-cycloalkenyl, —SO$_2$-substituted cycloalkenyl, —SO$_2$-aryl, —SO$_2$-substituted aryl, —SO$_2$-heteroaryl, —SO$_2$-substituted heteroaryl, —SO$_2$-heterocyclyl and —SO$_2$-substituted heterocyclyl, or wherein R$^{21}$ and R$^{22}$ are optionally joined, together with the nitrogen bound thereto to form a heterocyclic or substituted heterocyclic group, provided that R$^{21}$ and R$^{22}$ are both not hydrogen, and wherein said alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclyl and substituted heterocyclyl are as defined herein. When R$^{21}$ is hydrogen and $R^{22}$ is alkyl, the substituted amino group is herein sometimes referred to as alkylamino. When $R^{21}$ and $R^{22}$ are alkyl, the substituted amino group is herein sometimes referred to as dialkylamino. When referring to a monosubstituted amino, it is meant that either $R^{21}$ or $R^{22}$ is hydrogen but not both. When referring to a disubstituted amino, it is meant that neither $R^{21}$ nor $R^{22}$ are hydrogen.

"Hydroxyamino" refers to the group —NHOH.

"Alkoxyamino" refers to the group —NHO-alkyl wherein alkyl is defined herein.

"Aminocarbonyl" refers to the group —C(O)NR$^{23}$R$^{24}$ wherein $R^{23}$ and $R^{24}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclyl, substituted heterocyclyl, hydroxy, alkoxy, substituted alkoxy, amino, substituted amino and acylamino, or $R^{23}$ and $R^{24}$ are optionally joined together with the nitrogen bound thereto to form a heterocyclic or substituted heterocyclic group, and wherein alkyl, substituted alkyl, alkoxy, substituted alkoxy, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclyl and substituted heterocyclyl are as defined herein.

"Aminothiocarbonyl" refers to the group —C(S)NR$^{23}$R$^{24}$, wherein $R^{23}$ and $R^{24}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclyl, substituted heterocyclyl, hydroxy, alkoxy, substituted alkoxy, amino, substituted amino and acylamino, or $R^{23}$ and $R^{24}$ are optionally joined together with the nitrogen bound thereto to form a heterocyclic or substituted heterocyclic group, and wherein substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclyl and substituted heterocyclyl are as defined herein.

"Aminocarbonylamino" refers to the group —NR$^{20}$C(O)NR$^{23}$R$^{24}$ wherein $R^{20}$ is hydrogen or alkyl and $R^{23}$ and $R^{24}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclyl and substituted heterocyclyl, or $R^{23}$ and $R^{24}$ are optionally joined together with the nitrogen bound thereto to form a heterocyclic or substituted heterocyclic group, and wherein substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclyl and substituted heterocyclyl are as defined herein.

"Aminothiocarbonylamino" refers to the group —NR$^{20}$C(S)NR$^{23}$R$^{24}$ wherein $R^{20}$ is hydrogen or alkyl and $R^{23}$ and $R^{24}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclyl and substituted heterocyclyl, or $R^{23}$ and $R^{24}$ are optionally joined together with the nitrogen bound thereto to form a heterocyclic or substituted heterocyclic group, and wherein substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclyl and substituted heterocyclyl are as defined herein.

"Aminocarbonyloxy" refers to the group —O—C(O)NR$^{23}$R$^{24}$ wherein $R^{23}$ and $R^{24}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclyl, substituted heterocyclyl, hydroxy, alkoxy, substituted alkoxy, amino, substituted amino and acylamino, or $R^{23}$ and $R^{24}$ are optionally joined together with the nitrogen bound thereto to form a heterocyclic or substituted heterocyclic group, and wherein substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclyl and substituted heterocyclyl are as defined herein.

"Aminosulfonyl" refers to the group —SO$_2$NR$^{23}$R$^{24}$ wherein $R^{23}$ and $R^{24}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclyl, substituted heterocyclyl, hydroxy, alkoxy, substituted alkoxy, amino, substituted amino and acylamino, or $R^{23}$ and $R^{24}$ are optionally joined together with the nitrogen bound thereto to form a heterocyclic or substituted heterocyclic group, and wherein substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclyl and substituted heterocyclyl are as defined herein.

"Aminosulfonyloxy" refers to the group —O—SO$_2$NR$^{23}$R$^{24}$, wherein $R^{23}$ and $R^{24}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclyl, substituted heterocyclyl, hydroxy, alkoxy, substituted alkoxy, amino, substituted amino and acylamino, or $R^{23}$ and $R^{24}$ are optionally joined together with the nitrogen bound thereto to form a heterocyclic or substituted heterocyclic group, and wherein substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclyl and substituted heterocyclyl are as defined herein.

"Aminosulfonylamino" refers to the group —NR$^{20}$—SO$_2$NR$^{23}$R$^{24}$ wherein $R^{20}$ is hydrogen or alkyl and $R^{23}$ and $R^{24}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclyl and substituted heterocyclyl, or $R^{23}$ and $R^{24}$ are optionally joined together with the nitrogen bound thereto to form a heterocyclic or substituted heterocyclic group, and wherein substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclyl and substituted heterocyclyl are as defined herein.

"Amidino" refers to the group —C(=NR$^{25}$)NR$^{23}$R$^{24}$ wherein R$^{25}$, R$^{23}$ and R$^{24}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclyl and substituted heterocyclyl, or R$^{23}$ and R$^{24}$ are optionally joined together with the nitrogen bound thereto to form a heterocyclic or substituted heterocyclic group, and wherein substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclyl and substituted heterocyclyl are as defined herein.

"Aryl" or "Ar" refers to a monovalent aromatic carbocyclic group of from 6 to 14 carbon atoms having a single ring (e.g., phenyl) or multiple condensed rings (e.g., naphthyl or anthryl). In the multicyclic ring systems, one or more rings which are condensed with aryl may be cycloalkyl, cycloalkenyl, heterocyclyl, aryl or heteroaryl. Accordingly, aryl includes, for example, 2-benzoxazolinone, 1H-isothiochromenyl, isothiochromanyl, 2H-thiochromenyl, thiochromanyl, 9H-thioxanthenyl, thianthrenyl, phenoxathiinyl, benzothiophenyl, dibenzothiophenyl, benzofuranyl, dibenzofuranyl and 2H-1,4-benzoxazine-3(4H)-on-7-yl, provided that the point of attachment is at a carbon atom of an aryl ring comprising no hetero atom. Aryl groups typically include phenyl and naphthyl.

"Substituted aryl" refers to aryl groups which are substituted with 1 to 5, preferably 1 to 3, or more preferably 1 to 2 substituents selected from the group consisting of oxo, thione, alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, azide, carboxyl, carboxyl ester, (carboxyl ester)amino, (carboxyl ester)oxy, cyano, cyanate, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, hydroxyamino, alkoxyamino, hydrazino, substituted hydrazino, heteroaryl, substituted heteroaryl, heteroaryloxy, substituted heteroaryloxy, heteroarylthio, substituted heteroarylthio, heterocyclyl, substituted heterocyclyl, heterocyclyloxy, substituted heterocyclyloxy, heterocyclylthio, substituted heterocyclylthio, nitro, SO$_3$H, substituted sulfonyl, sulfonyloxy, thioacyl, thiocyanate, thiol, alkylthio and substituted alkylthio, wherein said substituents are defined herein. Substituents on a multicyclic ring system may be present at aryl group or one or more ring condensed with the aryl group.

"Aryloxy" refers to the group —O-aryl, where aryl is as defined herein, and includes, by way of example, phenoxy and naphthoxy.

"Substituted aryloxy" refers to the group —O— (substituted aryl) where substituted aryl is as defined herein.

"Arylthio" refers to the group —S-aryl, where aryl is as defined herein.

"Substituted arylthio" refers to —S-(substituted aryl), where substituted aryl is defined herein.

"Alkenyl" refers to a hydrocarbyl group having from 2 to 6 carbon atoms and preferably 2 to 4 carbon atoms and having at least 1 and preferably from 1 to 2 carbon-carbon double bond (C=C). Such groups are exemplified, for example, by vinyl, allyl and but-3-en-yl.

"Substituted alkenyl" refers to alkenyl groups having from 1 to 3 substituents, and preferably 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester) amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclyl, substituted heterocyclyl, heterocyclyloxy, substituted heterocyclyloxy, heterocyclylthio, substituted heterocyclylthio, nitro, SO$_3$H, substituted sulfonyl, sulfonyloxy, thioacyl, thiol, alkylthio and substituted alkylthio, wherein said substituents are defined herein and with the proviso that any hydroxy or thiol substitution is not attached to a vinyl (unsaturated) carbon atom.

"Alkynyl" refers to hydrocarbyl groups having from 2 to 6 carbon atoms and preferably 2 to 3 carbon atoms and having at least 1 and preferably from 1 to 2 carbon-carbon triple bond (C≡C).

"Substituted alkynyl" refers to alkynyl groups having from 1 to 3 substituents, and preferably 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester) amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclyl, substituted heterocyclyl, heterocyclyloxy, substituted heterocyclyloxy, heterocyclylthio, substituted heterocyclylthio, nitro, SO$_3$H, substituted sulfonyl, sulfonyloxy, thioacyl, thiol, alkylthio and substituted alkylthio, wherein said substituents are defined herein and with the proviso that any hydroxy or thiol substitution is not attached to an acetylenic (unsaturated) carbon atom.

"Azide" refers to the group —N$_3$.

"Hydrazino" refers to the group —NHNH$_2$.

"Substituted hydrazino" refers to the group —NR$^{26}$NR$^{27}$R$^{28}$ wherein R$^{26}$, R$^{27}$ and R$^{28}$ are independently selected from the group consisting of hydrogen, alkyl, substituted alkyl, alkenyl, substituted alkenyl, alkynyl, substituted alkynyl, aryl, substituted aryl, carboxyl ester, cycloalkyl, substituted cycloalkyl, cycloalkenyl, substituted cycloalkenyl, heteroaryl, substituted heteroaryl, heterocyclyl, substituted heterocyclyl, —SO$_2$-alkyl, —SO$_2$-substituted alkyl, —SO$_2$-alkenyl, —SO$_2$— substituted alkenyl, —SO$_2$-cycloalkyl, —SO$_2$-substituted cycloalkyl, —SO$_2$-cycloalkenyl, —SO$_2$-substituted cycloalkenyl, —SO$_2$-aryl, —SO$_2$-substituted aryl, —SO$_2$-heteroaryl, —SO$_2$-substituted heteroaryl, —SO$_2$-heterocyclyl and —SO$_2$-substituted heterocyclyl, or R$^{27}$ and R$^{28}$ are optionally joined together with the nitrogen bound thereto to form a heterocyclic or substituted heterocyclic group, provided that R$^{27}$ and R$^{28}$ are both not hydrogen, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclyl and substituted heterocyclyl are as defined herein.

"Cyano" or "carbonitrile" refers to the group —CN.

"Cyanate" refers to the group —OCN.

"Carbonyl" refers to the divalent group —C(O)— which is equivalent to —C(=O)—.

"Carboxyl" or "carboxy" refers to —COOH or salts thereof.

"Carboxyl ester" or "carboxy ester" refers to the groups —C(O)O-alkyl, —C(O)O-substituted alkyl, —C(O)O-alkenyl, —C(O)O-substituted alkenyl, —C(O)O-alkynyl, C(O)O-substituted alkynyl, —C(O)O-aryl, —C(O)O-substituted aryl, —C(O)O-cycloalkyl, —C(O)O-substituted cycloalkyl, C(O)O-cycloalkenyl, —C(O)O-substituted cycloalkenyl, C(O)O-heteroaryl, —C(O)O-substituted heteroaryl, —C(O)O-heterocyclyl and —C(O)O-substituted heterocyclyl, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclyl and substituted heterocyclyl are as defined herein.

"(Carboxyl ester)amino" refers to the group —NR$^{20}$—C(O)O-alkyl, —NR$^{20}$—C(O)O-substituted alkyl, —NR$^{20}$—C(O)O-alkenyl, —NR$^{20}$—C(O)O-substituted alkenyl, —NR$^{20}$—C(O)O-alkynyl, —NR$^{20}$—C(O)O-substituted alkynyl, —NR$^{20}$—C(O)O-aryl, —NR$^{20}$—C(O)O-substituted aryl, —NR$^{20}$—C(O)O-cycloalkyl, NR$^{20}$—C(O)O-substituted cycloalkyl, —NR$^{20}$—C(O)O-cycloalkenyl, —NR$^{20}$—C(O)O-substituted cycloalkenyl, —NR$^{20}$—C(O)O-heteroaryl, —NR$^{20}$—C(O)O-substituted heteroaryl, —NR$^{20}$—C(O)O-heterocyclyl or —NR$^{20}$—C(O)O-substituted heterocyclyl wherein R$^{20}$ is alkyl or hydrogen, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclyl and substituted heterocyclyl being as defined herein.

"(Carboxyl ester)oxy" refers to the group —O—C(O)O-alkyl, —O—C(O)O-substituted alkyl, —O—C(O)O-alkenyl, —O—C(O)O-substituted alkenyl, —O—C(O)O-alkynyl, —O—C(O)O-substituted alkynyl, —O—C(O)O-aryl, —O—C(O)O-substituted aryl, —O—C(O)O-cycloalkyl, —O—C(O)O-substituted cycloalkyl, —O—C(O)O-cycloalkenyl, —O—C(O)O-substituted cycloalkenyl, —O—C(O)O-heteroaryl, —O—C(O)O-substituted heteroaryl, —O—C(O)O-heterocyclyl or —O—C(O)O-substituted heterocyclyl wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclyl and substituted heterocyclyl are as defined herein.

"Cycloalkyl" refers to cyclic alkyl groups of from 3 to 10 carbon atoms having single or multiple cyclic rings including fused, bridged, and spiro ring systems. In multiple cyclic ring systems, one or more rings which is fused, bridged or spiro-linked with cycloalkyl can be cycloalkyl, cycloalkenyl, heterocyclyl, aryl or heteroaryl, provided that the point of attachment is through the cycloalkyl ring. Examples of suitable cycloalkyl groups include, for instance, adamantyl, cyclopropyl, cyclobutyl, cyclopentyl, and cyclooctyl. "C$_{x-y}$cycloalkyl" refers to cycloalkyl groups having x to y carbons.

"Cycloalkenyl" refers to non-aromatic cyclic alkyl groups of from 4 to 10 carbon atoms having single or multiple cyclic rings and having at least one >C=C< ring unsaturation and preferably from 1 to 2>C=C< ring unsaturation. In the multicyclic ring system, one or more ring which is fused, bridged or spiro-linked with cycloalkenyl may be cycloalkyl, heterocyclyl, aryl or heteroaryl, provided that the point of attachment is through the cycloalkenyl ring. "C$_{x-y}$cycloalkenyl" refers to cycloalkenyl groups having x to y carbons.

"Substituted cycloalkyl" and "substituted cycloalkenyl" refers to a cycloalkyl or cycloalkenyl group having from 1 to 5 or preferably 1 to 3 substituents selected from the group consisting of oxo, thione, alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, azide, carboxyl, carboxyl ester, (carboxyl ester)amino, (carboxyl ester)oxy, cyano, cyanate, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, hydroxyamino, alkoxyamino, hydrazino, substituted hydrazino, heteroaryl, substituted heteroaryl, heteroaryloxy, substituted heteroaryloxy, heteroarylthio, substituted heteroarylthio, heterocyclyl, substituted heterocyclyl, heterocyclyloxy, substituted heterocyclyloxy, heterocyclylthio, substituted heterocyclylthio, nitro, SO$_3$H, substituted sulfonyl, sulfonyloxy, thioacyl, thiocyanate, thiol, alkylthio and substituted alkylthio, wherein said substituents are as defined herein. Substituents on a multicyclic ring system may be present at cycloalkyl or cycloalkenyl group, or at one or more ring which is fused, bridged or spiro-linked with the cycloalkyl group or cycloalkenyl group.

"Cycloalkyloxy" refers to —O-cycloalkyl.

"Substituted cycloalkyloxy" refers to —O-(substituted cycloalkyl).

"Cycloalkylthio" refers to —S-cycloalkyl.

"Substituted cycloalkylthio" refers to —S-(substituted cycloalkyl).

"Cycloalkenyloxy" refers to —O-cycloalkenyl.

"Substituted cycloalkenyloxy" refers to —O— (substituted cycloalkenyl).

"Cycloalkenylthio" refers to —S-cycloalkenyl.

"Substituted cycloalkenylthio" refers to —S— (substituted cycloalkenyl).

"Guanidino" refers to the group —NHC(=NH)NH$_2$.

"Substituted guanidino" refers to —NR$^{29}$C(=NR$^{29}$)N(R$^{29}$)$_2$, wherein R$^{29}$ is independently selected from the group consisting of hydrogen, alkyl, substituted alkyl, aryl, substituted aryl, heteroaryl, substituted heteroaryl, heterocyclyl and substituted heterocyclyl, or two R$^{29}$ groups attached to a common guanidino nitrogen atom are optionally joined together with the nitrogen bound thereto to form a heterocyclic or substituted heterocyclic group, provided that at least one $R^{29}$ is not hydrogen, and wherein said substituents are as defined herein.

"Halo" or "halogen" refers to fluoro, chloro, bromo or iodo.

"Haloalkyl" refers to alkyl groups substituted by 1 to 5 or preferably 1 to 3 halo groups.

"Haloalkoxy" refers alkoxy groups substituted by 1 to 5 or preferably 1 to 3 halo groups.

"Hydroxy" or "hydroxyl" refers to the group —OH.

"Heteroaryl" refers to an aromatic group of from 1 to 12 carbon atoms and 1 to 4 heteroatoms selected from the group consisting of oxygen, nitrogen and sulfur within the ring. Such heteroaryl groups can have a single ring (e.g., pyridinyl or furyl) or multiple condensed rings (e.g., indolizinyl or benzothienyl) wherein the condensed rings may or may not be aromatic and/or contain a heteroatom provided that the point of attachment is through a carbon or heteroatom of the aromatic heteroaryl group. In one embodiment, the nitrogen and/or the sulfur ring atom(s) of the heteroaryl group are optionally oxidized to provide for the N-oxide (N→O), sulfinyl, or sulfonyl moieties. Heteroaryl includes pyridinyl, pyrrolyl, indolyl, thiophenyl and furanyl.

"Substituted heteroaryl" refers to heteroaryl groups that are substituted with from 1 to 5, preferably 1 to 3, or more preferably 1 to 2 substituents selected from the group consisting of the same group of substituents defined for substituted aryl.

"Heteroaryloxy" refers to —O-heteroaryl.

"Substituted heteroaryloxy" refers to the group —O—(substituted heteroaryl).

"Heteroarylthio" refers to the group —S-heteroaryl.

"Substituted heteroarylthio" refers to the group —S—(substituted heteroaryl).

"Heterocycle", "heterocyclyl" or "heterocycloalkyl" is used in an interchangeable manner, and refers to a saturated, partially saturated, or unsaturated group (but not aromatic) having a single ring or multiple condensed rings, including fused bridged and spirocycyl ring systems, from 1 to 4 hetero atoms selected from nitrogen, sulfur or oxygen within the ring wherein, in fused ring systems, one or more rings can be cycloalkyl, aryl or heteroaryl provided that the point of attachment is through the non-aromatic heterocycle. In one embodiment, the nitrogen and/or sulfur atom(s) of the heterocyclic group are optionally oxidized to provide for the N-oxide, sulfinyl, and sulfonyl moieties.

"Substituted heterocyclic", "substituted heterocyclyl" or "substituted heterocycloalkyl" refers to heterocyclyl groups that are substituted with from 1 to 5 or preferably 1 to 3 of the same substituents as defined for substituted cycloalkyl.

"Heterocyclyloxy" refers to the group —O-heterocyclyl.

"Substituted heterocyclyloxy" refers to the group —O-(substituted heterocyclyl).

"Heterocyclylthio" refers to the group —S-heterocyclyl.

"Substituted heterocyclylthio" refers to the group —S—(substituted heterocyclyl).

Examples of heterocycle and heteroaryl include, but not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thioxanthenyl, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine and tetrahydrofuranyl.

"Nitro" refers to the group —NO$_2$.

"Oxo" refers to the atom (=O).

"Oxide" refers to products resulting from the oxidation of one or more heteroatoms. Examples include N-oxides, sulfoxides, and sulfones.

"Spirocyclyl" refers to divalent cyclic groups of from 3 to 10 carbon atoms having a cycloalkyl ring with a spiro union (the union formed by a single atom which is the only common member of the rings) as exemplified by the following structure:

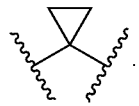 [SMILES: *C1(*)CC1]

"Spirocycloalkyl" or "spirocycloalkylidene" refers to divalent cyclic groups having a cycloalkyl ring with a spiro union, as described for spirocyclyl.

"sulfonyl" refers to the divalent group of —S(O)$_2$—.

"Substituted sulfonyl" refers to the group —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-cycloalkenyl, —SO$_2$-substituted cycloalkenyl, —SO$_2$-aryl, —SO$_2$-substituted aryl, —SO$_2$-heteroaryl, —SO$_2$-substituted heteroaryl, —SO$_2$-heterocyclyl or —SO$_2$-substituted heterocyclyl wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclyl and substituted heterocyclyl are as defined herein. Substituted sulfonyl includes groups such as methyl-SO$_2$—, phenyl-SO$_2$—, and 4-methylphenyl-SO$_2$—.

"Sulfonyloxy" refers to the group —OSO$_2$-alkyl, —OSO$_2$-substituted alkyl, —OSO$_2$-alkenyl, —OSO$_2$-substituted alkenyl, —OSO$_2$-alkynyl, —OSO$_2$-substituted alkynyl, —OSO$_2$-cycloalkyl, —OSO$_2$-substituted cycloalkyl, —OSO$_2$-cycloalkenyl, —OSO$_2$-substituted cycloalkenyl, —OSO$_2$-aryl, —OSO$_2$-substituted aryl, —OSO$_2$-heteroaryl, —OSO$_2$-substituted heteroaryl, OSO$_2$-heterocyclyl or —OSO$_2$-substituted heterocyclyl wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclyl and substituted heterocyclyl are as defined herein.

"Thioacyl" refers to the group H—C(S)—, alkyl-C(S)—, substituted alkyl-C(S)—, alkenyl-C(S)—, substituted alkenyl-C(S)—, alkynyl-C(S)—, substituted alkynyl-C(S)—, cycloalkyl-C(S)—, substituted cycloalkyl-C(S)—, cycloalkenyl-C(S)—, substituted cycloalkenyl-C(S)—, aryl-C(S)—, substituted aryl-C(S)—, heteroaryl-C(S)—, substituted heteroaryl-C(S)—, heterocyclyl-C(S)— or substituted heterocyclyl-C(S)— wherein said alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclyl and substituted heterocyclyl are as defined herein.

"Thiol" refers to the group —SH.

"Alkylthio" refers to the group —S-alkyl wherein alkyl is defined herein.

"Substituted alkylthio" refers to the group —S— (substituted alkyl) wherein substituted alkyl is defined herein.

"Thiocarbonyl" refers the divalent group —C(S)— which is equivalent to —C(=S)—.

"Thione" refers to the atom (=S).

"Thiocyanate" refers to the group —SCN.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group etc.) are not intended for inclusion herein. In such cases, the maximum number of such substitutions is three.

Similarly, it is understood that the above definitions are not intended to include impermissible substitution patterns (e.g., methyl substituted with 5 fluoro groups). Such impermissible substitution patterns are well known to the skilled artisan.

"Compound" and "compounds" as used herein refers to a compound encompassed by the generic formulae disclosed herein, any subgenus of those generic formulae, and any specific compounds within the generic and subgeneric formulae, including the oxide, ester, prodrug, pharmaceutically acceptable salt, or solvate thereof. The term further includes the stereoisomers and tautomers of the compound or compounds.

"Solvate" or "solvates" of a compound refer to those compounds, where the compound is as defined above, that are bound to a stoichiometric or non-stoichiometric amount of a solvent. Solvates includes solvates of the oxide, ester, prodrug, or pharmaceutically acceptable salt of the disclosed generic and subgeneric formulae. Preferred solvents are volatile, non-toxic, and/or acceptable for administration to humans in trace amounts. Suitable solvates include water.

"Stereoisomer" or "stereoisomers" refer to compounds that differ in the chirality of one or more stereocenters. Stereoisomers include enantiomers and diastereomers.

"Tautomer" refers to alternate forms of a compound that differ in the position of a proton, such as enol-keto and imine-enamine tautomers, or the tautomeric forms of heteroaryl groups containing a ring atom attached to both a ring —NH— moiety and a ring =N— moiety such as pyrazoles, imidazoles, benzimidazoles, triazoles, and tetrazoles.

"Prodrug" refers to any derivative of a compound of the embodiments that is capable of directly or indirectly providing a compound of the embodiments or an active metabolite or residue thereof when administered to a subject. Particularly favored derivatives and prodrugs are those that increase the bioavailability of the compounds of the embodiments when such compounds are administered to a subject (e.g., by allowing an orally administered compound to be more readily absorbed into the blood) or which enhance delivery of the parent compound to a biological compartment (e.g., the brain or lymphatic system) relative to the parent species. Prodrugs include ester forms of the compounds of the invention. Examples of ester prodrugs include formate, acetate, propionate, butyrate, acrylate, and ethylsuccinate derivatives. A general overview of prodrugs is provided in T. Higuchi and V. Stella, Pro drugs as Novel Delivery Systems, Vol. 14 of the A.C.S. Symposium Series and Edward B. Roche, ed., Bioreversible Carriers in Drug Design, American Pharmaceutical Association and Pergamon Press, 1987, both of which are incorporated herein by reference.

"Pharmaceutically acceptable salt" refers to pharmaceutically acceptable salts derived from a variety of organic and inorganic counter ions well known in the art and include, by way of example, salts of sodium, potassium, calcium, magnesium, ammonium, and tetraalkylammonium, and salts of organic or inorganic acids, such as hydrochloride, hydrobromide, tartrate, mesylate, acetate, maleate, and oxalate. Pharmaceutically acceptable salt of a compound refers to pharmaceutically acceptable salts including salts of the oxide, ester, or prodrug of the disclosed generic and subgeneric formulae.

"Subject" refers to mammals and includes humans and non-human mammals.

"Treating" or "treatment" of a disease in a subject refers to 1) preventing the disease from occurring in a subject that is predisposed or does not yet display symptoms of the disease; 2) inhibiting the disease or arresting its development; or 3) ameliorating or causing regression of the disease.

"VCP regulator" refers to a compound which can regulate, for example, enhance or inhibit, the ATPase activity of VCP. When the VCP regulator inhibits the ATPase activity, it sometimes referred to as a VCP inhibitor.

In one embodiment, the present invention relates to a compound of formula (II):

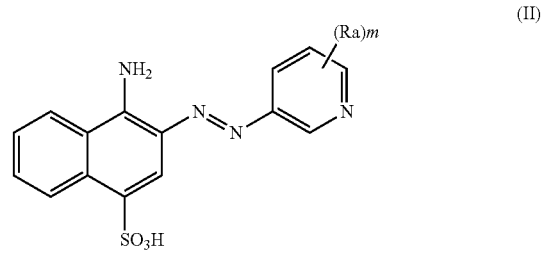

wherein Ra is as defined above, m is an integer selected from 0 to 4, or oxides, esters, prodrugs, pharmaceutically acceptable salts or solvates thereof, as well as compositions involving them and methods for using them.

In one embodiment, the present invention relates to a compound of formula (III):

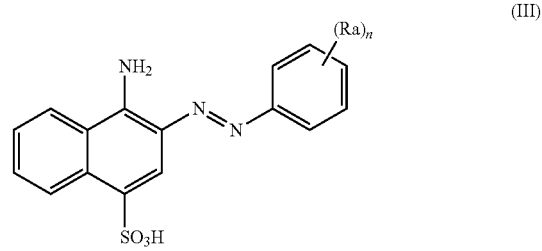

wherein Ra is as defined above, n is an integer selected from 0 to 5, or oxides, esters, prodrugs, pharmaceutically acceptable salts or solvates thereof, as well as compositions involving them and methods for using them.

In the compounds of formula (I) above, R is preferably selected from phenyl, pyridyl, quinolinyl and thiophenyl, which may be unsubstituted or substituted independently of one another with one or more Ra. The preferred scope of substituent Ra is listed below. It should be understood that when the compounds of the present invention have two or more Ra substituents, each Ra is not necessary to be selected from the identical scope. For example, when the compound of the present invention have two Ra substituents, one Ra may be selected from those within any of the following preferred scopes of Ra and other Ra may be selected from those within the scope of Ra of formula (I) above.

In the compounds of formula (I), (II) or (III) above, preferred substituent Ra is independently of one another selected from the group consisting of halo, alkyl, substituted alkyl, alkenyl, substituted alkenyl, aryl, substituted aryl, heteroaryl, substituted heteroaryl, heterocyclyl, substituted heterocyclyl, cyano, nitro, acyl, acylamino, alkoxy, substituted alkoxy, carboxyl, carboxyl ester, alkylthio, substituted alkylthio and aminocarbonyl. Further substituent on Ra is independently of one another selected from those described herein in the definition of formula (I) or each substituent.

In the compounds of formula (I), (II) or (III) above, more preferred substituent Ra is independently of one another selected from the group consisting of halo, alkyl, substituted alkyl, alkenyl, substituted alkenyl, aryl, substituted aryl, heteroaryl, substituted heteroaryl, heterocyclyl, substituted heterocyclyl, acyl, alkoxy and substituted alkoxy. Further substituent on Ra is independently of one another selected from those described herein in the definition of formula (I) or each substituent.

In the compounds of formula (I), (II) or (III) above, another more preferred substituent Ra is independently of one another selected from the group consisting of halo, alkyl, substituted alkyl, alkenyl, substituted alkenyl, aryl, substituted aryl, heteroaryl, substituted heteroaryl, cyano, nitro, acyl, acylamino, alkoxy, substituted alkoxy, carboxyl, carboxyl ester, alkylthio, substituted alkylthio and aminocarbonyl, especially alkenyl, substituted alkenyl, aryl, substituted aryl, heteroaryl, substituted heteroaryl, cyano, carboxyl ester alkylthio, substituted alkylthio and aminocarbonyl. Further substituent on Ra is independently of one another selected from those described herein in the definition of formula (I) or each substituent.

In one embodiment of the compounds of formula (I), (II) or (III) above, Ra is not present, that is, R is unsubstituted aryl or heteroaryl.

In one embodiment of the compounds of formula (I), (II) or (III) above, Ra is halo.

In one embodiment of the compounds of formula (I), (II) or (III) above, Ra is unsubstituted alkyl or alkyl substituted with 1, 2 or 3 substituents selected from halo.

In one embodiment of the compounds of formula (I), (II) or (III) above, Ra is alkenyl substituted with 1, 2 or 3 substituents selected from aryl and cyano.

In one embodiment of the compounds of formula (I), (II) or (III) above, Ra is unsubstituted aryl or aryl substituted with 1, 2 or 3 substituents selected from halo, alkyl, substituted alkyl, heterocyclyl, aryl, substituted aryl, heteroaryl, acyl, cyano, alkoxy, substituted alkoxy, aryloxy and hydroxyl.

In one embodiment of the compounds of formula (I), (II) or (III) above, Ra is unsubstituted heteroaryl or heteroaryl substituted with 1, 2 or 3 substituents selected from oxo, alkoxy and substituted alkoxy.

In one embodiment of the compounds of formula (I), (II) or (III) above, Ra is unsubstituted heterocyclyl.

In one embodiment of the compounds of formula (I), (II) or (III) above, Ra is cyano.

In one embodiment of the compounds of formula (I), (II) or (III) above, Ra is nitro.

In one embodiment of the compounds of formula (I), (II) or (III) above, Ra is acyl, for example, acyl selected from carboxyl ester substituted alkyl-C(O)— and substituted or unsubstituted aryl-C(O)—.

In one embodiment of the compounds of formula (I), (II) or (III) above, Ra is acylamino, for example, acylamino selected from substituted or unsubstituted heteroaryl-C(O)—.

In one embodiment of the compounds of formula (I), (II) or (III) above, Ra is unsubstituted alkoxy or alkoxy substituted with 1, 2 or 3 substituent independently selected from halo, heteroaryl, substituted heteroaryl, heterocyclyl, substituted heterocyclyl or alkoxy.

In one embodiment of the compounds of formula (I), (II) or (III) above, Ra is carboxyl, preferably carboxyl in the form of salt.

In one embodiment of the compounds of formula (I), (II) or (III) above, Ra is carboxyl ester.

In one embodiment of the compounds of formula (I), (II) or (III) above, Ra is alkylthio.

In one embodiment of the compounds of formula (I), (II) or (III) above, Ra is aminocarbonyl, for example, aminocarbonyl selected from substituted or unsubstituted aryl-NH—C(O)—.

In one embodiment of the compounds of formula (II) above, m is an integer selected from preferably 0 to 3, more preferably 0 to 2. In one embodiment of the compounds of formula (III) above, n is an integer selected from preferably 1 to 3, more preferably 1 to 2.

In one embodiment, the compounds selected from those listed in Tables 1 to 3 or oxides, esters, prodrugs, pharmaceutically acceptable salts or solvates thereof are provided.

TABLE 1

| No. | Structure | Compound name |
|---|---|---|
| 1 | 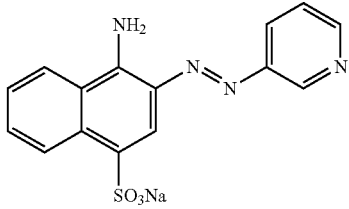 | 4-amino-3-(pyridine-3-ylazo)naphthalene-1-sulfonic acid sodium salt |

TABLE 1-continued

| No. | Structure | Compound name |
| --- | --- | --- |
| 2 | 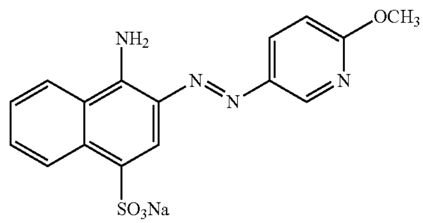 | 4-amino-3-(6-methoxypyridine-3-ylazo)naphthalene-1-sulfonic acid sodium salt |
| 3 | 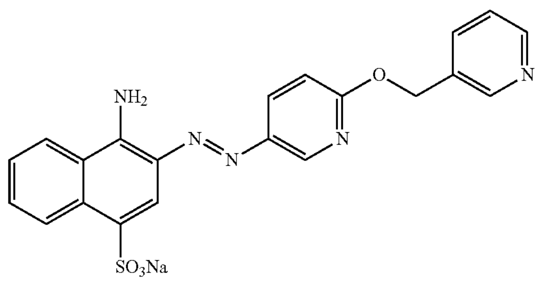 | 3-(2-pyridinomethoxy-5-pyridinoazo)-4-amino-1-naphthalenesulfonic acid sodium salt |
| 4 | 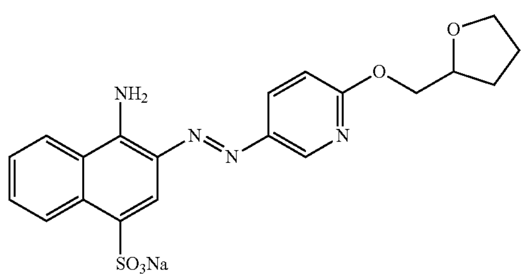 | 4-amino-3-[6-(tetrahydrofuran-2-ylmethoxy)pyridine-3-ylazo]-1-naphthalenesulfonic acid sodium salt |
| 5 | 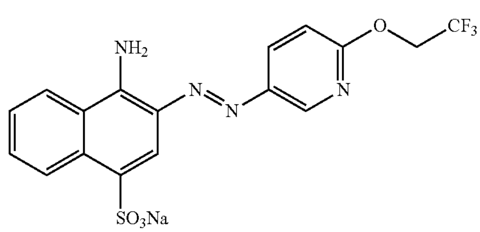 | 4-amino-3-[6-(2,2,2-trifluoroethoxy)pyridine-3-ylazo]naphthalene-1-sulfonic acid sodium salt |
| 6 | 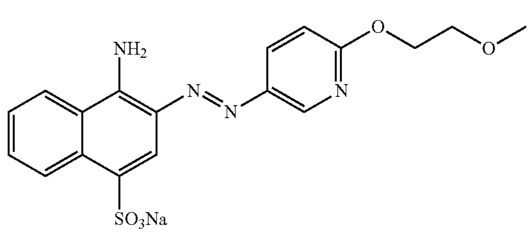 | 4-amino-3-[6-(2-methoxyethoxy)pyridine-3-ylazo]naphthalene-1-sulfonic acid sodium salt |
| 7 | 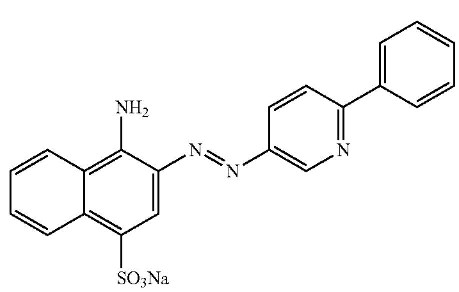 | 4-amino-3-(6-phenylpyridine-3-ylazo)naphthalene-1-sulfonic acid sodium salt |

TABLE 1-continued

| No. | Structure | Compound name |
|---|---|---|
| 8 | 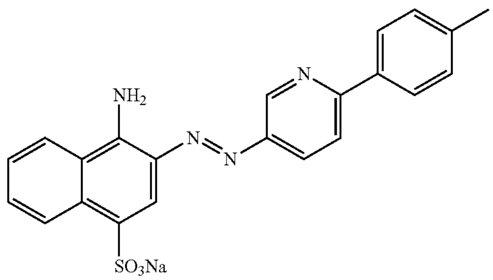 | 4-amino-3-(6-p-tolylpyridine-3-ylazo)naphthalene-1-sulfonic acid sodium salt |
| 9 | 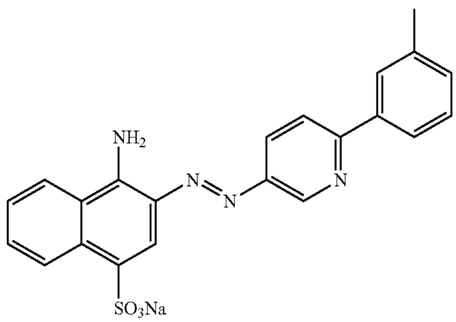 | 4-amino-3-(6-m-tolylpyridine-3-ylazo)naphthalene-1-sulfonic acid sodium salt |
| 10 | 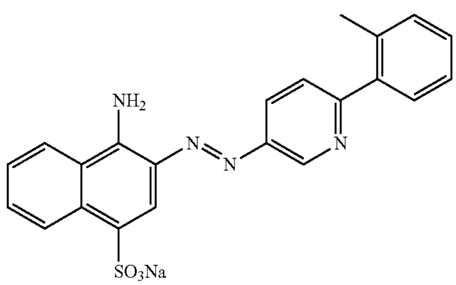 | 4-amino-3-(6-o-tolylpyridine-3-ylazo)naphthalene-1-sulfonic acid sodium salt |
| 11 | 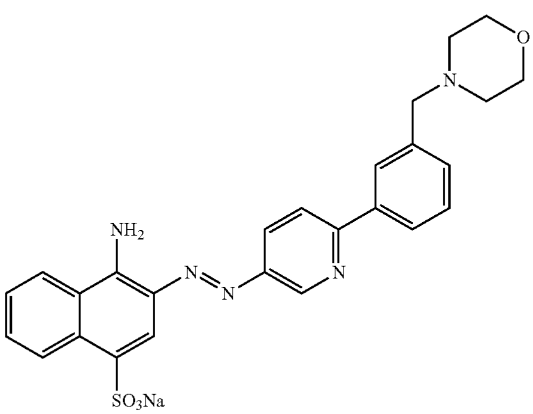 | 4-amino-3-[6-(3-morpholine-4-ylmethylphenyl)pyridine-3-ylazo]naphthalene-1-sulfonic acid sodium salt |

TABLE 1-continued

| No. | Structure | Compound name |
|---|---|---|
| 12 | 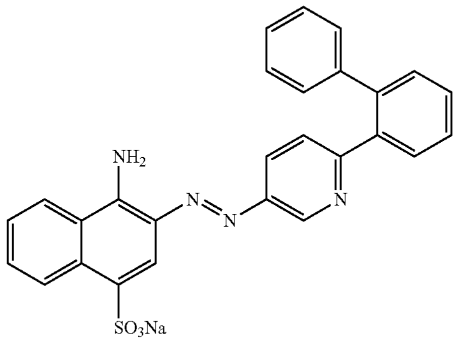 | 4-amino-3-(6-biphenyl-2-ylpyridine-3-ylazo)naphthalene-1-sulfonic acid sodium salt |
| 13 | 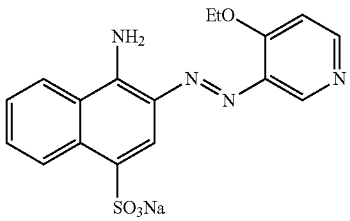 | 4-amino-3-(4-ethoxypyridine-3-ylazo)naphthalene-1-sulfonic acid sodium salt |
| 14 | 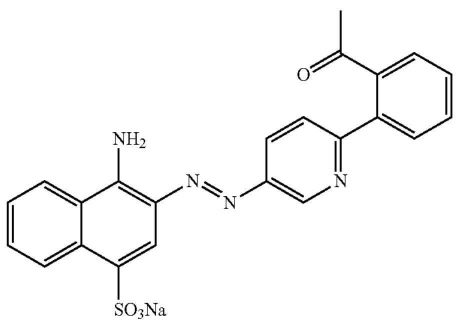 | 3-[6-(2-acetylphenyl)pyridine-3-ylazo]-4-aminonaphthalene-1-sulfonic acid sodium salt |
| 15 | 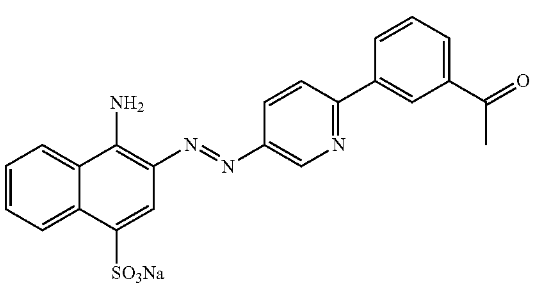 | 3-[6-(3-acetylphenyl)pyridine-3-ylazo]-4-aminonaphthalene-1-sulfonic acid sodium salt |
| 16 | 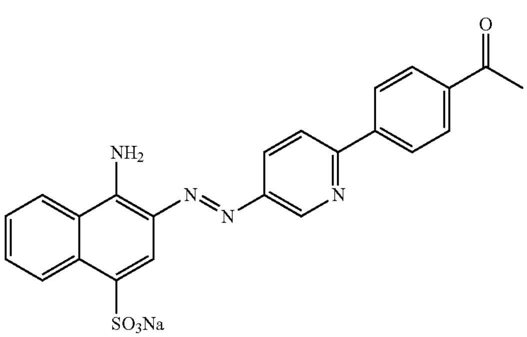 | 3-[6-(4-acetylphenyl)pyridine-3-ylazo]-4-aminonaphthalenesulfonic acid sodium salt |

TABLE 1-continued

| No. | Structure | Compound name |
|---|---|---|
| 17 | 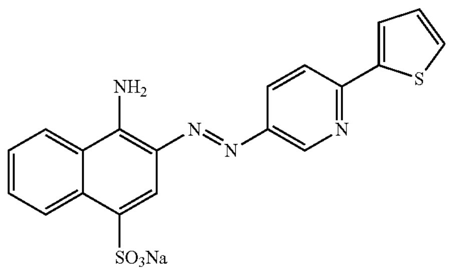 | 4-amino-3-(6-thiophene-2-ylpyridine-3-ylazo)naphthalene-1-sulfonic acid sodium salt |
| 18 | 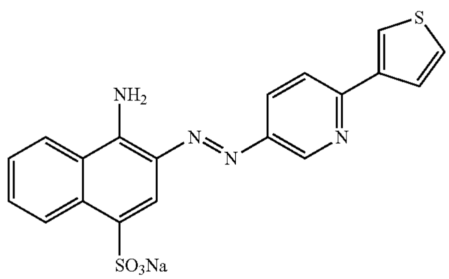 | 4-amino-3-(6-thiophene-3-ylpyridine-3-ylazo)naphthalene-1-sulfonic acid sodium salt |
| 19 | 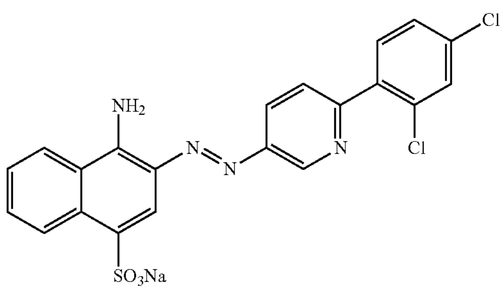 | 4-amino-3-[6-(2,4-dichlorophenyl)pyridine-3-ylazo]naphthalene-1-sulfonic acid sodium salt |
| 20 | 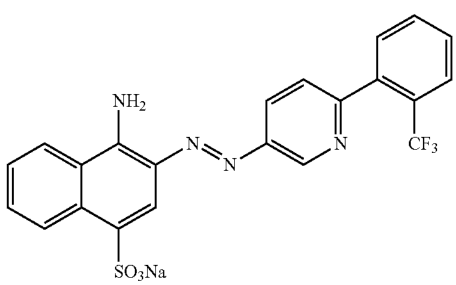 | 4-amino-3-[6-(2-trifluoromethylphenyl)pyridine-3-ylazo]naphthalene-1-sulfonic acid sodium salt |
| 21 | 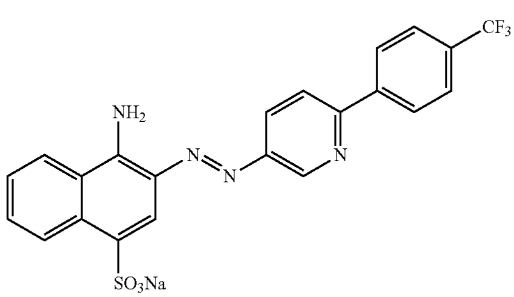 | 4-amino-3-[6-(4-trifluoromethylphenyl)pyridine-3-ylazo]naphthalene-1-sulfonic acid sodium salt |

TABLE 1-continued

| No. | Structure | Compound name |
|---|---|---|
| 22 | 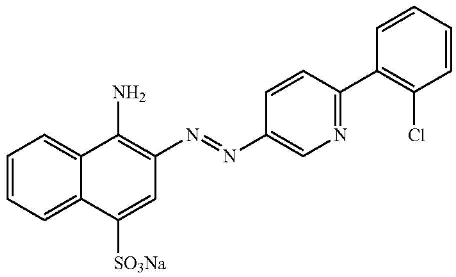 | 4-amino-3-[6-(2-chlorophenyl)pyridine-3-ylazo]naphthalene-1-sulfonic acid sodium salt |
| 23 | 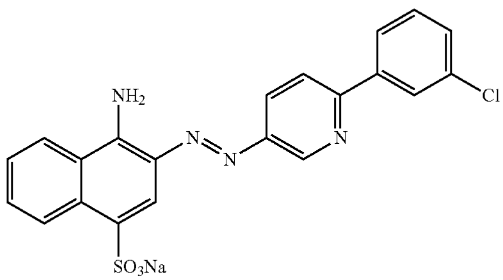 | 4-amino-3-[6-(3-chlorophenyl)pyridine-3-ylazo]naphthalene-1-sulfonic acid sodium salt |
| 24 | 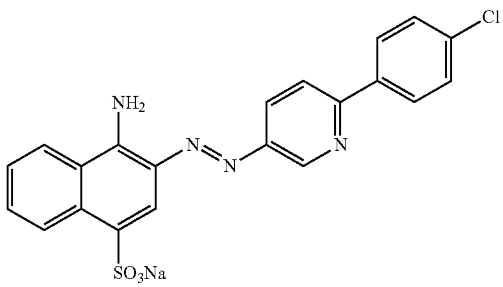 | 4-amino-3-[6-(4-chlorophenyl)pyridine-3-ylazo]naphthalene-1-sulfonic acid sodium salt |
| 25 | 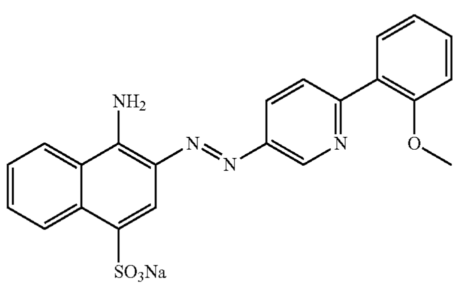 | 4-amino-3-[6-(2-methoxyphenyl)pyridine-3-ylazo]naphthalene-1-sulfonic acid sodium salt |
| 26 | 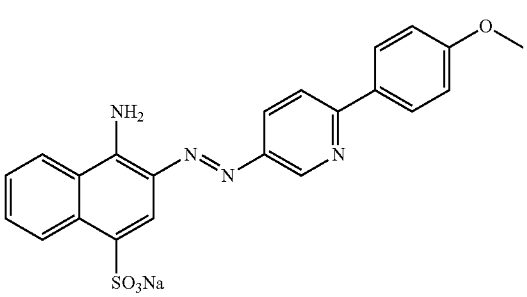 | 4-amino-3-[6-(4-methoxyphenyl)pyridine-3-ylazo]naphthalene-1-sulfonic acid sodium salt |

TABLE 1-continued

| No. | Structure | Compound name |
|---|---|---|
| 27 | 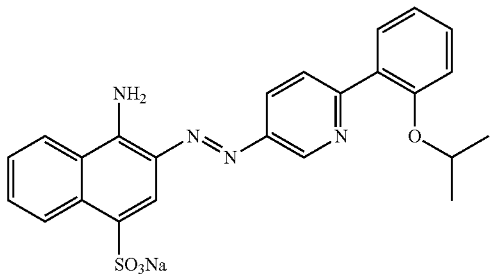 | 4-amino-3-[6-(2-isopropoxyphenyl)pyridine-3-ylazo]naphthalene-1-sulfonic acid sodium salt |
| 28 | 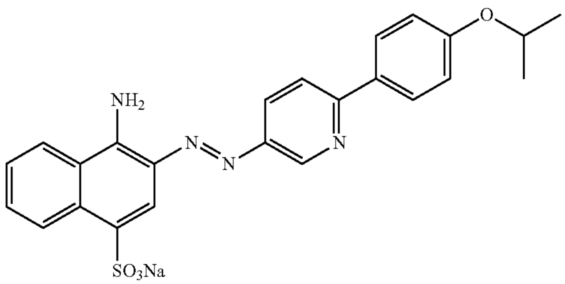 | 4-amino-3-[6-(4-isopropoxyphenyl)pyridine-3-ylazo]naphthalene-1-sulfonic acid sodium salt |
| 29 | 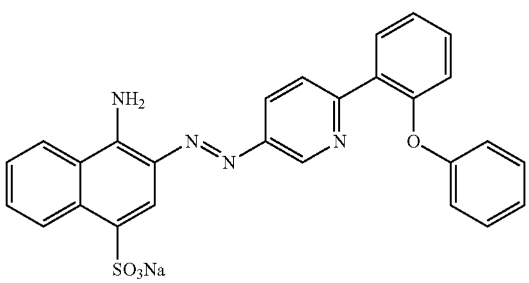 | 4-amino-3-[6-(2-phenoxyphenyl)pyridine-3-ylazo]naphthalene-1-sulfonic acid sodium salt |
| 30 | 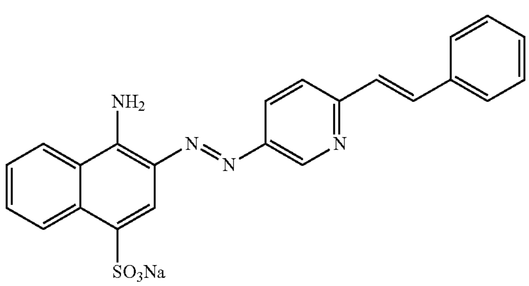 | 4-amino-3-(6-styrylpyridine-3-ylazo)naphthalenesulfonic acid sodium salt |
| 31 | 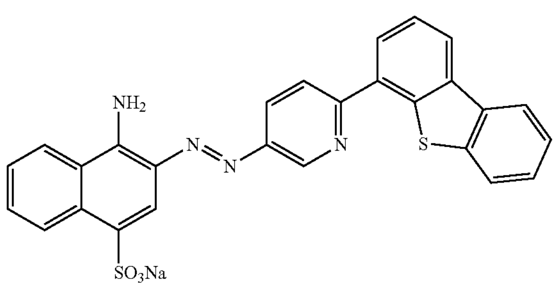 | 4-amino-3-(6-dibenzothiophene-4-ylpyridine-3-ylazo)naphthalene-1-sulfonic acid sodium salt |

TABLE 1-continued

| No. | Structure | Compound name |
|---|---|---|
| 32 | 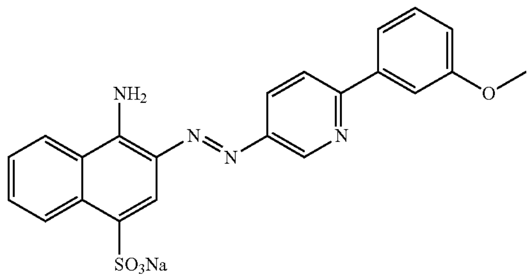 | 4-amino-3-[6-(3-methoxyphenyl)pyridine-3-ylazo]naphthalene-1-sulfonic acid sodium salt |
| 33 | 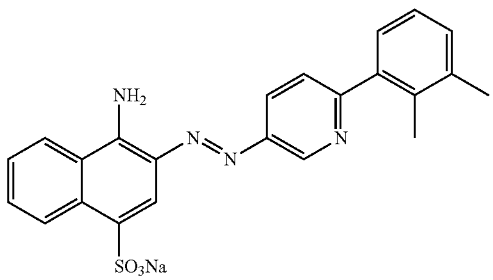 | 4-amino-3-[6-(2,3-dimethylphenyl)pyridine-3-ylazo]naphthalene-1-sulfonic acid sodium salt |
| 34 | 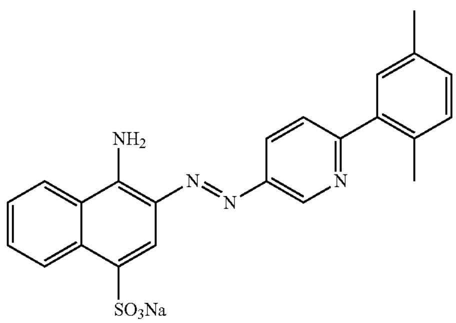 | 4-amino-3-[6-(2,5-dimethylphenyl)pyridine-3-ylazo]naphthalene-1-sulfonic acid sodium salt |
| 35 | 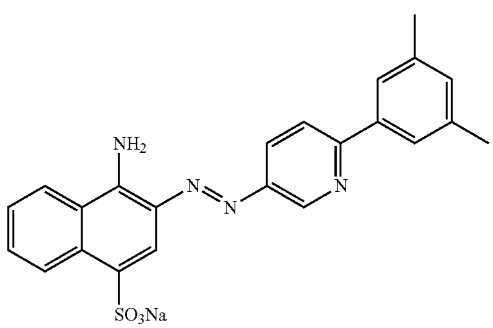 | 4-amino-3-[6-(3,5-dimethylphenyl)pyridine-3-ylazo]naphthalene-1-sulfonic acid sodium salt |
| 36 | 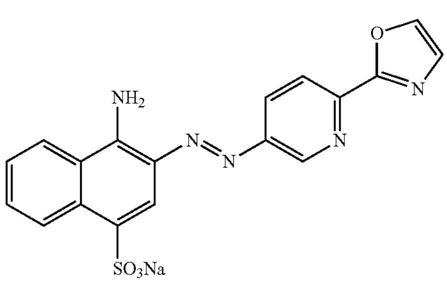 | 4-amino-3-(6-oxazole-2-ylpyridine-3-ylazo)naphthalene-1-sulfonic acid sodium salt |

TABLE 1-continued

| No. | Structure | Compound name |
|---|---|---|
| 37 | 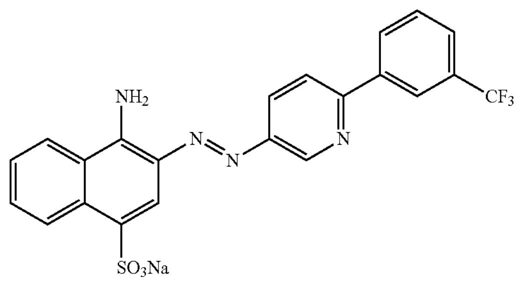 | 4-amino-3-[6-(3-trifluoromethylphenyl)pyridine-3-ylazo]naphthalene-1-sulfonic acid sodium salt |
| 38 | 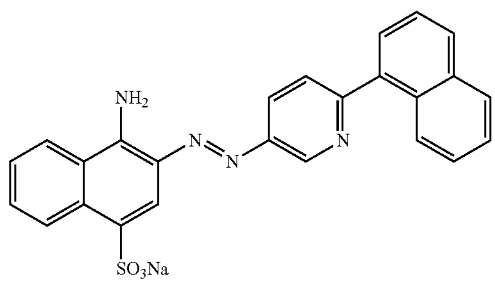 | 4-amino-3-(6-naphthalene-1-ylpyridine-3-ylazo)naphthalene-1-sulfonic acid sodium salt |
| 39 | 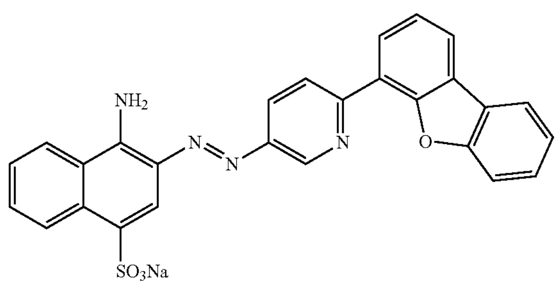 | 4-amino-3-(6-dibenzofuran-4-ylpyridine-3-ylazo)naphthalene-1-sulfonic acid sodium salt |
| 40 | 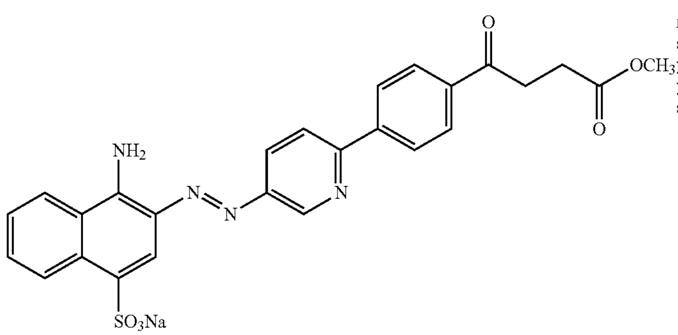 | methyl 4-{4-[5-(1-amino-4-sulfonaphthalene-2-ylazo)pyridine-2-yl]phenyl}-4-oxobutyrate sodium salt |
| 41 | 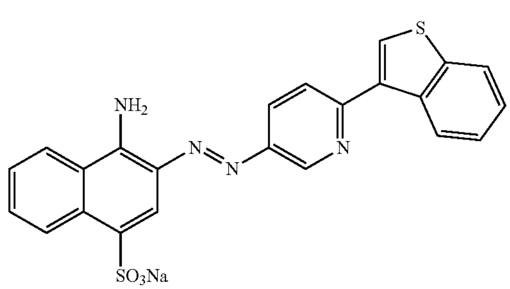 | 4-amino-3-(6-benzo[b]thiophene-3-ylpyridine-3-ylazo)naphthalene-1-sulfonic acid sodium salt |

TABLE 1-continued

| No. | Structure | Compound name |
|-----|-----------|---------------|
| 42 | 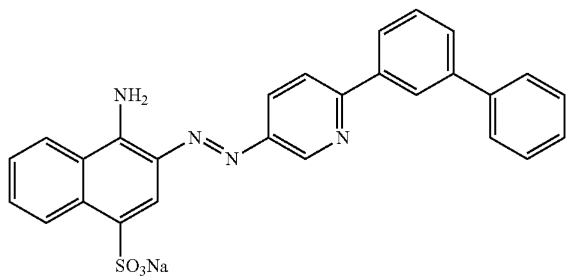 | 4-amino-3-(6-biphenyl-3-ylpyridine-3-ylazo)naphthalene-1-sulfonic acid sodium salt |
| 43 | 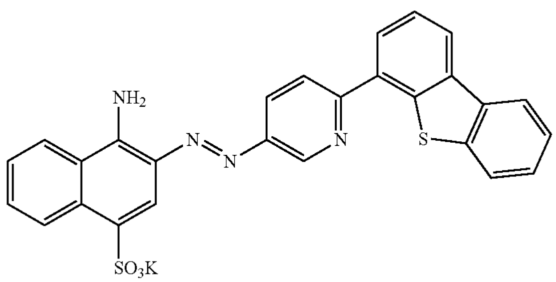 | 4-amino-3-(6-dibenzothiophene-4-ylpyridine-3-ylazo)naphthalene-1-sulfonic acid potassium salt |
| 44 | 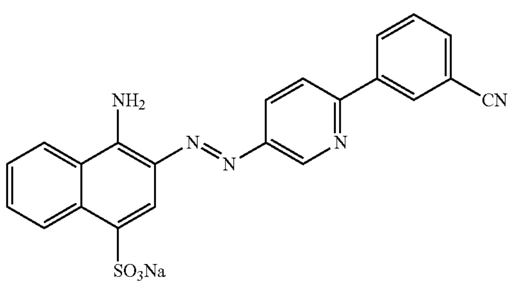 | 4-amino-3-[6-(3-cyanophenyl)pyridine-3-ylazo]naphthalene-1-sulfonic acid sodium salt |
| 45 | 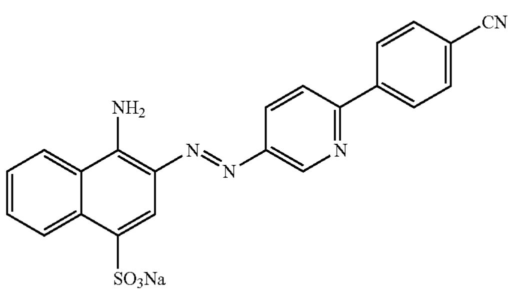 | 4-amino-3-[6-(4-cyanophenyl)pyridine-3-ylazo]naphthalene-1-sulfonic acid sodium salt |
| 46 | 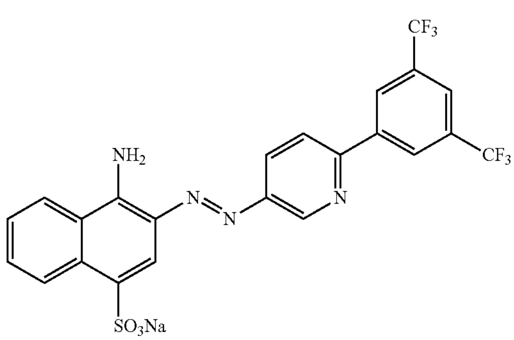 | 4-amino-3-[6-(3,5-bistrifluoromethylphenyl)pyridine-3-ylazo]naphthalenesulfonic acid sodium salt |

TABLE 1-continued

| No. | Structure | Compound name |
| --- | --- | --- |
| 47 | 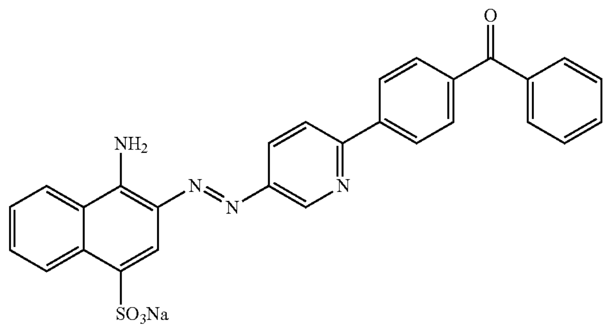 | 4-amino-3-[6-(4-benzoylphenyl)pyridine-3-ylazo]naphthalene-1-sulfonic acid sodium salt |
| 48 | 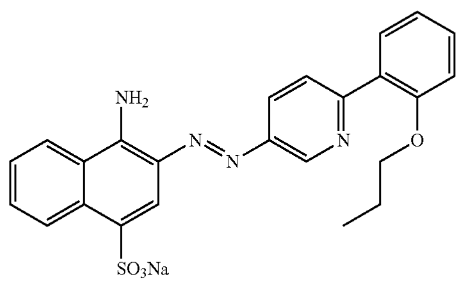 | 4-amino-3-[6-(2-propoxyphenyl)pyridine-3-ylazo]naphthalene-1-sulfonic acid sodium salt |
| 49 | 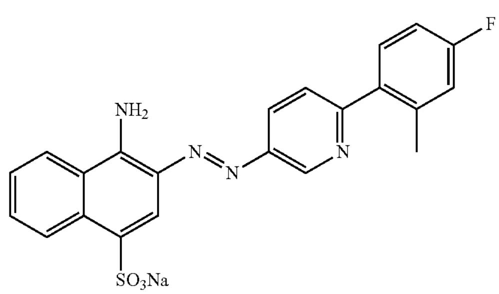 | 4-amino-3-[6-(4-fluoro-2-methylphenyl)pyridine-3-ylazo]naphthalene-1-sulfonic acid sodium salt |
| 50 | 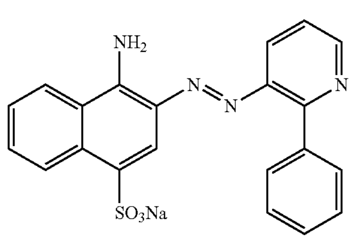 | 4-amino-3-(2-phenylpyridine-3-ylazo)naphthalene-1-sulfonic acid sodium salt |
| 51 | 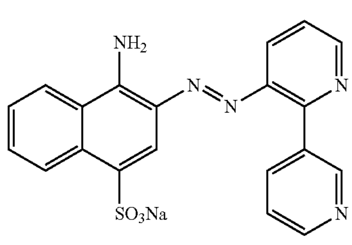 | 4-amino-3-([2,3']-bipyridinyl 3-ylazo)naphthalene-1-sulfonic acid sodium salt |

TABLE 1-continued

| No. | Structure | Compound name |
|---|---|---|
| 52 | 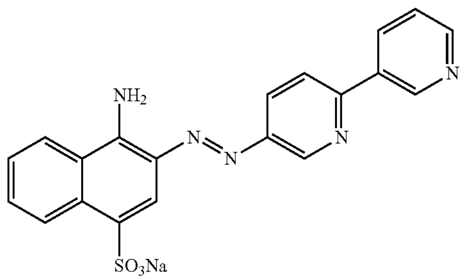 | 4-amino-3-([2,3']bipyridinyl-5-ylazo)naphthalene-1-sulfonic acid sodium salt |
| 53 | 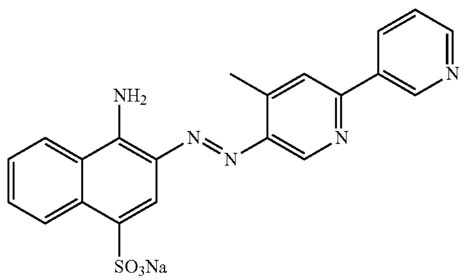 | 4-amino-3-(4-methyl-[2,3']bipyridinyl-5-ylazo)naphthalene-1-sulfonic acid sodium salt |
| 54 | 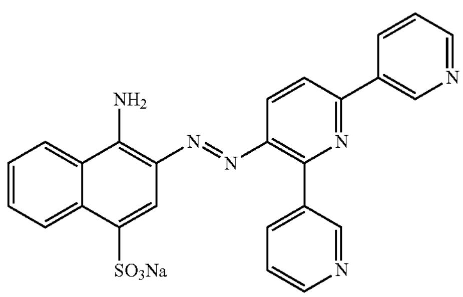 | 4-amino-3-([3,2'; 6',3'']terpyridine-3'-ylazo)naphthalene-1-sulfonic acid sodium salt |
| 55 | 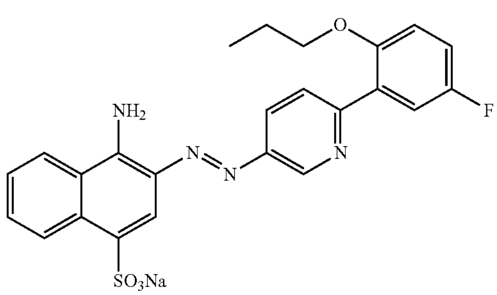 | 4-amino-3-[6-(5-fluoro-2-propoxyphenyl)pyridine-3-ylazo]naphthalene-1-sulfonic acid sodium salt |
| 56 | 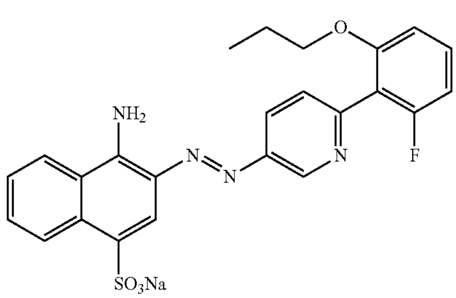 | 4-amino-3-[6-(2-fluoro-6-propoxyphenyl)pyridine-3-ylazo]naphthalene-1-sulfonic acid sodium salt |

TABLE 1-continued

| No. | Structure | Compound name |
|---|---|---|
| 57 | 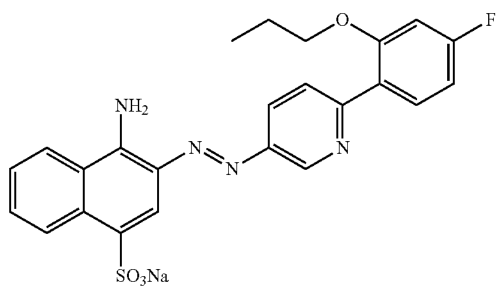 | 4-amino-3-[6-(4-fluoro-2-propoxyphenyl)pyridine-3-ylazo]naphthalene-1-sulfonic acid sodium salt |
| 58 | 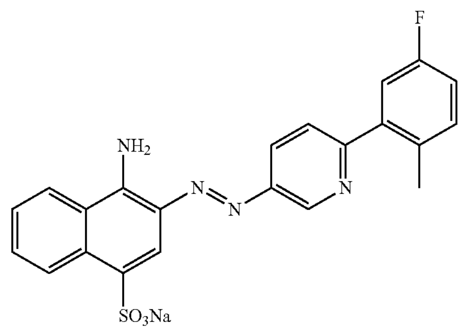 | 4-amino-3-[6-(5-fluoro-2-methylphenyl)pyridine-3-ylazo]naphthalene-1-sulfonic acid sodium salt |
| 59 | 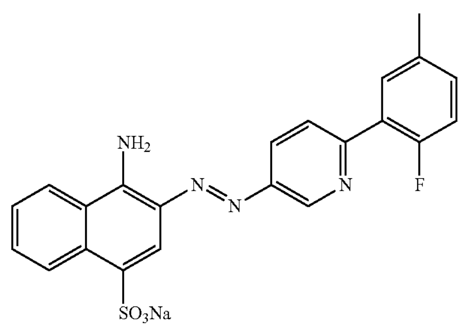 | 4-amino-3-[6-(2-fluoro-5-methylphenyl)pyridine-3-ylazo]naphthalene-1-sulfonic acid sodium salt |
| 60 | 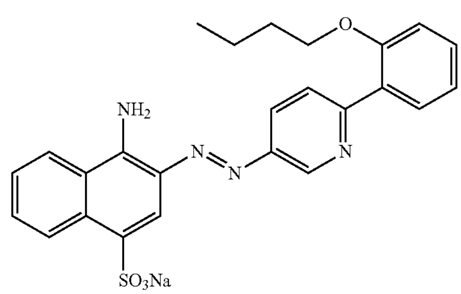 | 4-amino-3-[6-(2-butoxyphenyl)pyridine-3-ylazo]naphthalene-1-sulfonic acid sodium salt |
| 61 | 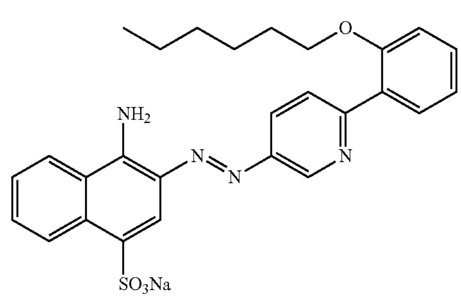 | 4-amino-3-[6-(2-hexyloxyphenyl)pyridine-3-ylazo]naphthalene-1-sulfonic acid sodium salt |

TABLE 1-continued

| No. | Structure | Compound name |
|---|---|---|
| 62 | 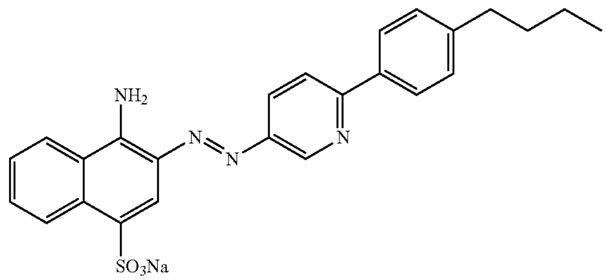 | 4-amino-3-[6-(4-butylphenyl)pyridine-3-ylazo]naphthalene-1-sulfonic acid sodium salt |
| 63 | 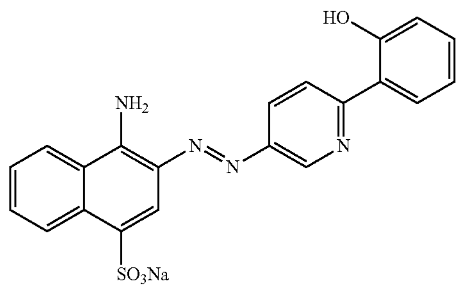 | 4-amino-3-[6-(2-hydroxyphenyl)pyridine-3-ylazo]naphthalene-1-sulfonic acid sodium salt |
| 64 | 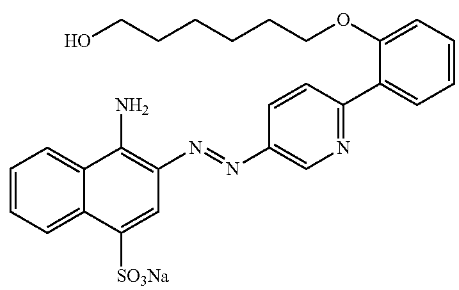 | 4-amino-3-{6-[2-(6-hydroxyhexyloxy)phenyl]pyridine-3-ylazo}naphthalene-1-sulfonic acid sodium salt |
| 65 | 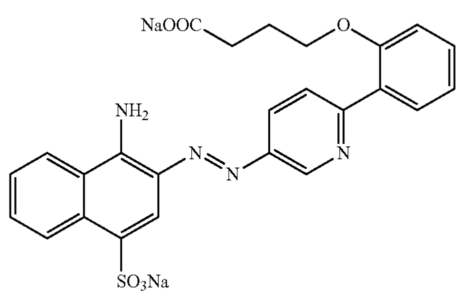 | 4-{2-[5-(1-amino-4-sulfonaphthalene-2-ylazo)pyridine-2-yl]phenoxy}butyric acid disodium salt |
| 66 | 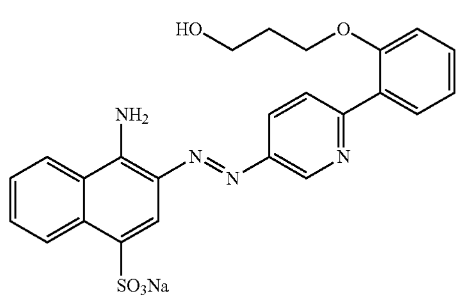 | 4-amino-3-{6-[2-(3-hydroxypropoxy)phenyl]pyridine-3-ylazo}naphthalene-1-sulfonic acid sodium salt |

TABLE 1-continued

| No. | Structure | Compound name |
|---|---|---|
| 67 | 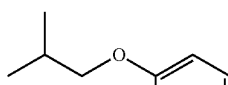 | 4-amino-3-[6-(2-isobutoxyphenyl)pyridine-3-ylazo]naphthalene-1-sulfonic acid sodium salt |
| 68 | 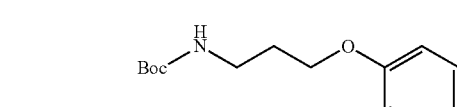 | 4-amino-3-{6-[2-(3-tert-butoxycarbonylaminopropoxy)phenyl]pyridine-3-ylazo}naphthalene-1-sulfonic acid sodium salt |
| 69 | 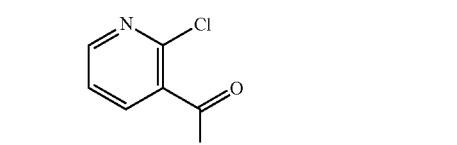 | 4-amino-3-[6-(2-{3-[(2-chloropyridine-3-carbonyl)amino]propoxy}phenyl)pyridine-3-ylazo]naphthalene-1-sulfonic acid sodium salt |
| 70 | 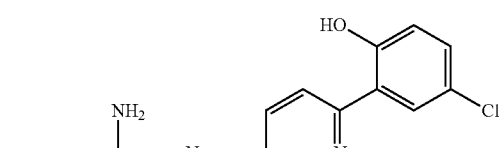 | 4-amino-3-[6-(5-chloro-2-hydroxyphenyl)pyridine-3-ylazo]naphthalene-1-sulfonic acid sodium salt |

TABLE 1-continued

| No. | Structure | Compound name |
|---|---|---|
| 71 | 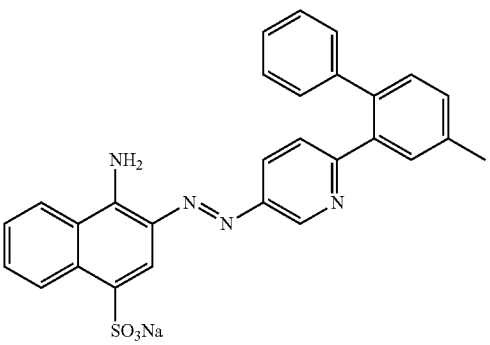 | 4-amino-3-[6-(4-methylbiphenyl-2-yl)pyridine-3-ylazo]naphthalene-1-sulfonic acid sodium salt |
| 72 | 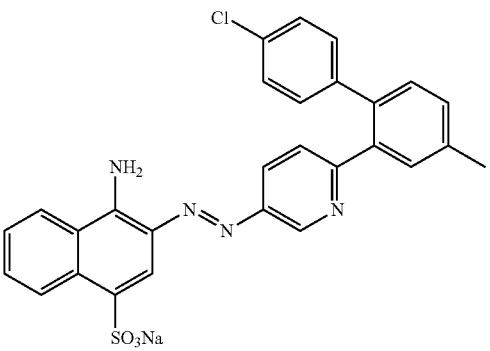 | 4-amino-3-[6-(4'-chloro-4-methylbiphenyl-2-yl)pyridine-3-ylazo]naphthalene-1-sulfonic acid sodium salt |
| 73 | 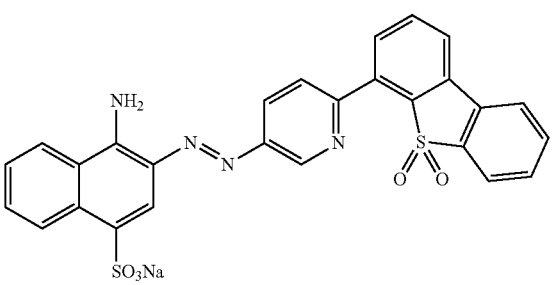 | 4-amino-3-[6-(5,5-dioxo-5H-5$\lambda^6$-dibenzothiophene-4-yl)pyridine-3-ylazo]naphthalene-1-sulfonic acid sodium salt |
| 74 | 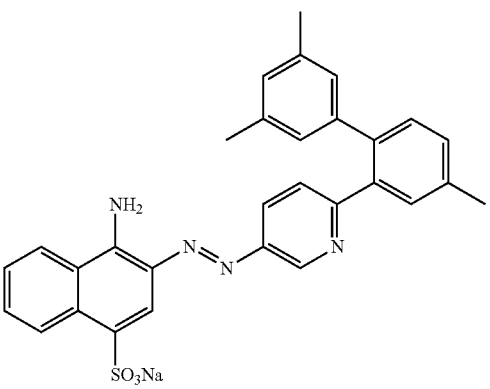 | 4-amino-3-[6-(4,3',5'-trimethylbiphenyl-2-yl)pyridine-3-ylazo]naphthalene-1-sulfonic acid sodium salt |

TABLE 1-continued

| No. | Structure | Compound name |
|---|---|---|
| 75 | 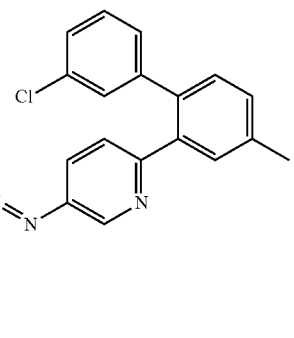 | 4-amino-3-[6-(3'-chloro-4-methylbiphenyl-2-yl)pyridine-3-ylazo]naphthalene-1-sulfonic acid sodium salt |
| 76 | 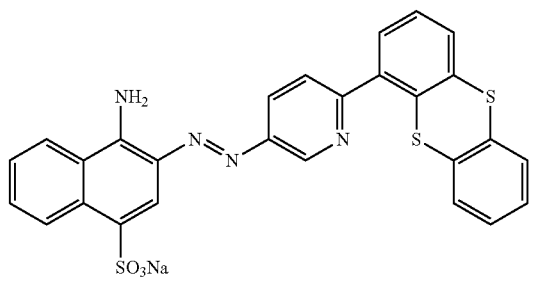 | 4-amino-3-(6-thianthrene-1-ylpyridine-3-ylazo)naphthalene-1-sulfonic acid sodium salt |
| 77 | 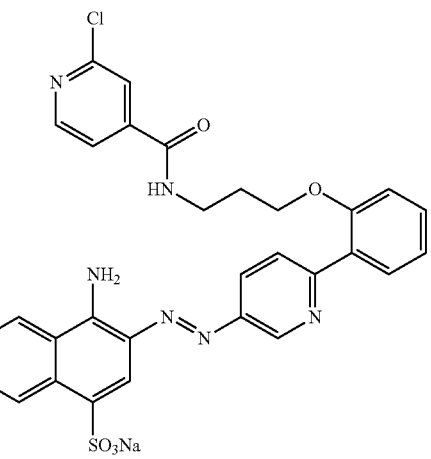 | 4-amino-3-[6-(2-{3-[(2-chloropyridine-4-carbonyl)amino]propoxy}phenyl)pyridine-3-ylazo]naphthalene-1-sulfonic acid sodium salt |
| 78 | 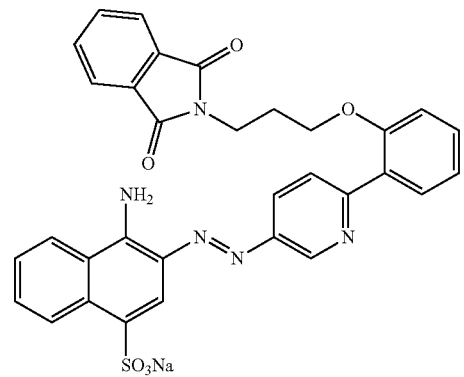 | 4-amino-3-(6-{2-[3-(1,3-dioxo-1,3-dihydroisoindole-2-yl)propoxy]phenyl}pyridine-3-ylazo)naphthalene-1-sulfonic acid sodium salt |

TABLE 1-continued

| No. | Structure | Compound name |
|---|---|---|
| 79 | 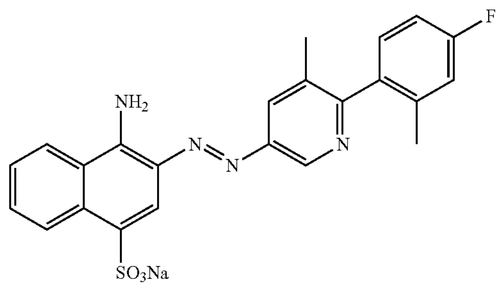 | 4-amino-3-[6-(4-fluoro-2-methylphenyl)-5-methylpyridine-3-ylazo]naphthalene-1-sulfonic acid sodium salt |
| 80 | 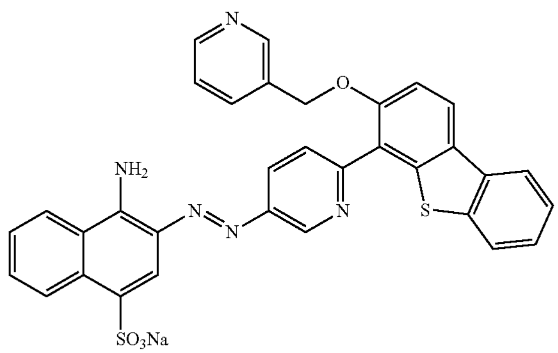 | 4-amino-3-{6-[3-(pyridine-3-ylmethoxy)dibenzothiophene-4-yl]pyridine-3-ylazo}naphthalene-1-sulfonic acid sodium salt |
| 81 | 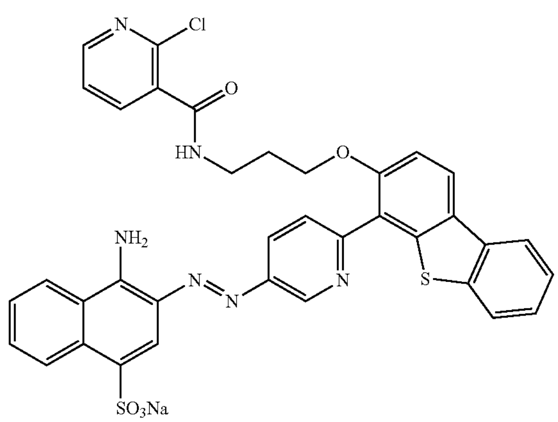 | 4-amino-3-[6-(3-{3-[(2-chloropyridine-3-carbonyl)amino]propoxy}dibenzothiophene-4-yl)pyridine-3-ylazo]naphthalene-1-sulfonic acid sodium salt |
| 82 | 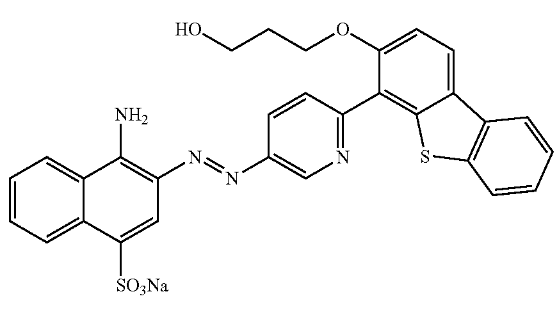 | 4-amino-3-{6-[3-(3-hydroxypropoxy)dibenzothiophene-4-yl]pyridine-3-ylazo}naphthalene-1-sulfonic acid sodium salt |

TABLE 1-continued

| No. | Structure | Compound name |
|---|---|---|
| 83 | 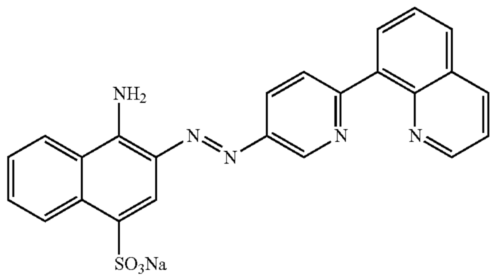 | 4-amino-3-(6-quinoline-8-ylpyridine-3-ylazo)naphthalene-1-sulfonic acid sodium salt |
| 84 | 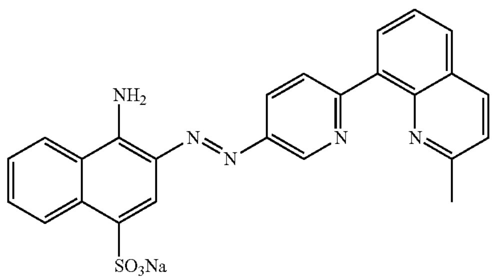 | 4-amino-3-[6-(2-methylquinoline-8-yl)pyridine-3-ylazo]naphthalene-1-sulfonic acid sodium salt |
| 85 | 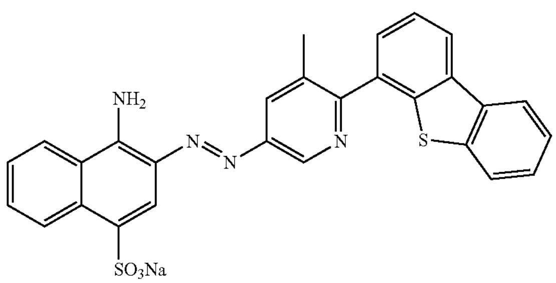 | 4-amino-3-(6-dibenzothiophene-4-yl-5-methylpyridine-3-ylazo)naphthalene-1-sulfonic acid sodium salt |
| 86 | 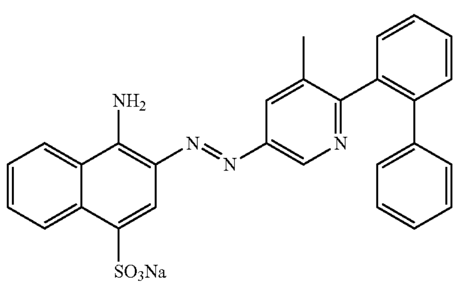 | 4-amino-3-(6-biphenyl-2-yl-5-methylpyridine-3-ylazo)naphthalene-1-sulfonic acid sodium salt |
| 87 | 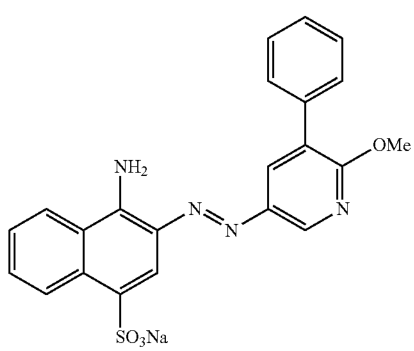 | 4-amino-3-(6-methoxy-5-phenylpyridine-3-ylazo)naphthalene-1-sulfonic acid sodium salt |

TABLE 1-continued

| No. | Structure | Compound name |
|---|---|---|
| 88 | 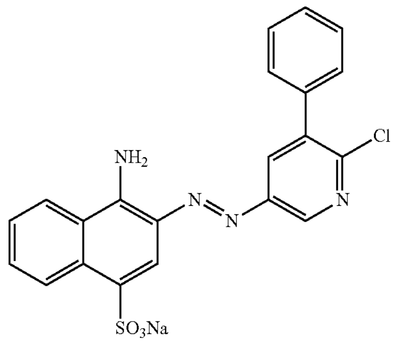 | 4-amino-3-(6-chloro-5-phenylpyridine-3-ylazo)naphthalene-1-sulfonic acid sodium salt |
| 89 | 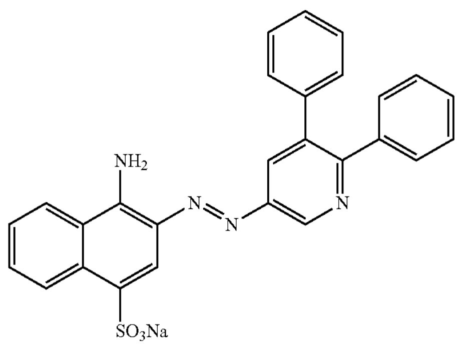 | 4-amino-3-(5,6-diphenylpyridine-3-ylazo)naphthalene-1-sulfonic acid sodium salt |
| 90 | 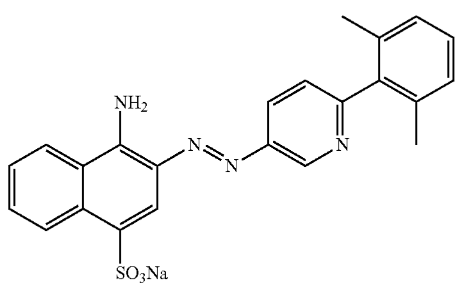 | 4-amino-3-[6-(2,6-dimethylphenyl)pyridine-3-ylazo]naphthalene-1-sulfonic acid sodium salt |
| 91 | 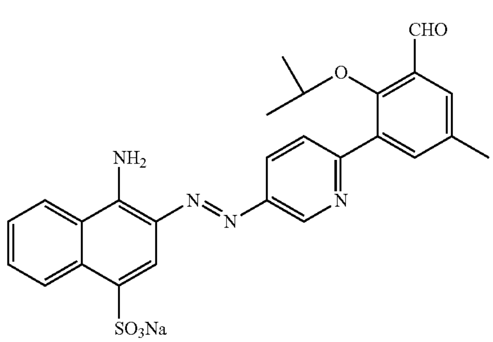 | 4-amino-3-[6-(3-formyl-2-isopropoxy-5-methylphenyl)pyridine-3-ylazo]naphthalene-1-sulfonic acid sodium salt |

TABLE 1-continued

| No. | Structure | Compound name |
| --- | --- | --- |
| 92 | 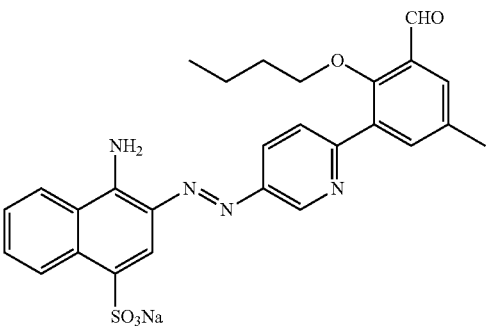 | 4-amino-3-[6-(3-formyl-2-butoxy-5-methylphenyl)pyridine-3-ylazo]naphthalene-1-sulfonic acid sodium salt |
| 193 | 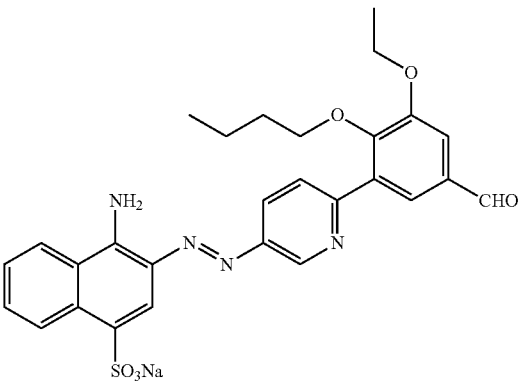 | 4-amino-3-[6-(2-butoxy-3-ethoxy-5-formylphenyl)pyridine-3-ylazo]naphthalene-1-sulfonic acid sodium salt |
| 194 | 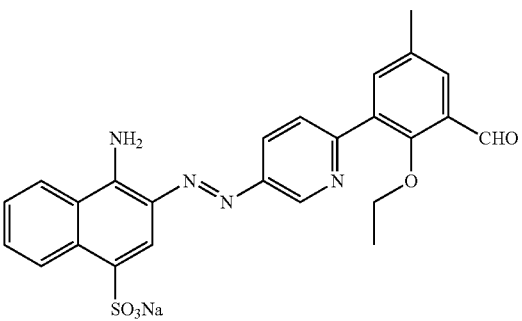 | 4-amino-3-[6-(2-ethoxy-3-formyl-5-methylphenyl)pyridine-3-ylazo]naphthalene-1-sulfonic acid sodium salt |

TABLE 2

| No. | Structure | Compound name |
| --- | --- | --- |
| 93 | 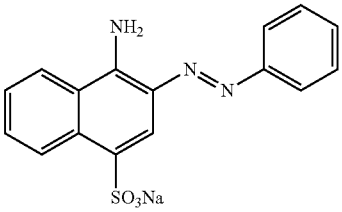 | 4-amino-3-phenylazonaphthalene-1-sulfonic acid sodium salt |

TABLE 2-continued

| No. | Structure | Compound name |
|---|---|---|
| 94 | 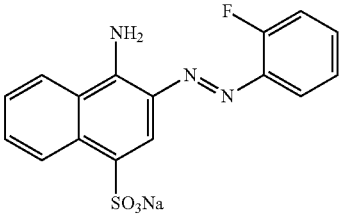 | 4-amino-3-(2-fluorophenylazo)naphthalene-1-sulfonic acid sodium salt |
| 95 | 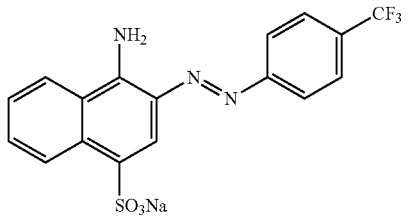 | 4-amino-3-(4-trifluoromethylphenylazo)naphthalene-1-sulfonic acid sodium salt |
| 96 | 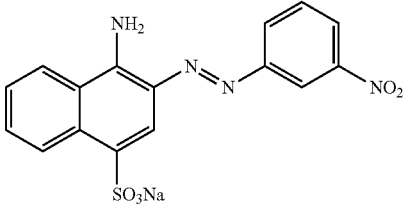 | 4-amino-3-(3-nitrophenylazo)naphthalene-1-sulfonic acid sodium salt |
| 97 | 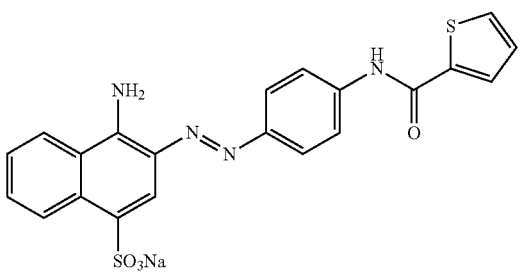 | 4-amino-3-[4-[(2-thienylcarbonyl)amino]phenylazo]-1-naphthalenesulfonic acid sodium salt |
| 98 | 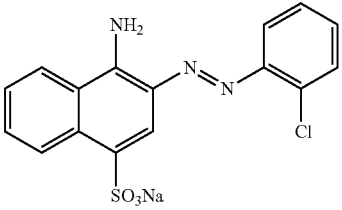 | 4-amino-3-(2-chlorophenylazo)naphthalene-1-sulfonic acid sodium salt |
| 99 | 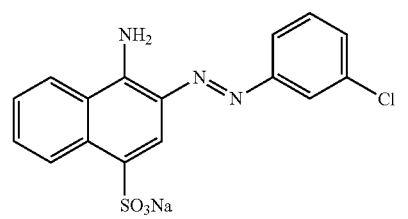 | 4-amino-3-(3-chlorophenylazo)naphthalene-1-sulfonic acid sodium salt |

TABLE 2-continued

| No. | Structure | Compound name |
|---|---|---|
| 100 | 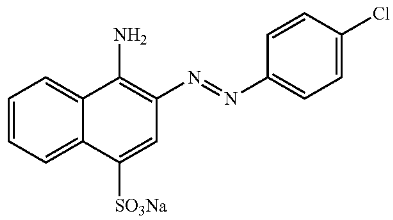 | 4-amino-3-(4-chlorophenylazo)naphthalene-1-sulfonic acid sodium salt |
| 101 | 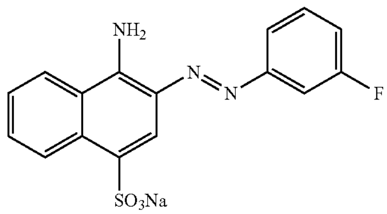 | 4-amino-3-(3-fluorophenylazo)naphthalene-1-sulfonic acid sodium salt |
| 102 | 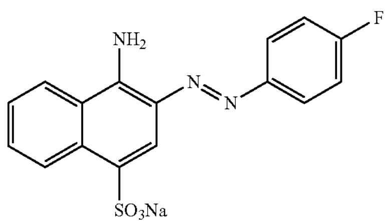 | 4-amino-3-(4-fluorophenylazo)naphthalene-1-sulfonic acid sodium salt |
| 103 | 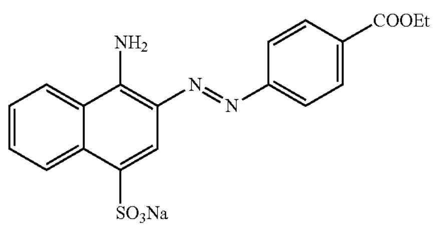 | ethyl 4-(1-amino-4-sulfonaphthalene-2-ylazo)benzoate sodium salt |
| 104 | 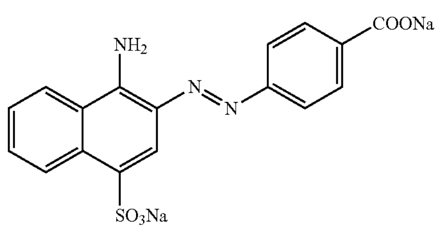 | 4-(1-amino-4-sulfonaphthalene-2-ylazo)benzoic acid disodium salt |
| 105 | 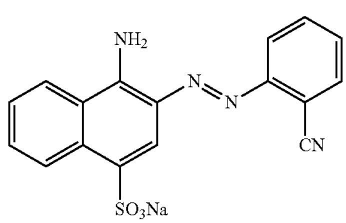 | 4-amino-3-(2-cyanophenylazo)naphthalene-1-sulfonic acid sodium salt |
| 106 | 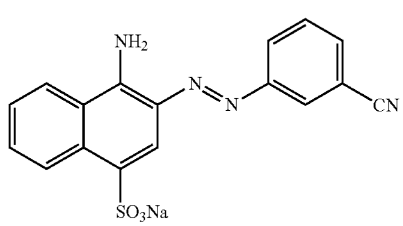 | 4-amino-3-(3-cyanophenylazo)naphthalene-1-sulfonic acid sodium salt |

TABLE 2-continued

| No. | Structure | Compound name |
|---|---|---|
| 107 | 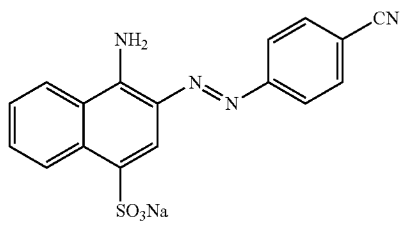 | 4-amino-3-(4-cyanophenylazo)naphthalene-1-sulfonic acid sodium salt |
| 108 | 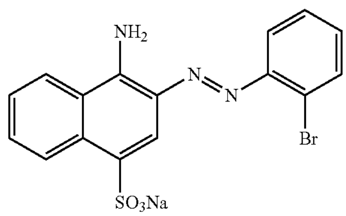 | 4-amino-3-(2-bromophenylazo)naphthalene-1-sulfonic acid sodium salt |
| 109 | 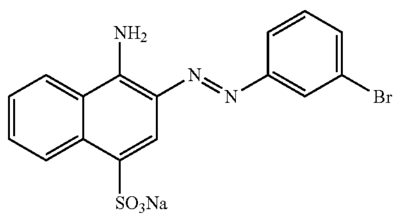 | 4-amino-3-(3-bromophenylazo)naphthalene-1-sulfonic acid sodium salt |
| 110 | 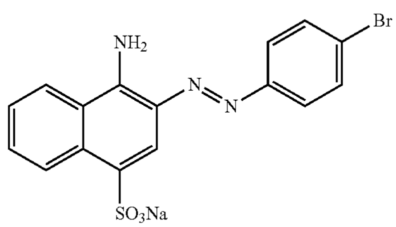 | 4-amino-3-(4-bromophenylazo)naphthalene-1-sulfonic acid sodium salt |
| 111 | 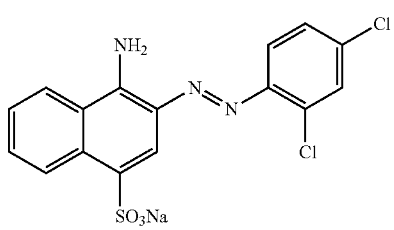 | 4-amino-3-(2,4-dichlorophenylazo)naphthalene-1-sulfonic acid sodium salt |
| 112 | 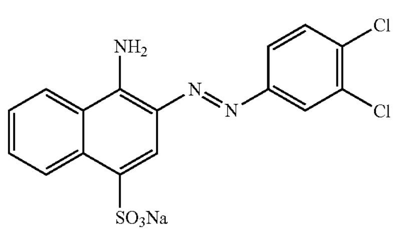 | 4-amino-3-(3,4-dichlorophenylazo)naphthalene-1-sulfonic acid sodium salt |
| 113 | 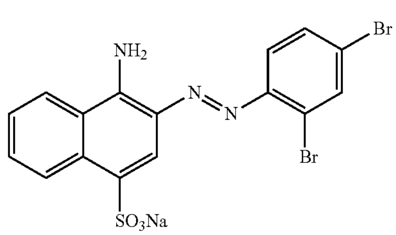 | 4-amino-3-(2,4-dibromophenylazo)naphthalene-1-sulfonic acid sodium salt |

TABLE 2-continued

| No. | Structure | Compound name |
|---|---|---|
| 114 | 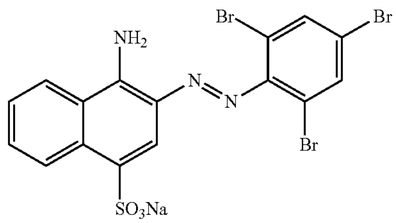 | 4-amino-3-(2,4,6-tribromophenylazo)naphthalene-1-sulfonic acid sodium salt |
| 115 | 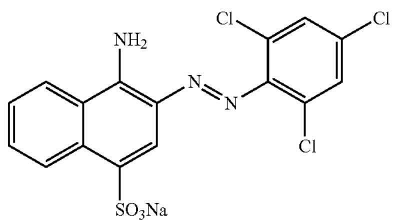 | 4-amino-3-(2,4,6-trichlorophenylazo)naphthalene-1-sulfonic acid sodium salt |
| 116 | 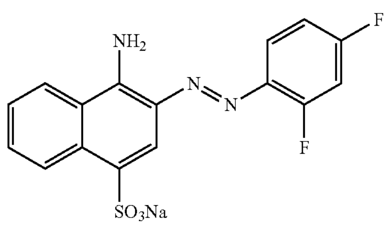 | 4-amino-3-(2,4-difluorophenylazo)naphthalene-1-sulfonic acid sodium salt |
| 117 | 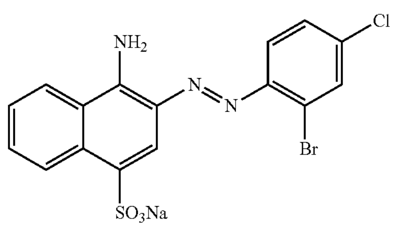 | 4-amino-3-(2-bromo-4-chlorophenylazo)naphthalene-1-sulfonic acid sodium salt |
| 118 | 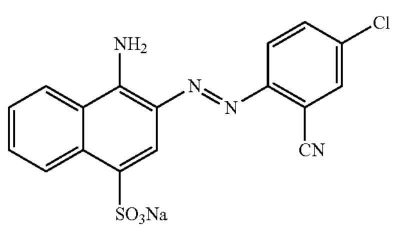 | 4-amino-3-(4-chloro-2-cyanophenylazo)naphthalene-1-sulfonic acid sodium salt |
| 119 | 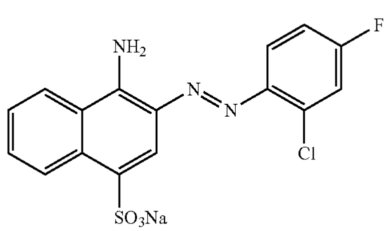 | 4-amino-3-(2-chloro-4-fluorophenylazo)naphthalene-1-sulfonic acid sodium salt |
| 120 | 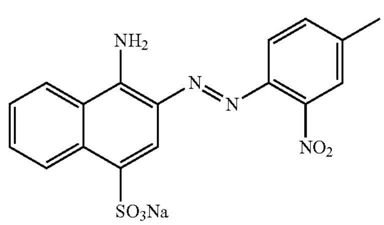 | 4-amino-3-(4-methyl-2-nitrophenylazo)naphthalene-1-sulfonic acid sodium salt |

TABLE 2-continued

| No. | Structure | Compound name |
|---|---|---|
| 121 | 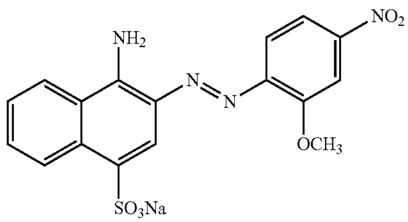 | 4-amino-3-(2-methoxy-4-nitrophenylazo)naphthalene-1-sulfonic acid sodium salt |
| 122 | 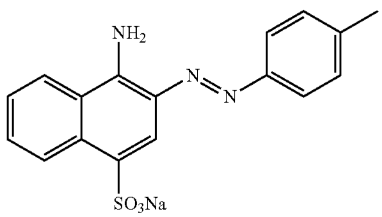 | 4-amino-3-p-tolylazonaphthalene-1-sulfonic acid sodium salt |
| 123 | 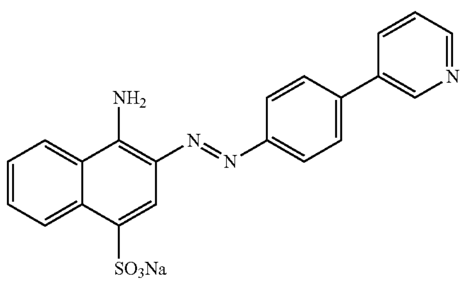 | 4-amino-3-(4-pyridine-3-ylphenylazo)-1-naphthalenesulfonic acid sodium salt |
| 124 | 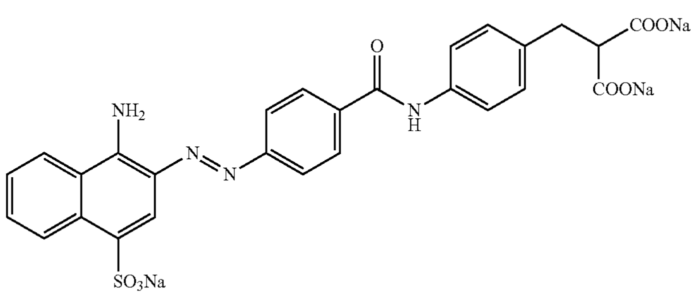 | 2-{4-[4-(1-amino-4-sulfonaphthalene-2-ylazo)benzoylamino]benzyl}malonic acid trisodium salt |
| 125 | 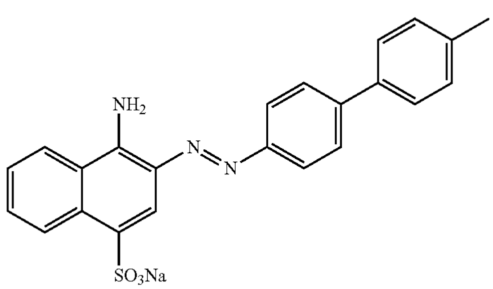 | 4-amino-3-(4'-methylbiphenyl-4-ylazo)naphthalene-1-sulfonic acid sodium salt |

TABLE 2-continued

| No. | Structure | Compound name |
|---|---|---|
| 126 | 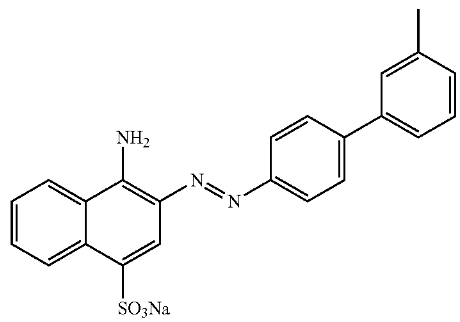 | 4-amino-3-(3'-methylbiphenyl-4-ylazo)naphthalene-1-sulfonic acid sodium salt |
| 127 | 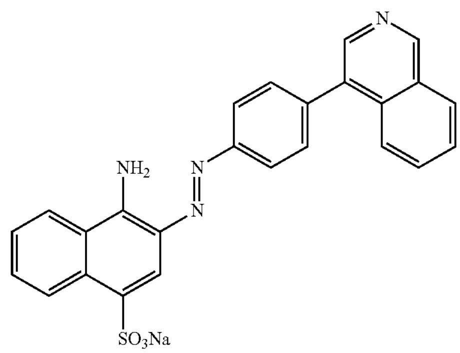 | 4-amino-3-(4-isoquinoline-1-ylphenylazo)naphthalene-1-sulfonic acid sodium salt |
| 128 | 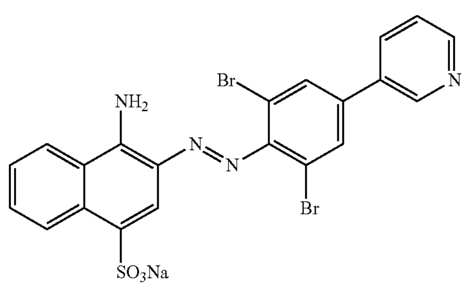 | 4-amino-3-(2,6-dibromo-4-pyridine-3-ylphenylazo)naphthalene-1-sulfonic acid sodium salt |
| 129 | 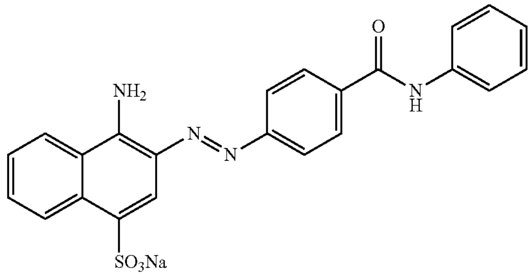 | 4-amino-3-(4-phenylcarbamoylphenylazo)naphthalene-1-sulfonic acid sodium salt |
| 130 | 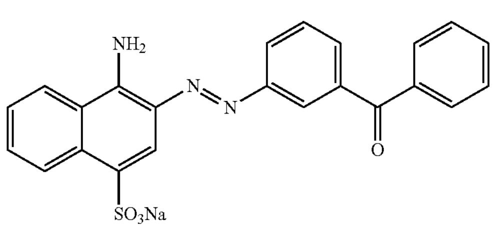 | 4-amino-3-(3-benzoylphenylazo)naphthalene-1-sulfonic acid sodium salt |

TABLE 2-continued

| No. | Structure | Compound name |
|---|---|---|
| 131 | 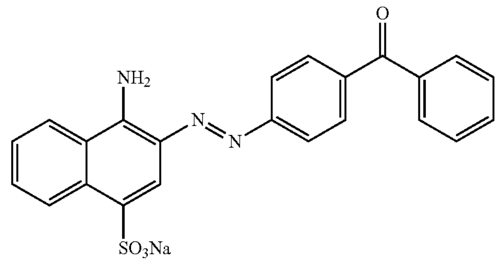 | 4-amino-3-(4-benzoylphenylazo)naphthalene-1-sulfonic acid sodium salt |
| 132 | 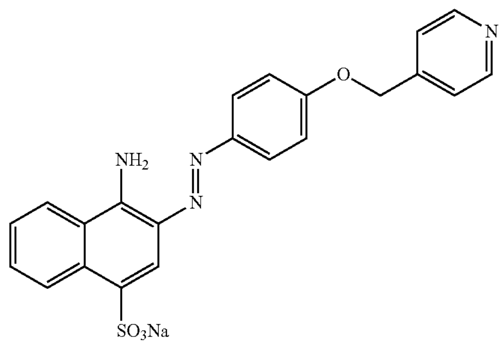 | 4-amino-3-[4-(pyridine-4-ylmethoxy)phenylazo]naphthalene-1-sulfonic acid sodium salt |
| 133 | 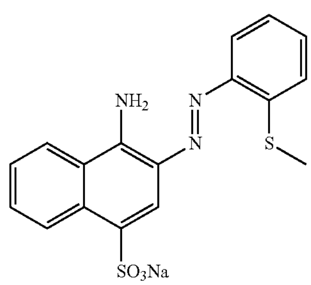 | 4-amino-3-(2-methylsulfanylphenylazo)naphthalene-1-sulfonic acid sodium salt |
| 134 | 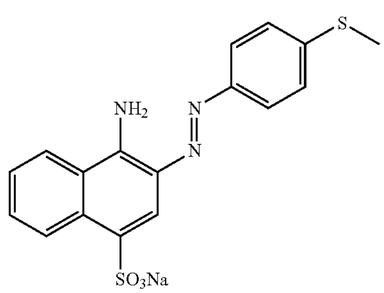 | 4-amino-3-(4-methylsulfanylphenylazo)naphthalene-1-sulfonic acid sodium salt |
| 135 | 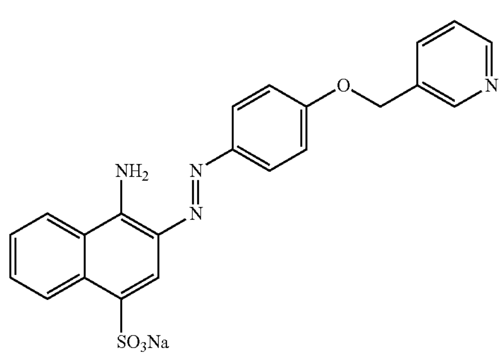 | 4-amino-3-[4-(pyridine-3-ylmethoxy)phenylazo]naphthalene-1-sulfonic acid sodium salt |

TABLE 2-continued

| No. | Structure | Compound name |
|---|---|---|
| 136 | 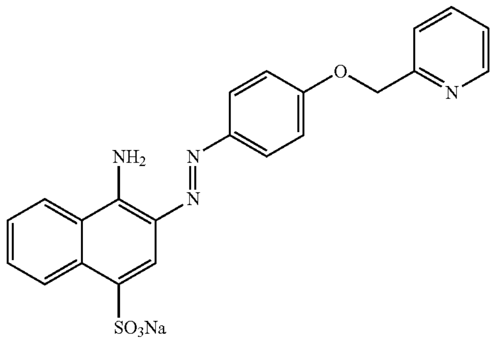 | 4-amino-3-[4-(pyridine-2-ylmethoxy)phenylazo]naphthalene-1-sulfonic acid sodium salt |
| 137 | 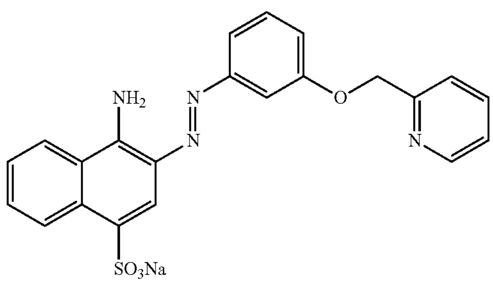 | 4-amino-3-[3-(pyridine-2-ylmethoxy)phenylazo]naphthalene-1-sulfonic acid sodium salt |
| 138 | 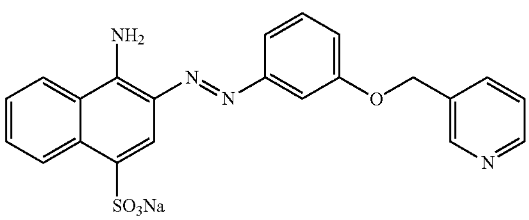 | 4-amino-3-[3-(pyridine-3-ylmethoxy)phenylazo]naphthalene-1-sulfonic acid sodium salt |
| 139 | 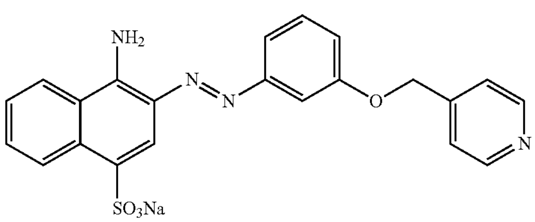 | 4-amino-3-[3-(pyridine-4-ylmethoxy)phenylazo]naphthalene-1-sulfonic acid sodium salt |
| 140 | 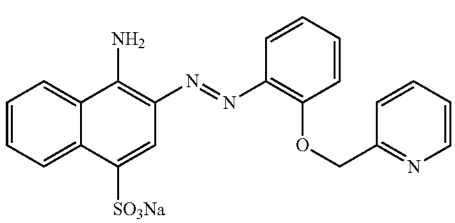 | 4-amino-3-[2-(pyridine-2-ylmethoxy)phenylazo]naphthalene-1-sulfonic acid sodium salt |
| 141 | 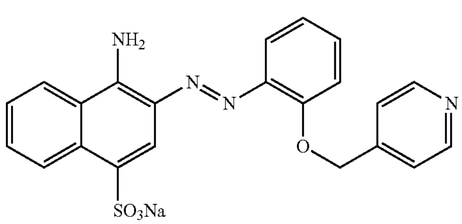 | 4-amino-3-[2-(pyridine-4-ylmethoxy)phenylazo]naphthalene-1-sulfonic acid sodium salt |

TABLE 2-continued

| No. | Structure | Compound name |
|---|---|---|
| 142 | 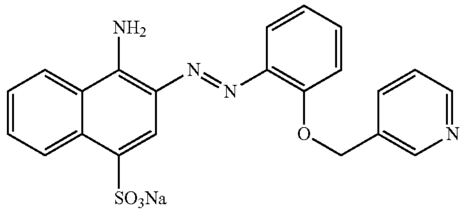 | 4-amino-3-[2-(pyridine-3-ylmethoxy)phenylazo]naphthalene-1-sulfonic acid sodium salt |
| 143 | 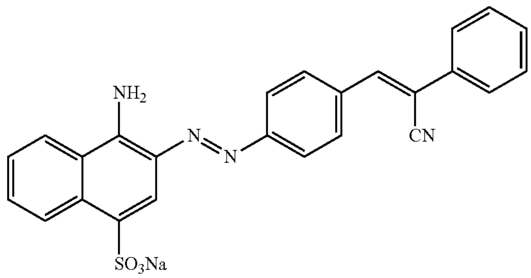 | 4-amino-3-[4-(2-cyano-2-phenylvinyl)phenylazo]naphthalene-1-sulfonic acid sodium salt |
| 144 | 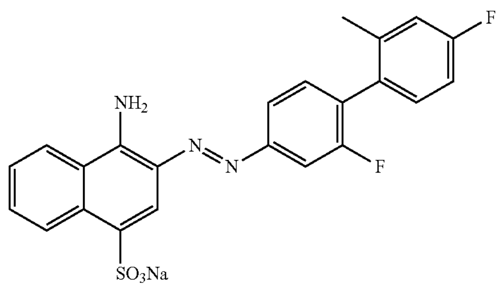 | 4-amino-3-(2,4'-difluoro-2'-methyl-diphenyl-4-ylazo)naphthalene-1-sulfonic acid sodium salt |

TABLE 3

| No. | Structure | Compound name |
|---|---|---|
| 145 | 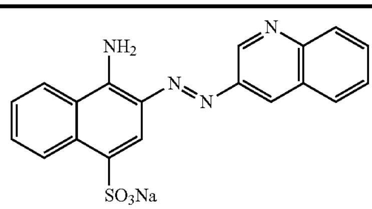 | 4-amino-3-(quinoline-3-ylazo)naphthalene-1-sulfonic acid sodium salt |
| 146 | 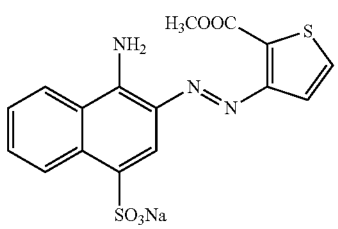 | methyl 3-(1-amino-4-sulfo-naphthalene-2-ylazo)thiophene-2-carboxylate sodium salt |
| 147 | 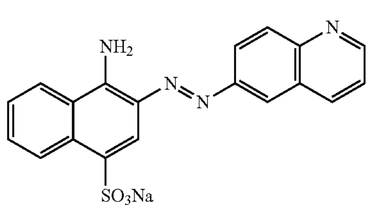 | 4-amino-3-(quinoline-6-ylazo)naphthalene-1-sulfonic acid sodium salt |

In a particularly preferred embodiment, the compounds selected from Compounds 1 to 92, 193 to 194, 105 to 107, 120, 123 to 130 and 132 to 147 listed in Tables 1 to 3 above or oxides, esters, prodrugs, pharmaceutically acceptable salts or solvates thereof are provided.

In one embodiment, provided is a pharmaceutical composition effective to regulate VCP activity in a human or animal subject when administered thereto, comprising a therapeutically effective amount of a compound of the invention including the compounds of formula (I), (II) or (III), or an oxide, ester, prodrug, solvate, or pharmaceutically acceptable salts thereof and a pharmaceutically acceptable carrier.

It will also be apparent to those skilled in the art that the compounds of the invention, including the compounds of formula (I), (II) or (III), or the pharmaceutically acceptable salts, esters, oxides, and prodrugs of any of them, may be subject to tautomerization and may therefore exist in various tautomeric forms.

The compounds of formula (I), (II) or (III) as well as the pharmaceutically acceptable salts, esters, oxides, and prodrugs of any of them may comprise asymmetrically substituted carbon atoms. Such asymmetrically substituted carbon atoms can result in the compounds existing in enantiomers, diastereomers, and other stereoisomeric forms that may be defined, in terms of absolute stereochemistry, such as in (R)- or (S)-forms. As a result, all such possible isomers, individual stereoisomers in their optically pure forms, mixtures thereof, racemic mixtures (or "racemates"), mixtures of diastereomers, as well as single diastereomers of the compounds are contemplated. The terms "S" and "R" configuration, as used herein, are as defined by the IUPAC 1974 RECOMMENDATIONS FOR SECTION E, FUNDAMENTAL STEREOCHEMISTRY, Pure Appl. Chem. 45:13-30 (1976).

VCP-Mediated Diseases

Nine human inherited neurodegenerative disorders, including Huntington's disease (HD), spinobulbar muscular atrophy, spinocerebellar ataxia type 1, spinocerebellar ataxia type 2, spinocerebellar ataxia type 3 (Machado-Joseph disease, MJD), spinocerebellar ataxia type 6, spinocerebellar ataxia type 7, spinocerebellar ataxia type 12, and dentatorubral-pallidoluysian atrophy have been shown to be caused by expanded CAG nucleotide repeats, encoding polyglutamine residues in the proteins responsible. Expanded polyglutamine tracts, typically of more than 40 repeats, possess an intrinsic ability to aggregate in a polyglutamine length and concentration-dependent manner. The ability of expanded polyglutamines to induce neurodegeneration in mice and cell death in cultured cells appears to be inseparable from their intrinsic ability to aggregate. This class of neurodegenerative disorders has thus been collectively called the "polyglutamine diseases". Accordingly, nuclear and/or cytoplasmic expanded aggregates or inclusions have been observed in neurons of patients suffering from essentially all polyglutamine diseases. Accumulation of abnormal proteins has also been observed in various other human neurodegenerative disorders (e.g. prion disease, Alzheimer's disease, amyotrophic lateral sclerosis and the Lewy body diseases, such as Parkinson's disease and dementia with Lewy bodies) (Trends Genet. 14: 396-402, 1998).

During the search for molecules which interact with expanded polyglutamines in mammalian cells, all cultured cells examined were found to contain a protein with a molecular mass of approx. 100 kDa which interacted with the GST (glutathione-S-transferase)-tagged MJD protein containing a 79-residue polyglutamine repeat (GST-MJD79) much more strongly than with GST-MJD containing a 35-residue polyglutamine repeat (GST-MJD35). This protein was then purified from both COS cells and HeLa cells by GST-MJD79-mediated affinity purification. MS and microsequencing analyses revealed that the protein isolated from both cell types was VCP, a member of the AAA (ATPase associated with various cellular activities) class of proteins (Cell Death Differ. 8: 977-984, 2001). In vitro pull-down assays revealed that VCP was no longer able to bind MJD proteins when the polyglutamine repeat portions were deleted. Northern blot analyses of human RNA showed that VCP was ubiquitously expressed in all tissues and throughout the brain. Expression of VCP(K524A), a dominant-negative mutant, led to cell death with accumulation of ubiquitinated proteins and formation of ER (endoplasmic reticulum)-derived vacuoles with ER stress (Cell Death Differ. 8: 977-984, 2001). Given that these phenotypes have been commonly observed in neurodegeneration, the potential involvement of VCP in neuronal cell death has been suggested. It is noteworthy that VCP has also been identified as a genetic modifier of expanded polyglutamine repeat-induced neurodegeneration in a *Drosophila* model of polyglutamine diseases (Cell Death Differ. 9: 264-273, 2002). These results strongly suggested the involvement of VCP in the pathogenesis of at least polyglutamine diseases.

Consistent with the in vitro pull-down results, endogenous VCP was found to co-localize with expanded polyglutamine repeat aggregates. An overexpressed FLAG-tagged 79-residue polyglutamine repeat aggregate was found to form aggregates both in the nucleus and in the cytoplasm in neuronally differentiated PC12 cells (pheochromocytoma cells), and to co-localize with endogenous VCP. Immunochemical analysis showed that in brain sections from HD and MJD patients, strong VCP signals were detected in the nuclear inclusions. Furthermore, VCP-positive staining of Lewy bodies was also observed in patients suffering from Parkinson's disease and in patients with dementia with Lewy bodies, indicating that VCP can recognize a broad range of abnormally folded proteins. VCP co-localization with abnormal protein aggregates was observed in other human neurodegenerative disorders. Indeed, VCP co-localization was observed in the inclusions in motor neurons of SOD1 (superoxide dismutase 1) mutant mice, a mouse model of amyotrophic lateral sclerosis, as well as in the neurons of patients suffering from motor neuron disease with dementia. Dystrophic neuritis in Alzheimer's disease and Marinesco bodies in Parkinson's disease were also VCP-positive. Consistent with these observations, strong VCP signals were observed in aggresomes, proteasome inhibitor-induced intracellular accumulations of ubiquitinated proteins, of cultured cells (Cell Death Differ. 8: 977-984, 2001, Neurosci. Lett. 343: 77-80, 2003, J. Biol. Chem. 279: 51376-51385, 2004).

Given that VCP belongs to the AAA class of ATPases, which includes several proteins functioning in protein control, and that VCP itself has been shown to function in such processes, an alternative possibility is that VCP has yet unknown biological effects on these aggregates. Aggresomes or aggregates of expanded polyglutamine repeats were generated, GFP (green fluorescent protein)-tagged VCP was co-expressed in cultured cells, and the GFP signals after aggregate formation ceased was traced. VCP-GFP co-localized with these protein aggregates, even when expressed after aggregate formation had occurred. The aggregates gradually shrank with continued culture of the cells, but VCP remained co-localized until the aggregates disappeared completely. After this, GFP signals were diffusely distributed throughout the cells. These observations suggest the possibility that VCP is capable of recognizing aggregates, even when aggregates are pre-formed, and remains associated with them until their complete disappearance. The clearance of such aggregates was delayed in cells in which VCP levels were mildly reduced by VCP siRNA (small interfering RNA), or where a dominant-negative VCP mutant was overexpressed (Genes Cells 12: 889-901, 2007), showing that VCP is involved in the processes of clearing the pre-formed aggresomes and expanded polyglutamine repeat aggregates.

These results suggest the possibility that VCP is able to function as an unfoldase towards aggregates. It was examined whether VCP has chaperone effects on denatured proteins, namely heat-denatured firefly luciferase. Cells expressing luciferase were heat-shocked at 45° C. for 15 min, and then incubated at 37° C. for several hours while new protein synthesis was inhibited by the addition of cycloheximide. Every 1 h, for up to 4 h after the heat shock, cells were harvested and their luciferase activity was measured. In this experiment, the luciferase activity from three types of cells was compared: control HeLa cells, VCP KD (knockdown) HeLa cells and VCP KD HeLa cells with wild-type VCP-GFP re-introduced. VCP KD cells failed to reactivate luciferase after the heat shock, when compared with control cells. However, the re-introduction of VCP-GFP into VCP KD cells led to a significant reactivation of luciferase activity, indistinguishable from that of control cells (Genes Cells 12: 889-901, 2007). To examine whether the ATPase activity of VCP is required for this reactivation, VCP(K251A), an ATPase activity-deficient mutant, was introduced into VCP KD cells. VCP(K251A)-GFP either reduced further or failed to reactivate luciferase activity (Genes Cells 12: 889-901, 2007). These results clearly indicate that VCP is involved in the re-folding and the reactivation of luciferase denatured by heat shock, and that its ATPase activity is essential for this function.

Luciferase levels in the aggregate fraction (insoluble fraction) increased remarkably just after the heat shock in both VCP KD cells and VCP KD cells expressing VCP-GFP, but luciferase levels were found to be reduced in VCP KD cells expressing VCP-GFP than in VCP KD cells 4 h after the heat shock. In VCP KD cells, the amount of luciferase stayed constant in the pellet fraction. Consistent with this, soluble luciferase levels increased in VCP KD cells expressing VCP-GFP, but not in VCP KD cells (Genes Cells 12: 889-901, 2007). These results indicate that VCP plays an important role in reactivating luciferase through resolubilizing it from aggregates.

Interestingly, VCP behaved in a totally opposite way in aggresome formation, compared with aggresome clearance. In cells treated with VCP siRNA or expressing VCP (K524M), another ATPase activity-deficient VCP, proteasome inhibitors could not efficiently induce aggresome formation (FEBS Lett. 580: 474-478, 2006). Furthermore, VCP siRNA dose-dependently suppressed the formation of aggregates by expanded polyglutamine repeats in PC12 cells. As observed with aggresome formation and clearance, VCP behaved in a totally different way depending on the expanded polyglutamine-expressing phases, namely during or after the expression. VCP was able to enhance aggregate formation during the expression of expanded polyglutamine repeats, and then VCP changed its function to eliminate the aggregates after expression of the expanded polyglutamine repeats was shut down. These results as a whole suggest the possibility that VCP catalyses both aggregate formation and clearance, depending on the concentration of soluble aggregate-prone proteins, rather than on the concentration of already aggregated or insoluble proteins. Namely, during the expression of expanded polyglutamine repeats, it is expected that the concentration of soluble aggregate-prone expanded polyglutamine repeats is high, and after shutting off the expanded polyglutamine repeat expression, the concentration decreases. Indeed, each condition induced aggregate formation and clearance respectively, and both aggregate formation and clearance were inhibited by VCP KD (Genes Cells 12: 889-901, 2007).

Existence of VCP-positive inclusions has been observed not only in neurons of patients suffering from several neurodegenerative disorders, but also in the muscles of several myopathies with rimmed vacuoles. These findings led to the discovery of the VCP gene as the gene responsible for IBMPFD (inclusion body myopathy with Paget disease of bone and frontotemporal dementia: OMIM 605382) (Nat. Genet. 36: 377-381, 2004). To date, 14 missense mutations have been identified in the VCP coding region. Given that VCP possesses both aggregate-forming and -clearing activities, it is expected that the former activity is dominant over the latter for the VCP mutations involved in IBMPFD. Indeed, cells expressing any of the IBMPFD VCP mutations showed an increased formation of both aggresome and expanded polyglutamine aggregates when compared with cells expressing wild-type VCP. Biochemically, all assayed IBMPFD VCP mutants showed elevated ATPase activities, as well as elevated binding affinities for several VCP cofactors and for ubiquitinated proteins. It is noteworthy that the rimmed vacuoles in muscles contain amyloid β-peptide (Aβ), α-synuclein, tau and ubiquitinated proteins, which are all found in neuronal inclusions in neurodegenerative disorders. These observations further support and enhance the potential roles of VCP as a common player in the pathogenesis among human neurodegenerative disorders, as well as in human muscular disorders. VCP may also play important roles in several bone disorders.

The compounds of the present invention can regulate ATPase activity of VCP. Therefore, in one embodiment, the compounds of present invention can be used for treating VCP-mediated diseases, for example, IBMPFD, neurodegenerative diseases, muscle (including cardiac muscle) diseases and bone diseases. The diseases which can be treated with the compounds of the present invention are, especially, motor neuron diseases represented by amyotrophic lateral sclerosis, Parkinson's syndrome including Parkinson's disease, dementia represented by Alzheimer's disease, progressive supranuclear palsy, Huntington's disease, multiple system atrophy including striatonigral degeneration, Shy-Drager syndrome and olivopontocerebellar atrophy, any type of spinocerebellar ataxia including spinocerebellar ataxia type 1, spinocerebellar ataxia type 2, spinocerebellar ataxia type 3 (Machado-Joseph disease, MJD), spinocerebellar ataxia type 6, spinocerebellar ataxia type 7, spinocerebellar ataxia type 12 and dentatorubral-pallidoluysian atrophy, or neurodegenerative diseases such as multiple sclerosis, muscular or myocardial diseases such as myopathy, and bone diseases such as osteoporosis or Paget's disease.

VCP is also known to be involved in degradation of proteins by ubiquitin-proteasome system. VCP does not recognize limited types of proteins as its substrates, but is characterized by its function regulating the efficiency of the protein degradation system. Since it has been known that the system involves proteins which are significant for occurrence of diseases, the compounds of the present invention can treat the diseases involving the ubiquitin-proteasome system.

It has been known that among the proteins which are degraded by the ubiquitin-proteasome system IκB forms a heterodimer with NFκB, the degradation of IκB plays an important role in the intracellular signal transduction of many inflammatory cytokines or physical stimulation to the cell and the degradation of IκB involves VCP (J. Biol. Chem. 273: 3562-3567, 1998). The stimulation includes, but not limited to, TNF-α, IL-1, viruses, LPS, ultraviolet light, radiation, lymphocyte stimulator, and reactive oxygen. The compounds of the present invention may also influence the production of biological factors which are regulated by NFκB. The factors include, but not limited to, TNF-α, INF-γ, IL-1, IL-2, IL-6, IL-8, IL-12, RANTES, Eotaxin, VCAM, ICAM, colony-stimulating factor, COX2 and the like.

Therefore, the compounds of the present invention can treat the diseases involving NFκB-IκB, especially various inflammatory diseases or allergic reactions. The diseases include rheumatic diseases such as rheumatoid arthritis or systemic lupus erythematosus, atopic dermatitis, nephritis, and pancreatitis. The inflammatory diseases further include various diseases which involve inflammatory reaction as a secondary cause, for example, stroke, cerebral infarction, ischemic diseases such as myocardial infarction, or Crohn's disease or ulcerative colitis and the like.

Furthermore, it has been known that VCP plays a central role in synthesis or degradation of proteins in endoplasmic reticulum. Therefore, expression of many membrane proteins and secreted proteins may be influenced by the compounds of the present invention. It is well known that the protein degradation by VCP in endoplasmic reticulum is carried out in association with the protein degradation by ubiquitin-proteasome system, but the role of VCP is not limited to those associated with ubiquitin-proteasome system.

Among the membrane proteins, degradation of CFTR which is a pathogenic protein of cystic fibrosis is known to be especially influenced by VCP (J. Biol. Chem. 277: 47358-47365, 2002). Thus, the compounds of the present invention can treat the diseases which are caused by abnormality of amount, distribution or morphology of the membrane protein, especially cystic fibrosis.

Among the membrane proteins, MHC class I protein is a membrane protein which plays a central role in self- or nonself-recognition of cells, and plays an important role in diseases of immune system or viral infections. VCP has been known to control the degradation of the protein (Nature 429: 841-847, 2004). Therefore, the diseases which can be treated with the compounds of the present invention include the diseases involving MHC class I proteins, for example, autoimmune diseases, viral infections (including HIV, hepatitis B and hepatitis C) and benign or malignant tumors (including leukemia and lymphoma).

Experiments using cells of various organisms have revealed that VCP is an essential protein in the course of cell cycle such as regeneration of Golgi body or extension of nuclear membrane (Cell 82: 905-914, 1995, Nature 450: 1258-1262, 2007). Furthermore, it is known that reduced expression of VCP by the means of RNAi causes arrest of cell cycle or cell death (J. Cell. Sci. 117: 281-292, 2004). These facts indicate the association between VCP and oncogenesis or proliferation and metastasis of cancer. Indeed, overexpression of VCP is observed in certain cancers in human (Ann. Oncol. 15: 1432-1438, 2004). Therefore, the compounds of the present invention can inhibit the occurrence, proliferation and metastasis of tumor cells by regulating VCP in tumor cells such as cancer, or can treat various tumor diseases by causing cell death in association with the inhibition of proliferation process. The cancers of which the association with VCP is strongly suggested and that can be treated by the compounds of the present invention include, but not limited to, squamous cell carcinoma and adenocarcinoma, and in view of the derived organ, gastric cancer, colon cancer, liver cancer, lung cancer, prostate cancer, thyroid cancer, leukemia and lymphoma.

Some membrane proteins are synthesized so that they are present at cellular membrane temporally or permanently, even though their essential activities do not need membrane localization. Among them the amount of HMG-CoA reductase is known to be regulated by Ufd1-Np14-VCP and protein degradation system in endoplasmic reticulum involving Insig-1 (J. Biol. Chem. 279: 38184-38193, 2004). Therefore, the compounds of the present invention may be useful for treating diseases involving HMG-CoA reductase, for example, dyslipidemia such as hyperlipidemia and hypercholesterolemia.

Among the membrane proteins, IP3 receptor is present on endoplasmic reticulum and used by inositol 3-phosphate produced in several intracellular signal transduction systems to transduce its effect as increase in intracellular calcium. The amount, localization or morphology of IP3 receptor is known to be regulated by VCP (Biochim. Biophys. Acta. 1793: 1710-1718, 2009). Therefore, the compounds of the present invention can treat various diseases involving abnormality in the intracellular signal transduction system including inositol 3-phosphate by regulating the signal transduction system. The signal transduction systems causing the activation of inositol 3-phosphate include, but not limited to, muscarinic acetylcholine receptors, alpha-adrenergic receptors, histamine receptors, serotonin receptors, metabotropic glutamate receptors, substance P receptors, endothelin receptors and the like. Therefore, the diseases which can be treated by the compounds of the present invention also include hypertension, benign prostatic hyperplasia, chronic obstructive pulmonary disease, urinary frequency, urinary incontinence, irritable bowel syndrome, allergic disease, gastric ulcer, duodenal ulcer, depression, anxiety, schizophrenia, migraine, pain, vomiting and the like.

In another aspect, a method of treating a VCP-mediated disease, for example, any one of the above-mentioned diseases, comprising administering to a human or animal subject in need thereof a therapeutically effective amount of the compound of formula (I), (II) or (III) is provided.

In further another aspect, a method of treating a VCP-mediated disease comprising administering to a human or animal subject in need thereof a therapeutically effective amount of the compound of formula (I), (II) or (III) and at least one further agent is provided.

In another aspect, a method of regulating ATPase activity of VCP comprising contacting a cell with the compound of formula (I), (II) or (III) in vivo or ex vivo.

In one embodiment, "neurodegenerative disease" as used herein refers to motor neuron diseases represented by amyotrophic lateral sclerosis, Parkinson's syndrome including Parkinson's disease, dementia represented by Alzheimer's disease, progressive supranuclear palsy, Huntington's disease, multiple system atrophy including striatonigral degeneration, Shy-Drager syndrome and olivopontocerebellar atrophy, any type of spinocerebellar ataxia including spinocerebellar ataxia type 1, spinocerebellar ataxia type 2, spinocerebellar ataxia type 3 (Machado-Joseph disease, MJD), spinocerebellar ataxia type 6, spinocerebellar ataxia type 7, spinocerebellar ataxia type 12 and dentatorubral-pallidoluysian atrophy, or multiple sclerosis.

In one embodiment, "muscle disease" as used herein refers to myopathy including cardiac myopathy.

In one embodiment, "bone disease" as used herein refers to Paget's disease or osteoporosis.

In one aspect, the effect of VCP regulators for regulating ATPase activity is determined, for example by the following exemplary assay. Mouse VCP cDNA (the amino acid sequence is completely identical among mouse, rat and human) is added with a DNA sequence corresponding to a histidine tag at the amino-terminal, subcloned into a baculovirus vector pVL1392 (BD Bioscience), and expressed in Sf-9 insect cells. The protein is purified with a nickel column. After the purification the concentration of the protein is adjusted to 0.25-0.5 μg/ml and the protein is stored in a solution containing 50 mM TrisCl pH 8.0, 5 mM EDTA, 10% glycerol, and 15 mM DTT at 4° C. 500 ng of the purified VCP is mixed with 100 μM [$\gamma$-$^{32}$P]ATP (18.5 GBq/mmol) and the test substance in 20 μL of ATPase buffer (20 mM HEPES (pH7.4), 50 mM KCl, 5 mM MgCl$_2$, 15 mM DTT), and incubated at 37° C. for 10 minutes. The enzyme reaction is stopped with addition of 200 μL of an ice-cold solution containing 7% TCA and 1 mM K$_2$HPO$_4$. 50μ of a solution containing 3.75% ammonium molybdate and 0.02M tungstate silicic/3 N H$_2$SO$_4$ is added, followed by 300 μL of n-butylacetic acid, and then the liberated phosphate is extracted into the organic layer. The reaction tube is centrifuged for 5 minutes at 20,000 g to separate the aqueous layer and the organic layer, 200 μL of the organic layer is taken, and the beta ray radiated from the liberated phosphate is quantified with liquid scintillation counter. By measuring the ATPase activity in the presence of the test substance at various concentrations, ATPase inhibitory activity of the test substance is measured.

The compounds of the present invention regulate, typically enhance or inhibit, especially inhibit, ATPase activity of VCP. When measured according the assay above, the compounds of the present invention preferably has $IC_{50}$ value less than 10 μM, preferably less than 5 μM, more preferably less than 1 μM, and most preferably less than 0.5 μM.

The further agents which can be used in combination with the compounds of the present invention may be agents which can be used for the treatment of any one of the diseases listed above and has been approved by the authorities. For example, examples of the further agents for the treatment of neurodegenerative diseases, muscle diseases or bone disease include, but not limited to, L-dopa, anticholinergic agents (for example, commercially available one such as trade name Artane or Parkin), amantadine hydrochloride (for example, commercially available one such as Symmetrel), ergot- or nonergot-alkaloid, for example, bromocriptine mesylate (for example, commercially available one such as Parlodel), cabergoline (for example, commercially available one such as Cabaser), talipexole hydrochloride (for example, commercially available one such as Domin) and pergolide mesylate (for example, commercially available one such as Permax), selegiline hydrochloride (for example, commercially available one such as FP tablet), L-DOPS (for example, commercially available one such as DOPS), other antidepressive agents or psychotropic agents, donepezil or salts thereof such as hydrochloride (for example, commercially available one such as Aricept).

The compounds of the embodiments and the further agents can be administered at the recommended maximum clinical dosage or at lower doses. Dosage levels of the active compounds in the compositions of the embodiments may be varied so as to obtain a desired therapeutic response depending on the route of administration, severity of the disease and the response of the patient. The combination can be administered as separate compositions or as a single dosage form containing both agents. When administered as a combination, the therapeutic agents can be formulated as separate compositions, which are given at the same time or different times, or the therapeutic agents, can be given as a single composition.

Synthetic Methods

In other aspects, provided are methods of manufacture of compounds of formula (I), (II) or (III) as described herein.

The compounds disclosed herein can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, Protecting Groups in Organic Synthesis, Third Edition, Wiley, New York, 1999, and references cited therein.

Furthermore, the compounds disclosed herein may contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of the embodiments, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures described in standard reference texts such as Fieser and Fieser's Reagents for Organic Synthesis, Volumes 1-15 (John Wiley and Sons, 1991), Rodd's Chemistry of Carbon Compounds, Volumes 1-5 and Supplementals (Elsevier Science Publishers, 1989), Organic Reactions, Volumes 1-40 (John Wiley and Sons, 1991), March's Advanced Organic Chemistry (John Wiley and Sons, 4$^{th}$ Edition) and Larock's Comprehensive Organic Transformations (VCH Publishers Inc., 1989), or obvious modifications thereof, for instance, the disclosure of Examples herein.

The various starting materials, intermediates, and compounds of the embodiments may be isolated and purified where appropriate using conventional techniques such as precipitation, filtration, crystallization, evaporation, distillation, and chromatography. Characterization of these compounds may be performed using conventional methods such as by melting point, mass spectrum, nuclear magnetic resonance, and various other spectroscopic analyses.

Compounds of the embodiments may generally be prepared using a number of methods familiar to one of skill in the art, and may generally be made in accordance with the following reaction Scheme 1, which is described in detail in the Examples below.

General Schemes:

Scheme 1 illustrates a general method for the preparation of intermediates and compounds of the invention. These compounds are prepared from starting materials that are known in the art or are commercially available, or starting materials which can be easily prepared from such starting materials by those skilled in the art.

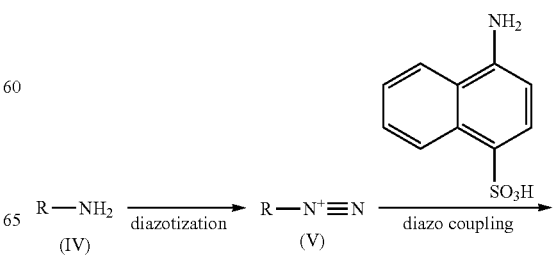

Scheme 1

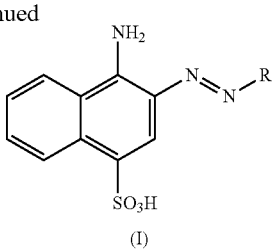

(I)

wherein R in formulae (IV), (V) and (I) is as defined above in formula (I). The details and reaction conditions of diazotization of primary amine and diazo coupling of diazotized compound are well known to those skilled in the art, and they can conveniently select a suitable reaction condition from such well-known reaction conditions.

In scheme 1, typically the compound of formula (IV) is suspended in a suitable solvent, for example, water, acetic acid or tetrahydrofuran or the mixture thereof, and reacted with nitrous acid or a salt or ester thereof, for example, nitrites such as potassium nitrite, calcium nitrite, silver nitrite, sodium nitrite or barium nitrite, or nitrite esters such as ethyl nitrite, isopentyl nitrite (also called as isoamyl nitrite), isobutyl nitrite, isopropyl nitrite or isopentyl nitrite with cooling, for example, below 10° C., preferably below 5° C. to achieve diazotization, resulting in the compound of formula (V).

In scheme 1, typically 4-amino-naphthalene-1-sulfonic acid can be suspended in a suitable solvent, for example water, and then subjected to diazo-coupling with the compound of formula (V) obtained above under a basic condition (for example, by addition of aqueous sodium hydroxide), for example, at pH7 to 11, preferably at pH8 to 10, with cooling, for example, at 0 to 15° C., preferably at 0 to 10° C. to give the compound of formula (I).

The following applies in general to all processes mentioned hereinbefore and hereinafter, while reaction conditions specifically mentioned above or below are preferred.

In any of the reactions mentioned hereinbefore and hereinafter, protecting groups may be used where appropriate or desired, even if this is not mentioned specifically, to protect functional groups that are not intended to take part in a given reaction, and they can be introduced and/or removed at appropriate or desired stages. Reactions comprising the use of protecting groups are therefore included as possible also in cases where reactions without specific mentioning of protection and/or deprotection are described in this specification.

Within the scope of this disclosure only a readily removable group that is not a constituent of the particular desired end product of formula I is designated a "protecting group", unless the context indicates otherwise. The protection of functional groups by such protecting groups, the protecting groups themselves, and the reactions appropriate for their introduction and removal are described for example in standard reference works, such as J. F. W. McOmie, "Protective Groups in Organic Chemistry", Plenum Press, London and New York 1973, T. W. Greene and P. G. M. Wuts, "Protective Groups in Organic Synthesis", Third edition, Wiley, New York 1999, "The Peptides"; Volume 3 (editors: E. Gross and J. Meienhofer), Academic Press, London and New York 1981, "Methoden der organischen Chemie" (Methods of Organic Chemistry), Houben Weyl, 4th edition, Volume 15/I, Georg Thieme Verlag, Stuttgart 1974, H.-D. Jakubke and H. Jeschkeit, "Aminosaeuren, Peptide, Proteine" (Amino acids, Peptides, Proteins), Verlag Chemie, Weinheim, Deerfield Beach, and Basel 1982, and Jochen Lehmann, "Chemie der Kohlenhydrate: Monosaccharide and Derivate" (Chemistry of Carbohydrates: Monosaccharides and Derivatives), Georg Thieme Verlag, Stuttgart 1974. A characteristic of protecting groups is that they can be removed readily (i.e. without the occurrence of undesired secondary reactions) for example by solvolysis, reduction, photolysis or alternatively under physiological conditions (e.g. by enzymatic cleavage).

All the above-mentioned process steps can be carried out under reaction conditions that are known per se, preferably those mentioned specifically, in the absence or, customarily, in the presence of solvents or diluents, preferably solvents or diluents that are inert towards the reagents used and dissolve them, in the absence or presence of catalysts, condensation or neutralizing agents, for example ion exchangers, such as cation exchangers, e.g. in the $H^+$ form, depending on the nature of the reaction and/or of the reactants at reduced, normal or elevated temperature, for example in a temperature range of from about −100° C. to about 190° C., preferably from approximately −80° C. to approximately 150° C., for example at from −80 to −60° C., at room temperature, at from −20 to 40° C. or at reflux temperature, under atmospheric pressure or in a closed vessel, where appropriate under pressure, and/or in an inert atmosphere, for example under an argon or nitrogen atmosphere.

The solvents from which those solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofuran or dioxane, liquid aromatic hydrocarbons, such as benzene or toluene, alcohols, such as methanol, ethanol or 1- or 2-propanol, nitriles, such as acetonitrile, halogenated hydrocarbons, such as methylene chloride or chloroform, acid amides, such as N,N-dimethylformamide or N,N-dimethylacetamide, bases, such as heterocyclic nitrogen bases, for example pyridine or N-methylpyrrolidin-2-one, carboxylic acid anhydrides, such as lower alkanoic acid anhydrides, for example acetic anhydride, cyclic, linear or branched hydrocarbons, such as cyclohexane, hexane or isopentane, or mixtures of these, for example aqueous solutions, unless otherwise indicated in the description of the processes. Such solvent mixtures may also be used in working up, for example by chromatography or partitioning.

The invention relates also to those forms of the process in which a compound obtainable as intermediate at any stage of the process is used as starting material and the remaining process steps are carried out, or in which a starting material is formed under the reaction conditions or is used in the form of a derivative, for example in protected form or in the form of a salt, or a compound obtainable by the process according to the invention is produced under the process conditions and processed further in situ. In the process of the present invention those starting materials are preferably used which result in compounds of formula I described as being preferred. Special preference is given to reaction conditions that are identical or analogous to those mentioned in Examples.

In one aspect, the present invention provides the process for preparing the compounds of formula (I), (II) or (III), comprising (1) reacting the compound of formula (IV)

R—NH$_2$       (IV)

in which R is as defined above, with nitrous acid or a salt or ester thereof with cooling to give the compound of formula (V)

R—N⁺≡N  (V)

in which R is as defined above,
(2) reacting the resulting compound of formula (V) with 4-amino-naphthalene-1-sulfonic acid under a basic condition to give the compound of formula (I), (II) or (III),
(3) isolating the resulting compound of formula (I), (II) or (III) from the reaction mixture,
and optionally, converting the compound of formula (I), (II) or (III) into another compound of formula (I), (II) or (III), converting the resulting salt of the compound of formula (I), (II) or (III) into a free compound or another salt, converting the resulting free compound of formula (I), (II) or (III) into a salt and/or ester thereof, and/or separating the resulting isomeric mixture of the compound of formula (I), (II) or (III) into respective isomers.

Administration and Pharmaceutical Compositions

In other aspects, pharmaceutical compositions comprising at least one compound of formula (I), (II), or (III) together with a pharmaceutically acceptable carrier suitable for administration to a human or animal subject, either alone or together with other agents are provided.

In another aspects, the compounds of formula (I), (II) or (III) for treating a VCP-mediated disease and use of the compounds of formula (I), (II) or (III) in the preparation of a pharmaceutical for treating a VCP-mediated disease are provided.

In general, the compounds of the embodiments will be administered in a therapeutically effective amount by any of the accepted modes of administration for agents that serve similar utilities. The actual amount of the compound, i.e., the active ingredient, will depend upon numerous factors such as the severity of the disease to be treated, the age and relative health of the subject, the potency of the compound used, the route and form of administration, and other factors. The drug can be administered more than once a day, preferably once or twice a day. All of these factors are within the skill of the attending clinician.

The amount of active ingredient that may be combined with the carrier materials to produce a single dosage form will vary depending upon the host treated and the particular mode of administration. It will be understood, however, that the specific dose level for any particular subject will depend upon a variety of factors including the activity of the specific compound employed, the age, body weight, general health, sex, diet, time of administration, route of administration, rate of excretion, drug combination, and the severity of the particular disease undergoing therapy. The therapeutically effective amount for a given situation can be readily determined by routine experimentation and is within the skill and judgment of the ordinary clinician.

A therapeutically effective dose generally can be a total daily dose administered to a host in single or divided doses which may be in amounts, for example, of from about 0.001 to about 1000 mg/kg body weight daily and from about 1.0 to about 30 mg/kg body weight daily. Dosage unit compositions may contain such amounts of submultiples thereof to make up the daily dose.

The choice of formulation depends on various factors such as the mode of drug administration and bioavailability of the drug substance. The drug can be administered as pharmaceutical compositions by any one of the following routes: oral, systemic (e.g., transdermal, intranasal or by suppository), or parenteral (e.g., intramuscular, intravenous or subcutaneous) administration. One manner of administration is oral using a convenient daily dosage regimen that can be adjusted according to the degree of affliction. Compositions can take the form of tablets, pills, capsules, semi-solids, powders, sustained release formulations, solutions, suspensions, elixirs, aerosols, or any other appropriate compositions. Another manner for administration is inhalation such as for delivering a therapeutic agent directly to the respiratory tract (see U.S. Pat. No. 5,607,915).

Suitable pharmaceutically acceptable carriers or excipients include, for example, processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-β-cyclodextrin, polyvinylpyrrolidinone, low melting waxes, ion exchange resins, and the like, as well as combinations of any two or more thereof. Liquid and semisolid excipients can be selected from glycerol, propylene glycol, water, ethanol and various oils, including those of petroleum, animal, vegetable or synthetic origin, e.g., peanut oil, soybean oil, mineral oil, sesame oil, etc. In some embodiments liquid carriers, particularly for injectable solutions, include water, saline, aqueous dextrose, and glycols. Other suitable pharmaceutically acceptable excipients are described in "Remington's Pharmaceutical Sciences," Mack Pub. Co., New Jersey (1991).

As used herein, the term "pharmaceutically acceptable salts" refers to the nontoxic acid or alkaline earth metal salts of the compounds of formulae (I), (II), or (III). These salts can be prepared in situ during the final isolation and purification of the compounds of formulae (I), (II), or (III), or by separately reacting the base or acid functions with a suitable organic or inorganic acid or base, respectively. Representative salts include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesulfonate, lactate, maleate, methanesulfonate, nicotinate, 2-naphthalenesulfonate, oxalate, pamoate, pectinate, persulfate, 3-phenylproionate, picrate, pivalate, propionate, succinate, sulfate, tartrate, thiocyanate, p-toluenesulfonate and undecanoate. Also, the basic nitrogen-containing groups can be quaternized with agents such as alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl chlorides, and others. Water or oil-soluble or dispersible products are thereby obtained.

Examples of acids which may be employed to form pharmaceutically acceptable acid addition salts include such inorganic acids as hydrochloric acid, sulfuric acid and phosphoric acid and such organic acids as oxalic acid, maleic acid, methanesulfonic acid, succinic acid and citric acid. Basic addition salts can be prepared in situ during the final isolation and purification of the compounds of formula (I), (II), or (III), or separately by reacting carboxylic acid moieties with a suitable base such as the hydroxide, carbonate or bicarbonate of a pharmaceutically acceptable metal cation or with ammonia, or an organic primary, secondary or tertiary amine. Pharmaceutically acceptable salts include, but are not limited to, cations based on the alkali and alkaline earth metals, such as sodium, lithium, potassium, calcium, magnesium, aluminum salts and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. Other representative organic amines useful for the formation of base addition salts include diethylamine, ethylenediamine, ethanolamine, diethanolamine, piperazine and the like.

As used herein, the term "pharmaceutically acceptable ester" refers to esters, which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates.

The term "pharmaceutically acceptable prodrugs" as used herein refers to those prodrugs of the compounds which are, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the embodiments. The term "prodrug" refers to compounds that are rapidly transformed in vivo to yield the parent compound of the above formula, for example by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

It will be apparent to those skilled in the art that the compounds of formula (I), (II) or (III) or the pharmaceutically acceptable salts, esters, oxides, and prodrugs of any of them, may be processed in vivo through metabolism in a human or animal body or cell to produce metabolites. The term "metabolite" as used herein refers to the formula of any derivative produced in a subject after administration of a parent compound. The derivatives may be produced from the parent compound by various biochemical transformations in the subject such as, for example, oxidation, reduction, hydrolysis, or conjugation and include, for example, oxides and demethylated derivatives. The metabolites of a compound of the embodiments may be identified using routine techniques known in the art. See, e.g., Bertolini, G. et al., J. Med. Chem. 40:2011-2016 (1997); Shan, D. et al., J. Pharm. Sci. 86(7):765-767; Bagshawe K., Drug Dev. Res. 34:220-230 (1995); Bodor, N., Advances in Drug Res. 13:224-331 (1984); Bundgaard, H., Design of Prodrugs (Elsevier Press 1985); and Larsen, I. K., Design and Application of Prodrugs, Drug Design and Development (Krogsgaard-Larsen et al., eds., Harwood Academic Publishers, 1991). It should be understood that individual chemical compounds that are metabolites of the compounds of formulas (I), (II) or (III) or the pharmaceutically acceptable salts, esters, oxides and prodrugs of any of them, are included within the embodiments provided herein.

The compounds of the preferred embodiments may be administered orally, parenterally, sublingually, by aerosolization or inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or ionophoresis devices. The term parenteral as used herein includes subcutaneous injections, intravenous, intrathecal, intramuscular, intrasternal injection, or infusion techniques.

Injectable preparations, for example, sterile injectable aqueous or oleaginous suspensions may be formulated according to the known art using suitable dispersing or wetting agents or suspending agents. The sterile injectable preparation may also be a sterile injectable solution or suspension in a nontoxic parenterally acceptable diluent or solvent, for example, as a solution in 1,3-propanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols, which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose, lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, cyclodextrins, and sweetening, flavoring, and perfuming agents.

The compounds of the embodiments can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain stabilizers, preservatives, excipients, and the like. Examples of lipids are the phospholipids and phosphatidylcholines (lecithins), both natural and synthetic. Methods to form liposomes are known in the art. See, for example, Prescott, Ed., Methods in Cell Biology, Volume XIV, Academic Press, New York, N. W., p. 33 et seq. (1976).

Compressed gases may be used to disperse a compound of the embodiments in aerosol form. Inert gases suitable for this purpose are nitrogen, carbon dioxide, etc. Other suitable pharmaceutical excipients and their formulations are described in Remington's Pharmaceutical Sciences, edited by E. W. Martin (Mack Publishing Company, 18th ed., 1990).

For delivery via inhalation the compound can be formulated as liquid solution, suspensions, aerosol propellants or dry powder and loaded into a suitable dispenser for administration. There are several types of pharmaceutical inhalation devices, nebulizer, inhalers, metered dose inhalers (MDI) and dry powder inhalers (DPI). Nebulizer devices produce a stream of high velocity air that causes the therapeutic agents (which are formulated in a liquid form) to spray as a mist that is carried into the subject's respiratory tract. MDI's typically are formulation packaged with a compressed gas. Upon actuation, the device discharges a measured amount of therapeutic agent by compressed gas, thus affording a reliable method of administering a set amount of agent. DPI dispenses therapeutic agents in the form of a free flowing powder that can be dispersed in the subject's inspiratory air-stream during breathing by the device. In order to achieve a free flowing powder, the therapeutic agent is formulated with an excipient such as lactose. A measured amount of the therapeutic agent is stored in a capsule form and is dispensed with each actuation.

The following Examples illustrate the present invention, but not limit the scope thereof.

EXAMPLES

Example 1

Synthesis of 4-amino-3-(pyridine-3-ylazo)naphthalene-1-sulfonic acid sodium salt

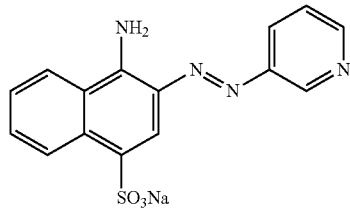

3-Aminopyridine (1.50 g, 16 mmol) was suspended in water (10 ml), added dropwise with 35% hydrochloric acid (4.15 g, 40 mmol). The suspension was cooled below 5° C., added dropwise with an aqueous solution of sodium nitrite (1.15 g, 17 mmol), and reacted below 5° C. for about 5 minutes. After the completion of the reaction, excess sodium nitrite was decomposed with amidosulfuric acid to obtain diazo solution. 4-Amino-1-naphthalenesulfonic acid (3.38 g, 15 mmol) was suspended in water (25 ml), and the pH of the suspension was adjusted to pH 8 to 10 with 10% aqueous sodium hydroxide, and with cooling on ice added with the diazo solution, during which 10% aqueous sodium hydroxide was added dropwise to keep the pH at 7 to 10. After the reaction at pH 7 to 10 below 10° C. for 1 hour, the temperature was raised to 40 to 50° C. with hot water, and salting-out was performed with addition of sodium chloride. After cooling to the room temperature, the precipitated crystals were filtered with suction. After purification by column chromatography, the products were purified by recrystallization to give the title compound (3.10 g, 59.0%).

$^1$H-NMR (DMSO-d6) δ [ppm]=9.14 (1H, d, J=2.1), 8.75 (1H, dd, J=8.4 Hz, 1.2 Hz), 8.59 (1H, dd, J=4.5 Hz, 1.5 Hz), 8.45 (1H, d, J=7.8 Hz), 8.36 (1H, ddd, J=8.2 Hz, 2.1 Hz, 1.5 Hz), 8.29 (1H, s), 7.77 (2H, s), 7.77-7.46 (3H, m)

$^{13}$C-NMR (DMSO-d6) δ [ppm]=155.2, 147.0, 132.4, 132.2, 128.9, 128.8, 128.4, 128.3, 126.3, 126.1, 125.2, 124.2, 124.1, 122.7, 117.6

Example 2

Synthesis of 4-amino-3-(6-methoxypyridine-3-ylazo)naphthalene-1-sulfonic acid sodium salt

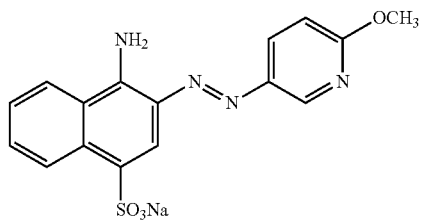

The title compound was synthesized in a manner analogous to Example 1, except for replacing 3-aminopyridine with 3-amino-6-methoxypyridine.

$^1$H-NMR (DMSO-d6) δ [ppm]=8.77 (1H, d, J=2.7 Hz), 8.74 (1H, d, J=8.1 Hz), 8.43 (1H, d, J=9.0 Hz), 8.42 (1H, d, J=8.7 Hz), 8.28 (1H, s), 7.44-7.58 (4H, m), 6.94 (1H, d, J=8.7 Hz), 3.95 (3H, s)

$^{13}$C-NMR (DMSO-d6) δ [ppm]=164.0, 146.1, 145.3, 144.4, 132.3, 131.7, 129.4, 128.8, 128.2, 127.9, 124.8, 124.1, 123.6, 116.1, 111.3, 53.7

Example 3

Synthesis of 3-(2-pyridinomethoxy-5-pyridinoazo)-4-amino-1-naphthalenesulfonic acid sodium salt

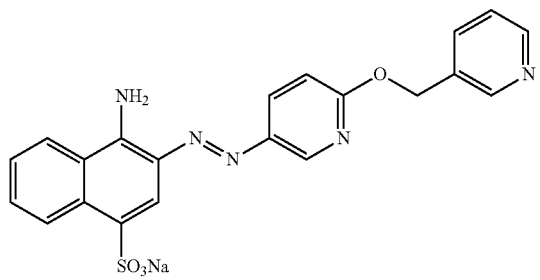

(i) 5-Nitro-2-pyridinomethoxypyridine

To a suspension of 60% sodium hydrid (0.72 g, 18 mmol) in tetrahydrofuran (20 ml), 3-pyridinemethanol (1.03 g, 9 mmol) was added dropwise with cooling on ice. After reacting for 10 minutes, a solution of 2-chloro-5-nitropyridine (1.5 g, 9 mmol) in tetrahydrofuran was added dropwise with cooling on ice. With cooling on ice, the reaction was carried out for 30 minutes and quenched with methanol (5 ml), and then the reaction mixture was poured into cold water (200 ml). The precipitated crystals were filtered with suction to give the title compound (2.16 g, 103.8%).

(ii) 5-Amino-2-pyridinomethoxypyridine

Iron powder (100 mesh, 0.56 g, 10 mmol) was added to ethanol:water=2:1 (15 ml), and the temperature was raised to 70° C. Ammonium chloride (0.04 g, 0.7 mmol) was added, followed by 5-nitro-2-pyridinomethoxypyridine (1.00 g, 4 mmol) synthesized in (i). The temperature was raised to 80° C., and the reaction was carried out for 1 hour. The reaction solution was filtered via Celite, concentrated under reduced pressure, and ethanol was distilled off. The concentrate was neutralized with saturated sodium bicarbonate water, and extracted with ethyl acetate. The organic layer was dried with anhydrous sodium sulfate, concentrated under reduced pressure to give the title compound (0.61 g, 75.8%).

(iii) 3-(2-Pyridinomethoxy-5-pyridinoazo)-4-amino-1-naphthalenesulfonic acid sodium salt The title compound was synthesized in a manner analogous to Example 1, except for replacing 3-aminopyridine with 5-amino-2-pyridinomethoxypyridine synthesized in (ii).

$^1$H-NMR (DMSO-d6) δ [ppm]=8.81 (1H, d, J=2.1 Hz), 8.73 (1H, m), 8.72 (1H, s), 8.55 (1H, dd, J=4.8 Hz, 1.8 Hz), 8.49 (1H, dd, J=9.0 Hz, 2.1 Hz), 8.41 (1H, d, J=8.1 Hz), 8.28 (1H, d, J=3.1 Hz) 7.94-7.90 (1H, m), 7.60-7.41 (5H, m), 7.03 (1H, d, J=9.0 Hz)
$^{13}$C-NMR (DMSO-d6) δ [ppm]=163.2, 149.4, 149.2, 146.4, 145.2, 144.8, 136.2, 132.7, 132.2, 131.8, 129.9, 128.8, 128.3, 128.1, 125.0, 124.2, 123.8, 123.7, 116.0, 111.7, 65.4

Example 4

Synthesis of 4-amino-3-[6-(tetrahydrofuran-2-ylmethoxy)pyridine-3-ylazo]-1-naphthalenesulfonic acid sodium salt

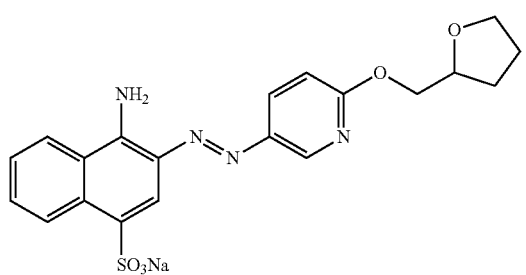

(i) 5-Nitro-2-(tetrahydrofuran-2-ylmethoxy)pyridine

The title compound was synthesized in a manner analogous to Example 3 (i), except for replacing 3-pyridinemethanol with tetrahydrofurfuryl alcohol.

(ii) 6-(Tetrahydrofuran-2-ylmethoxy)pyridine-3-ylamine

The title compound was synthesized in a manner analogous to Example 3 (ii), except for replacing 5-nitro-2-pyridinomethoxypyridine with 5-nitro-2-(tetrahydrofuran-2-ylmethoxy)pyridine synthesized in (i).

(iii) 4-Amino-3-[6-(tetrahydrofuran-2-ylmethoxy)pyridine-3-ylazo]-1-naphthalenesulfonic acid sodium salt The title compound was synthesized in a manner analogous to Example 1, except for replacing 3-aminopyridine with 6-(tetrahydrofuran-2-ylmethoxy)pyridine-3-ylamine synthesized in (ii).

$^1$H-NMR (DMSO-d6) δ [ppm]=8.76 (1H, d, J=9.0, 2.7 Hz), 8.72 (1H, dd, J=8.4, 0.9 Hz), 8.46 (1H, dd, J=9.0, 2.7 Hz), 8.26 (1H, s), 7.56 (1H, dd, J=7.0, 0.9 Hz), 7.50-7.47 (3H, m)
$^{13}$C-NMR (DMSO-d6) δ [ppm]=163.6, 146.2, 145.4, 144.5, 132.3, 131.7, 129.5, 128.8, 128.2, 128.0, 124.8, 124.2, 123.7, 115.9, 111.5, 76.2, 68.3, 67.4, 27.7, 25.2

Example 5

Synthesis of 4-amino-3-[6-(2,2,2-trifluoroethoxy)pyridine-3-ylazo]naphthalene-1-sulfonic acid sodium salt

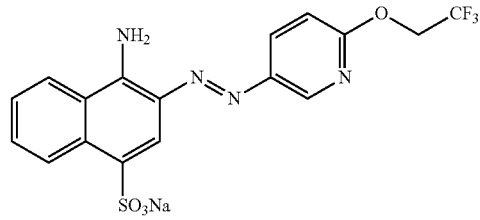

(i) 5-Nitro-2-(2,2,2-trifluoroethoxy)pyridine

The title compound was synthesized in a manner analogous to Example 3 (i), except for replacing 3-pyridinemethanol with 2,2,2-trifluoroethanol.

(ii) 6-(2,2,2-Trifluoroethoxy)pyridine-3-ylamine

The title compound was synthesized in a manner analogous to Example 3 (ii), except for replacing 5-nitro-2-pyridinomethoxypyridine with 5-nitro-2-(2,2,2-trifluoroethoxy)pyridine.

(iii) 4-Amino-3-[6-(2,2,2-trifluoroethoxy)pyridine-3-ylazo]naphthalene-1-sulfonic acid sodium salt The title compound was synthesized in a manner analogous to Example 1, except for replacing 3-aminopyridine with 6-(2,2,2-trifluoroethoxy)pyridine-3-ylamine synthesized in (ii).

$^1$H-NMR (DMSO-d6) δ [ppm]=8.81 (1H, d, J=2.1 Hz), 8.73 (1H, m), 8.72 (1H, s), 8.55 (1H, dd, J=4.8 Hz, 1.8 Hz), 8.49 (1H, dd, J=9.0 Hz, 2.1 Hz), 8.41 (1H, d, J=8.1 Hz), 8.28 (1H, d, J=3.1 Hz) 7.94-7.90 (1H, m), 7.60-7.41 (5H, m), 7.03 (1H, d, J=9.0 Hz)
$^{13}$C-NMR (DMSO-d6) δ [ppm]=161.3, 146.7, 145.4, 144.6, 132.4, 131.9, 130.5, 128.8, 128.3, 128.1, 124.9, 124.2, 123.7, 115.8, 111.4, 62.0

Example 6

Synthesis of 4-amino-3-[6-(2-methoxyethoxy)pyridine-3-ylazo]naphthalene-1-sulfonic acid sodium salt

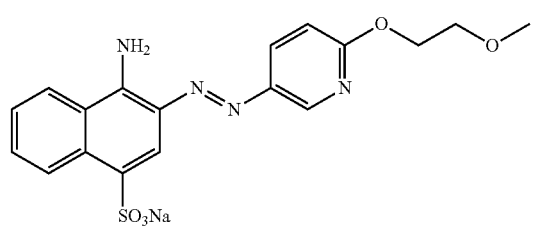

(i) 2-(2-Methoxyethoxy)-5-nitropyridine

The title compound was synthesized in a manner analogous to Example 3 (i), except for replacing 3-pyridinemethanol with 2-methoxyethanol.

(ii) 6-(2-Methoxyethoxy)pyridine-3-ylamine

The title compound was synthesized in a manner analogous to Example 3 (ii), except for replacing 5-nitro-2-pyridinomethoxypyridine with 2-(2-methoxyethoxy)-5-nitropyridine synthesized in (i).

(iii) 4-Amino-3-[6-(2-methoxyethoxy)pyridine-3-ylazo]naphthalene-1-sulfonic acid sodium salt The title compound was synthesized in a manner analogous to Example 1, except for replacing 3-aminopyridine with 6-(2-methoxyethoxy)pyridine-3-ylamine synthesized in (ii).

$^1$H-NMR (DMSO-d6) δ [ppm]=8.81 (1H, d, J=2.1 Hz), 8.73 (1H, m), 8.72 (1H, s), 8.55 (1H, dd, J=4.8 Hz, 1.8 Hz), 8.49 (1H, dd, J=9.0 Hz, 2.1 Hz), 8.41 (1H, d, J=8.1 Hz), 8.28 (1H, d, J=3.1 Hz) 7.94-7.90 (1H, m), 7.60-7.41 (5H, m), 7.03 (1H, d, J=9.0 Hz)

$^{13}$C-NMR (DMSO-d6) δ [ppm]=163.6, 146.4, 145.5, 144.5, 132.3, 131.8, 129.6, 128.8, 128.7, 128.2, 124.9, 124.2, 123.7, 115.9, 111.6, 70.2, 65.3, 58.2

Example 7

Synthesis of 4-amino-3-(6-phenylpyridine-3-ylazo)naphthalene-1-sulfonic acid sodium salt

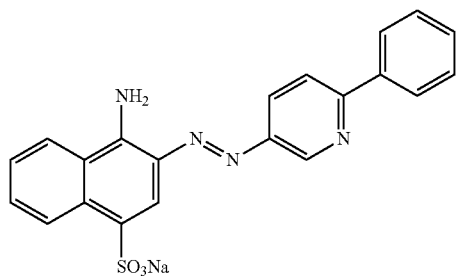

(i) 2-Phenyl-5-nitropyridine

2-Chloro-5-nitropyridine (3.0 g, 18.9 mmol), phenylboronic acid (2.5 g, 20.8 mmol), and tetrakis(triphenylphosphine)palladium (0.2 g, 0.2 mmol) were added to 1,2-dimethoxyethan (30 ml), then degassed and purged with nitrogen three times under reduced pressure. Under nitrogen atmosphere the mixture was stirred at room temperature for 20 minutes, then 1M aqueous sodium carbonate (40 ml) was poured in, and the temperature was raised to 80° C. After the reaction at 80° C. for 6 hours, the mixture was cooled to room temperature and crystallized with addition of water. The precipitated crystals were filtered to give the title compound (3.7 g, 96.8%).

(ii) 2-Phenyl-5-aminopyridine

Ethanol (20 ml) and water (5 ml) was mixed, added with iron powder, and heated to 70-80° C. Ammonium chloride (0.1 g, 2.1 mmol) was added, followed by 2-phenyl-5-nitropyridine (2.0 g, 10.0 mmol) obtained in (i). The reaction was carried out at 70-80° C. for 1 hour. After the completion of the reaction, the iron powder was filtered while hot through Celite, and the filtrate was concentrated under reduced pressure. The residue was dissolved in isopropyl alcohol, crystallized and filtered with addition of water to give the title compound (1.4 g, 81.9%).

(iii) 4-Amino-3-(6-phenylpyridine-3-ylazo)naphthalene-1-sulfonic acid sodium salt 2-Phenyl-5-aminopyridine (1.0 g, 5.9 mmol) obtained in (ii) was suspended in water, and added with 35% hydrochloric acid (2 ml) to form hydrochloride. With cooling on ice, an aqueous solution of sodium nitrite (0.4 g, 6.2 mmol) was added dropwise at 0 to 5° C., and the reaction was carried out for about 5 minutes. Amide sulfuric acid was added and the reaction was carried out for additional 5 minutes, resulting in diazo solution.

4-Amino-1-naphthalenesulfonic acid (1.3 g, 5.6 mmol) was suspended in water, and the pH of the suspension was adjusted to pH 8 to 9 with 10% aqueous sodium hydroxide. The mixture was cooled to 5-10° C., the obtained diazo solution was added dropwise at 5-10° C., during which 10% aqueous sodium hydroxide was added dropwise to keep the pH at 7 to 9. After the completion of the addition, the reaction was carried out at 5-10° C. for 1 hour, then the temperature was raised to room temperature. Saturated sodium chloride solution was added, and the precipitated crystals were filtered with suction. The products were purified by column chromatography to give the title compound (1.2 g, 48.3%).

$^1$H-NMR (DMSO-d6) δ [ppm]=9.21 (1H, d, J=2.7), 8.75 (1H, dd, J=8.6, 0.9), 8.55 (1H, dd, J=8.7, 2.7), 8.46 (1H, d, J=7.8), 8.31 (1H, s), 8.20 (2H, d, J=8.0), 8.12 (1H, d, J=8.7), 7.79 (2H, bs), 7.63-7.46 (5H, m)

$^{13}$C-NMR (DMSO-d6) δ [ppm]=155.9, 147.4, 147.2, 146.3, 138.1, 132.5, 132.1, 129.4, 129.3, 128.9, 128.5, 128.4, 127.6, 126.7, 125.1, 124.2, 124.0, 120.7, 116.3

Example 8

Synthesis of 4-amino-3-(6-p-tolylpyridine-3-ylazo)naphthalene-1-sulfonic acid sodium salt

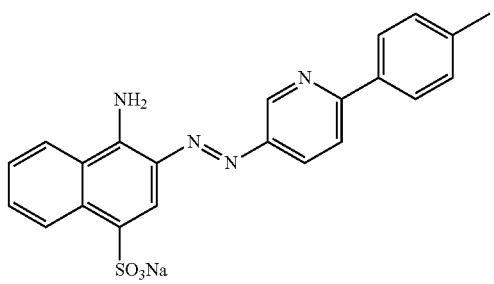

(i) 5-Nitro-2-p-tolylpyridine

2-Chloro-5-nitropyridine (5.0 g, 31.5 mmol) and tetrakis(triphenylphosphine)palladium (0.35 g, 0.3 mmol) were added to 1,2-dimethoxyethan (50 ml), then degassed and purged with nitrogen three times under reduced pressure.

Under nitrogen atmosphere the mixture was stirred at room temperature for 20 minutes, 4-methylphenylboronic acid (4.29 g, 31.5 mmol) and 2M aqueous sodium carbonate (31.5 ml) were poured in, and the temperature was raised to 80° C. After the reaction at 80° C. for 3 hours, the mixture was cooled to room temperature and extracted with addition of ethyl acetate and water. The organic layer was dried with anhydrous sodium sulfate, and concentrated under reduced pressure. The products were purified by column chromatography to give the title compound (80.0% 5.4 g, yield).

(ii) 6-p-Tolylpyridine-3-ylamine

The title compound was synthesized in a manner analogous to Example 7 (ii), except for replacing 2-phenyl-5-nitropyridine with 5-nitro-2-p-tolylpyridine obtained in (i).

(iii) 4-Amino-3-(6-p-tolylpyridine-3-ylazo)naphthalene-1-sulfonic acid sodium salt The title compound was synthesized in a manner analogous to Example 7 (iii), except for replacing 2-phenyl-5-aminopyridine with 6-p-tolylpyridine-3-ylamine obtained in (ii).

$^1$H-NMR (DMSO-d6) δ [ppm]=9.20 (1H, d, J=2.4 Hz), 8.75 (1H, d, J=8.4 Hz), 8.45 (1H, d, J=8.7 Hz), 8.44 (1H, d, J=8.7 Hz), 8.29 (1H, s), 8.10 (2H, d, J=7.5 Hz), 8.07 (1H, d, J=7.8 Hz), 7.74 (2H, bs), 7.59 (1H, dd, J=7.5, 7.2 Hz), 7.47 (1H, dd, J=7.2 Hz), 7.33 (2H, d, J=8.1 Hz), 2.38 (3H, s)

$^{13}$C-NMR (DMSO-d6) δ [ppm]=155.9, 147.2, 146.9, 146.3, 139.0, 135.4, 132.6, 132.1, 129.5, 129.3, 128.4, 127.5, 126.6, 125.0, 124.2, 123.8, 120.2, 116.4, 20.9

Example 9

Synthesis of 4-amino-3-(6-m-tolylpyridine-3-ylazo)naphthalene-1-sulfonic acid sodium salt

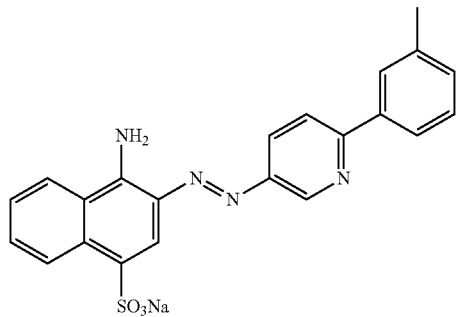

(i) 5-Nitro-2-m-tolylpyridine

The title compound was synthesized in a manner analogous to Example 7 (i), except for replacing phenylboronic acid with 3-methylphenylboronic acid.

(ii) 6-m-Tolylpyridine-3-ylamine

The title compound was synthesized in a manner analogous to Example 7 (ii), except for replacing 2-phenyl-5-nitropyridine with 5-nitro-2-m-tolylpyridine obtained in (i).

(iii) 4-Amino-3-(6-m-tolylpyridine-3-ylazo)naphthalene-1-sulfonic acid sodium salt The title compound was synthesized in a manner analogous to Example 7 (iii), except for replacing 2-phenyl-5-aminopyridine with 6-m-tolylpyridine-3-ylamine obtained in (ii).

$^1$H-NMR (DMSO-d6) δ [ppm]=9.22 (1H, dd, J=2.4, 0.6), 8.76 (1H, dd, J=8.4, 1.2), 8.46 (1H, J=8.7), 8.45 (1H, J=8.7), 8.31 (1H, s), 8.09 (1H, d, J=8.7), 8.03 (1H, s), 7.97 (1H, d, J=7.8), 7.77 (2H, bs), 7.56 (1H, m), 7.49 (1H, m), 7.40 (1H, dd, J=7.8, 7.5), 7.27 (1H, d, J=7.5), 2.42 (3H, s)

$^{13}$C-NMR (DMSO-d6) δ [ppm]=156.0, 147.3, 146.9, 146.2, 138.0, 132.6, 132.5, 132.1, 130.0, 129.3, 128.7, 128.4, 128.3, 127.4, 127.3, 125.0, 124.2, 123.9, 120.6, 116.5, 21.1

Example 10

Synthesis of 4-amino-3-(6-o-tolylpyridine-3-ylazo)naphthalene-1-sulfonic acid sodium salt

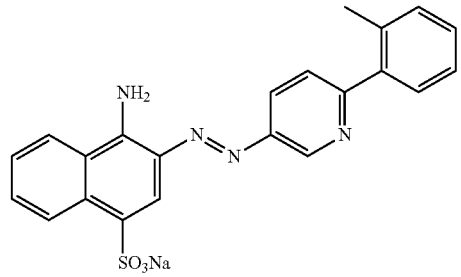

(i) 5-Nitro-2-o-tolylpyridine

The title compound was synthesized in a manner analogous to Example 8 (i), except for replacing 4-methylphenylboronic acid with 2-methylphenylboronic acid.

(ii) 6-o-Tolylpyridine-3-ylamine

The title compound was synthesized in a manner analogous to Example 7 (ii), except for replacing 2-phenyl-5-nitropyridine with 5-nitro-2-o-tolylpyridine obtained in (i).

(iii) 4-Amino-3-(6-o-tolylpyridine-3-ylazo)naphthalene-1-sulfonic acid sodium salt The title compound was synthesized in a manner analogous to Example 7 (iii), except for replacing 2-phenyl-5-aminopyridine with 6-o-tolylpyridine-3-ylamine obtained in (ii).

$^1$H-NMR (DMSO-d6) δ [ppm]=9.23 (1H, d, J=2.1 Hz), 8.76 (1H, d, J=8.1 Hz), 8.46 (1H, d, J=8.1 Hz), 8.45 (1H, dd, J=8.1, 2.1 Hz), 8.32 (1H, s), 7.78 (2H, bs), 7.66 (1H, d, J=8.1), 7.60 (1H, dd, J=7.8, 7.2), 7.52-7.48 (2H, m), 7.33-7.30 (3H, m), 2.41 (3H, s)

$^{13}$C-NMR (DMSO-d6) δ [ppm]=159.2, 147.0, 146.7, 145.3, 139.6, 135.6, 132.5, 132.1, 130.8, 129.7, 129.2, 128.5, 128.4, 128.3, 127.2, 125.9, 125.0, 124.5, 124.2, 123.9, 116.5, 20.4

Example 11

Synthesis of 4-amino-3-[6-(3-morpholine-4-ylmethylphenyl)pyridine-3-ylazo]naphthalene-1-sulfonic acid sodium salt

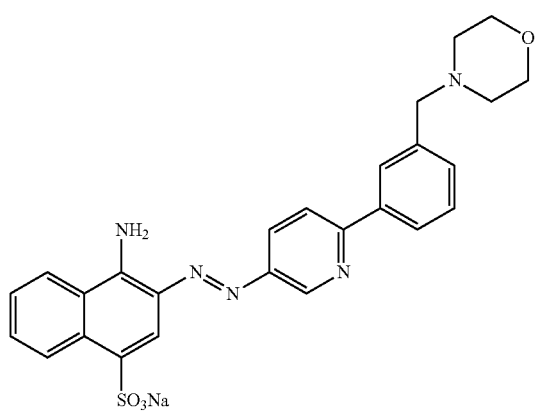

(i) 5-Nitro-2-m-tolylpyridine

The title compound was synthesized in a manner analogous to Example 7 (i), except for replacing phenylboronic acid with 3-methylphenylboronic acid.

(ii) 2-(3-Bromomethylphenyl)-5-nitropyridine

5-Nitro-2-m-tolylpyridine (2.0 g, 9.3 mmol) obtained in (i) and acetonitrile (20 ml) were charged, refluxed with heating. A solution of N-bromosuccinimide (1.68 g, 9.4 mmol) and azobisisobutyronitrile (0.02 g, 0.12 mmol) in acetonitrile was added dropwise. The reaction was carried out for 1 hour under reflux. The reaction solution was cooled and extracted with addition of toluene and water. The organic layer was dried with anhydrous sodium sulfate and concentrated under reduced pressure. Purification by recrystallization gave the title compound (1.94 g, 73.5%).

(iii) 4-[3-(5-Nitropyridine-2-yl)benzyl]morpholine 2-(3-Bromomethylphenyl)-5-nitropyridine (1.5 g, 5.1 mmol) obtained in (ii), morpholine (0.53 g, 6.1 mmol), potassium carbonate (1.41 g, 10.2 mmol), and acetonitrile (30 ml) were charged, and reacted under reflux for 2 hours. The reaction solution was cooled and extracted with addition of ethyl acetate and water. The organic layer was dried with anhydrous sodium sulfate, concentrated to dryness to give the title compound (1.42 g, 94.9%).

(iv) 6-(3-Morpholine-4-ylmethylphenyl)pyridine-3-ylamine

The title compound was synthesized in a manner analogous to Example 7 (ii), except for replacing 2-phenyl-5-nitropyridine with 4-[3-(5-nitropyridine-2-yl)benzyl]morpholine obtained in (iii).

(v) 4-Amino-3-[6-(3-morpholine-4-ylmethylphenyl)pyridine-3-ylazo]naphthalene-1-sulfonic acid sodium salt The title compound was synthesized in a manner analogous to Example 7 (iii), except for replacing 2-phenyl-5-aminopyridine with 6-(3-morpholine-4-ylmethylphenyl)pyridine-3-ylamine obtained in (iv).

$^1$H-NMR (DMSO-d6) δ [ppm]=9.23 (1H, d, J=2.4), 8.75 (1H, d, J=7.5), 8.47 (1H, dd, J=8.7, 2.4), 8.45 (1H, d, J=8.1), 8.32 (1H, s), 8.14 (1H, m), 8.06 (1H, d, J=7.8), 7.79 (2H, bs), 7.62-7.58 (1H, m), 7.52-7.44 (2H, m), 7.39 (1H, d, J=7.5), 3.60-3.56 (6H, m), 2.40 (4H, t, J=4.2)

$^{13}$C-NMR (DMSO-d6) δ [ppm]=155.9, 147.3, 147.0, 146.3, 138.5, 138.0, 132.5, 132.1, 130.1, 129.3, 128.8, 128.5, 128.3, 127.5, 127.3, 125.5, 125.1, 124.2, 123.9, 120.7, 116.5, 66.2, 62.5, 53.2

Example 12

Synthesis of 4-amino-3-(6-biphenyl-2-ylpyridine-3-ylazo)naphthalene-1-sulfonic acid sodium salt

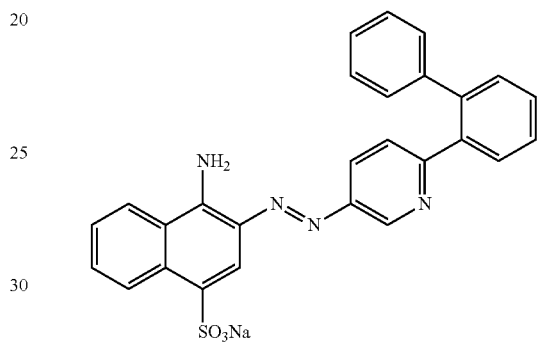

(i) 2-Biphenyl-2-yl-5-nitropyridine

The title compound was synthesized in a manner analogous to Example 7 (i), except for replacing phenylboronic acid with biphenyl-2-ylboronic acid.

(ii) 6-Biphenyl-2-ylpyridine-3-ylamine

To methanol (250 ml), 2-biphenyl-2-yl-5-nitropyridine (16.3 g, 58.9 mmol) obtained in (i) and 10% palladium carbon (1.2 g) were added, reduced at 45° C. under hydrogen pressure of 0.7 MPa. The palladium catalyst was filtered through Celite, and the filtrate was concentrated to dryness under reduced pressure to give title compound (16.6 g, 114.4% yield).

(iii) 4-Amino-3-(6-biphenyl-2-ylpyridine-3-ylazo)naphthalene-1-sulfonic acid sodium salt 6-Biphenyl-2-ylpyridine-3-ylamine (16.6 g, 58.9 mmol) obtained in (ii) was dissolved in 99% acetic acid (50 ml), and added with 35% hydrochloric acid (25 g) to form hydrochloride. With cooling on ice a 36% aqueous solution of sodium nitrite (12 g, 62.5 mmol) was added dropwise at 0-5° C., and the reaction was carried out for about 15 minutes. Amide sulfuric acid was added and the reaction was carried out for additional 5 minutes, resulting in diazo solution. 4-Amino-1-naphthalenesulfonic acid (13.0 g, 58.4 mmol) was suspended in water (130 ml), and the pH of the suspension was adjusted to pH 8 to 9 with 10% aqueous sodium hydroxide. The mixture was cooled to 5-10° C., and added dropwise with the obtained diazo solution at 5-10° C., during which 10% aqueous sodium hydroxide was added dropwise to keep the pH at 7 to 9. After the completion of the addition, the reaction was carried out at 5-10° C. for 1 hour, then the temperature was raised to room temperature. Salting-out was performed with saturated aqueous sodium chloride, and the precipitated crystals were filtered with suction. Purification by column chromatography gave the title compound (19.4 g, 66.1% yield).

$^1$H-NMR (DMSO-d6) δ [ppm]=9.14 (1H, d, J=2.4), 8.74 (1H, d, J=8.4), 8.45 (1H, d, J=7.8), 8.29 (1H, s), 8.17 (1H, dd, J=8.4, 2.4), 7.75-7.72 (3H, m), 7.62-7.44 (6H, m), 7.32-7.25 (1H, m), 7.29 (2H, d, J=7.2), 7.16 (2H, d, J=7.2), 7.03 (1H, d, J=8.4)

$^{13}$C-NMR (DMSO-d6) δ [ppm]=158.7, 147.2, 146.5, 146.3, 140.9, 140.3, 138.7, 132.3, 132.1, 130.5, 129.4, 129.2, 128.9, 128.5, 128.4, 128.3, 127.6, 127.0, 125.8, 125.4, 125.1, 124.2, 124.0, 116.2

Example 13

Synthesis of 4-amino-3-(4-ethoxypyridine-3-ylazo)naphthalene-1-sulfonic acid sodium salt

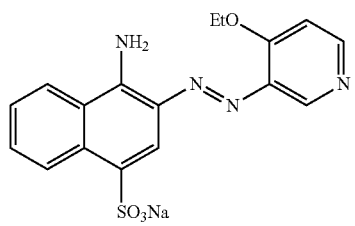

(i) 4-Ethoxypyridine-3-ylamine

The title compound was synthesized in a manner analogous to Example 7 (ii), except for replacing 2-phenyl-5-nitropyridine with 4-ethoxy-3-nitropyridine.

(ii) 4-Amino-3-(4-ethoxypyridine-3-ylazo)naphthalene-1-sulfonic acid sodium salt The title compound was synthesized in a manner analogous to Example 7 (iii), except for replacing 2-phenyl-5-aminopyridine with 4-ethoxypyridine-3-ylamine obtained in (i).

$^1$H-NMR (DMSO-d6) δ [ppm]=8.75 (1H, d, J=7.2 Hz), 8.73 (1H, s), 8.47 (1H, d, J=8.1 Hz), 8.41 (3H, m), 8.26 (1H, s), 7.57-7.62 (1H, m), 7.46-7.51 (1H, m), 7.24 (1H, d, J=6.0 Hz), 4.31 (2H, q, J=6.6 Hz), 1.44 (3H, t, J=6.6 Hz)

$^{13}$C-NMR (DMSO-d6) δ [ppm]=159.6, 151.2, 144.2, 138.0, 137.6, 132.0, 131.5, 129.4, 128.4, 128.1, 125.0, 124.3, 124.0, 121.7, 109.1, 64.3, 14.5

Example 14

Synthesis of 3-[6-(2-acetylphenyl)pyridine-3-ylazo]-4-aminonaphthalene-1-sulfonic acid sodium salt

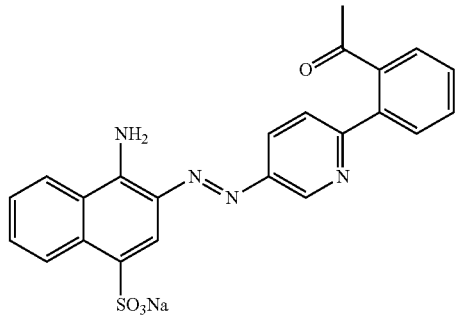

(i) (2-Acetylphenyl)-2-yl-5-nitropyridine

The title compound was synthesized in a manner analogous to Example 8 (i), except for replacing 4-methylphenylboronic acid with 2-acetylphenylboronic acid.

(ii) 6-(2-Acetylphenyl)pyridine-3-ylamine

The title compound was synthesized in a manner analogous to Example 7 (ii), except for replacing 2-phenyl-5-nitropyridine with (2-acetylphenyl)-2-yl-5-nitropyridine obtained in (i).

(iii) 3-[6-(2-Acetylphenyl)pyridine-3-ylazo]-4-aminonaphthalene-1-sulfonic acid sodium salt The title compound was synthesized in a manner analogous to Example 7 (iii), except for replacing 2-phenyl-5-aminopyridine with 6-(2-acetylphenyl)pyridine-3-ylamine obtained in (ii).

$^1$H-NMR (DMSO-d6) δ [ppm]=9.16 (1H, d, J=2.1 Hz), 8.75 (1H, d, J=7.8 Hz), 8.49 (1H, dd, J=8.7, 2.1 Hz), 8.46 (1H, m), 8.30 (1H, s), 7.94 (1H, d, J=8.7 Hz), 7.83 (1H, d, J=7.2 Hz), 7.82 (2H, bs), 7.64-7.50 (5H, m), 2.25 (3H, s)

$^{13}$C-NMR (DMSO-d6) δ [ppm]=203.1, 156.5, 147.2, 147.1, 144.8, 141.7, 137.6, 132.6, 132.2, 130.3, 129.3, 129.2, 128.9, 128.6, 128.4, 128.4, 127.4, 125.1, 124.2, 124.0, 123.0, 116.5, 30.5

Example 15

Synthesis of 3-[6-(3-acetylphenyl)pyridine-3-ylazo]-4-aminonaphthalene-1-sulfonic acid sodium salt

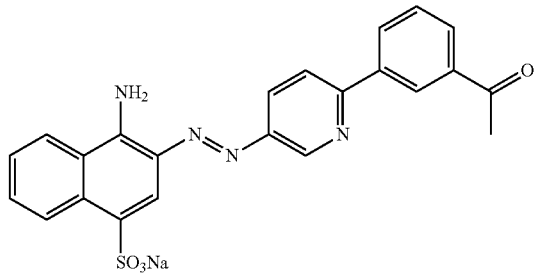

(i) (3-Acetylphenyl)-2-yl-5-nitropyridine

The title compound was synthesized in a manner analogous to Example 8 (i), except for replacing 4-methylphenylboronic acid with 3-acetylphenylboronic acid.

(ii) 6-(3-Acetylphenyl)pyridine-3-ylamine

The title compound was synthesized in a manner analogous to Example 7 (ii), except for replacing 2-phenyl-5-nitropyridine with (3-acetylphenyl)-2-yl-5-nitropyridine obtained in (i).

(iii) 3-[6-(3-Acetylphenyl)pyridine-3-ylazo]-4-aminonaphthalene-1-sulfonic acid sodium salt The title compound was synthesized in a manner analogous to Example 7 (iii), except for replacing 2-phenyl-5-aminopyridine with 6-(3-acetylphenyl)pyridine-3-ylamine obtained in (ii).

$^1$H-NMR (DMSO-d6) δ [ppm]=9.32 (1H, d, J=2.1 Hz), 8.82-8.78 (2H, m), 8.55 (1H, dd, J=8.7, 2.1 Hz), 8.54-8.50 (1H, m), 8.47 (1H, d, J=8.1 Hz), 8.38 (1H, s), 8.27 (1H, d, J=8.7 Hz), 8.08 (1H, d, J=8.1 Hz), 7.89 (2H, bs), 7.74-7.63 (2H, m), 7.58-7.53 (1H, m), 2.73 (3H, s)

$^{13}$C-NMR (DMSO-d6) δ [ppm]=198.0, 154.9, 147.6, 147.2, 146.4, 138.5, 137.5, 132.5, 132.2, 131.2, 129.4, 129.4, 128.9, 128.7, 128.3, 127.8, 126.3, 125.2, 124.2, 124.0, 121.1, 116.6, 27.0

Example 16

Synthesis of 3-[6-(4-acetylphenyl)pyridine-3-ylazo]-4-aminonaphthalenesulfonic acid sodium salt

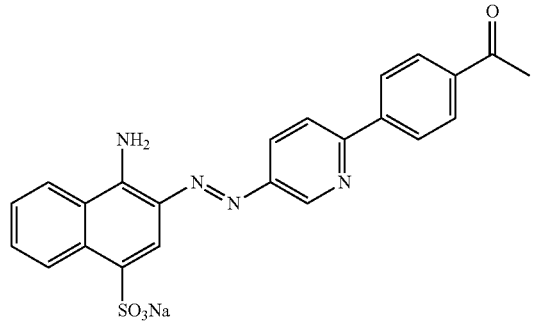

(i) (4-Acetylphenyl)-2-yl-5-nitropyridine

The title compound was synthesized in a manner analogous to Example 8 (i), except for replacing 4-methylphenylboronic acid with 4-acetylphenylboronic acid.

(ii) 6-(4-Acetylphenyl)pyridine-3-ylamine

The title compound was synthesized in a manner analogous to Example 7 (ii), except for replacing 2-phenyl-5-nitropyridine with (4-acetylphenyl)-2-yl-5-nitropyridine obtained in (i).

(iii) 3-[6-(4-Acetylphenyl)pyridine-3-ylazo]-4-aminonaphthalenesulfonic acid sodium salt The title compound was synthesized in a manner analogous to Example 7 (iii), except for replacing 2-phenyl-5-aminopyridine with 6-(4-acetylphenyl)pyridine-3-ylamine obtained in (ii).

$^1$H-NMR (DMSO-d6) δ [ppm]=9.27 (1H, d, J=2.1 Hz), 8.77 (1H, d, J=8.4 Hz), 8.51-8.46 (2H, m), 8.34-8.31 (3H, m), 8.20 (1H, d, J=8.7 Hz), 8.07 (2H, d, J=8.1 Hz), 7.87 (2H, bs), 7.50 (1H, dd, J=7.8, 7.2 Hz), 7.61 (1H, dd, J=7.8, 7.2 Hz), 2.62 (3H, s)

$^{13}$C-NMR (DMSO-d6) δ [ppm]=197.7, 154.5, 147.7, 147.3, 146.4, 142.1, 136.9, 132.4, 132.2, 129.4, 128.8, 128.3, 127.7, 126.8, 125.2, 124.2, 124.0, 121.5, 116.6, 26.9

Example 17

Synthesis of 4-amino-3-(6-thiophene-2-ylpyridine-3-ylazo)naphthalene-1-sulfonic acid sodium salt

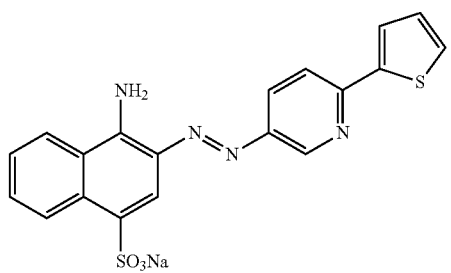

(i) 5-Nitro-2-thiophene-2-ylpyridine

The title compound was synthesized in a manner analogous to Example 8 (i), except for replacing 4-methylphenylboronic acid with 2-thiopheneboronic acid.

(ii) 6-Thiophene-2-ylpyridine-3-ylamine

The title compound was synthesized in a manner analogous to Example 7 (ii), except for replacing 2-phenyl-5-nitropyridine with 5-nitro-2-thiophene-2-ylpyridine obtained in (i).

(iii) 4-Amino-3-(6-thiophene-2-ylpyridine-3-ylazo)naphthalene-1-sulfonic acid sodium salt The title compound was synthesized in a manner analogous to Example 7 (iii), except for replacing 2-phenyl-5-aminopyridine with 6-thiophene-2-ylpyridine-3-ylamine obtained in (ii).

$^1$H-NMR (DMSO-d6) δ [ppm]=9.10 (1H, d, J=2.1), 8.78 (1H, d, J=8.1), 8.47 (1H, d, J=8.1), 8.42 (1H, dd, J=8.4, 2.1), 8.36 (1H, s), 8.02 (1H, d, J=8.4), 7.88 (1H, dd, J=3.6, 0.9), 7.80 (2H, bs), 7.68 (1H, dd, J=5.1, 0.9), 7.61 (1H, dd, J=8.1, 7.2), 7.50 (1H, dd, J=7.5, 6.9), 7.18 (1H, dd, J=5.1, 3.6)

$^{13}$C-NMR (DMSO-d6) δ [ppm]=152.0, 147.2, 147.1, 146.6, 144.2, 132.3, 132.0, 129.4, 129.3, 128.8, 128.7, 128.3, 127.4, 126.2, 125.2, 124.3, 124.0, 119.3, 116.7

Example 18

Synthesis of 4-amino-3-(6-thiophene-3-ylpyridine-3-ylazo)naphthalene-1-sulfonic acid sodium salt

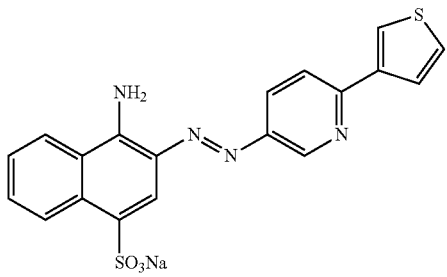

(i) 5-Nitro-2-thiophene-3-ylpyridine

The title compound was synthesized in a manner analogous to Example 7 (i), except for replacing phenylboronic acid with 3-thiopheneboronic acid.

(ii) 6-thiophene-3-ylpyridine-3-ylamine

The title compound was synthesized in a manner analogous to Example 7 (ii), except for replacing 2-phenyl-5-nitropyridine with 5-nitro-2-thiophene-3-ylpyridine obtained in (i).

(iii) 4-Amino-3-(6-thiophene-3-ylpyridine-3-ylazo)naphthalene-1-sulfonic acid sodium salt The title compound was synthesized in a manner analogous to Example 7 (iii), except for replacing 2-phenyl-5-aminopyridine with 6-thiophene-3-ylpyridine-3-ylamine obtained in (ii).

$^1$H-NMR (DMSO-d6) δ [ppm]=9.14 (1H, d, J=2.1 Hz), 8.75 (1H, dd, J=8.4, 1.2 Hz), 8.45-8.42 (1H, m), 8.41 (1H, dd, J=8.4, 2.1 Hz), 8.31 (1H, s), 8.29 (1H, dd, J=3.0, 1.2 Hz), 8.00 (1H, d, J=8.4 Hz), 7.84 (1H, dd, J=5.1, 1.2 Hz), 7.75 (2H, bs), 7.67 (1H, dd, J=5.1, 3.0 Hz), 7.63-7.57 (1H, m), 7.52-7.47 (1H, m)

$^{13}$C-NMR (DMSO-d6) δ [ppm]=152.9, 147.0, 146.9, 146.5, 141.5, 132.4, 132.0, 129.3, 128.6, 128.3, 127.4, 127.3, 126.5, 125.2, 124.9, 124.2, 123.9, 120.9, 116.7

Example 19

Synthesis of 4-amino-3-[6-(2,4-dichlorophenyl)pyridine-3-ylazo]naphthalene-1-sulfonic acid sodium salt

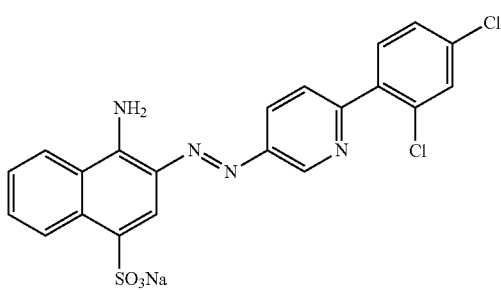

(i) 2-(2,4-Dichlorophenyl)-5-nitropyridine

The title compound was synthesized in a manner analogous to Example 7 (i), except for replacing phenylboronic acid with 2,4-dichlorophenylboronic acid.

(ii) 6-(2,4-Dichlorophenyl)pyridine-3-ylamine

The title compound was synthesized in a manner analogous to Example 7 (ii), except for replacing 2-phenyl-5-nitropyridine with 2-(2,4-dichlorophenyl)-5-nitropyridine obtained in (i).

(iii) 4-Amino-3-[6-(2,4-dichlorophenyl)pyridine-3-ylazo]naphthalene-1-sulfonic acid sodium salt The title compound was synthesized in a manner analogous to Example 7 (iii), except for replacing 2-phenyl-5-aminopyridine with 6-(2,4-dichlorophenyl)pyridine-3-ylamine obtained in (ii).

$^1$H-NMR (DMSO-d6) δ [ppm]=9.25 (1H, dd, J=2.4, 0.6 Hz), 8.75 (1H, dd, J=8.4, 0.9 Hz), 8.48 (1H, dd, J=8.4, 2.4 Hz), 8.46 (1H, d, J=8.1 Hz), 8.31 (1H, s), 7.85 (2H, bs), 7.82 (1H, dd, J=8.4, 0.6 Hz), 7.76 (1H, d, J=2.4 Hz), 7.72 (1H, d, J=8.1 Hz), 7.57 (1H, dd, J=8.1, 2.4 Hz), 7.63-7.59 (1H, m), 7.53-7.50 (1H, m)

$^{13}$C-NMR (DMSO-d6) δ [ppm]=154.8, 147.4, 145.8, 137.4, 134.0, 133.1, 132.5, 132.3, 132.2, 129.5, 129.3, 128.7, 128.3, 127.7, 127.1, 125.2, 124.2, 124.0, 116.6

Example 20

Synthesis of 4-amino-3-[6-(2-trifluoromethylphenyl)pyridine-3-ylazo]naphthalene-1-sulfonic acid sodium salt

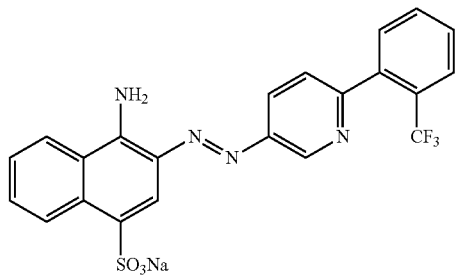

(i) 5-Nitro-2-(2-trifluoromethylphenyl)pyridine

The title compound was synthesized in a manner analogous to Example 8 (i), except for replacing 4-methylphenylboronic acid with 2-trifluoromethylphenylboronic acid.

(ii) 6-(2-Trifluoromethylphenyl)pyridine-3-ylamine

The title compound was synthesized in a manner analogous to Example 7 (ii), except for replacing 2-phenyl-5-nitropyridine with 5-nitro-2-(2-trifluoromethylphenyl)pyridine obtained in (i).

(iii) 4-Amino-3-[6-(2-trifluoromethylphenyl)pyridine-3-ylazo]naphthalene-1-sulfonic acid sodium salt The title compound was synthesized in a manner analogous to Example 7 (iii), except for replacing 2-phenyl-5-aminopyridine with 6-(2-trifluoromethylphenyl)pyridine-3-ylamine obtained in (ii).

$^1$H-NMR (DMSO-d6) δ [ppm]=9.23 (1H, d, J=1.8 Hz), 8.77 (1H, d, J=8.1 Hz), 8.49 (1H, d, J=8.4 Hz), 8.48 (1H, d, J=8.1 Hz), 8.34 (1H, s), 7.89-7.48 (9H, m)

$^{13}$C-NMR (DMSO-d6) δ [ppm]=157.2, 147.3, 145.1, 139.4, 132.4, 132.3, 132.2, 131.7, 129.3, 129.0, 128.6, 128.3, 127.3, 127.1, 126.7, 126.5, 126.4, 126.0, 125.1, 124.3, 124.2, 124.0, 122.4, 116.5

Example 21

Synthesis of 4-amino-3-[6-(4-trifluoromethylphenyl)pyridine-3-ylazo]naphthalene-1-sulfonic acid sodium salt

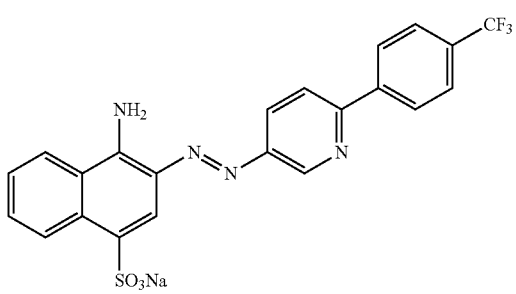

(i) 5-Nitro-2-(4-trifluoromethylphenyl)pyridine

The title compound was synthesized in a manner analogous to Example 8 (i), except for replacing 4-methylphenylboronic acid with 4-trifluoromethylphenylboronic acid.

(ii) 6-(4-Trifluoromethylphenyl)pyridine-3-ylamine

The title compound was synthesized in a manner analogous to Example 7 (ii), except for replacing 2-phenyl-5-nitropyridine with 5-nitro-2-(4-trifluoromethylphenyl)pyridine obtained in (i).

(iii) 4-Amino-3-[6-(4-trifluoromethylphenyl)pyridine-3-ylazo]naphthalene-1-sulfonic acid sodium salt The title compound was synthesized in a manner analogous to Example 7 (iii), except for replacing 2-phenyl-5-aminopyridine with 6-(4-trifluoromethylphenyl)pyridine-3-ylamine obtained in (ii).

$^1$H-NMR (DMSO-d6) δ [ppm]=9.27 (1H, d, J=2.4 Hz), 8.77 (1H, dd, J=8.4, 1.2 Hz), 8.51 (1H, dd, J=8.4, 2.4 Hz), 8.46 (1H, d, J=8.1 Hz), 8.40 (2H, d, J=8.1 Hz), 8.33 (1H, s), 8.21 (1H, d, J=8.4 Hz), 7.86 (2H, d, J=8.1 Hz), 7.85 (2H, bs), 7.63-7.58 (1H, m), 7.53-7.47 (1H, m)

$^{13}$C-NMR (DMSO-d6) δ [ppm]=154.0, 147.8, 147.2, 146.2, 141.9, 132.6, 132.2, 129.4, 129.0, 128.6, 128.3, 127.8, 127.3, 125.7, 125.6, 125.0, 124.2, 123.9, 121.4, 116.6

Example 22

Synthesis of 4-amino-3-[6-(2-chlorophenyl)pyridine-3-ylazo]naphthalene-1-sulfonic acid sodium salt

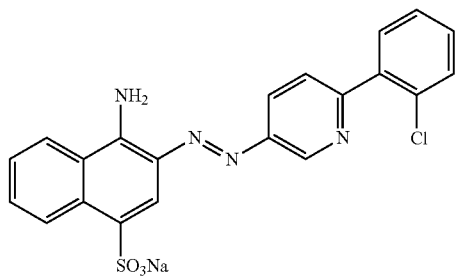

(i) 2-(2-Chlorophenyl)-5-nitropyridine

The title compound was synthesized in a manner analogous to Example 7 (i), except for replacing phenylboronic acid with 2-chlorophenylboronic acid.

(ii) 6-(2-Chlorophenyl)pyridine-3-ylamine

The title compound was synthesized in a manner analogous to Example 7 (ii), except for replacing 2-phenyl-5-nitropyridine with 2-(2-chlorophenyl)-5-nitropyridine obtained in (i).

(iii) 4-Amino-3-[6-(2-chlorophenyl)pyridine-3-ylazo]naphthalene-1-sulfonic acid sodium salt The title compound was synthesized in a manner analogous to Example 7 (iii), except for replacing 2-phenyl-5-aminopyridine with 6-(2-chlorophenyl)pyridine-3-ylamine obtained in (ii).

$^1$H-NMR (DMSO-d6) δ [ppm]=8.76 (1H, d, J=2.4 Hz), 8.27 (1H, d, J=8.4 Hz), 7.99 (1H, dd, J=8.4, 2.4 Hz), 7.96 (1H, d, J=8.4 Hz), 7.83 (1H, s), 7.33 (2H, bs), 7.32 (1H, d, J=8.4 Hz), 7.20-7.18 (1H, m), 7.14-7.09 (2H, m), 7.03-6.97 (3H, m)

$^{13}$C-NMR (DMSO-d6) δ [ppm]=155.8, 147.3, 147.2, 145.7, 138.4, 132.4, 132.2, 131.7, 131.2, 130.2, 130.1, 129.3, 128.6, 128.3, 127.4, 126.7, 125.1, 124.2, 124.0, 116.5

Example 23

Synthesis of 4-amino-3-[6-(3-chlorophenyl)pyridine-3-ylazo]naphthalene-1-sulfonic acid sodium salt

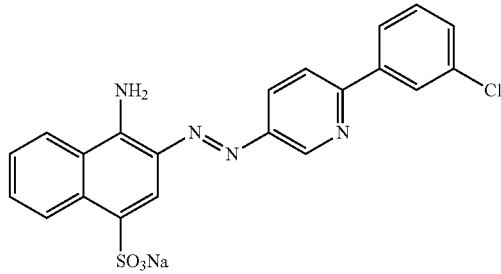

(i) 2-(3-Chlorophenyl)-5-nitropyridine

The title compound was synthesized in a manner analogous to Example 7 (i), except for replacing phenylboronic acid with 3-chlorophenylboronic acid.

(ii) 6-(3-Chlorophenyl)pyridine-3-ylamine

The title compound was synthesized in a manner analogous to Example 7 (ii), except for replacing 2-phenyl-5-nitropyridine with 2-(3-chlorophenyl)-5-nitropyridine obtained in (i).

(iii) 4-Amino-3-[6-(3-chlorophenyl)pyridine-3-ylazo]naphthalene-1-sulfonic acid sodium salt The title compound was synthesized in a manner analogous to Example 7 (iii), except for replacing 2-phenyl-5-aminopyridine with 6-(3-chlorophenyl)pyridine-3-ylamine obtained in (ii).

$^1$H-NMR (DMSO-d6) δ [ppm]=9.24 (1H, d, J=2.4 Hz), 8.76 (1H, d, J=8.4 Hz), 8.49 (1H, dd, J=8.4, 2.4 Hz), 8.47 (1H, d, J=6.9 Hz), 8.33 (1H, s), 8.24 (1H, d, J=2.1 Hz), 8.17 (1H, d, J=8.4 Hz), 8.17-8.14 (1H, m), 7.84 (2H, bs), 7.63-7.57 (1H, m), 7.55-7.47 (3H, m)

$^{13}$C-NMR (DMSO-d6) δ [ppm]=154.1, 147.7, 147.2, 146.3, 140.1, 133.8, 132.5, 132.1, 130.7, 129.4, 129.0, 128.6, 128.3, 127.7, 126.3, 125.2, 125.1, 124.2, 124.0, 121.1, 116.5

Example 24

Synthesis of 4-amino-3-[6-(4-chlorophenyl)pyridine-3-ylazo]naphthalene-1-sulfonic acid sodium salt

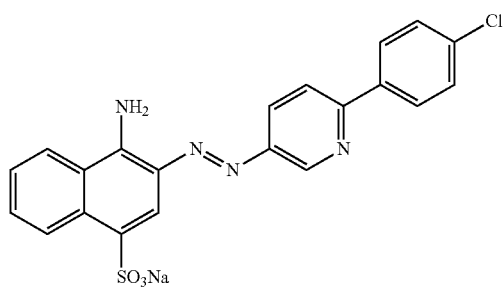

(i) 2-(4-Chlorophenyl)-5-nitropyridine

The title compound was synthesized in a manner analogous to Example 7 (i), except for replacing phenylboronic acid with 4-chlorophenylboronic acid.

(ii) 6-(4-Chlorophenyl)pyridine-3-ylamine

The title compound was synthesized in a manner analogous to Example 7 (ii), except for replacing 2-phenyl-5-nitropyridine with 2-(4-chlorophenyl)-5-nitropyridine obtained in (i).

(iii) 4-Amino-3-[6-(4-chlorophenyl)pyridine-3-ylazo]naphthalene-1-sulfonic acid sodium salt The title compound was synthesized in a manner analogous to Example 7 (iii), except for replacing 2-phenyl-5-aminopyridine with 6-(4-chlorophenyl)pyridine-3-ylamine obtained in (ii).

$^1$H-NMR (DMSO-d6) δ [ppm]=9.18 (1H, d, J=1.8 Hz), 8.70 (1H, d, J=8.1 Hz), 8.06 (1H, d, J=8.4 Hz), 8.45-8.40 (2H, m), 8.28 (1H, s), 8.16 (2H, d, J=8.4 Hz), 7.78 (2H, bs), 7.58-7.42 (4H, m)

$^{13}$C-NMR (DMSO-d6) δ [ppm]=154.6, 147.5, 147.4, 146.5, 136.9, 134.2, 132.4, 132.2, 129.3, 128.9, 128.7, 128.5, 128.3, 127.7, 125.2, 124.2, 124.1, 120.8, 116.4

Example 25

Synthesis of 4-amino-3-[6-(2-methoxyphenyl)pyridine-3-ylazo]naphthalene-1-sulfonic acid sodium salt

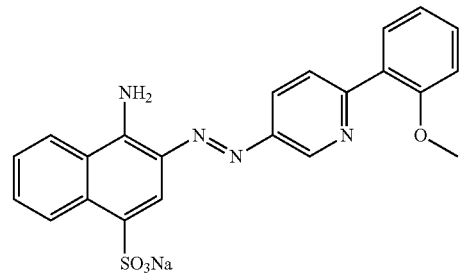

(i) 2-(2-Methoxyphenyl)-5-nitropyridine

The title compound was synthesized in a manner analogous to Example 7 (i), except for replacing phenylboronic acid with 2-methoxyphenylboronic acid.

(ii) 6-(2-Methoxyphenyl)pyridine-3-ylamine

The title compound was synthesized in a manner analogous to Example 7 (ii), except for replacing 2-phenyl-5-nitropyridine with 2-(2-methoxyphenyl)-5-nitropyridine obtained in (i).

(iii) 4-Amino-3-[6-(2-methoxyphenyl)pyridine-3-ylazo]naphthalene-1-sulfonic acid sodium salt The title compound was synthesized in a manner analogous to Example 7 (iii), except for replacing 2-phenyl-5-aminopyridine with 6-(2-methoxyphenyl)pyridine-3-ylamine obtained in (ii).

$^1$H-NMR (DMSO-d6) δ [ppm]=9.23 (1H, d, J=2.1 Hz), 8.76 (1H, dd, J=8.4, 2.1 Hz), 8.46 (1H, d, J=8.4 Hz), 8.40 (1H, dd, J=8.4, 1.8 Hz), 8.33 (1H, s), 8.03 (1H, d, J=8.4 Hz), 7.88 (1H, dd, J=7.8, 1.8 Hz), 7.76 (2H, bs), 7.63-7.58 (1H, m), 7.52-7.47 (1H, m), 7.46-7.40 (1H, m), 7.18 (1H, d, J=8.1 Hz), 7.12-7.07 (1H, m), 3.87 (3H, s)

$^{13}$C-NMR (DMSO-d6) δ [ppm]=157.0, 155.2, 146.9, 146.7, 145.8, 132.4, 132.0, 130.7, 130.5, 129.2, 128.4, 128.3, 127.7, 126.4, 125.1, 124.2, 123.9, 120.7, 116.5, 112.1, 55.7

Example 26

Synthesis of 4-amino-3-[6-(4-methoxyphenyl)pyridine-3-ylazo]naphthalene-1-sulfonic acid sodium salt

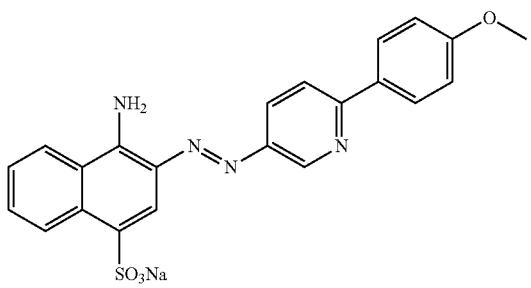

(i) 2-(4-Methoxyphenyl)-5-nitropyridine

The title compound was synthesized in a manner analogous to Example 7 (i), except for replacing phenylboronic acid with 4-methoxyphenylboronic acid.

(ii) 6-(4-Methoxyphenyl)pyridine-3-ylamine

The title compound was synthesized in a manner analogous to Example 7 (ii), except for replacing 2-phenyl-5-nitropyridine with 2-(4-methoxyphenyl)-5-nitropyridine obtained in (i).

(iii) 4-Amino-3-[6-(4-methoxyphenyl)pyridine-3-ylazo]naphthalene-1-sulfonic acid sodium salt The title compound was synthesized in a manner analogous to Example 7 (iii), except for replacing 2-phenyl-5-aminopyridine with 6-(4-methoxyphenyl)pyridine-3-ylamine obtained in (ii).

$^1$H-NMR (DMSO-d6) δ [ppm]=9.19 (1H, d, J=2.1 Hz), 8.75 (1H, dd, J=8.1, 0.9 Hz), 8.47-8.42 (2H, m), 8.32 (1H, s), 8.16 (2H, d, J=9.0 Hz), 8.04 (1H, d, J=8.7 Hz), 7.75 (2H, bs), 7.63-7.57 (1H, m), 7.52-7.47 (1H, m), 7.06 (2H, d, J=9.0 Hz), 3.82 (3H, s)

$^{13}$C-NMR (DMSO-d6) δ [ppm]=160.5, 155.8, 146.9, 146.8, 146.5, 132.4, 132.0, 130.6, 129.3, 128.4, 128.3, 128.2, 127.4, 125.1, 124.2, 123.9, 119.8, 116.3, 114.3, 55.3

Example 27

Synthesis of 4-amino-3-[6-(2-isopropoxyphenyl)pyridine-3-ylazo]naphthalene-1-sulfonic acid sodium salt

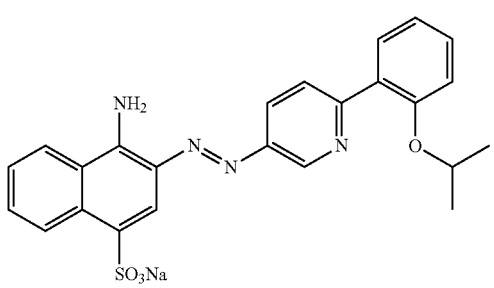

(i) 2-(2-Isopropoxyphenyl)-5-nitropyridine

The title compound was synthesized in a manner analogous to Example 7 (i), except for replacing phenylboronic acid with 2-isopropoxyphenylboronic acid.

(ii) 6-(2-Isopropoxyphenyl)pyridine-3-ylamine

The title compound was synthesized in a manner analogous to Example 7 (ii), except for replacing 2-phenyl-5-nitropyridine with 2-(2-isopropoxyphenyl)-5-nitropyridine obtained in (i).

(iii) 4-Amino-3-[6-(2-isopropoxyphenyl)pyridine-3-ylazo]naphthalene-1-sulfonic acid sodium salt The title compound was synthesized in a manner analogous to Example 7 (iii), except for replacing 2-phenyl-5-aminopyridine with 6-(2-isopropoxyphenyl)pyridine-3-ylamine obtained in (ii).

$^1$H-NMR (DMSO-d6) δ [ppm]=9.23 (1H, d, J=2.1 Hz), 8.77 (1H, d, J=8.4 Hz), 8.52-8.45 (2H, m), 8.36 (1H, s), 8.10 (1H, d, J=8.7 Hz), 7.90 (1H, dd, J=7.5, 1.2 Hz), 7.82 (2H, bs), 7.64-7.58 (1H, m), 7.52-7.48 (1H, m), 7.41-7.35 (1H, m), 7.14 (1H, d, J=8.4 Hz), 7.08-7.03 (1H, m), 4.72-4.65 (1H, m), 1.28 (6H, d, J=6.0 Hz)

$^{13}$C-NMR (DMSO-d6) δ [ppm]=155.4, 155.2, 147.2, 146.7, 146.5, 132.4, 132.1, 131.1, 130.4, 129.2, 128.5, 128.4, 128.3, 125.7, 125.2, 125.1, 124.2, 123.9, 120.6, 116.2, 114.5, 70.1, 21.9

Example 28

Synthesis of 4-amino-3-[6-(4-isopropoxyphenyl)pyridine-3-ylazo]naphthalene-1-sulfonic acid sodium salt

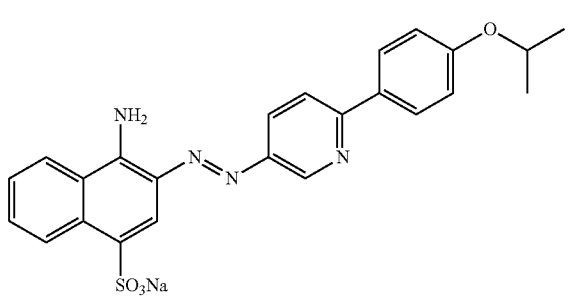

(i) 2-(4-Isopropoxyphenyl)-5-nitropyridine

The title compound was synthesized in a manner analogous to Example 7 (i), except for replacing phenylboronic acid with 4-isopropoxyphenylboronic acid.

(ii) 6-(4-Isopropoxyphenyl)pyridine-3-ylamine

The title compound was synthesized in a manner analogous to Example 7 (ii), except for replacing 2-phenyl-5-nitropyridine with 2-(4-isopropoxyphenyl)-5-nitropyridine obtained in (i).

(iii) 4-Amino-3-[6-(4-isopropoxyphenyl)pyridine-3-ylazo]naphthalene-1-sulfonic acid sodium salt The title compound was synthesized in a manner analogous to Example 7 (iii), except for replacing 2-phenyl-5-aminopyridine with 6-(4-isopropoxyphenyl)pyridine-3-ylamine obtained in (ii).

$^1$H-NMR (DMSO-d6) δ [ppm]=9.17 (1H, dd, J=2.4, 0.6 Hz), 8.77 (1H, dd, J=8.4, 1.2 Hz), 8.45 (1H, d, J=8.4 Hz), 8.41 (1H, dd, J=8.7, 2.4 Hz), 8.33 (1H, s), 8.12 (2H, d, J=9.0 Hz), 8.01 (1H, d, J=8.7 Hz), 7.74 (2H, bs), 7.62-7.57 (1H, m), 7.52-7.47 (1H, m), 7.02 (2H, d, J=9.0 Hz), 4.73-4.65 (1H, m), 1.29 (6H, d, J=5.7 Hz)

$^{13}$C-NMR (DMSO-d6) δ [ppm]=158.7, 155.8, 146.7, 146.6, 146.2, 132.5, 132.0, 130.2, 129.2, 128.3, 128.2, 127.4, 124.9, 124.2, 123.8, 119.6, 116.6, 115.7, 69.3, 21.8

Example 29

Synthesis of 4-amino-3-[6-(2-phenoxyphenyl)pyridine-3-ylazo]naphthalene-1-sulfonic acid sodium salt

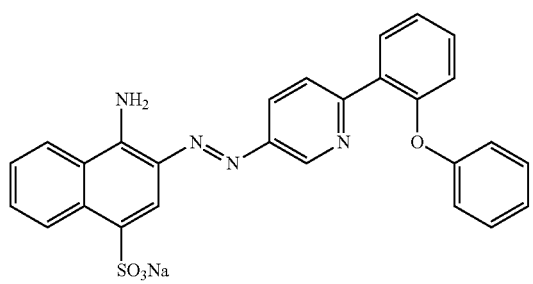

(i) 5-Nitro-2-(2-phenoxyphenyl)pyridine

The title compound was synthesized in a manner analogous to Example 8 (i), except for replacing 4-methylphenylboronic acid with 2-phenoxyphenylboronic acid.

(ii) 6-(2-Phenoxyphenyl)pyridine-3-ylamine

The title compound was synthesized in a manner analogous to Example 7 (ii), except for replacing 2-phenyl-5-nitropyridine with 5-nitro-2-(2-phenoxyphenyl)pyridine obtained in (i).

(iii) 4-Amino-3-[6-(2-phenoxyphenyl)pyridine-3-ylazo]naphthalene-1-sulfonic acid sodium salt The title compound was synthesized in a manner analogous to Example 7 (iii), except for replacing 2-phenyl-5-aminopyridine with 6-(2-phenoxyphenyl)pyridine-3-ylamine obtained in (ii).

$^1$H-NMR (DMSO-d6) δ [ppm]=9.23 (1H, d, J=2.1 Hz), 8.74 (1H, d, J=8.4 Hz), 8.45 (1H, d, J=8.4 Hz), 8.40 (1H, dd, J=8.7, 2.1 Hz), 8.30 (1H, s), 8.03 (1H, dd, J=7.5, 1.5 Hz), 7.97 (1H, d, J=8.7), 7.75 (2H, bs), 7.62-7.57 (1H, m), 7.51-7.44 (2H, m), 7.38-7.33 (3H, m), 7.10-6.98 (4H, m)

$^{13}$C-NMR (DMSO-d6) δ [ppm]=157.0, 154.3, 153.7, 147.5, 147.1, 146.5, 132.4, 132.2, 131.4, 131.1, 130.8, 130.2, 129.2, 128.6, 128.4, 126.6, 125.2, 124.7, 124.5, 124.2, 124.0, 123.2, 120.3, 117.9, 116.0

Example 30

Synthesis of 4-amino-3-(6-styrylpyridine-3-ylazo)naphthalenesulfonic acid sodium salt

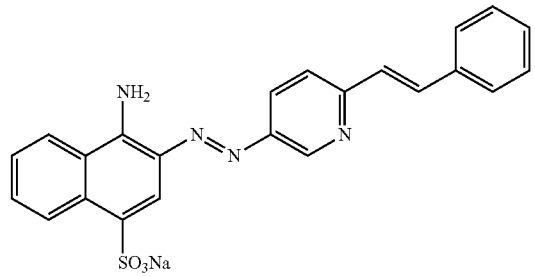

(i) 5-Nitro-2-styrylpyridine

The title compound was synthesized in a manner analogous to Example 7 (i), except for replacing phenylboronic acid with E-phenylethenylboronic acid.

(ii) 6-Styrylpyridine-3-ylamine

The title compound was synthesized in a manner analogous to Example 7 (ii), except for replacing 2-phenyl-5-nitropyridine with 5-nitro-2-styrylpyridine obtained in (i).

(iii) 4-Amino-3-(6-styrylpyridine-3-ylazo)naphthalenesulfonic acid sodium salt

The title compound was synthesized in a manner analogous to Example 7 (iii), except for replacing 2-phenyl-5-aminopyridine with 6-styrylpyridine-3-ylamine obtained in (ii).

$^1$H-NMR (DMSO-d6) δ [ppm]=9.15 (1H, d, J=1.8 Hz), 8.76 (1H, d, J=8.4 Hz), 8.46 (1H, d, J=8.4 Hz), 8.40 (1H, dd, J=8.4, 1.8 Hz), 8.23 (1H, s), 7.81-7.68 (2H, m), 7.76 (2H, bs), 7.63-7.58 (1H, m), 7.52-7.30 (7H, m)

$^{13}$C-NMR (DMSO-d6) δ [ppm]=155.2, 147.2, 146.9, 136.4, 132.9, 132.5, 132.0, 129.3, 128.9, 128.5, 128.4, 128.3, 127.6, 127.2, 126.8, 125.0, 124.2, 123.9, 123.1, 116.5

Example 31

Synthesis of 4-amino-3-(6-dibenzothiophene-4-ylpyridine-3-ylazo)naphthalene-1-sulfonic acid sodium salt

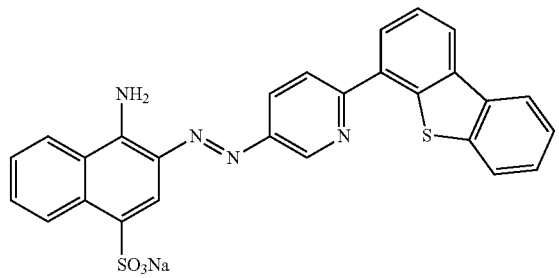

(i) 2-Dibenzothiophene-4-yl-5-nitropyridine

The title compound was synthesized in a manner analogous to Example 7 (i), except for replacing phenylboronic acid with 4-dibenzothiopheneboronic acid.

(ii) 6-Dibenzothiophene-4-ylpyridine-3-ylamine

The title compound was synthesized in a manner analogous to Example 7 (ii), except for replacing 2-phenyl-5-nitropyridine with 2-dibenzothiophene-4-yl-5-nitropyridine obtained in (i).

(iii) 4-Amino-3-(6-dibenzothiophene-4-ylpyridine-3-ylazo)naphthalene-1-sulfonic acid sodium salt 6-Dibenzothiophene-4-ylpyridine-3-ylamine (39.5 g, 143.0 mmol) obtained in (ii) was dissolved in tetrahydrofuran/water (2600 ml), added with 98% sulfuric acid (42.5 g) to form sulfate. With cooling on ice, an aqueous solution of sodium nitrite (13.3 g, 192.5 mmol) was added dropwise at 0-5° C., and the reaction was carried out for about 15 minutes. Amide sulfuric acid was added and the reaction was carried out for additional 5 minutes, resulting in diazo solution. 4-Amino-1-naphthalenesulfonic acid (31.6 g, 141.5 mmol) was suspended in water, and the pH of the suspension was adjusted to pH 8 to 9 with 10% aqueous sodium hydroxide. The mixture was cooled to 5-10° C., and added dropwise with the obtained diazo solution at 5-10° C., during which 10% aqueous sodium hydroxide was added dropwise to keep the pH at 7 to 9. After the completion of the addition, the reaction was carried out at 5-10° C. for 1 hour, then the temperature was raised to room temperature. Under reduced pressure tetrahydrofuran was distilled off and saturated sodium chloride solution was added. The precipitated crystals were filtered with suction, purified by column chromatography to give the title compound (29.0 g, 38.1%).

$^1$H-NMR (DMSO-d6) δ [ppm]=9.40 (1H, d, J=2.4 Hz), 8.77 (1H, d, J=8.1 Hz), 8.61 (1H, dd, J=8.7, 2.4 Hz), 8.51 (1H, J=7.8 Hz), 8.50 (1H, d, J=8.7 Hz), 8.44-8.39 (3H, m), 8.36 (1H, s), 8.10-8.07 (1H, m), 7.88 (2H, bs), 7.72-7.66 (1H, m), 7.65-7.60 (1H, m), 7.56-7.49 (3H, m)

$^{13}$C-NMR (DMSO-d6) δ [ppm]=154.7, 147.6, 147.2, 144.7, 141.6, 136.9, 136.5, 134.2, 132.5, 132.2, 132.1, 129.4, 128.7, 128.4, 127.9, 127.2, 125.6, 125.2, 125.1, 124.6, 124.3, 124.1, 123.1, 122.6, 121.9, 121.4, 116.1

Example 32

Synthesis of 4-amino-3-[6-(3-methoxyphenyl)pyridine-3-ylazo]naphthalene-1-sulfonic acid sodium salt

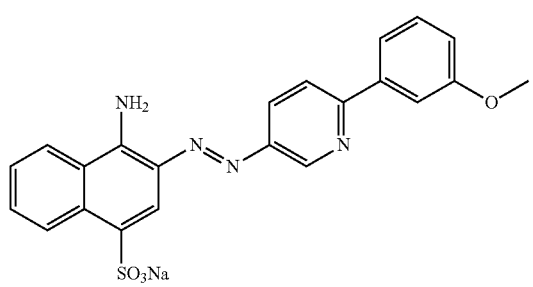

(i) 2-(3-Methoxyphenyl)-5-nitropyridine

The title compound was synthesized in a manner analogous to Example 8 (i), except for replacing 4-methylphenylboronic acid with 3-methoxyphenylboronic acid.

(ii) 6-(3-Methoxyphenyl)pyridine-3-ylamine

The title compound was synthesized in a manner analogous to Example 7 (ii), except for replacing 2-phenyl-5-nitropyridine with 2-(3-methoxyphenyl)-5-nitropyridine obtained in (i).

(iii) 4-Amino-3-[6-(3-methoxyphenyl)pyridine-3-ylazo]naphthalene-1-sulfonic acid sodium salt The title compound was synthesized in a manner analogous to Example 7 (iii), except for replacing 2-phenyl-5-aminopyridine with 6-(3-methoxyphenyl)pyridine-3-ylamine obtained in (ii).

$^1$H-NMR (DMSO-d6) δ [ppm]=9.23 (1H, d, J=2.4 Hz), 8.78 (1H, dd, J=8.4, 1.2 Hz), 8.47 (1H, d, J=8.1 Hz), 8.45 (1H, dd, J=8.7, 2.4 Hz), 8.35 (1H, s), 8.11 (1H, d, J=8.7 Hz), 7.76-7.74 (4H, m), 7.63-7.58 (1H, m), 7.53-7.47 (1H, m), 7.24 (1H, dd, J=8.1 Hz), 7.05-7.01 (1H, m), 3.86 (3H, s)

$^{13}$C-NMR (DMSO-d6) δ [ppm]=159.7, 155.6, 147.4, 146.9, 146.0, 139.5, 132.5, 132.1, 129.9, 129.3, 128.5, 128.3, 127.6, 125.0, 124.2, 123.9, 120.8, 119.0, 116.6, 115.2, 111.7, 55.2

Example 33

Synthesis of 4-amino-3-[6-(2,3-dimethylphenyl)pyridine-3-ylazo]naphthalene-1-sulfonic acid sodium salt

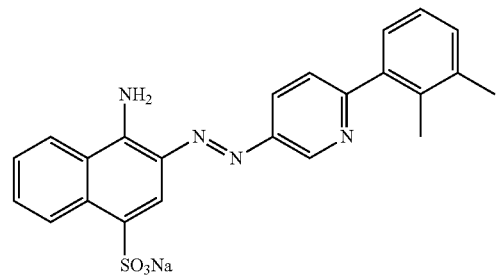

(i) 2-(2,3-Dimethylphenyl)-5-nitropyridine

The title compound was synthesized in a manner analogous to Example 8 (i), except for replacing 4-methylphenylboronic acid with 2,3-dimethylphenylboronic acid.

(ii) 6-(2,3-Dimethylphenyl)pyridine-3-ylamine

The title compound was synthesized in a manner analogous to Example 7 (ii), except for replacing 2-phenyl-5-nitropyridine with 2-(2,3-dimethylphenyl)-5-nitropyridine obtained in (i).

(iii) 4-Amino-3-[6-(2,3-dimethylphenyl)pyridine-3-ylazo]naphthalene-1-sulfonic acid sodium salt The title compound was synthesized in a manner analogous to Example 7 (iii), except for replacing 2-phenyl-5-aminopyridine with 6-(2,3-dimethylphenyl)pyridine-3-ylamine obtained in (ii).

$^1$H-NMR (DMSO-d6) δ [ppm]=9.23 (1H, d, J=2.1 Hz), 8.77 (1H, d, J=8.1 Hz), 8.48-8.43 (2H, m), 8.35 (1H, s), 7.79 (2H, bs), 7.63-7.57 (2H, m), 7.53-7.48 (1H, m), 7.28-7.16 (3H, m), 2.32 (3H, s), 2.23 (3H, s)

$^{13}$C-NMR (DMSO-d6) δ [ppm]=160.0, 147.0, 146.7, 145.3, 140.2, 137.1, 134.1, 132.4, 132.1, 129.8, 129.2, 128.5, 128.3, 127.5, 127.0, 125.3, 125.1, 124.8, 124.2, 123.9, 116.6, 20.2, 16.6

Example 34

Synthesis of 4-amino-3-[6-(2,5-dimethylphenyl)pyridine-3-ylazo]naphthalene-1-sulfonic acid sodium salt

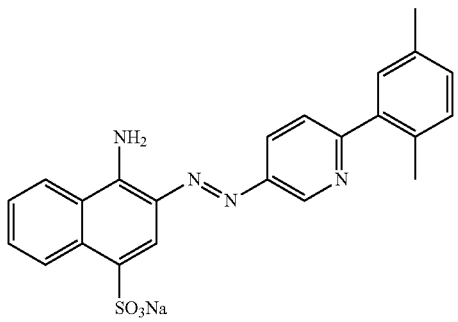

(i) 2-(2,5-Dimethylphenyl)-5-nitropyridine

The title compound was synthesized in a manner analogous to Example 8 (i), except for replacing 4-methylphenylboronic acid with 2,5-dimethylphenylboronic acid.

(ii) 6-(2,5-Dimethylphenyl)pyridine-3-ylamine

The title compound was synthesized in a manner analogous to Example 7 (ii), except for replacing 2-phenyl-5-nitropyridine with 2-(2,5-dimethylphenyl)-5-nitropyridine obtained in (i).

(iii) 4-Amino-3-[6-(2,5-dimethylphenyl)pyridine-3-ylazo]naphthalene-1-sulfonic acid sodium salt The title compound was synthesized in a manner analogous to Example 7 (iii), except for replacing 2-phenyl-5-aminopyridine with 6-(2,5-dimethylphenyl)pyridine-3-ylamine obtained in (ii).

$^1$H-NMR (DMSO-d6) δ [ppm]=9.22 (1H, d, J=2.1 Hz), 8.75 (1H, dd, J=8.4, 1.2 Hz), 8.46 (1H, d, J=8.4 Hz), 8.45 (1H, d, J=8.4 Hz), 8.32 (1H, s), 7.78 (2H, bs), 7.65 (1H, d, J=8.4 Hz), 7.63-7.58 (1H, m), 7.52-7.47 (1H, m), 7.31 (1H, s), 7.21 (1H, d, J=7.8 Hz), 7.14 (1H, dd, J=7.8, 1.2 Hz), 2.35 (3H, s), 2.33 (3H, s)

$^{13}$C-NMR (DMSO-d6) δ [ppm]=159.4, 147.1, 146.7, 145.5, 139.4, 134.9, 132.4, 132.4, 132.1, 130.8, 130.3, 129.2, 129.1, 128.5, 128.3, 127.1, 125.1, 124.5, 124.2, 123.9, 116.4, 20.6, 20.0

Example 35

Synthesis of 4-amino-3-[6-(3,5-dimethylphenyl)pyridine-3-ylazo]naphthalene-1-sulfonic acid sodium salt

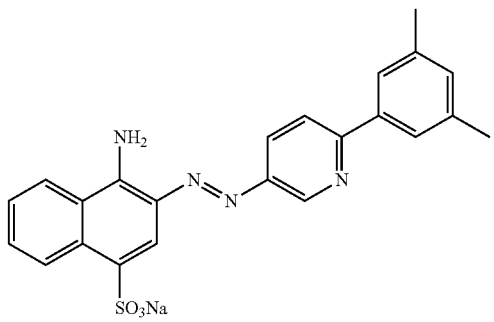

(i) 2-(3,5-Dimethylphenyl)-5-nitropyridine

The title compound was synthesized in a manner analogous to Example 7 (i), except for replacing phenylboronic acid with 3,5-dimethylphenylboronic acid.

(ii) 6-(3,5-Dimethylphenyl)pyridine-3-ylamine

The title compound was synthesized in a manner analogous to Example 7 (ii), except for replacing 2-phenyl-5-nitropyridine with 2-(3,5-dimethylphenyl)-5-nitropyridine obtained in (i).

(iii) 4-Amino-3-[6-(3,5-dimethylphenyl)pyridine-3-ylazo]naphthalene-1-sulfonic acid sodium salt The title compound was synthesized in a manner analogous to Example 7 (iii), except for replacing 2-phenyl-5-aminopyridine with 6-(3,5-dimethylphenyl)pyridine-3-ylamine obtained in (ii).

$^1$H-NMR (DMSO-d6) δ [ppm]=9.21 (1H, d, J=2.4 Hz), 8.76 (1H, d, J=7.8 Hz), 8.47-8.44 (2H, m), 8.33 (1H, s), 8.07 (1H, d, J=8.7), 7.81 (4H, s), 7.63-7.58 (1H, m), 7.53-7.48 (1H, m), 7.09 (1H, s), 2.37 (6H, s)

$^{13}$C-NMR (DMSO-d6) δ [ppm]=156.1, 147.3, 146.9, 146.4, 138.0, 137.9, 132.5, 132.1, 130.8, 129.3, 128.5, 128.3, 127.2, 125.1, 124.5, 124.2, 123.9, 120.6, 116.6, 21.1

Example 36

Synthesis of 4-amino-3-(6-oxazole-2-ylpyridine-3-ylazo)naphthalene-1-sulfonic acid sodium salt

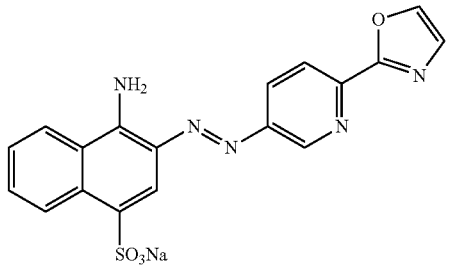

(i) 5-Nitro-2-oxazole-2-ylpyridine

The title compound was synthesized in a manner analogous to Example 7 (i), except for replacing phenylboronic acid with oxazole-2-boronic acid.

(ii) 6-Oxazole-2-ylpyridine-3-ylamine

The title compound was synthesized in a manner analogous to Example 7 (ii), except for replacing 2-phenyl-5-nitropyridine with 5-nitro-2-oxazole-2-ylpyridine obtained in (i).

(iii) 4-Amino-3-(6-oxazole-2-ylpyridine-3-ylazo)naphthalene-1-sulfonic acid sodium salt The title compound was synthesized in a manner analogous to Example 7 (iii), except for replacing 2-phenyl-5-aminopyridine with 6-oxazole-2-ylpyridine-3-ylamine obtained in (ii).

$^1$H-NMR (DMSO-d6) δ [ppm]=8.71 (1H, s), 8.69 (1H, s), 8.5 (1H, s), 8.40 (1H, d, J=8.1 Hz), 8.27 (1H, s), 8.01 (2H, d, J=8.4 Hz), 7.90 (2H, d, J=8.4 Hz), 7.69 (2H, bs), 7.51-7.56 (1H, m), 7.41-7.46 (1H, m)

$^{13}$C-NMR (DMSO-d6) δ [ppm]=152.9, 152.3, 146.0, 138.8, 135.8, 132.3, 131.7, 131.5, 128.8, 128.2, 126.0, 124.9, 124.2, 123.8, 122.8, 117.5

Example 37

Synthesis of 4-amino-3-[6-(3-trifluoromethylphenyl)pyridine-3-ylazo]naphthalene-1-sulfonic acid sodium salt

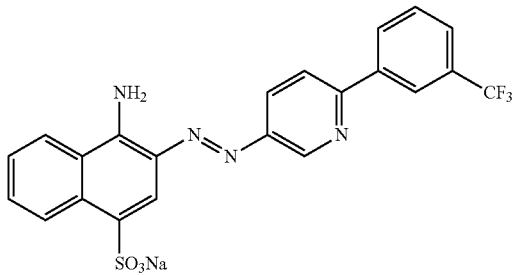

(i) 5-Nitro-2-(3-trifluoromethylphenyl)pyridine

The title compound was synthesized in a manner analogous to Example 8 (i), except for replacing 4-methylphenylboronic acid with 3-trifluoromethylphenylboronic acid.

(ii) 6-(3-Trifluoromethylphenyl)pyridine-3-ylamine

The title compound was synthesized in a manner analogous to Example 7 (ii), except for replacing 2-phenyl-5-nitropyridine with 5-nitro-2-(3-trifluoromethylphenyl)pyridine obtained in (i).

(iii) 4-Amino-3-[6-(3-trifluoromethylphenyl)pyridine-3-ylazo]naphthalene-1-sulfonic acid sodium salt The title compound was synthesized in a manner analogous to Example 7 (iii), except for replacing 2-phenyl-5-aminopyridine with 6-(3-trifluoromethylphenyl)pyridine-3-ylamine obtained in (ii).

$^1$H-NMR (DMSO-d6) δ [ppm]=9.27 (1H, d, J=2.4 Hz), 8.77 (1H, d, J=7.2 Hz), 8.53-8.47 (4H, m), 8.35 (1H, s), 7.87 (2H, bs), 7.81 (1H, d, J=7.8 Hz), 7.75 (1H, dd, J=7.8 Hz), 7.64-7.58 (1H, m), 7.53-7.48 (1H, m)

$^{13}$C-NMR (DMSO-d6) δ [ppm]=153.9, 147.8, 147.3, 146.4, 139.0, 132.5, 132.2, 130.5, 130.1, 130.0, 129.6, 129.4, 128.6, 128.3, 127.8, 126.1, 125.7, 125.1, 124.2, 124.0, 123.0, 122.9, 122.5, 121.2, 116.6, 62.0

Example 38

Synthesis of 4-amino-3-(6-naphthalene-1-ylpyridine-3-ylazo)naphthalene-1-sulfonic acid sodium salt

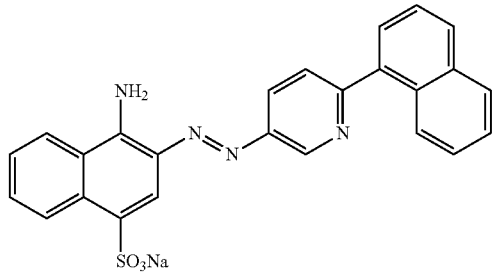

(i) 2-Naphthalene-1-yl-5-nitropyridine

The title compound was synthesized in a manner analogous to Example 7 (i), except for replacing phenylboronic acid with 1-naphthaleneboronic acid.

(ii) 6-Naphthalene-1-ylpyridine-3-ylamine

The title compound was synthesized in a manner analogous to Example 7 (ii), except for replacing 2-phenyl-5-nitropyridine with 2-naphthalene-1-yl-5-nitropyridine obtained in (i).

(iii) 4-Amino-3-(6-naphthalene-1-ylpyridine-3-ylazo)naphthalene-1-sulfonic acid sodium salt The title compound was synthesized in a manner analogous to Example 7 (iii), except for replacing 2-phenyl-5-aminopyridine with 6-naphthalene-1-ylpyridine-3-ylamine obtained in (ii).

$^1$H-NMR (DMSO-d6) δ [ppm]=9.34 (1H, d, J=2.1 Hz), 8.80 (1H, d, J=8.1 Hz), 8.54 (1H, dd, J=8.4, 2.1 Hz), 8.49 (1H, d, J=8.1 Hz), 8.39 (1H, s), 8.24-8.21 (1H, m), 8.04-8.02 (2H, m), 7.85 (2H, bs), 7.81 (1H, d, J=8.4 Hz), 7.72 (1H, d, J=6.3 Hz), 7.66-7.49 (5H, m)

$^{13}$C-NMR (DMSO-d6) δ [ppm]=158.4, 147.0, 145.5, 137.5, 133.5, 132.4, 132.1, 130.5, 129.3, 128.9, 128.5, 128.3, 127.7, 127.5, 126.5, 126.0, 125.6, 125.4, 125.3, 125.0, 124.2, 123.9, 116.7

Example 39

Synthesis of 4-amino-3-(6-dibenzofuran-4-ylpyridine-3-ylazo)naphthalene-1-sulfonic acid sodium salt

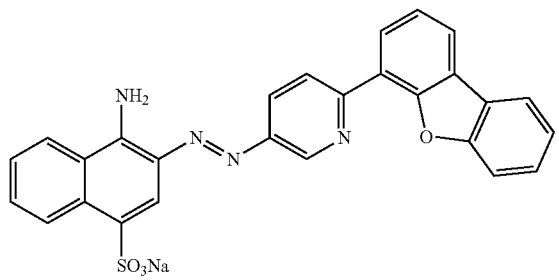

(i) 2-Dibenzofuran-4-yl-5-nitropyridine

The title compound was synthesized in a manner analogous to Example 8 (i), except for replacing 4-methylphenylboronic acid with dibenzofuran-4-ylboronic acid.

(ii) 6-Dibenzofuran-4-ylpyridine-3-ylamine

The title compound was synthesized in a manner analogous to Example 7 (ii), except for replacing 2-phenyl-5-nitropyridine with 2-dibenzofuran-4-yl-5-nitropyridine obtained in (i).

(iii) 4-Amino-3-(6-dibenzofuran-4-ylpyridine-3-ylazo)naphthalene-1-sulfonic acid sodium salt The title compound was synthesized in a manner analogous to Example 7 (iii), except for replacing 2-phenyl-5-aminopyridine with 6-dibenzofuran-4-ylpyridine-3-ylamine obtained in (ii).

$^1$H-NMR (DMSO-d6) δ [ppm]=9.31 (1H, s), 8.72 (1H, d, J=8.4 Hz), 8.58-8.51 (2H, m), 8.43 (1H, d, J=8.1 Hz), 8.34 (1H, d, J=7.5 Hz), 8.29 (1H, s), 8.21 (1H, d, J=7.8 Hz), 8.17 (1H, d, J=8.1 Hz), 7.80-7.77 (3H, m), 7.59-7.38 (5H, m)

$^{13}$C-NMR (DMSO-d6) δ [ppm]=155.4, 153.0, 152.4, 147.4, 146.1, 132.6, 132.2, 129.4, 128.6, 128.4, 127.9, 127.8, 127.1, 125.1, 124.8, 124.2, 124.1, 124.0, 123.6, 123.5, 123.2, 123.1, 122.2, 121.3, 116.2, 111.9

Example 40

Synthesis of methyl 4-{4-[5-(1-amino-4-sulfonaphthalene-2-ylazo)pyridine-2-yl]phenyl}-4-oxobutyrate sodium salt

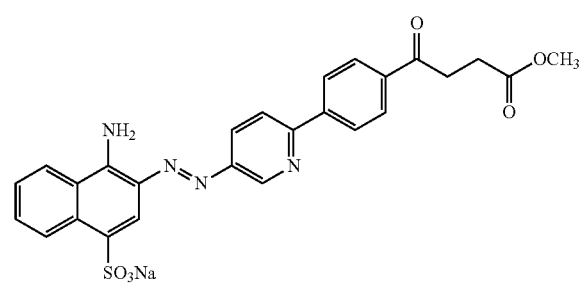

(i) Methyl 4-(4-bromophenyl)-4-oxobutyrate

To a solution of 4-(4-bromophenyl)-4-oxobutylic acid (5.0 g, 19.4 mmol) in methanol (40 ml) trimethyl orthoformate (4 ml) and 98% sulfuric acid (0.5 g) was added and refluxed with heating. After the completion of the reaction and the concentration under reduced pressure, the products were crystallized with addition of water. The resulting crystals were filtered with suction to give the title compound (4.13 g, 97.9%).

(ii) Methyl 4-oxo-4-[4-(4,4,5,5-tetramethyl-[1,3,2] dioxaborolane-2-yl)phenyl]butyrate To a solution of methyl 4-(4-bromophenyl)-4-oxobutyrate (0.54 g, 2.0 mmol) obtained in (i) and [1,1'-bis(diphenylphosphino)ferrocene]palladium(II) dichloride (0.05 g, 0.06 mmol) in dimethylsulfoxide, bis(pinacolato)diborane (0.51 g, 2.0 mmol) and potassium acetate (0.6 g, 6.0 mmol) were added, and reacted under nitrogen at 80° C. for 1 hour. After cooling, water was added and the mixture was extracted with ethyl acetate. The organic layer was washed with aqueous sodium chloride, concentrated under reduced pressure, and purified by column chromatography to give the title compound (0.67 g, 105.3%).

(iii) Methyl 4-[4-(5-nitropyridine-2-yl)phenyl]-4-oxobutyrate

To a solution of 2-chloro-5-nitropyridine (0.30 g, 1.9 mmol) and methyl 4-oxo-4-[4-(4,4,5,5-tetramethyl-[1,3,2]dioxaborolane-2-yl)phenyl]butyrate (0.60 g, 1.9 mmol) obtained in (ii) in 1,2-dimethoxyethan (5 ml), [1,1'-bis(diphenylphosphino)ferrocene]palladium(II) dichloride (0.02 g, 0.02 mmol) and potassium carbonate (0.52 g, 3.8 mmol) were added. The reaction was carried out under nitrogen atmosphere at 80° C. for 4 hours. After cooling, the mixture was extracted with ethyl acetate, the organic layer was concentrated and purified by column chromatography to give the title compound (0.58 g, 97.1%).

(iv) Methyl 4-[4-(5-aminopyridine-2-yl)phenyl]-4-oxobutyrate

The title compound was synthesized in a manner analogous to Example 7 (ii), except for replacing 2-phenyl-5-nitropyridine with methyl 4-[4-(5-nitropyridine-2-yl)phenyl]-4-oxobutyrate obtained in (iii).

(v) Methyl 4-{4-[5-(1-amino-4-sulfonaphthalene-2-ylazo)pyridine-2-yl]phenyl}-4-oxobutyrate sodium salt The title compound was synthesized in a manner analogous to Example 7 (iii), except for replacing 2-phenyl-5-aminopyridine with methyl 4-[4-(5-aminopyridine-2-yl)phenyl]-4-oxobutyrate obtained in (iv).

$^1$H-NMR (DMSO-d6) δ [ppm]=9.27 (1H, d, J=2.1 Hz), 8.77 (1H, d, J=8.1 Hz), 8.52-8.46 (2H, m), 8.34 (1H, s), 8.33 (2H, d, J=8.1 Hz), 8.20 (1H, d, J=8.7 Hz), 8.09 (2H, d, J=8.1 Hz), 7.87 (2H, bs), 7.64-7.59 (1H, m), 7.53-7.48 (1H, m), 3.60 (3H, s), 3.34 (2H, t, J=6.3 Hz), 2.67 (2H, t, J=6.3 Hz)

$^{13}$C-NMR (DMSO-d6) δ [ppm]=198.0, 172.9, 154.4, 147.8, 147.3, 146.4, 142.2, 136.4, 132.5, 132.2, 129.4, 128.7, 128.5, 128.3, 127.7, 126.9, 125.2, 124.2, 124.0, 121.5, 116.6, 51.4, 33.2, 27.6

Example 41

Synthesis of 4-amino-3-(6-benzo[b]thiophene-3-ylpyridine-3-ylazo)naphthalene-1-sulfonic acid sodium salt

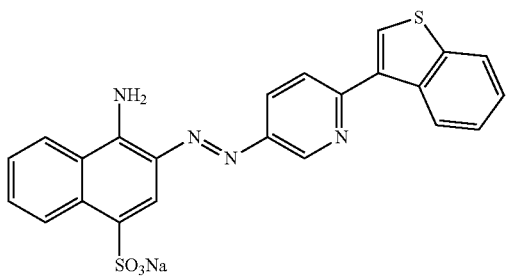

(i) 2-Benzo[b]thiophene-3-yl-5-nitropyridine

The title compound was synthesized in a manner analogous to Example 7 (i), except for replacing phenylboronic acid with benzo[b]thiophene-3-ylboronic acid.

(ii) 6-Benzo[b]thiophene-3-ylpyridine-3-ylamine

The title compound was synthesized in a manner analogous to Example 7 (ii), except for replacing 2-phenyl-5-nitropyridine with 2-benzo[b]thiophene-3-yl-5-nitropyridine obtained in (i).

(iii) 4-Amino-3-(6-benzo[b]thiophene-3-ylpyridine-3-ylazo)naphthalene-1-sulfonic acid sodium salt The title compound was synthesized in a manner analogous to Example 7 (iii), except for replacing 2-phenyl-5-aminopyridine with 6-benzo[b]thiophene-3-ylpyridine-3-ylamine obtained in (ii).

$^1$H-NMR (DMSO-d6) δ [ppm]=9.30 (1H, d, J=2.1 Hz), 8.87 (1H, d, J=7.8 Hz), 8.78 (1H, d, J=8.1 Hz), 8.53-8.46 (3H, m), 8.36 (1H, s), 8.08 (2H, m), 7.80 (2H, bs), 7.64-7.59 (1H, m), 7.54-7.43 (3H, m)

$^{13}$C-NMR (DMSO-d6) δ [ppm]=154.0, 147.0, 146.8, 145.8, 140.2, 136.9, 134.9, 132.5, 132.1, 129.3, 128.5, 128.4, 128.3, 127.5, 125.0, 124.8, 124.2, 123.9, 122.9, 122.8, 116.5

Example 42

Synthesis of 4-amino-3-(6-biphenyl-3-ylpyridine-3-ylazo)naphthalene-1-sulfonic acid sodium salt

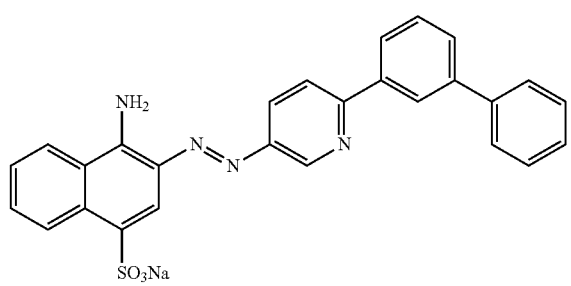

(i) 2-Biphenyl-3-yl-5-nitropyridine

The title compound was synthesized in a manner analogous to Example 8 (i), except for replacing 4-methylphenylboronic acid with 3-biphenylboronic acid.

(ii) 6-Biphenyl-3-ylpyridine-3-ylamine

The title compound was synthesized in a manner analogous to Example 7 (ii), except for replacing 2-phenyl-5-nitropyridine with 2-biphenyl-3-yl-5-nitropyridine obtained in (i).

(iii) 4-Amino-3-(6-biphenyl-3-ylpyridine-3-ylazo)naphthalene-1-sulfonic acid sodium salt The title compound was synthesized in a manner analogous to Example 12 (iii), except for replacing 6-biphenyl-2-ylpyridine-3-ylamine with 6-biphenyl-3-ylpyridine-3-ylamine obtained in (ii).

$^1$H-NMR (DMSO-d6) δ [ppm]=9.28 (1H, d, J=2.1 Hz), 8.78 (1H, d, J=8.4 Hz), 8.52-8.46 (3H, m), 8.37 (1H, s), 8.25 (1H, d, J=8.7 Hz), 8.19 (1H, d, J=7.5 Hz), 7.84 (2H, bs), 7.79-7.74 (3H, m), 7.64-7.59 (2H, m), 7.53-7.48 (3H, m), 7.42-7.38 (1H, m)

$^{13}$C-NMR (DMSO-d6) δ [ppm]=155.8, 147.5, 147.1, 146.3, 140.8, 140.0, 138.8, 132.4, 132.1, 129.6, 129.3, 129.0, 128.6, 128.3, 127.7, 127.6, 126.9, 125.8, 125.1, 125.0, 124.2, 124.0, 121.0, 116.6

Example 43

Synthesis of 4-amino-3-(6-dibenzothiophene-4-ylpyridine-3-ylazo)naphthalene-1-sulfonic acid potassium salt

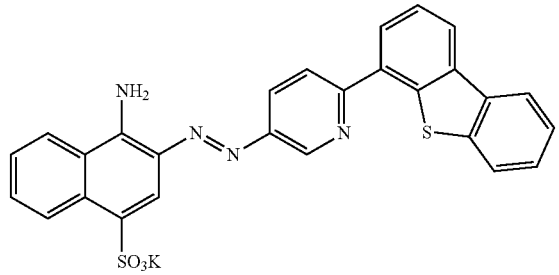

4-Amino-3-(6-dibenzothiophene-4-ylpyridine-3-ylazo)naphthalene-1-sulfonic acid potassium salt In Example 31 (iii), the title compound was obtained by neutralizing with potassium carbonate in place of sodium hydroxide.

$^1$H-NMR (DMSO-d6) δ [ppm]=9.41 (1H, d, J=2.4 Hz), 8.81 (1H, d, J=7.8 Hz), 8.59 (1H, dd, J=8.7, 2.4 Hz), 8.51 (1H, d, J=8.7 Hz), 8.49 (1H, d, J=7.2 Hz), 8.43-8.37 (4H, m), 8.10-8.07 (1H, m), 7.89 (2H, bs), 7.70-7.63 (2H, m), 7.60-7.47 (3H, m)

$^{13}$C-NMR (DMSO-d6) δ [ppm]=154.6, 147.4, 147.1, 144.5, 141.6, 136.8, 136.5, 134.1, 132.6, 132.2, 132.0, 129.4, 128.6, 128.4, 127.9, 127.1, 125.6, 125.1, 125.0, 124.5, 124.2, 124.0, 123.0, 122.5, 121.8, 121.4, 116.4

Example 44

Synthesis of 4-amino-3-[6-(3-cyanophenyl)pyridine-3-ylazo]naphthalene-1-sulfonic acid sodium salt

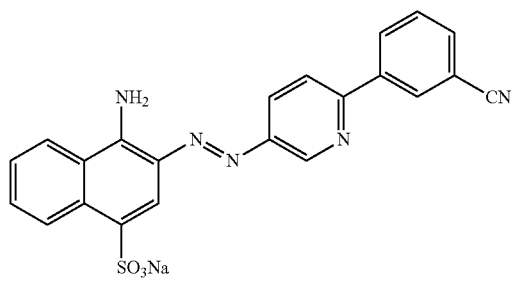

(i) 3-(5-Nitropyridine-2-yl)benzonitrile

The title compound was synthesized in a manner analogous to Example 8 (i), except for replacing 4-methylphenylboronic acid with 3-cyanophenylboronic acid.

(ii) 3-(5-Aminopyridine-2-yl)benzonitrile

The title compound was synthesized in a manner analogous to Example 7 (ii), except for replacing 2-phenyl-5-nitropyridine with 3-(5-nitropyridine-2-yl)benzonitrile obtained in (i).

(iii) 4-Amino-3-[6-(3-cyanophenyl)pyridine-3-ylazo]naphthalene-1-sulfonic acid sodium salt The title compound was synthesized in a manner analogous to Example 7 (iii), except for replacing 2-phenyl-5-aminopyridine with 3-(5-aminopyridine-2-yl)benzonitrile obtained in (ii).

$^1$H-NMR (DMSO-d6) δ [ppm]=9.26 (1H, d, J=2.1 Hz), 8.76 (1H, dd, J=7.5, 0.9 Hz), 8.61 (1H, m), 8.53-8.46 (3H, m), 8.34 (1H, s), 8.23 (1H, d, J=8.7 Hz), 7.92-7.87 (3H, m), 7.72 (1H, m), 7.61 (1H, m), 7.50 (1H, m)

$^{13}$C-NMR (DMSO-d6) δ [ppm]=153.5, 147.9, 147.4, 146.4, 139.2, 132.7, 132.5, 132.2, 131.3, 130.2, 130.1, 129.4, 128.7, 128.3, 127.8, 125.2, 124.2, 124.0, 121.3, 118.8, 116.5, 112.1

Example 45

Synthesis of 4-amino-3-[6-(4-cyanophenyl)pyridine-3-ylazo]naphthalene-1-sulfonic acid sodium salt

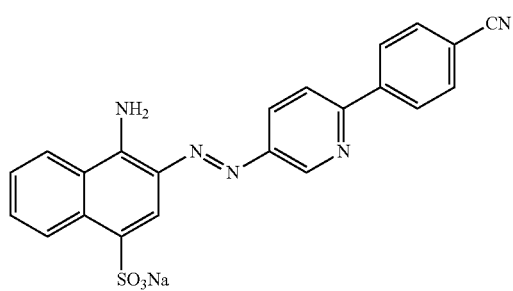

(i) 4-(5-Nitropyridine-2-yl)benzonitrile

The title compound was synthesized in a manner analogous to Example 8 (i), except for replacing 4-methylphenylboronic acid with 4-cyanophenylboronic acid.

(ii) 4-(5-Aminopyridine-2-yl)benzonitrile

The title compound was synthesized in a manner analogous to Example 7 (ii), except for replacing 2-phenyl-5-nitropyridine with 4-(5-nitropyridine-2-yl)benzonitrile obtained in (i).

(iii) 4-Amino-3-[6-(4-cyanophenyl)pyridine-3-ylazo]naphthalene-1-sulfonic acid sodium salt The title compound was synthesized in a manner analogous to Example 7 (iii), except for replacing 2-phenyl-5-aminopyridine with 4-(5-aminopyridine-2-yl)benzonitrile obtained in (ii).

$^1$H-NMR (DMSO-d6) δ [ppm]=9.27 (1H, dd, J=7.5, 0.9 Hz), 8.76 (1H, dd, J=7.5, 0.9 Hz), 8.52-8.46 (2H, m), 8.38-8.33 (3H, m), 8.21 (1H, d, J=8.4 Hz), 7.95 (2H, d, J=8.7 Hz), 7.89 (2H, bs), 7.64-7.59 (1H, m), 7.52-7.47 (1H, m)

$^{13}$C-NMR (DMSO-d6) δ [ppm]=153.6, 147.9, 147.5, 146.4, 142.2, 132.8, 132.5, 132.2, 129.4, 128.7, 128.3, 127.9, 127.3, 125.2, 124.2, 124.0, 121.7, 118.9, 116.5, 111.5

Example 46

Synthesis of 4-amino-3-[6-(3,5-bistrifluoromethylphenyl)pyridine-3-ylazo]naphthalenesulfonic acid sodium salt

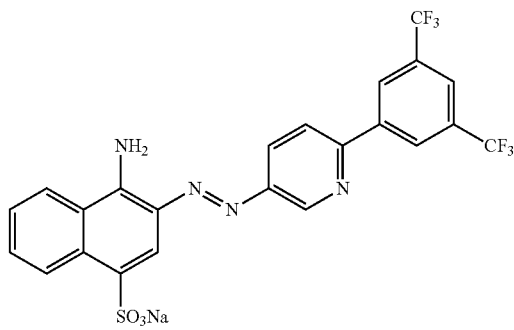

(i) 2-(3,5-Bistrifluoromethylphenyl)-5-nitropyridine

The title compound was synthesized in a manner analogous to Example 8 (i), except for replacing 4-methylphenylboronic acid with 3,5-bistrifluoromethylphenylboronic acid.

(ii) 6-(3,5-Bistrifluoromethylphenyl)pyridine-3-ylamine

The title compound was synthesized in a manner analogous to Example 7 (ii), except for replacing 2-phenyl-5-nitropyridine with 2-(3,5-bistrifluoromethylphenyl)-5-nitropyridine obtained in (i).

(iii) 4-Amino-3-[6-(3,5-bistrifluoromethylphenyl)pyridine-3-ylazo]naphthalenesulfonic acid sodium salt The title compound was synthesized in a manner analogous to Example 7 (iii), except for replacing 2-phenyl-5-aminopyridine with 6-(3,5-bistrifluoromethylphenyl)pyridine-3-ylamine obtained in (ii).

$^1$H-NMR (DMSO-d6) δ [ppm]=9.29 (1H, d, J=1.5 Hz), 8.83 (2H, bs), 8.76 (1H, d, J=7.8 Hz), 8.55-8.33 (4H, m), 8.16 (1H, bs), 7.92 (2H, bs), 7.66-7.48 (2H, m)

$^{13}$C-NMR (DMSO-d6) δ [ppm]=152.0, 148.2, 147.5, 146.5, 140.5, 132.6, 132.3, 131.6, 131.2, 130.8, 130.3, 129.5, 128.8, 128.4, 127.9, 127.0, 125.2, 124.2, 124.1, 121.9, 121.6, 116.6, 115.4

Example 47

Synthesis of 4-amino-3-[6-(4-benzoylphenyl)pyridine-3-ylazo]naphthalene-1-sulfonic acid sodium salt

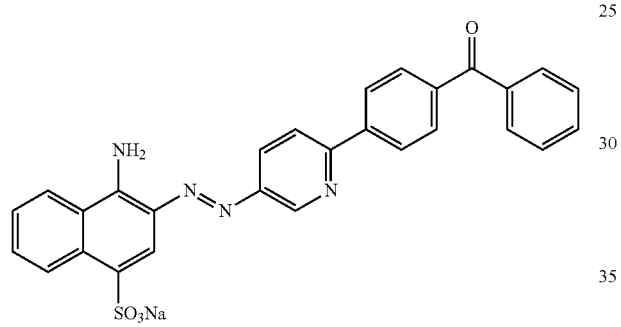

(i) [4-(5-Nitropyridine-2-yl)phenyl]phenylmethanone

The title compound was synthesized in a manner analogous to Example 7 (i), except for replacing phenylboronic acid with 4-benzoylphenylboronic acid.

(ii) [4-(5-Aminopyridine-2-yl)phenyl]phenylmethanone

The title compound was synthesized in a manner analogous to Example 7 (ii), except for replacing 2-phenyl-5-nitropyridine with [4-(5-nitropyridine-2-yl)phenyl]phenylmethanone obtained in (i).

(iii) 4-Amino-3-[6-(4-benzoylphenyl)pyridine-3-ylazo]naphthalene-1-sulfonic acid sodium salt The title compound was synthesized in a manner analogous to Example 7 (iii), except for replacing 2-phenyl-5-aminopyridine with [4-(5-aminopyridine-2-yl)phenyl]phenylmethanone obtained in (ii).

$^1$H-NMR (DMSO-d6) δ [ppm]=9.28 (1H, d, J=1.2 Hz), 8.76 (1H, dd, J=8.3, 1.2 Hz), 8.52 (1H, dd, J=8.7, 2.4 Hz), 8.47 (1H, d, J=8.1 Hz), 8.39-8.33 (3H, m), 8.23 (1H, d, J=8.3 Hz), 7.89-7.77 (6H, m), 7.70-7.50 (5H, m)

$^{13}$C-NMR (DMSO-d6) δ [ppm]=195.4, 154.5, 147.8, 147.3, 146.4, 141.8, 137.2, 137.1, 132.8, 132.6, 132.2, 130.3, 129.6, 129.4, 128.7, 128.4, 128.4, 127.8, 126.8, 125.1, 124.2, 124.0, 121.5, 116.5

Example 48

Synthesis of 4-amino-3-[6-(2-propoxyphenyl)pyridine-3-ylazo]naphthalene-1-sulfonic acid sodium salt

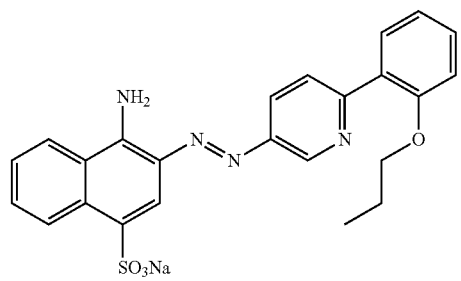

(i) 5-Nitro-2-(2-propoxyphenyl)pyridine

The title compound was synthesized in a manner analogous to Example 7 (i), except for replacing phenylboronic acid with 2-propoxyphenylboronic acid.

(ii) 6-(2-Propoxyphenyl)pyridine-3-ylamine

The title compound was synthesized in a manner analogous to Example 7 (ii), except for replacing 2-phenyl-5-nitropyridine with 5-nitro-2-(2-propoxyphenyl)pyridine obtained in (i).

(iii) 4-Amino-3-[6-(2-propoxyphenyl)pyridine-3-ylazo]naphthalene-1-sulfonic acid sodium salt The title compound was synthesized in a manner analogous to Example 7 (iii), except for replacing 2-phenyl-5-aminopyridine with 6-(2-propoxyphenyl)pyridine-3-ylamine obtained in (ii).

$^1$H-NMR δ [ppm]=9.23 (1H, dd, J=2.4, 0.6 Hz), 8.76 (1H, dd, J=8.4, 0.9 Hz), 8.43-8.48 (2H, m), 8.34 (1H, s), 8.13 (1H, d, J=8.7 Hz), 7.92 (1H, dd, J=7.5, 1.5 Hz), 7.76 (2H, bs), 7.368-7.631 (3H, m), 7.04-7.16 (2H, m), 4.04 (2H, t, J=6.3 Hz), 1.73-1.797 (2H, m), 1.04 (3H, t, J=6.6 Hz)

$^{13}$C-NMR δ [ppm]=147.0, 146.7, 146.4, 132.4, 132.1, 130.8, 130.5, 129.3, 128.4, 128.3, 127.7, 125.8, 125.1, 124.2, 123.9, 120.6, 116.3, 112.9, 69.6, 22.1, 10.8

Example 49

Synthesis of 4-amino-3-[6-(4-fluoro-2-methylphenyl)pyridine-3-ylazo]naphthalene-1-sulfonic acid sodium salt

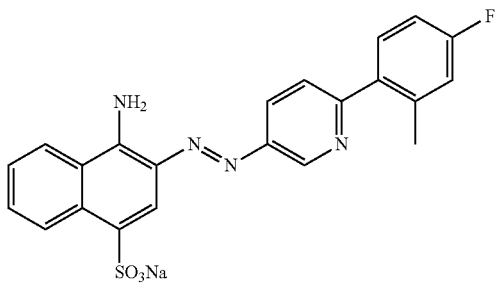

(i) 2-(4-Fluoro-2-methylphenyl)-5-nitropyridine

The title compound was synthesized in a manner analogous to Example 8 (i), except for replacing 4-methylphenylboronic acid with 4-fluoro-2-methylphenylboronic acid.

(ii) 6-(4-Fluoro-2-methylphenyl)pyridine-3-ylamine

The title compound was synthesized in a manner analogous to Example 7 (ii), except for replacing 2-phenyl-5-nitropyridine with 2-(4-fluoro-2-methylphenyl)-5-nitropyridine obtained in (i).

(iii) 4-Amino-3-[6-(4-fluoro-2-methylphenyl)pyridine-3-ylazo]naphthalene-1-sulfonic acid sodium salt The title compound was synthesized in a manner analogous to Example 12 (iii), except for replacing 6-biphenyl-2-ylpyridine-3-ylamine with 6-(4-fluoro-2-methylphenyl)pyridine-3-ylamine obtained in (ii).

$^1$H-NMR δ [ppm]=9.22 (1H, d, J=2.4 Hz), 8.76 (1H, d, J=8.1), 8.49-8.44 (2H, m), 8.34 (1H, s), 7.82 (2H, bs), 7.67-7.47 (4H, m), 7.21-7.11 (2H, m), 2.41 (3H, s)

$^{13}$C-NMR (DMSO-d6) δ [ppm]=163.5, 160.3, 158.2, 147.1, 146.7, 145.4, 138.8, 138.7, 136.1, 136.1, 132.4, 132.1, 131.8, 131.7, 129.2, 128.6, 128.3, 127.2, 125.1, 124.6, 124.2, 124.0, 117.3, 117.1, 116.6, 112.9, 112.6, 20.4. 20.4

Example 50

Synthesis of 4-amino-3-(2-phenylpyridine-3-ylazo)naphthalene-1-sulfonic acid sodium salt

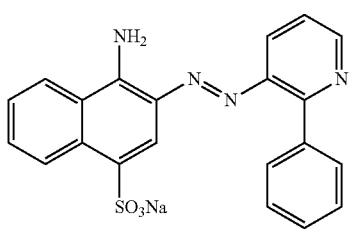

(i) 2-Phenylpyridine-3-ylamine

3-Amino-2-chloropyridine (0.5 g, 3.9 mmol), phenylboronic acid (0.47 g, 3.9 mmol), and bis(triphenylphosphine)palladium dichloride (0.137 g, 0.195 mmol) were added to 1,4-dioxane (20 ml). Under nitrogen atmosphere the mixture was stirred at room temperature for 30 minutes. 1M aqueous sodium carbonate (8 ml) was poured in, and the temperature was raised to 80° C. After the reaction at 80° C. for 8 hours, the mixture was distilled off under reduced pressure. The residue was extracted with addition of ethyl acetate and water. The impurities were filtered off from the organic layer, and the solvent was distilled off under reduced pressure. The purification by column chromatography gave the title compound (0.47 g, 71.0% yield).

(ii) 4-Amino-3-(2-phenylpyridine-3-ylazo)naphthalene-1-sulfonic acid sodium salt The title compound was synthesized in a manner analogous to Example 7 (iii), except for replacing 2-phenyl-5-aminopyridine with 2-phenylpyridine-3-ylamine obtained in (i).

$^1$H-NMR δ [ppm]=8.73 (1H, d, J=8.4 Hz), 8.70 (1H, dd, J=4.8, 1.5 Hz), 8.45 (1H, d, J=8.1 Hz), 8.34 (1H, dd, J=8.1, 1.5 Hz), 8.21 (1H, s), 8.08 (2H, bs), 7.83 (2H, dd, J=7.8, 1.8 Hz), 7.43-7.62 (6H, m)

$^{13}$C-NMR δ [ppm]=154.7, 149.6, 146.1, 145.0, 138.5, 132.4, 131.8, 130.5, 129.4, 128.5, 128.4, 128.2, 127.9, 125.0, 124.5, 124.1, 124.1, 123.4, 120.5

Example 51

Synthesis of 4-amino-3-([2,3']-bipyridinyl3-ylazo)naphthalene-1-sulfonic acid sodium salt

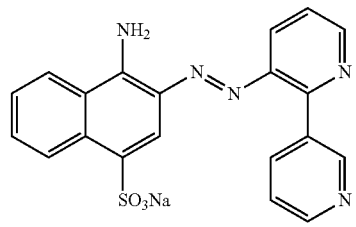

(i) [2,3']-Bipyridinyl-3-ylamine

The title compound was synthesized in a manner analogous to Example 50 (i), except for replacing phenylboronic acid with 3-pyridinylboronic acid.

(ii) 4-Amino-3-([2,3']-bipyridinyl3-ylazo)naphthalene-1-sulfonic acid sodium salt The title compound was synthesized in a manner analogous to Example 7 (iii), except for replacing 2-phenyl-5-aminopyridine with [2,3']-bipyridinyl-3-ylamine obtained in (i).

$^1$H-NMR δ [ppm]=8.97 (1H, d, J=2.1 Hz), 8.639-8.734 (3H, m), 8.42-8.47 (2H, m), 8.21 (1H, d, J=8.1 Hz), 8.15 (1H, s), 7.99 (2H, bs), 7.45-7.62 (4H, m)

$^{13}$C-NMR δ [ppm]=152.2, 150.5, 149.8, 149.2, 146.4, 146.1, 137.9, 134.1, 132.5, 132.0, 129.5, 128.7, 128.2, 125.1, 124.7, 124.1, 123.0, 118.9

Example 52

Synthesis of 4-amino-3-([2,3']bipyridinyl-5-ylazo)naphthalene-1-sulfonic acid sodium salt

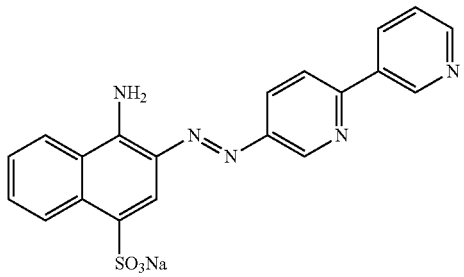

(i) 5-Nitro-[2,3']bipyridinyl

The title compound was synthesized in a manner analogous to Example 7 (i), except for replacing phenylboronic acid with 3-pyridinylboronic acid.

(ii) [2,3']Bipyridinyl-5-ylamine

The title compound was synthesized in a manner analogous to Example 7 (ii), except for replacing 2-phenyl-5-nitropyridine with 5-nitro-[2,3']bipyridinyl obtained in (i).

(iii) 4-Amino-3-([2,3']bipyridinyl-5-ylazo)naphthalene-1-sulfonic acid sodium salt The title compound was synthesized in a manner analogous to Example 7 (iii), except for replacing 2-phenyl-5-aminopyridine with [2,3']bipyridinyl-5-ylamine obtained in (ii).

$^1$H-NMR (DMSO-d6) δ [ppm]=9.37 (1H, s), 9.27 (1H, s), 8.76 (1H, d, J=8.4), 8.64 (1H, d, J=3.6), 8.54-8.46 (3H, m), 8.34 (1H, s), 8.20 (1H, d, J=8.4), 7.85 (2H, bs), 7.64-7.48 (3H, m)

$^{13}$C-NMR (DMSO-d6) δ [ppm]=153.6, 150.0, 147.9, 147.7, 147.2, 146.3, 134.0, 133.5, 132.5, 132.1, 129.4, 128.6, 128.3, 127.8, 125.1, 124.2, 124.0, 123.9, 121.1, 116.5

Example 53

Synthesis of 4-amino-3-(4-methyl-[2,3']bipyridinyl-5-ylazo)naphthalene-1-sulfonic acid sodium salt

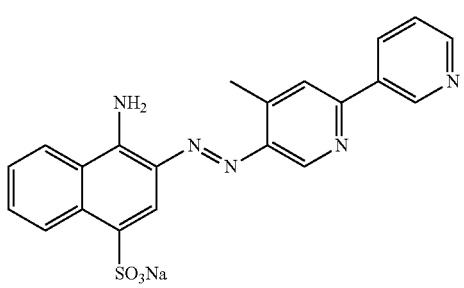

(i) 4-Methyl-5-nitro-[2,3']bipyridinyl

The title compound was synthesized in a manner analogous to Example 7 (i), except for replacing 2-chloro-5-nitropyridine with 2-chloro-4-methyl-5-nitropyridine, and replacing phenylboronic acid with 3-pyridinylboronic acid.

(ii) 4-Methyl-[2,3']bipyridinyl-5-ylamine

The title compound was synthesized in a manner analogous to Example 7 (ii), except for replacing 2-phenyl-5-nitropyridine with 4-methyl-5-nitro-[2,3']bipyridinyl obtained in (i).

(iii) 4-Amino-3-(4-methyl-[2,3']bipyridinyl-5-ylazo)naphthalene-1-sulfonic acid sodium salt The title compound was synthesized in a manner analogous to Example 7 (iii), except for replacing 2-phenyl-5-aminopyridine with 4-methyl-[2,3']bipyridinyl-5-ylamine obtained in (ii).

$^1$H-NMR (DMSO-d6) δ [ppm]=9.33 (1H, d, J=2.1), 9.05 (1H, s), 8.77 (1H, d, J=8.1), 8.62 (1H, dd, J=4.5, 2.1), 8.50-8.44 (2H, m), 8.32 (1H, s), 8.11 (1H, s), 7.96 (2H, bs), 7.63-7.47 (3H, m), 2.25 (3H, s)

$^{13}$C-NMR (DMSO-d6) δ [ppm]=152.7, 149.8, 147.7, 146.3, 145, 7, 144.3, 138.1, 133.8, 133.7, 132.5, 132.0, 129.8, 128.5, 128.3, 125.1, 124.2, 123.9, 123.8, 122.6, 117.9, 17.2

Example 54

Synthesis of 4-amino-3-([3,2';6',3'']terpyridine-3'-ylazo)naphthalene-1-sulfonic acid sodium salt

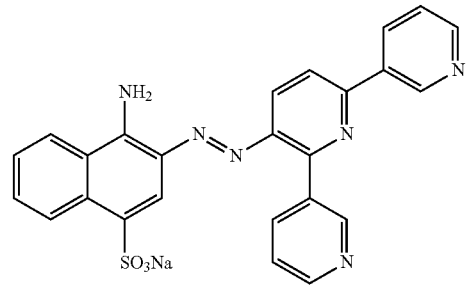

(i) [3,2';6',3'']Terpyridine-3'-ylamine

6-Bromo-2-chloropyridine-3-ylamine (0.50 g, 2.1 mmol), 3-pyridinylboronic acid (0.52 g, 4.2 mmol), and tetrakis(triphenylphosphine)palladium(0) (0.12 g, 0.11 mmol) were dissolved in dioxane (32 ml) and degassed. After stirring at room temperature for 30 minutes, 1M aqueous sodium carbonate (13 ml) was poured in, and the temperature was raised to 80° C. After the reaction at 80° C. for 4 hours, the mixture was concentrated and passed through an alumina column. The mixture was added with aqueous hydrochloric acid and neutralized. The precipitated crystals were filtered and dried to give the title compound (0.53 g, 101.7% yield).

(ii) 4-Amino-3-([3,2';6',3"]terpyridine-3'-ylazo) naphthalene-1-sulfonic acid sodium salt The title compound was synthesized in a manner analogous to Example 7 (iii), except for replacing 2-phenyl-5-aminopyridine[3,2';6',3"]terpyridine-3'-ylamine obtained in (i).

$^1$H-NMR δ [ppm]=9.43 (1H, d, J=1.5 Hz), 9.13 (1H, d, J=2.1 Hz), 8.60-8.76 (4H, m), 8.58 (1H, d, J=8.7 Hz), 8.44 (1H, d, J=8.1 Hz), 8.34-8.38 (1H, m), 8.18-8.24 (2H, m), 8.02 (2H, bs), 7.45-7.63 (4H, m)

$^{13}$C-NMR δ [ppm]=153.3, 152.2, 150.6, 150.2, 150.1, 149.3, 148.0, 146.2, 145.7, 138.0, 134.2, 134.1, 133.4, 132.9, 132.1, 129.8, 128.7, 128.3, 125.9, 125.0, 124.1, 124.0, 124.0, 123.9, 123.0, 120.8, 118.7

Example 55

Synthesis of 4-amino-3-[6-(5-fluoro-2-propoxyphenyl)pyridine-3-ylazo]naphthalene-1-sulfonic acid sodium salt

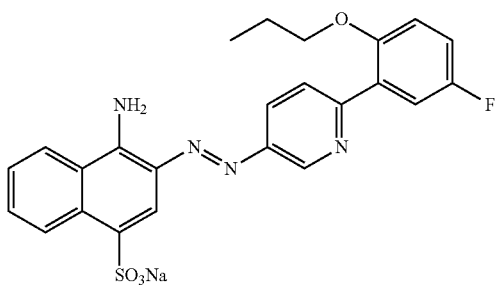

(i) 2-(5-Fluoro-2-propoxyphenyl)-5-nitropyridine

The title compound was synthesized in a manner analogous to Example 7 (i), except for replacing phenylboronic acid with 5-fluoro-2-propoxyphenylboronic acid.

(ii) 6-(5-Fluoro-2-propoxyphenyl)pyridine-3-ylamine

The title compound was synthesized in a manner analogous to Example 7 (ii), except for replacing 2-phenyl-5-nitropyridine with 2-(5-fluoro-2-propoxyphenyl)-5-nitropyridine obtained in (i).

(iii) 4-Amino-3-[6-(5-fluoro-2-propoxyphenyl)pyridine-3-ylazo]naphthalene-1-sulfonic acid sodium salt The title compound was synthesized in a manner analogous to Example 7 (iii), except for replacing 2-phenyl-5-aminopyridine with 6-(5-fluoro-2-propoxyphenyl)pyridine-3-ylamine obtained in (ii).

$^1$H-NMR δ [ppm]=9.23 (1H, d, J=2.4), 8.75 (1H, dd, J=8.4, 0.9), 8.48-8.45 (2H, m), 8.32 (1H, s), 8.17 (1H, d, J=8.4), 7.78 (2H, bs), 7.73 (1H, dd, J=9.9, 3.0), 7.63-7.48 (2H, m), 7.27-7.15 (2H, m), 4.03 (2H, t, J=6.3), 1.82-1.73 (2H, m), 0.99 (3H, t, J=7.2)

$^{13}$C-NMR (DMSO-d6) δ [ppm]=158.0, 154.8, 153.6, 153.6, 153.0, 152.9, 147.2, 147.0, 146.3, 132.5, 132.1, 129.3, 128.9, 128.8, 128.5, 128.3, 126.1, 125.0, 124.1, 123.9, 116.7, 116.3, 114.7, 114.6, 70.4, 22.1, 10.7

Example 56

Synthesis of 4-amino-3-[6-(2-fluoro-6-propoxyphenyl)pyridine-3-ylazo]naphthalene-1-sulfonic acid sodium salt

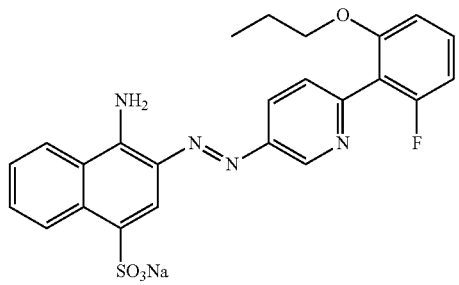

(i) 2-(2-Fluoro-6-propoxyphenyl)-5-nitropyridine

The title compound was synthesized in a manner analogous to Example 8 (i), except for replacing 4-methylphenylboronic acid with 2-fluoro-6-propoxyphenylboronic acid.

(ii) 6-(2-Fluoro-6-propoxyphenyl)pyridine-3-ylamine

The title compound was synthesized in a manner analogous to Example 7 (ii), except for replacing 2-phenyl-5-nitropyridine with 2-(2-fluoro-6-propoxyphenyl)-5-nitropyridine obtained in (i).

(iii) 4-Amino-3-[6-(2-fluoro-6-propoxyphenyl)pyridine-3-ylazo]naphthalene-1-sulfonic acid sodium salt The title compound was synthesized in a manner analogous to Example 7 (iii), except for replacing 2-phenyl-5-aminopyridine with 6-(2-fluoro-6-propoxyphenyl)pyridine-3-ylamine obtained in (ii).

$^1$H-NMR (DMSO-d6) δ [ppm]=9.20 (1H, dd, J=2.4, 0.6), 8.75 (1H, dd, J=8.4, 1.2), 8.48 (1H, d, J=8.1), 8.44 (1H, dd, J=8.4, 2.4), 8.32 (1H, s), 7.83 (2H, bs), 7.64-7.38 (4H, m), 6.99-6.88 (2H, m), 3.96 (2H, t, J=6.3), 1.62-1.55 (2H, m), 0.83 (3H, t, J=7.2)

$^{13}$C-NMR (DMSO-d6) δ [ppm]=161.7, 158.5, 157.4, 157.3, 151.5, 147.0, 147.0, 145.6, 132.4, 132.1, 130.6, 130.4, 129.2, 128.5, 128.3, 126.5, 126.3, 125.0, 124.2, 124.0, 118.0, 117.7, 116.6, 108.6, 108.0, 107.7, 70.0, 21.9, 10.4

Example 57

Synthesis of 4-amino-3-[6-(4-fluoro-2-propoxyphenyl)pyridine-3-ylazo]naphthalene-1-sulfonic acid sodium salt

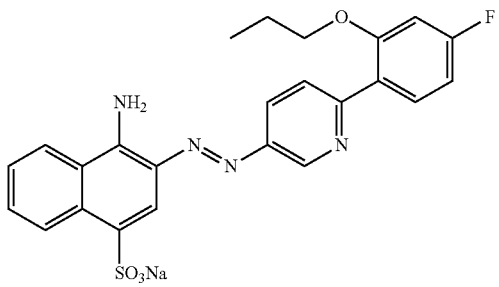

(i) 2-(4-Fluoro-2-propoxyphenyl)-5-nitropyridine

The title compound was synthesized in a manner analogous to Example 8 (i), except for replacing 4-methylphenylboronic acid with 4-fluoro-2-propoxyphenylboronic acid.

(ii) 6-(4-Fluoro-2-propoxyphenyl)pyridine-3-ylamine

The title compound was synthesized in a manner analogous to Example 7 (ii), except for replacing 2-phenyl-5-nitropyridine with 2-(4-fluoro-2-propoxyphenyl)-5-nitropyridine obtained in (i).

(iii) 4-Amino-3-[6-(4-fluoro-2-propoxyphenyl)pyridine-3-ylazo]naphthalene-1-sulfonic acid sodium salt The title compound was synthesized in a manner analogous to Example 7 (iii), except for replacing 2-phenyl-5-aminopyridine with 6-(4-fluoro-2-propoxyphenyl)pyridine-3-ylamine obtained in (ii).

$^1$H-NMR (DMSO-d6) δ [ppm]=9.21 (1H, d, J=2.1 Hz), 8.75 (1H, d, J=7.8 Hz), 8.49-8.42 (2H, m), 8.32 (1H, s), 8.06 (1H, d, J=8.7 Hz), 7.97 (1H, dd, J=8.7, 7.2 Hz), 7.74 (2H, bs), 7.62-7.47 (2H, m), 7.09-6.88 (2H, m), 4.07 (2H, t, J=6.3 Hz), 1.83-1.72 (2H, m), 1.00 (3H, t, J=7.2 Hz)

$^{13}$C-NMR (DMSO-d6) δ [ppm]=165.0, 161.8, 157.9, 157.7, 154.3, 146.9, 146.7, 146.3, 132.5, 132.3, 132.1, 132.1, 129.3, 128.4, 128.3, 125.9, 125.0, 124.7, 124.2, 124.1, 124.1, 123.9, 107.3, 107.4, 100.9, 100.6, 70.2, 21.9, 10.7

Example 58

Synthesis of 4-amino-3-[6-(5-fluoro-2-methylphenyl)pyridine-3-ylazo]naphthalene-1-sulfonic acid sodium salt

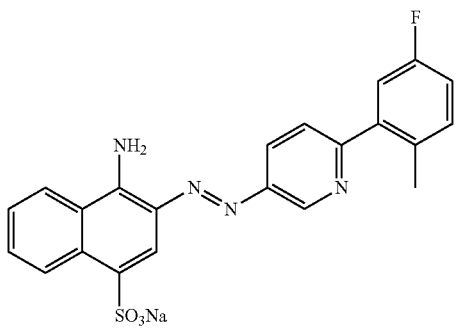

(i) 2-(5-Fluoro-2-methylphenyl)-5-nitropyridine

The title compound was synthesized in a manner analogous to Example 8 (i), except for replacing 4-methylphenylboronic acid with 5-fluoro-2-methylphenylboronic acid.

(ii) 6-(5-Fluoro-2-methylphenyl)pyridine-3-ylamine

The title compound was synthesized in a manner analogous to Example 7 (ii), except for replacing 2-phenyl-5-nitropyridine with 2-(5-fluoro-2-methylphenyl)-5-nitropyridine obtained in (i).

(iii) 4-Amino-3-[6-(5-fluoro-2-methylphenyl)pyridine-3-ylazo]naphthalene-1-sulfonic acid sodium salt The title compound was synthesized in a manner analogous to Example 7 (iii), except for replacing 2-phenyl-5-aminopyridine with 6-(5-fluoro-2-methylphenyl)pyridine-3-ylamine obtained in (ii).

$^1$H-NMR (DMSO-d6) δ [ppm]=9.24 (1H, d, J=2.4 Hz), 8.75 (1H, dd, J=8.4, 0.9 Hz), 8.49-8.44 (2H, m), 8.32 (1H, s), 7.80 (2H, bs), 7.71 (1H, d, J=8.4 Hz), 7.70-7.15 (5H, m), 2.37 (3H, s)

$^{13}$C-NMR (DMSO-d6) δ [ppm]=147.1, 146.9, 145.4, 141.3, 141.2, 132.6, 132.5, 132.1, 131.7, 131.7, 129.3, 128.5, 128.3, 127.3, 125.1, 124.6, 124.2, 123.9, 116.4, 116.2, 115.9, 115.2, 114.9, 19.6

Example 59

Synthesis of 4-amino-3-[6-(2-fluoro-5-methylphenyl)pyridine-3-ylazo]naphthalene-1-sulfonic acid sodium salt

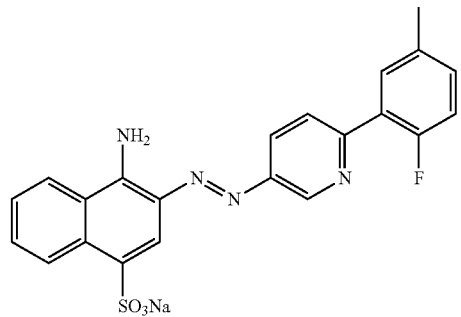

(i) 2-(2-Fluoro-5-methylphenyl)-5-nitropyridine

The title compound was synthesized in a manner analogous to Example 7 (i), except for replacing phenylboronic acid with 2-fluoro-5-methylphenylboronic acid.

(ii) 6-(2-Fluoro-5-methylphenyl)pyridine-3-ylamine

The title compound was synthesized in a manner analogous to Example 7 (ii), except for replacing 2-phenyl-5-nitropyridine with 2-(2-fluoro-5-methylphenyl)-5-nitropyridine obtained in (i).

(iii) 4-Amino-3-[6-(2-fluoro-5-methylphenyl)pyridine-3-ylazo]naphthalene-1-sulfonic acid sodium salt The title compound was synthesized in a manner analogous to Example 7 (iii), except for replacing 2-phenyl-5-aminopyridine with 6-(2-fluoro-5-methylphenyl)pyridine-3-ylamine obtained in (ii).

$^1$H-NMR (DMSO-d6) δ [ppm]=9.26 (1H, d, J=2.7 Hz), 8.78 (1H, dd, J=8.4, 0.9 Hz), 8.48-8.45 (2H, m), 8.35 (1H, s), 7.93-7.84 (4H, m), 7.64-7.48 (2H, m), 7.30-7.19 (2H, m), 2.37 (3H, s)

$^{13}$C-NMR (DMSO-d6) δ [ppm]=159.9, 156.6, 152.4, 147.2, 147.1, 133.9, 132.5, 132.1, 130.9, 129.3, 128.6, 128.3, 127.2, 126.0, 125.8, 125.1, 124.5, 124.4, 124.2, 123.9, 116.7, 116.3, 116.0, 20.2

Example 60

Synthesis of 4-amino-3-[6-(2-butoxyphenyl)pyridine-3-ylazo]naphthalene-1-sulfonic acid sodium salt

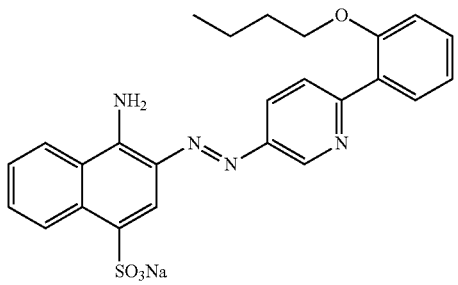

(i) 2-(2-Butoxyphenyl)-5-nitropyridine

The title compound was synthesized in a manner analogous to Example 7 (i), except for replacing phenylboronic acid with 2-butoxyphenylboronic acid.

(ii) 6-(2-Butoxyphenyl)pyridine-3-ylamine

The title compound was synthesized in a manner analogous to Example 7 (ii), except for replacing 2-phenyl-5-nitropyridine with 2-(2-butoxyphenyl)-5-nitropyridine obtained in (i).

(iii) 4-Amino-3-[6-(2-butoxyphenyl)pyridine-3-ylazo]naphthalene-1-sulfonic acid sodium salt The title compound was synthesized in a manner analogous to Example 7 (iii), except for replacing 2-phenyl-5-aminopyridine with 6-(2-butoxyphenyl)pyridine-3-ylamine obtained in (ii).

$^1$H-NMR (DMSO-d6) δ [ppm]=9.22 (1H, d, J=2.4 Hz), 8.77 (1H, d, J=8.4 Hz), 8.46 (1H, d, J=7.5 Hz), 8.43 (1H, dd, J=8.7, 2.4 Hz), 8.34 (1H, s), 8.08 (1H, d, J=8.7 Hz), 7.91 (1H, dd, J=7.8, 1.8 Hz), 7.76 (2H, bs), 7.63-7.37 (3H, m), 7.15 (1H, d, J=8.1 Hz), 7.08 (1H, dd, J=7.8, 7.8 Hz), 4.08 (2H, t, J=6.6 Hz), 1.74 (2H, tt, J=6.6, 6.6 Hz), 1.44 (2H, tt, J=7.2, 6.6 Hz), 0.92 (3H, t, J=7.2 Hz)

$^{13}$C-NMR (DMSO-d6) δ [ppm]=156.4, 155.2, 146.9, 146.7, 146.3, 132.4, 132.0, 130.8, 130.4, 129.3, 128.4, 128.3, 127.7, 125.8, 125.0, 125.0, 124.2, 123.9, 120.6, 116.4, 112.9, 67.8, 30.8, 18.9, 13.7

Example 61

Synthesis of 4-amino-3-[6-(2-hexyloxyphenyl)pyridine-3-ylazo]naphthalene-1-sulfonic acid sodium salt

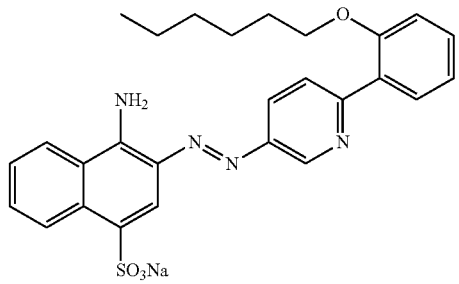

(i) 2-(2-Hexyloxyphenyl)-5-nitropyridine

The title compound was synthesized in a manner analogous to Example 7 (i), except for replacing phenylboronic acid with 2-hexyloxyphenylboronic acid.

(ii) 6-(2-Hexyloxyphenyl)pyridine-3-ylamine

The title compound was synthesized in a manner analogous to Example 7 (ii), except for replacing 2-phenyl-5-nitropyridine with 2-(2-hexyloxyphenyl)-5-nitropyridine obtained in (i).

(iii) 4-Amino-3-[6-(2-hexyloxyphenyl)pyridine-3-ylazo]naphthalene-1-sulfonic acid sodium salt The title compound was synthesized in a manner analogous to Example 7 (iii), except for replacing 2-phenyl-5-aminopyridine with 6-(2-hexyloxyphenyl)pyridine-3-ylamine obtained in (ii).

$^1$H-NMR (DMSO-d6) δ [ppm]=9.16 (1H, d, J=2.4 Hz), 8.69 (1H, dd, J=8.4, 0.9 Hz), 8.42 (1H, d, J=6.0 Hz), 8.36 (1H, dd, J=8.7, 2.4 Hz), 8.27 (1H, s), 8.01 (1H, d, J=8.7 Hz), 7.84 (1H, dd, J=7.5, 1.8 Hz), 7.20 (2H, bs), 7.58-7.30 (3H, m), 7.07 (1H, d, J=8.1 Hz), 7.01 (1H, dd, J=8.1, 8.1 Hz), 3.99 (2H, t, J=6.6 Hz), 1.69-1.64 (2H, m), 1.35-1.18 (6H, m), 0.76 (3H, t, J=6.9 Hz)

$^{13}$C-NMR (DMSO-d6) δ [ppm]=156.5, 155.1, 147.0, 146.7, 146.1, 132.4, 132.1, 130.8, 130.5, 129.3, 128.5, 128.3, 127.6, 126.1, 125.1, 125.1, 124.2, 123.9, 120.6, 116.5, 113.0, 68.2, 30.9, 28.6, 25.3, 22.0, 13.9

Example 62

Synthesis of 4-amino-3-[6-(4-butylphenyl)pyridine-3-ylazo]naphthalene-1-sulfonic acid sodium salt

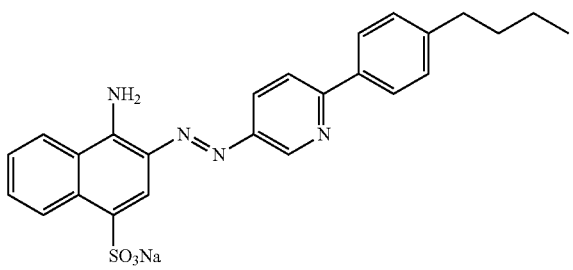

(i) 2-(4-Butylphenyl)-5-nitropyridine

The title compound was synthesized in a manner analogous to Example 7 (i), except for replacing phenylboronic acid with 4-butylphenylboronic acid.

(ii) 6-(4-Butylphenyl)pyridine-3-ylamine

The title compound was synthesized in a manner analogous to Example 7 (ii), except for replacing 2-phenyl-5-nitropyridine with 2-(4-butylphenyl)-5-nitropyridine obtained in (i).

(iii) 4-Amino-3-[6-(4-butylphenyl)pyridine-3-ylazo]naphthalene-1-sulfonic acid sodium salt The title compound was synthesized in a manner analogous to Example 7 (iii), except for replacing 2-phenyl-5-aminopyridine with 6-(4-butylphenyl)pyridine-3-ylamine obtained in (ii).

$^1$H-NMR (DMSO-d6) δ [ppm]=9.21 (1H, d, J=2.4 Hz), 8.77 (1H, d, J=8.4 Hz), 8.48-8.43 (2H, m), 8.33 (1H, s), 8.11-8.05 (3H, m), 7.78 (2H, bs), 7.63-7.48 (2H, m), 7.31 (2H, d, J=8.1 Hz), 2.63 (2H, t, J=7.5 Hz), 1.61-1.56 (2H, m), 1.35-1.28 (2H, m), 0.90 (3H, t, J=7.2 Hz)

$^{13}$C-NMR (DMSO-d6) δ [ppm]=156.0, 147.2, 146.9, 146.3, 143.9, 135.6, 132.4, 132.0, 129.3, 128.8, 128.5, 128.3, 127.5, 126.6, 125.1, 124.2, 123.9, 120.3, 116.6, 34.6, 33.0, 21.8, 13.8

Example 63

Synthesis of 4-amino-3-[6-(2-hydroxyphenyl)pyridine-3-ylazo]naphthalene-1-sulfonic acid sodium salt

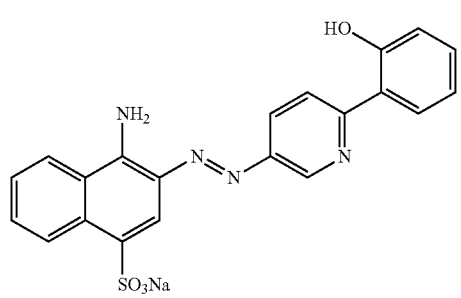

(i) 2-(5-Nitropyridine-2-yl)phenol

The title compound was synthesized in a manner analogous to Example 7 (i), except for replacing phenylboronic acid with 2-hydroxyphenylboronic acid.

(ii) 2-(5-Aminopyridine-2-yl)phenol

The title compound was synthesized in a manner analogous to Example 7 (ii), except for replacing 2-phenyl-5-nitropyridine with 2-(5-nitropyridine-2-yl)phenol obtained in (i).

(iii) 4-Amino-3-[6-(2-hydroxyphenyl)pyridine-3-ylazo]naphthalene-1-sulfonic acid sodium salt The title compound was synthesized in a manner analogous to Example 7 (iii), except for replacing 2-phenyl-5-aminopyridine with 2-(5-aminopyridine-2-yl)phenol obtained in (ii).

$^1$H-NMR (DMSO-d6) δ [ppm]=14.09 (1H, bs), 9.22 (1H, d, J=2.4 Hz), 8.75 (1H, d, J=7.8 Hz), 8.61 (1H, dd, J=9.0, 2.4 Hz), 8.47 (1H, d, J=7.8 Hz), 8.35 (1H, s), 8.32 (1H, s), 8.10 (1H, d, J=7.8 Hz), 7.84 (2H, bs), 7.59-7.63 (1H, m), 7.48-7.53 (1H, m), 7.30-7.36 (1H, m), 6.92-6.97 (2H, m)

$^{13}$C-NMR (DMSO-d6) δ [ppm]=159.2, 156.6, 147.5, 146.8, 142.9, 132.6, 132.2, 131.7, 129.3, 129.0, 128.7, 128.4, 127.4, 125.1, 124.2, 124.0, 120.6, 119.1, 118.9, 118.0, 116.2

Example 64

Synthesis of 4-amino-3-{6-[2-(6-hydroxyhexyloxy)phenyl]pyridine-3-ylazo}naphthalene-1-sulfonic acid sodium salt

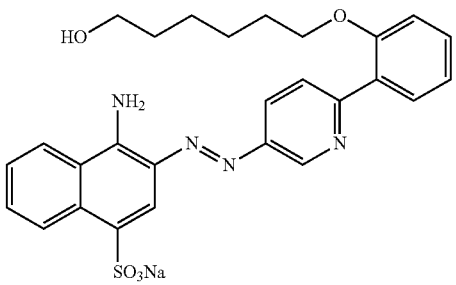

(i) 6-[2-(5-Nitropyridine-2-yl)phenoxy]hexane-1-ol

To a solution of 2-(5-nitropyridine-2-yl)phenol (1.0 g, 4.6 mmol) synthesized in Example 63 (i), 6-chlorohexanol (0.76 g, 5.6 mmol), and potassium carbonate (1.28 g, 9.3 mmol) in N,N-dimethylformamide (5 ml), potassium iodide (0.154 g, 0.93 mmol) was added and the reaction was carried out at 80° C. for 4 hours. The mixture was cooled, added with water and extracted with methylene chloride. The organic layer was dried with anhydrous sodium sulfate, concentrated to dryness under reduced pressure, and purified by column chromatography. Recrystallization gave the title compound (1.08 g, 74.5%).

(ii) 6-[2-(5-Aminopyridine-2-yl)phenoxy]hexane-1-ol

The title compound was synthesized in a manner analogous to Example 7 (ii), except for replacing 2-phenyl-5-nitropyridine with 6-[2-(5-nitropyridine-2-yl)phenoxy]hexane-1-ol obtained in (i).

(iii) 4-Amino-3-{6-[2-(6-hydroxyhexyloxy)phenyl]pyridine-3-ylazo}naphthalene-1-sulfonic acid sodium salt The title compound was synthesized in a manner analogous to Example 7 (iii), except for replacing 2-phenyl-5-aminopyridine with 6-[2-(5-aminopyridine-2-yl)phenoxy]hexane-1-ol obtained in (ii).

$^1$H-NMR (DMSO-d6) δ [ppm]=9.23 (1H, s), 8.76 (1H, d, J=8.4 Hz), 8.42-8.48 (2H, m), 8.33 (1H, s), 8.09 (1H, d, J=8.4 Hz), 7.92 (1H, d, J=7.5 Hz), 7.76 (2H, bs), 7.61-7.63 (1H, m), 7.48-7.53 (1H, m), 7.37-7.43 (1H, m), 7.05-7.17 (2H, m), 4.36 (1H, t, J=4.8 Hz), 4.07 (2H, t, J=6.0 Hz), 1.40-1.75 (10H, m)

$^{13}$C-NMR (DMSO-d7) δ [ppm]=156.5, 155.2, 147.0, 146.7, 146.2, 132.4, 132.1, 130.8, 130.5, 129.3, 128.4, 128.3, 127.7, 126.0, 125.0, 124.2, 123.9, 120.6, 116.3, 112.9, 68.1, 60.6, 32.5, 28.7, 25.5, 25.2

Example 65

Synthesis of 4-{2-[5-(1-amino-4-sulfonaphthalene-2-ylazo)pyridine-2-yl]phenoxy}butyric acid disodium salt

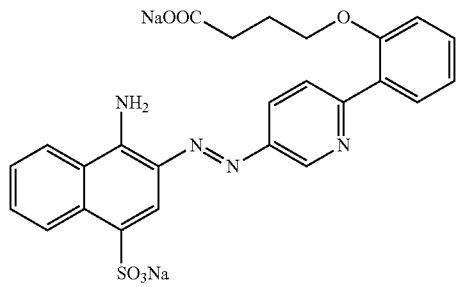

(i) 4-[2-(5-Nitropyridine-2-yl)phenoxy]butyric acid

To a solution of 2-(5-nitropyridine-2-yl)phenol (0.75 g, 3.5 mmol) synthesized in Example 63 (i), ethyl 4-bromo-n-butyrate (0.81 g, 4.2 mmol) and potassium carbonate (0.96 g, 6.9 mmol) in acetonitrile (10 ml), potassium iodide (0.115 g, 0.69 mmol) was added and the reaction was carried out at 80° C. for 2 hours. The mixture was cooled, and extracted with addition of water and methylene chloride. The organic layer was dried with anhydrous sodium sulfate, and concentrated under reduced pressure. Hydrolysis was carried out with aqueous sodium hydroxide in methanol for 1 hour, and the reaction was neutralized with addition of hydrochloric acid. The precipitated solids were filtered to give the title compound (0.92 g, 87.0%).

(ii) 4-[2-(5-Aminopyridine-2-yl)phenoxy]butyric acid

The title compound was synthesized in a manner analogous to Example 7 (ii), except for replacing 2-phenyl-5-nitropyridine with 4-[2-(5-nitropyridine-2-yl)phenoxy]butyric acid obtained in (i).

(iii) 4-{2-[5-(1-Amino-4-sulfonaphthalene-2-ylazo)pyridine-2-yl]phenoxy}butyric acid disodium salt The title compound was synthesized in a manner analogous to Example 7 (iii), except for replacing 2-phenyl-5-aminopyridine with 4-[2-(5-aminopyridine-2-yl)phenoxy]butyric acid obtained in (ii).

$^1$H-NMR (DMSO-d6) δ [ppm]=9.21 (1H, d, J=2.1 Hz), 8.76 (1H, d, J=8.4 Hz), 8.46 (1H, d, J=8.1 Hz), 8.41 (1H, dd, J=8.4, 2.1 Hz), 8.32 (1H, s), 8.13 (1H, d, J=8.4 Hz), 7.92 (1H, d, J=7.5 Hz), 7.76 (2H, bs), 7.57-7.62 (1H, m), 7.47-7.49 (1H, m), 7.36-7.41 (1H, m), 7.16 (1H, d, J=8.4 Hz), 7.03-7.08 (1H, m), 4.11 (2H, t, J=6.6 Hz), 2.06-2.11 (2H, m), 1.94 (2H, t, J=6.6 Hz)

$^{13}$C-NMR (DMSO-d6) δ [ppm]=176.8, 156.6, 155.2, 146.8, 146.6, 146.1, 132.5, 132.0, 130.7, 130.4, 129.3, 128.3, 128.3, 127.5, 125.8, 125.0, 125.0, 124.2, 123.9, 120.4, 116.5, 112.8, 68.5, 34.1, 26.1

Example 66

Synthesis of 4-amino-3-{6-[2-(3-hydroxypropoxy)phenyl]pyridine-3-ylazo}naphthalene-1-sulfonic acid sodium salt

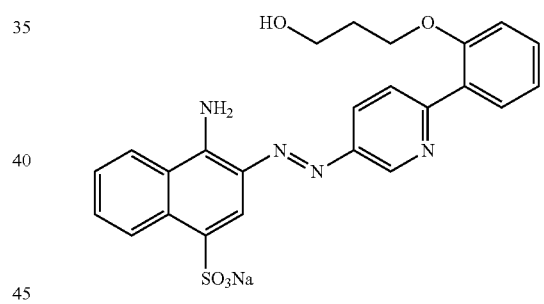

(i) 3-[2-(5-Nitropyridine-2-yl)phenoxy]propane-1-ol

To a solution of 2-(5-nitropyridine-2-yl)phenol (0.50 g, 2.3 mmol) synthesized in Example 63 (i), 3-bromopropanol (0.39 g, 2.8 mmol) and potassium carbonate (0.64 g, 4.6 mmol) in acetonitrile (8 ml), potassium iodide (0.077 g, 0.46 mmol) was added and the reaction was carried out at 80° C. for 4 hours. The mixture was cooled, added with water and extracted with methylene chloride. The organic layer was dried with anhydrous sodium sulfate, concentrated to dryness under reduced pressure, and purified by column chromatography. Recrystallization gave the title compound (0.47 g, 74.5%).

(ii) 3-[2-(5-Aminopyridine-2-yl)phenoxy]propane-1-ol

The title compound was synthesized in a manner analogous to Example 7 (ii), except for replacing 2-phenyl-5-nitropyridine with 3-[2-(5-nitropyridine-2-yl)phenoxy]propane-1-ol obtained in (i).

(iii) 4-Amino-3-{6-[2-(3-hydroxypropoxy)phenyl]pyridine-3-ylazo}naphthalene-1-sulfonic acid sodium salt The title compound was synthesized in a manner analogous to Example 7 (iii), except for replacing 2-phenyl-5-aminopyridine with 3-[2-(5-aminopyridine-2-yl)phenoxy]propane-1-ol obtained in (ii).

$^1$H-NMR (DMSO-d6) δ [ppm]=9.21 (1H, dd, J=2.4, 0.6 Hz), 8.76 (1H, dd, J=8.1, 1.2 Hz), 8.40-8.47 (2H, m), 8.32 (1H, s), 8.08 (1H, dd, J=8.4, 0.6 Hz), 7.91 (1H, dd, J=7.8, 1.8 Hz), 7.74 (2H, bs), 7.57-7.62 (1H, m), 7.47-7.52 (1H, m), 7.38-7.44 (1H, m), 7.05-7.19 (2H, m), 4.56 (1H, t, J=5.4 Hz), 4.16 (2H, t, J=6.0 Hz), 3.54-3.61 (2H, m), 1.89-1.93 (2H, m)

$^{13}$C-NMR (DMSO-d6) δ [ppm]=156.4, 155.2, 146.8, 146.6, 146.3, 146.2, 132.5, 132.0, 130.4, 129.3, 128.4, 128.2, 127.7, 124.9, 124.2, 123.9, 123.8, 120.6, 116.5, 116.4, 112.8, 65.2, 57.4, 32.1

Example 67

Synthesis of 4-amino-3-[6-(2-isobutoxyphenyl)pyridine-3-ylazo]naphthalene-1-sulfonic acid sodium salt

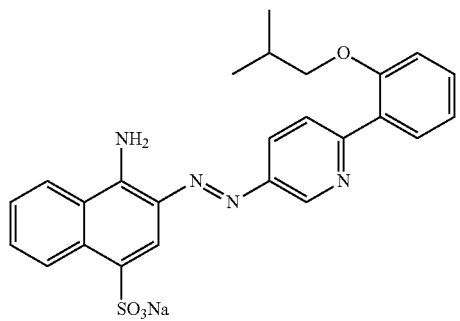

(i) 2-(2-Isobutoxyphenyl)-5-nitropyridine

To a solution of 2-(5-nitropyridine-2-yl)phenol (0.60 g, 2.8 mmol) synthesized in Example 63 (i), isobutyl bromide (0.46 g, 3.3 mmol) and potassium carbonate (0.77 g, 5.6 mmol) in acetonitrile (3 ml), potassium iodide (0.092 g, 0.56 mmol) was added and the reaction was carried out at 80° C. for 4 hours. The mixture was cooled, added with water, crystallized and filtered. The crystals were purified by column chromatography to give the title compound (0.62 g, 81.3%).

(ii) 6-(2-Isobutoxyphenyl)pyridine-3-ylamine

The title compound was synthesized in a manner analogous to Example 7 (ii), except for replacing 2-phenyl-5-nitropyridine with 2-(2-isobutoxyphenyl)-5-nitropyridine obtained in (i).

(iii) 4-Amino-3-[6-(2-isobutoxyphenyl)pyridine-3-ylazo]naphthalene-1-sulfonic acid sodium salt The title compound was synthesized in a manner analogous to Example 7 (iii), except for replacing 2-phenyl-5-aminopyridine with 6-(2-isobutoxyphenyl)pyridine-3-ylamine obtained in (ii).

$^1$H-NMR (DMSO-d6) δ [ppm]=9.23 (1H, d, J=2.4 Hz), 8.75 (1H, d, J=8.7 Hz), 8.45-8.48 (2H, m), 8.33 (1H, s), 8.08 (1H, d, J=8.7 Hz), 7.90 (1H, dd, J=2.5, 1.8 Hz), 7.75 (2H, bs), 7.58-7.63 (1H, m), 7.47-7.52 (1H, m), 7.37-7.40 (1H, m), 7.05-7.16 (2H, m), 3.87 (2H, d, J=6.3 Hz), 1.99-2.09 (1H, m), 0.99 (6H, d, J=6.6 Hz)

$^{13}$C-NMR (DMSO-d6) δ [ppm]=156.5, 155.3, 147.2, 146.7, 132.4, 132.1, 130.9, 130.5, 129.3, 128.5, 128.4, 128.3, 127.7, 125.7, 125.1, 124.2, 124.0, 120.6, 116.2, 116.1, 112.8, 74.4, 27.9, 19.4, 19.3

Example 68

Synthesis of 4-amino-3-{6-[2-(3-tert-butoxycarbonylaminopropoxy)phenyl]pyridine-3-ylazo}naphthalene-1-sulfonic acid sodium salt

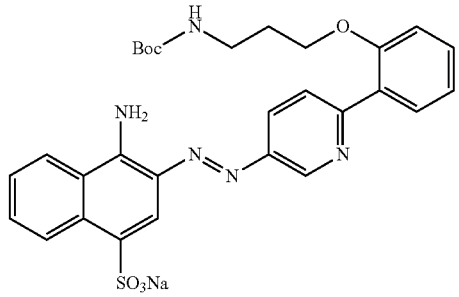

(i) tert-Butyl{3-[2-(5-nitropyridine-2-yl)phenoxy]propyl}carbamate

Di-tert-butyl dicarbonate (1.01 g, 4.6 mmol) was dissolved in N,N-dimethylacetamide (12 ml) and added with 3-bromoaminopropane hydrobromide (1.01 g, 4.6 mmol) and potassium carbonate (0.64 g, 4.6 mmol). The reaction was carried out at 45-50° C. for 1 hour. 2-(5-Nitropyridine-2-yl)phenol (0.50 g, 2.3 mmol) synthesized in Example 63 (i) and potassium carbonate (0.64 g, 4.6 mmol) were added. The reaction was carried out at 50° C. for 20 minutes and at 75-80° C. for 1 hour. The reaction was cooled and extracted with addition of water and ethyl acetate. The organic layer was dried with anhydrous sodium sulfate and concentrated under reduced pressure. The precipitated crystals were filtered with addition of water. The resulting crystals were dissolved in methanol, and hydrolyzed with dropwise addition of hydrochloric acid at 50° C. The solution was concentrated and neutralized with saturated aqueous sodium bicarbonate. The precipitated crystals were filtered to give the title compound (0.57 g, 66.4%).

(ii) tert-Butyl {3-[2-(5-aminopyridine-2-yl)phenoxy]propyl}carbamate

The title compound was synthesized in a manner analogous to Example 7 (ii), except for replacing 2-phenyl-5-nitropyridine with tert-butyl {3-[2-(5-nitropyridine-2-yl)phenoxy]propyl}carbamate obtained in (i).

(iii) 4-Amino-3-{6-[2-(3-tert-butoxycarbonylaminopropoxy)phenyl]pyridine-3-ylazo}naphthalene-1-sulfonic acid sodium salt The title compound was synthesized in a manner analogous to Example 7 (iii), except for replacing 2-phenyl-5- aminopyridine with tert-butyl{3-[2-(5-aminopyridine-2-yl)phenoxy]propyl}carbamate obtained in (ii).

¹H-NMR (DMSO-d6) δ [ppm]=9.23 (1H, d, J=1.8 Hz), 8.74 (1H, d, J=8.4 Hz), 8.41-8.47 (2H, m), 8.32 (1H, s), 8.12 (1H, d, J=8.7 Hz), 7.90 (1H, d, J=7.8 Hz), 7.77 (2H, bs), 7.57-7.63 (1H, m), 7.47-7.5 (1H, m), 7.38-7.40 (1H, m), 6.90-7.16 (3H, m), 4.09 (2H, t, J=5.7 Hz), 3.11-3.15 (2H, m), 1.85-1.89 (2H, m), 1.36 (9H, s)

¹³C-NMR (DMSO-d6) δ [ppm]=156.4, 155.7, 155.3, 145.0, 146.7, 146.4, 132.4, 132.1, 130.9, 130.5, 129.3, 128.5, 128.4, 128.3, 127.7, 125.9, 125.9, 125.9, 125.3, 125.2, 125.1, 124.2, 124.0, 120.7, 116.4, 112.7, 77.6, 65.7, 48.7

Example 69

Synthesis of 4-amino-3-[6-(2-{3-[(2-chloropyridine-3-carbonyl)amino]propoxy}phenyl)pyridine-3-ylazo]naphthalene-1-sulfonic acid sodium salt

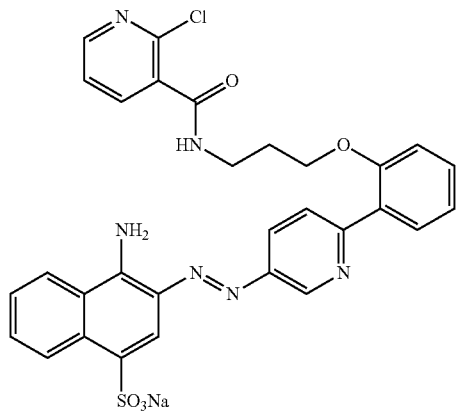

(i) N-(3-Bromopropyl)-2-chloronicotinamide

3-Bromopropylamine hydrobromide (2.08 g, 9.5 mmol), triethylamine (2.89 g, 28.6 mmol), and methylene chloride (10 ml) were charged, and added dropwise with a solution of 2-chloronicotinic acid chloride, which was obtained by conventional acid chloride reaction of 2-chloronicotinic acid (1.50 g, 9.5 mmol), in methylene chloride. The reaction was carried out at room temperature. The mixture was extracted with ethyl acetate. The organic layer was dried with anhydrous sodium sulfate, concentrated to dryness under reduced pressure, and then purified by column chromatography to give the title compound (1.78 g, 67.5%).

(ii) 2-Chloro-N-{3-[2-(5-nitropyridine-2-yl)phenoxy]propyl}nicotinamide 2-(5-Nitropyridine-2-yl)phenol (0.54 g, 2.5 mmol) synthesized in Example 63 (i) and THF (2.5 ml) were charged, cooled to 0 to 10° C., and added with sodium hydride (0.12 g, 5 mmol). A solution of N-(3-bromopropyl)-2-chloronicotinamide (0.69 g, 2.5 mmol) synthesized in (i) in THF (2.5 ml) was added dropwise, and the reaction was carried out at room temperature for 7 hour. The reaction was quenched with aqueous ammonium chloride and the mixture was extracted with ethyl acetate. The organic layer was dried with anhydrous sodium sulfate, concentrated to dryness under reduced pressure, and purified by column chromatography to give the title compound (1.07 g, 103.6% yield).

(iii) N-{3-[2-(5-Aminopyridine-2-yl)phenoxy]propyl}-2-chloronicotinamide

The title compound was synthesized in a manner analogous to Example 7 (ii), except for replacing 2-phenyl-5-nitropyridine with 2-chloro-N-{3-[2-(5-nitropyridine-2-yl)phenoxy]propyl}nicotinamide obtained in (ii).

(iv) 4-Amino-3-[6-(2-{3-[(2-chloropyridine-3-carbonyl)amino]propoxy}phenyl)pyridine-3-ylazo]naphthalene-1-sulfonic acid sodium salt The title compound was synthesized in a manner analogous to Example 7 (iii), except for replacing 2-phenyl-5-aminopyridine with N-{3-[2-(5-aminopyridine-2-yl)phenoxy]propyl}-2-chloronicotinamide obtained in (iii).

¹H-NMR (DMSO-d6) δ [ppm]=9.23 (1H, d, J=1.8 Hz), 8.74-8.77 (2H, m), 8.42-8.47 (3H, m), 8.32 (1H, s), 8.14 (1H, d, J=8.4 Hz), 7.87-7.90 (2H, m), 7.77 (2H, bs), 7.39-7.66 (4H, m), 7.18 (1H, d, J=8.7 Hz), 7.07-7.12 (1H, m), 4.19 (2H, t, J=5.7 Hz), 3.44 (2H, t, J=6.0 Hz), 2.00-2.04 (2H, m)

¹³C-NMR (DMSO-d6) δ [ppm]=165.2, 156.3, 155.3, 150.2, 150.1, 147.0, 146.7, 146.5, 133.3, 132.4, 132.1, 130.9, 130.5, 129.3, 128.5, 128.4, 128.3, 127.8, 126.0, 125.2, 125.1, 124.2, 124.0, 123.1, 120.7, 116.5, 112.8, 65.4, 36.0, 28.7

Example 70

Synthesis of 4-amino-3-[6-(5-chloro-2-hydroxyphenyl)pyridine-3-ylazo]naphthalene-1-sulfonic acid sodium salt

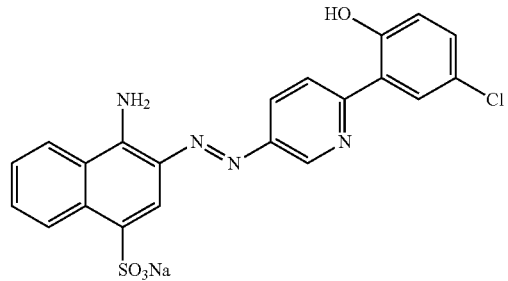

(i) 2-(3-Chlorophenyl)-5-nitropyridine

The title compound was synthesized in a manner analogous to Example 7 (i), except for replacing phenylboronic acid with 3-chlorophenylboronic acid.

(ii) 4-Chloro-2-(5-nitropyridine-2-yl)phenol

To toluene (14.0 ml) and acetic anhydride (14.0 ml), 2-(3-chlorophenyl)-5-nitropyridine (1.05 g, 4.5 mmol) obtained in (i), diacetoxyiodobenzene (1.60 g, 5.0 mmol) and palladium acetate (0.08 g, 0.36 mmol) were added, and reacted under atmosphere of air at 100° C. for 1 hour. The solvent was distilled off under reduced pressure. Purification by column chromatography resulted in an oil. The resulting oil was dissolved in methanol, added with 35% hydrochloric acid, and hydrolyzed at room temperature for 2 hours. The precipitated crystals were filtered to give the title compound (1.0 g, 89.2%).

(iii) 2-(5-Aminopyridine-2-yl)-4-chlorophenol

The title compound was synthesized in a manner analogous to Example 7 (ii), except for replacing 2-phenyl-5-nitropyridine with 4-chloro-2-(5-nitropyridine-2-yl)phenol obtained in (ii).

(iv) 4-Amino-3-[6-(5-chloro-2-hydroxyphenyl)pyridine-3-ylazo]naphthalene-1-sulfonic acid sodium salt The title compound was synthesized in a manner analogous to Example 7 (iii), except for replacing 2-phenyl-5-aminopyridine with 2-(5-aminopyridine-2-yl)-4-chlorophenol obtained in (iii).

$^1$H-NMR (DMSO-d6) δ [ppm]=14.05 (1H, s), 9.22 (1H, d, J=2.1 Hz), 8.75 (1H, d, J=8.7 Hz), 8.61 (1H, dd, J=8.7, 2.1 Hz), 8.47 (1H, d, J=8.1 Hz), 8.41 (1H, d, J=8.7 Hz), 8.31 (1H, s), 8.17 (1H, s), 7.87 (2H, bs), 7.58-7.63 (1H, m), 7.47-7.53 (1H, m), 7.35 (1H, dd, J=9.0, 2.4 Hz), 6.99 (1H, d, J=9.0 Hz)

$^{13}$C-NMR (DMSO-d6) δ [ppm]=157.8, 154.9, 147.6, 147.1, 143.1, 143.0, 132.6, 132.3, 131.1, 129.4, 128.7, 128.3, 126.8, 126.7, 125.1, 124.2, 122.8, 120.6, 119.7, 116.2, 116.1

Example 71

Synthesis of 4-amino-3-[6-(4-methylbiphenyl-2-yl)pyridine-3-ylazo]naphthalene-1-sulfonic acid sodium salt

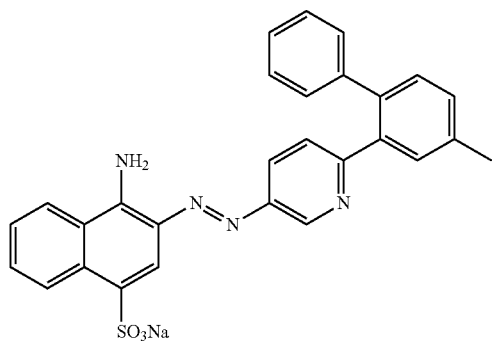

(i) Diphenyliodonium tetrafluoroborate

Phenylboronic acid (0.79 g, 6.5 mmol), methylene chloride (62 ml), and boron trifluoride ethyl ether complex (0.97 g, 6.8 mmol) were charged and cooled to 0° C. A solution of diacetoxy iodobenzene (2.0 g, 6.2 mmol) in methylene chloride (62 ml) was added dropwise. The reaction was carried out at 0° C. for 1.5 hours. A saturated aqueous solution of sodium fluoroborate (13.6 g, 124.2 mmol) was added dropwise, and the mixture was extracted with addition of water and methylene chloride. The organic layer was dried with anhydrous sodium sulfate, concentrated to dryness under reduced pressure, and purified by recrystallization to give the title compound (2.13 g, 93.5%).

(ii) 6-(4-Methylbiphenyl-2-yl)pyridine-3-ylamine

N-(6-m-Tolylpyridine-3-yl)acetamide (0.50 g, 2.2 mmol) which was obtained by conventional acetylation of 6-m-tolylpyridine-3-ylamine synthesized in Example 9 (ii), diphenyliodonium tetrafluoroborate (1.22 g, 3.3 mmol) synthesized in (i) and palladium acetate (0.025 g, 0.11 mmol) were added to acetic acid (17 ml), and reacted at 100° C. for 1 hour. The solvent was distilled off under reduced pressure, and the extraction was carried out with addition of saturated aqueous sodium bicarbonate and methylene chloride. The organic layer was dried with anhydrous sodium sulfate, and concentrated to dryness under reduced pressure. Methanol and 98% sulfuric acid were added to the products, and the hydrolysis was carried out at 70° C. for 2 hours. Methanol was distilled off under reduced pressure to give the title compound (0.34 g, 59.4%).

(iii) 4-Amino-3-[6-(4-methylbiphenyl-2-yl)pyridine-3-ylazo]naphthalene-1-sulfonic acid sodium salt The title compound was synthesized in a manner analogous to Example 7 (iii), except for replacing 2-phenyl-5-aminopyridine with 6-(4-methylbiphenyl-2-yl)pyridine-3-ylamine obtained in (ii).

$^1$H-NMR (DMSO-d6) δ [ppm]=9.14 (1H, d, J=2.4 Hz), 8.73 (1H, d, J=8.4 Hz), 8.47 (1H, d, J=8.1 Hz), 8.29 (1H, s), 8.16 (1H, dd, J=8.4, 2.4 Hz), 7.74 (2H, bs), 7.45-7.62 (3H, m), 7.20-7.33 (6H, m), 7.12 (1H, d, J=6.3 Hz), 6.99 (1H, d, J=8.4 Hz), 2.42 (3H, s)

$^{13}$C-NMR (DMSO-d6) δ [ppm]=158.8, 147.3, 146.6, 146.5, 140.9, 138.5, 137.5, 136.9, 132.2, 132.1, 131.1, 130.5, 129.5, 129.4, 129.1, 128.6, 128.3, 126.8, 125.6, 125.5, 125.4, 125.1, 124.2, 124.1, 116.1, 20.7

Example 72

Synthesis of 4-amino-3-[6-(4'-chloro-4-methylbiphenyl-2-yl)pyridine-3-ylazo]naphthalene-1-sulfonic acid sodium salt

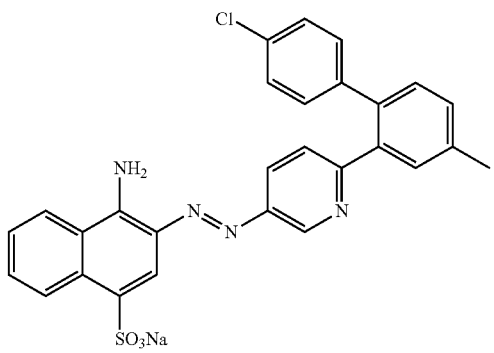

(i) Diacetoxy(2,4,6-trimethylphenyl)iodine (III)

1,3,5-Trimethyl-2-iodobenzene (20.0 g, 81.3 mmol) and acetic acid (720 ml) were charged and added portionwise with sodium perborate tetrahydrate (125 g, 813 mmol). The mixture was reacted for 3 hours, concentrated, and extracted with addition of water and methylene chloride. The organic layer was dried with anhydrous sodium sulfate, concentrated to dryness under reduced pressure, and purified by recrystallization to give the title compound (1.36 g, 37.3%).

(ii) (4-Chlorophenyl)(2,4,6-trimethylphenyl)iodonium tetrafluoroborate

4-Chlorophenylboronic acid (3.0 g, 8.2 mmol), methylene chloride (82 ml) and boron trifluoride ethyl ether complex (1.29 g, 9.1 mmol) were charged and cooled to 0° C. A solution of diacetoxy(2,4,6-trimethylphenyl)iodine (III) (3.0 g, 8.2 mmol) synthesized in (i) in methylene chloride (82 ml) was added dropwise, and the reaction was carried out at 0° C. for 1.5 hours. A saturated aqueous solution of sodium fluoroborate (18.1 g, 164.8 mmol) was added dropwise, and the mixture was extracted with addition of water and methylene chloride. The organic layer was dried with anhydrous sodium sulfate, concentrated to dryness under reduced pressure, and purified by recrystallization to give the title compound (3.36 g, 93.5%).

(iii) 6-(4'-Chloro-4-methylbiphenyl-2-yl)pyridine-3-ylamine

To acetic acid (17 ml), N-(6-m-tolylpyridine-3-yl)acetamide (0.50 g, 2.2 mmol), (4-chlorophenyl)(2,4,6-trimethylphenyl)iodonium tetrafluoroborate (1.13 g, 2.5 mmol) synthesized in (ii) and palladium acetate (0.025 g, 0.11 mmol) were added, and reacted at 100° C. for 1 hour. The solvent was distilled off under reduced pressure, and the residue was purified by column chromatography. The solvent was distilled off under reduced pressure. Methanol and 35% hydrochloric acid were added, and the hydrolysis was carried out at 65° C. for 2 hours. Methanol was distilled off under reduced pressure. Purification by column chromatography gave the title compound (0.47 g, 72.5%).

(iv) 4-Amino-3-[6-(4'-chloro-4-methylbiphenyl-2-yl)pyridine-3-ylazo]naphthalene-1-sulfonic acid sodium salt The title compound was synthesized in a manner analogous to Example 7 (iii), except for replacing 2-phenyl-5-aminopyridine with 6-(4'-chloro-4-methylbiphenyl-2-yl)pyridine-3-ylamine obtained in (iii).
$^1$H-NMR (DMSO-d6) δ [ppm]=9.13 (1H, d, J=2.4), 8.73 (1H, d, J=8.4), 8.43 (1H, d, J=8.1), 8.28 (1H, s), 8.23 (1H, dd, J=8.4, 2.4), 7.71 (NH$_2$, s), 7.61-7.55 (2H, m), 7.51-7.46 (1H, m), 7.36-7.33 (4H, m), 7.14 (2H, d, J=8.4), 7.08 (1H, d, J=8.4)
$^{13}$C-NMR (DMSO-d6) δ [ppm]=166.7, 158.5, 147.2, 146.4, 139.8, 138.5, 137.4, 136.2, 132.5, 132.1, 131.6, 131.2, 131.1, 130.4, 129.6, 129.2, 128.5, 125.9, 125.4, 125.1, 124.2, 123.9, 116.1, 20.7

Example 73

Synthesis of 4-amino-3-[6-(5,5-dioxo-5H-5λ$^6$-dibenzothiophene-4-yl)pyridine-3-ylazo]naphthalene-1-sulfonic acid sodium salt

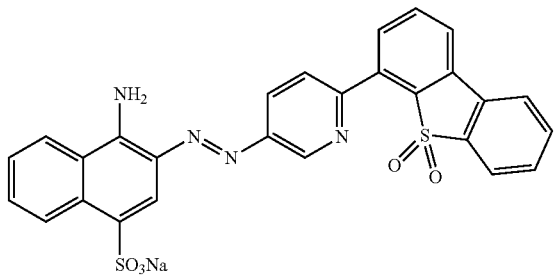

(i) 2-(5,5-Dioxo-5H-5λ$^6$-dibenzothiophene-4-yl)-5-nitropyridine

2-Dibenzothiophene-4-yl-5-nitropyridine (1.20 g, 3.92 mmol) synthesized in Example 31 (i) was suspended in acetic acid (16 ml). The temperature was raised to 45° C. Sodium perborate (2.02 g, 11.75 mmol) was added to the suspension, and the reaction was carried out at 45° C. for 3 hours. The reaction was cooled, and the precipitated crystals were filtered and purified by column chromatography to give the title compound (1.21 g, 91.2%).

(ii) 6-(5,5-Dioxo-5H-5λ$^6$-dibenzothiophene-4-yl)pyridine-3-ylamine

The title compound was obtained in a manner analogous to Example 7 (ii), except for replacing 2-phenyl-5-nitropyridine with 2-(5,5-dioxo-5H-5λ$^6$-dibenzothiophene-4-yl)-5-nitropyridine obtained in (i).

(iii) 4-Amino-3-[6-(5,5-dioxo-5H-5λ$^6$-dibenzothiophene-4-yl)pyridine-3-ylazo]naphthalene-1-sulfonic acid sodium salt The title compound was obtained in a manner analogous to Example 7 (iii), except for replacing 2-phenyl-5-aminopyridine with 6-(5,5-dioxo-5H-5λ$^6$-dibenzothiophene-4-yl)pyridine-3-ylamine obtained in (ii).
$^1$H-NMR (DMSO-d6) δ [ppm]=9.30 (1H, s), 8.76 (1H, d, J=8.4 Hz), 8.58 (1H, d, J=8.4 Hz), 8.48 (1H, d, J=8.4 Hz), 8.33 (1H, s), 8.28-8.30 (2H, m), 8.24 (1H, d, J=7.8 Hz), 8.13 (1H, d, J=7.8 Hz), 7.89-7.96 (4H, m), 7.78-7.83 (1H, m), 7.59-7.69 (2H, m), 7.49-7.53 (1H, m)
$^{13}$C-NMR (DMSO-d6) δ [ppm]=152.4, 147.9, 147.7, 145.6, 137.7, 137.2, 134.7, 134.5, 134.3, 132.8, 132.6, 132.3, 131.3, 131.2, 129.9, 129.5, 128.7, 128.4, 127.7, 125.2, 124.2, 124.0, 123.7, 123.1, 122.5, 121.7, 116.4

Example 74

Synthesis of 4-amino-3-[6-(4,3',5'-trimethylbiphenyl-2-yl)pyridine-3-ylazo]naphthalene-1-sulfonic acid sodium salt

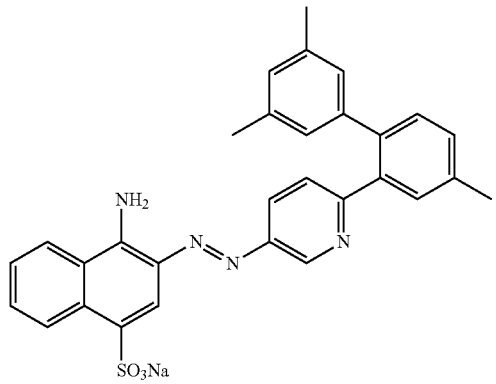

(i) (3,5-Dimethylphenyl)(2,4,6-trimethylphenyl)iodonium tetrafluoroborate

The title compound was obtained in a manner analogous to Example 72(ii), except for replacing 4-chlorophenylboronic acid with 3,5-dimethylphenylboronic acid.

(ii) 6-(4,3',5'-Trimethylbiphenyl-2-yl)pyridine-3-ylamine

The title compound was obtained in a manner analogous to Example 72 (iii), except for replacing (4-chlorophenyl)(2,4,6-trimethylphenyl)iodonium tetrafluoroborate with (3,5-dimethylphenyl)(2,4,6-trimethylphenyl)iodonium tetrafluoroborate obtained in (i).

(iii) 4-Amino-3-[6-(4,3',5'-trimethylbiphenyl-2-yl)pyridine-3-ylazo]naphthalene-1-sulfonic acid sodium salt The title compound was synthesized in a manner analogous to Example 7 (iii), except for replacing 2-phenyl-5-aminopyridine with 6-(4,3',5'-trimethylbiphenyl-2-yl)pyridine-3-ylamine obtained in (ii).

$^1$H-NMR (DMSO-d6) δ [ppm]=9.16 (1H, d, J=2.4), 8.72 (1H, d, J=8.4), 8.44 (1H, d, J=8.4), 8.27 (1H, s), 8.18 (1H, dd, J=8.4, 2.4), 7.69 (NH$_2$, s), 7.61-7.55 (2H, m), 7.50-7.45 (1H, m), 7.30 (2H, s), 6.99 (1H, d, J=8.4), 6.86 (1H, s), 6.73 (2H, s), 2.41 (3H, s), 2.15 (6H, s)

$^{13}$C-NMR (DMSO-d6) δ [ppm]=166.8, 158.9, 147.2, 146.5, 140.8, 138.4, 137.7, 137.2, 136.7, 132.4, 132.1, 131.0, 130.4, 129.4, 129.2, 128.5, 128.3, 128.2, 127.2, 125.4, 125.3, 125.1, 124.2, 123.9, 116.0, 20.9, 20.7

Example 75

Synthesis of 4-amino-3-[6-(3'-chloro-4-methylbiphenyl-2-yl)pyridine-3-ylazo]naphthalene-1-sulfonic acid sodium salt

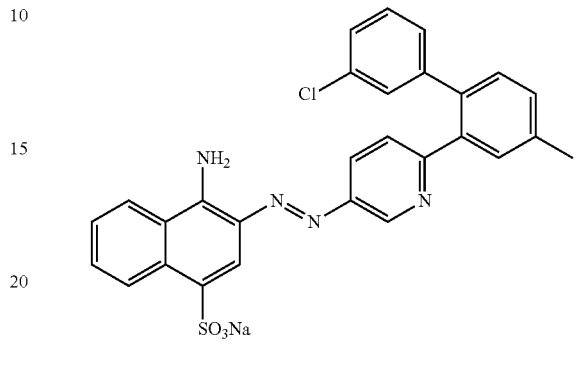

(i) (3-Chlorophenyl)(2,4,6-trimethylphenyl)iodonium tetrafluoroborate

The title compound was obtained in a manner analogous to Example 72(ii), except for replacing 4-chlorophenylboronic acid with 3-chlorophenylboronic acid.

(ii) 6-(3'-Chloro-4-methylbiphenyl-2-yl)pyridine-3-ylamine

The title compound was obtained in a manner analogous to Example 72 (iii), except for replacing (4-chlorophenyl)(2,4,6-trimethylphenyl)iodonium tetrafluoroborate with (3-chlorophenyl)(2,4,6-trimethylphenyl)iodonium tetrafluoroborate obtained in (i).

(iii) 4-Amino-3-[6-(3'-chloro-4-methylbiphenyl-2-yl)pyridine-3-ylazo]naphthalene-1-sulfonic acid sodium salt The title compound was synthesized in a manner analogous to Example 7 (iii), except for replacing 2-phenyl-5-aminopyridine with 6-(3'-chloro-4-methylbiphenyl-2-yl)pyridine-3-ylamine obtained in (ii).

$^1$H-NMR (DMSO-d6) δ [ppm]=9.12 (1H, d, J=2.4), 8.72 (1H, d, J=8.4), 8.45 (1H, d, J=8.4), 8.27 (1H, s), 8.24 (1H, dd, J=8.7, 2.4), 7.74 (NH$_2$, s), 7.61-7.55 (2H, m), 7.50-7.45 (1H, m), 7.36 (2H, s), 7.31-7.22 (3H, m), 7.00 (1H, d, J=6.6), 2.43 (3H, s)

$^{13}$C-NMR (DMSO-d6) δ [ppm]=166.9, 158.5, 147.3, 146.6, 146.3, 143.1, 138.6, 137.6, 136.0, 132.9, 132.4, 132.1, 131.1, 130.5, 130.0, 129.6, 129.2, 128.9, 128.5, 128.2, 126.7, 126.0, 125.4, 125.1, 124.2, 124.0, 116.1, 20.7

Example 76

Synthesis of 4-amino-3-(6-thianthrene-1-ylpyridine-3-ylazo)naphthalene-1-sulfonic acid sodium salt

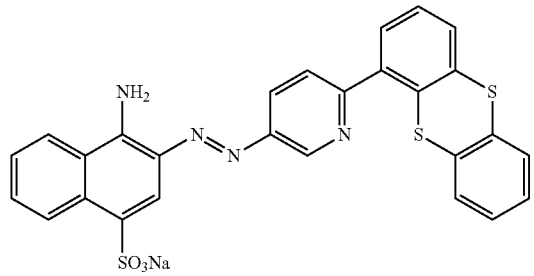

(i) 5-Nitro-2-thianthrene-1-ylpyridine

The title compound was synthesized in a manner analogous to Example 7 (i), except for replacing phenylboronic acid with thianthrene-1-ylboronic acid.

(ii) 6-Thianthrene-1-ylpyridine-3-ylamine

The title compound was synthesized in a manner analogous to Example 7 (ii), except for replacing 2-phenyl-5-nitropyridine with 5-nitro-2-thianthrene-1-ylpyridine obtained in (i).

(iii) 4-Amino-3-(6-thianthrene-1-ylpyridine-3-ylazo)naphthalene-1-sulfonic acid sodium salt The title compound was synthesized in a manner analogous to Example 31 (iii), except for replacing 6-dibenzothiophene-4-ylpyridine-3-ylamine with 6-thianthrene-1-ylpyridine-3-ylamine obtained in (ii).

$^1$H-NMR (DMSO-d6) δ [ppm]=9.29 (1H, d, J=2.4), 8.70 (1H, d, J=8.4), 8.50-8.44 (2H, m), 8.29 (1H, s), 7.86 (NH$_2$, s), 7.78 (1H, d, J=8.7), 7.64-7.18 (7H, m), 7.30-7.24 (1H, m), 7.21-7.16 (1H, m)

$^{13}$C-NMR (DMSO-d6) δ [ppm]=156.7, 147.4, 147.2, 144.4, 140.4, 135.7, 135.53, 135.50, 134.2, 132.4, 132.2, 129.6, 129.4, 129.2, 128.7, 128.6, 128.5, 128.3, 128.2, 128.1, 128.0, 127.5, 125.1, 124.2, 124.1, 116.5

Example 77

Synthesis of 4-amino-3-[6-(2-{3-[(2-chloropyridine-4-carbonyl)amino]propoxy}phenyl)pyridine-3-ylazo]naphthalene-1-sulfonic acid sodium salt

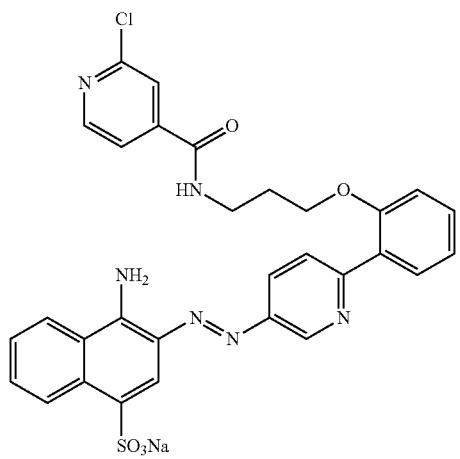

(i) N-(3-Bromopropyl)-2-chloroisonicotinamide

The title compound was synthesized in a manner analogous to Example 69 (i), except for replacing 2-chloronicotinic acid with 2-chloroisonicotinic acid.

(ii) 2-Chloro-N-{3-[2-(5-nitropyridine-2-yl)phenoxy]propyl}isonicotinamide 2-(5-Nitropyridine-2-yl)phenol (0.50 g, 2.3 mmol) synthesized in Example 63 (i) and N-(3-bromopropyl)-2-chloroisonicotinamide (0.77 g, 2.8 mmol) synthesized in (i) were charged, and added with potassium carbonate (0.48 g, 3.5 mmol). The reaction was carried out at 80° C. for 6 hours. The mixture was concentrated, added with acetonitrile, and concentrated to dryness after removing impurities. Purification by column chromatography gave the title compound (0.55 g, 57.9%).

(iii) N-{3-[2-(5-Aminopyridine-2-yl)phenoxy]propyl}-2-chloroisonicotinamide

The title compound was synthesized in a manner analogous to Example 7 (ii), except for replacing 2-phenyl-5-nitropyridine with 2-chloro-N-{3-[2-(5-nitropyridine-2-yl)phenoxy]propyl}isonicotinamide obtained in (ii).

(iv) 4-Amino-3-[6-(2-{3-[(2-chloropyridine-4-carbonyl)amino]propoxy}phenyl)pyridine-3-ylazo]naphthalene-1-sulfonic acid sodium salt The title compound was synthesized in a manner analogous to Example 7 (iii), except for replacing 2-phenyl-5-aminopyridine with N-{3-[2-(5-aminopyridine-2-yl)phenoxy]propyl}-2-chloroisonicotinamide obtained in (iii).

$^1$H-NMR (DMSO-d6) δ [ppm]=9.22 (1H, d, J=2.4), 8.99-8.96 (1H, m), 8.75 (1H, d, J=8.1), 8.52 (1H, d, J=5.1), 8.47-8.40 (2H, m), 8.31 (1H, s), 8.14 (1H, d, J=8.7), 7.89 (1H, dd, J=7.5, 1.8), 7.83 (1H, s), 7.76 (NH$_2$, s), 7.74 (1H, dd, J=5.1, 1.5), 7.62-7.57 (1H, m), 7.52-7.50 (1H, m), 7.41-7.38 (1H, m), 7.17 (1H, d, J=8.4), 7.11-7.06 (1H, m), 4.16 (2H, t, J=6.3), 3.51-3.45 (2H, m), 2.05-2.01 (2H, m)

$^{13}$C-NMR (DMSO-d6) δ [ppm]=163.4, 156.4, 155.3, 150.9, 150.7, 147.0, 146.7, 146.3, 145.0, 132.5, 132.1, 130.9, 130.5, 129.3, 128.5, 128.3, 127.7, 126.0, 125.2, 125.1, 124.2, 123.9, 122.0, 121.0, 120.7, 116.5, 112.8, 65.7, 38.7, 28.7

Example 78

Synthesis of 4-amino-3-(6-{2-[3-(1,3-dioxo-1,3-dihydroisoindole-2-yl)propoxy]phenyl}pyridine-3-ylazo)naphthalene-1-sulfonic acid sodium salt

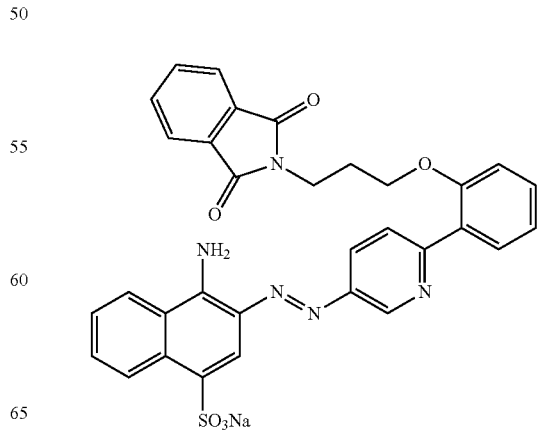

(i) 2-{3-[2-(5-Nitropyridine-2-yl)phenoxy]propyl}isoindole-1,3-dione 2-(5-Nitropyridine-2-yl)phenol (0.80 g, 3.7 mmol) synthesized in Example 63 (i), 3-bromopropylphthalimide (1.5 g, 4.4 mmol) and potassium carbonate (1.02 g, 7.4 mmol) were dissolved in acetonitrile (25 ml) and reacted at 80° C. for 4 hours. The mixture was cooled, added with water, and extracted with methylene chloride. The organic layer was dried with anhydrous sodium sulfate, and concentrated to dryness under reduced pressure. Purification by column chromatography gave the title compound (1.45 g, 97.1%).

(ii) 2-{3-[2-(5-Aminopyridine-2-yl)phenoxy]propyl}isoindole-1,3-dione

The title compound was synthesized in a manner analogous to Example 7 (ii), except for replacing 2-phenyl-5-nitropyridine with 2-{3-[2-(5-nitropyridine-2-yl)phenoxy]propyl}isoindole-1,3-dione obtained in (i).

(iii) 4-Amino-3-(6-{2-[3-(1,3-dioxo-1,3-dihydroisoindole-2-yl)propoxy]phenyl}pyridine-3-ylazo)naphthalene-1-sulfonic acid sodium salt The title compound was synthesized in a manner analogous to Example 7 (iii), except for replacing 2-phenyl-5-aminopyridine with 2-{3-[2-(5-aminopyridine-2-yl)phenoxy]propyl}isoindole-1,3-dione obtained in (ii).

$^1$H-NMR (DMSO-d6) δ [ppm]=9.15 (1H, d, J=2.4), 8.75 (1H, d, J=8.0), 8.46 (1H, d, J=8.1), 8.35-8.31 (2H, m), 8.16 (1H, d, J=8.7), 7.87 (1H, dd, J=7.5, 1.8), 7.80-7.73 (6H, m), 7.63-7.58 (1H, m), 7.53-7.48 (1H, m), 7.42-7.36 (1H, m), 7.12-7.05 (2H, m)

$^{13}$C-NMR (DMSO-d6) δ [ppm]=168.1, 156.3, 155.1, 146.9, 146.6, 146.1, 134.3, 132.5, 132.1, 131.7, 130.9, 130.5, 129.3, 128.5, 128.4, 127.7, 126.1, 125.1, 124.2, 124.0, 123.0, 120.7, 116.6, 112.6, 100.2, 65.9, 35.2, 28.0

Example 79

Synthesis of 4-amino-3-[6-(4-fluoro-2-methylphenyl)-5-methylpyridine-3-ylazo]naphthalene-1-sulfonic acid sodium salt

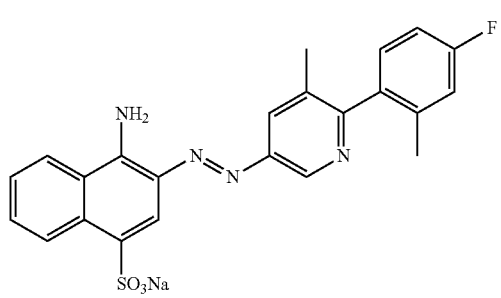

(i) 2-(4-Fluoro-2-methylphenyl)-3-methyl-5-nitropyridine

The title compound was synthesized in a manner analogous to Example 7 (i), except for replacing 2-chloro-5-nitropyridine with 2-chloro-3-methyl-5-nitropyridine and replacing phenylboronic acid with 4-fluoro-2-methylphenylboronic acid.

(ii) 6-(4-Fluoro-2-methylphenyl)-5-methylpyridine-3-ylamine

The title compound was synthesized in a manner analogous to Example 7 (ii), except for replacing 2-phenyl-5-nitropyridine with 2-(4-fluoro-2-methylphenyl)-3-methyl-5-nitropyridine obtained in (i).

(iii) 4-Amino-3-[6-(4-fluoro-2-methylphenyl)-5-methylpyridine-3-ylazo]naphthalene-1-sulfonic acid sodium salt The title compound was synthesized in a manner analogous to Example 7 (iii), except for replacing 2-phenyl-5-aminopyridine with 6-(4-fluoro-2-methylphenyl)-5-methylpyridine-3-ylamine obtained in (ii).

$^1$H-NMR (DMSO-d6) δ [ppm]=9.02 (1H, d, J=2.1 Hz), 8.73 (1H, d, J=8.4 Hz), 8.50 (1H, d, J=8.4 Hz), 8.37 (1H, d, J=2.1 Hz), 8.31 (1H, s), 7.83 (2H, bs), 7.57-7.63 (1H, m), 7.47-7.52 (1H, m), 7.07-7.29 (3H, m), 2.15 (3H, s), 2.07 (3H, s)

$^{13}$C-NMR (DMSO-d6) δ [ppm]=163.2, 160.0, 158.4, 147.4, 147.1, 143.3, 138.5, 138.4, 136.3, 136.3, 132.4, 132.2, 132.1, 130.7, 130.6, 129.1, 128.6, 128.3, 128.1, 125.1, 124.3, 124.1, 116.7, 116.6, 116.5, 112.6, 112.3, 19.3, 19.3

Example 80

Synthesis of 4-amino-3-{6-"3-(pyridine-3-ylmethoxy)dibenzothiophene-4-yl]pyridine-3-ylazo}naphthalene-1-sulfonic acid sodium salt

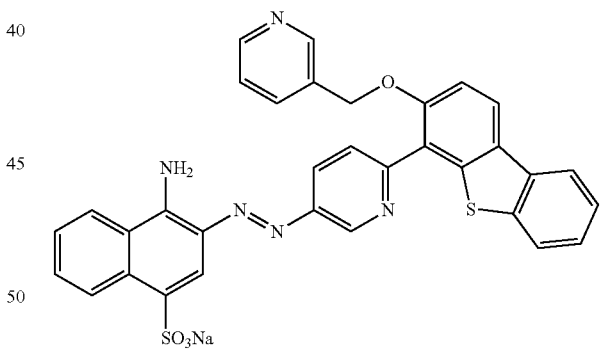

(i) 4-(5-Nitropyridine-2-yl)dibenzothiophene-3-ol

To toluene (6.1 ml) and acetic anhydride (6.1 ml), 2-dibenzothiophene-4-yl-5-nitropyridine (0.62 g, 2.0 mmol), diacetoxyiodobenzene (0.72 g, 2.2 mmol) and palladium acetate (0.02 g, 0.1 mmol) were added, and reacted under air atmosphere at 100° C. for 1 hour. The solvent was distilled off under reduced pressure. Purification by column chromatography resulted in yellow crystals. The crystals were dissolved in methanol, added with a 30% aqueous solution of sodium hydroxide, and the hydrolysis was carried out at room temperature for 2 hours. Methanol was distilled off under reduced pressure. The mixture was added with water and neutralized with 35% hydrochloric acid. The precipitated crystals were filtered to give the title compound (0.47 g, 64%).

(ii) 3-[4-(5-Nitropyridine-2-yl)dibenzothiophene-3-yloxymethyl]pyridine

To acetonitrile (5.0 ml) and N,N-dimethylformamide (5.0 ml), 4-(5-nitropyridine-2-yl)dibenzothiophene-3-ol (0.50 g, 1.6 mmol) obtained in (i), 3-chloromethylpyridine hydrochloride (0.28 g, 1.7 mmol), potassium carbonate (0.43 g, 3.1 mmol) and a catalytic amount of potassium iodide were added, and reacted at 70° C. for 8 hours. The mixture was concentrated under reduced pressure and purified by column chromatography to give the title compound (0.44 g, 66.5%).

(iii) 6-[3-(Pyridine-3-ylmethoxy)dibenzothiophene-4-yl]pyridine-3-ylamine

The title compound was synthesized in a manner analogous to Example 7 (ii), except for replacing 2-phenyl-5-nitropyridine with 3-[4-(5-nitropyridine-2-yl)dibenzothiophene-3-yloxymethyl]pyridine obtained in (ii).

(iv) 4-Amino-3-{6-"3-(pyridine-3-ylmethoxy)dibenzothiophene-4-yl]pyridine-3-ylazo}naphthalene-1-sulfonic acid sodium salt The title compound was synthesized in a manner analogous to Example 7 (iii), except for replacing 2-phenyl-5-aminopyridine with 6-[3-(pyridine-3-ylmethoxy)dibenzothiophene-4-yl]pyridine-3-ylamine obtained in (iii).

$^1$H-NMR (DMSO-d6) δ [ppm]=9.34 (1H, s), 8.77 (1H, d, J=8.4 Hz), 8.72 (1H, s), 8.41-8.55 (4H, m), 8.36 (1H, s), 8.30 (1H, d, J=6.9 Hz), 8.22 (1H, d, J=8.4 Hz), 7.92-7.96 (2H, m), 7.88 (2H, bs), 7.41-7.64 (6H, m), 5.43 (2H, s)

$^{13}$C-NMR (DMSO-d6) δ [ppm]=155.3, 153.9, 149.3, 149.0, 147.4, 146.8, 144.8, 140.3, 140.0, 135.7, 134.5, 132.3, 132.2, 130.1, 129.3, 128.6, 128.3, 126.7, 126.1, 126.1, 125.1, 124.5, 124.2, 124.1, 123.7, 123.3, 122.4, 121.9, 121.2, 116.5, 112.1, 68.6

Example 81

Synthesis of 4-amino-3-[6-(3-{3-[(2-chloropyridine-3-carbonyl)amino]propoxy}dibenzothiophene-4-yl)pyridine-3-ylazo]naphthalene-1-sulfonic acid sodium salt

(i) 2-Chloro-N-{3-[4-(5-nitropyridine-2-yl)dibenzothiophene-3-yloxy]propyl}nicotinamide 4-(5-Nitropyridine-2-yl)dibenzothiophene-3-ol (0.50 g, 1.6 mmol) synthesized in Example 80 (i), N-(3-bromopropyl)-2-chloronicotinamide (0.52 g, 1.9 mmol) synthesized in Example 69 (i), potassium carbonate (0.43 g, 3.1 mmol), and tetrahydrofuran (25 ml) were charged, and reacted at 70° C. for 6 hours. The mixture was extracted with addition of water and methylene chloride. The organic layer was dried with anhydrous sodium sulfate, and concentrated to dryness under reduced pressure. Purification by column chromatography and recrystallization gave the title compound (0.66 g, 79.5%).

(ii) N-{3-[4-(5-Aminopyridine-2-yl)dibenzothiophene-3-yloxy]propyl}-2-chloronicotinamide The title compound was synthesized in a manner analogous to Example, except for replacing 7 (ii), 2-phenyl-5-nitropyridine with 2-chloro-N-{3-[4-(5-nitropyridine-2-yl)dibenzothiophene-3-yloxy]propyl}nicotinamide obtained in (i).

(iii) 4-Amino-3-[6-(3-{3-[(2-chloropyridine-3-carbonyl)amino]propoxy}dibenzothiophene-4-yl)pyridine-3-ylazo]naphthalene-1-sulfonic acid sodium salt The title compound was synthesized in a manner analogous to Example 7 (iii), except for replacing 2-phenyl-5-aminopyridine with N-{3-[4-(5-aminopyridine-2-yl)dibenzothiophene-3-yloxy]propyl}-2-chloronicotinamide obtained in (ii).

$^1$H-NMR (DMSO-d6) δ [ppm]=9.36 (1H, d, J=2.1 Hz), 8.75-8.77 (2H, m), 8.28-8.55 (7H, m), 7.84-7.96 (4H, m), 7.40-7.64 (6H, m), 4.34 (2H, t, J=5.6 Hz), 3.45-3.49 (2H, m), 2.08 (2H, t, J=5.9 Hz)

$^{13}$C-NMR (DMSO-d6) δ [ppm]=165.3, 155.9, 154.1, 150.2, 147.2, 146.8, 146.5, 144.6, 250.3, 140.0, 138.1, 134.5, 133.3, 132.6, 132.2, 129.7, 129.4, 128.6, 128.3, 126.7, 126.2, 126.0, 125.1, 124.5, 124.2, 124.0, 123.3, 123.1, 122.4, 121.4, 121.1, 116.5, 111.4, 66.6, 36.0, 28.8

Example 82

Synthesis of 4-amino-3-{6-[3-(3-hydroxypropoxy)dibenzothiophene-4-yl]pyridine-3-ylazo}naphthalene-1-sulfonic acid sodium salt

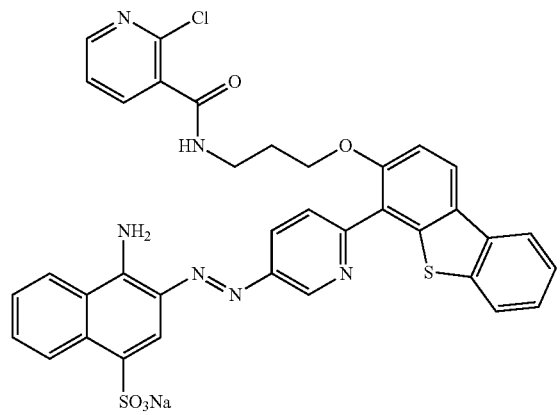

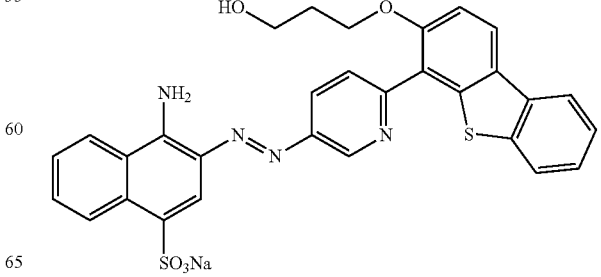

(i) 3-[4-(5-Nitropyridine-2-yl)dibenzothiophene-3-yloxy]propane-1-ol

To a solution of 4-(5-nitropyridine-2-yl)dibenzothiophene-3-ol (0.50 g, 1.6 mmol) synthesized in Example 80 (i), 3-bromo-1-propanol (0.26 g, 1.9 mmol) and potassium carbonate (0.43 g, 3.1 mmol) in acetonitrile (10 ml), potassium iodide (0.01 g, 0.08 mmol) was added, and the reaction was carried out at 80° C. for 4 hours. After the mixture was cooled, crystallized with addition of water and filtered, the crystals were purified by column chromatography to give the title compound (0.43 g, 70.6%).

(ii) 3-[4-(5-Aminopyridine-2-yl)dibenzothiophene-3-yloxy]propane-1-ol

The title compound was synthesized in a manner analogous to Example 7 (ii), except for replacing 2-phenyl-5-nitropyridine with 3-[4-(5-nitropyridine-2-yl)dibenzothiophene-3-yloxy]propane-1-ol obtained in (i).

(iii) 4-Amino-3-{6-[3-(3-hydroxypropoxy)dibenzothiophene-4-yl]pyridine-3-ylazo}naphthalene-1-sulfonic acid sodium salt The title compound was synthesized in a manner analogous to Example 7 (iii), except for replacing 2-phenyl-5-aminopyridine with 3-[4-(5-aminopyridine-2-yl)dibenzothiophene-3-yloxy]propane-1-ol obtained in (ii).

$^1$H-NMR (DMSO-d6) δ [ppm]=9.35 (1H, s), 8.77 (1H, d, J=8.7 Hz), 8.53 (1H, d, J=8.7 Hz), 8.47 (1H, d, J=8.7 Hz), 8.40 (1H, d, J=8.7 Hz), 8.34 (1H, s), 8.26-8.29 (2H, m), 7.95 (1H, d, J=6.9 Hz), 7.80 (2H, bs), 7.58-7.63 (1H, m), 7.40-7.53 (4H, m), 4.61 (1H, bs), 4.32 (2H, t, J=6.0 Hz), 3.60-3.70 (2H, m), 1.96 (2H, t, J=6.0 Hz)

$^{13}$C-NMR (DMSO-d6) δ [ppm]=156.0, 154.0, 147.1, 146.7, 144.5, 140.2, 140.1, 134.5, 132.7, 132.2, 129.6, 129.4, 128.4, 128.4, 126.5, 125.9, 125.9, 125.0, 124.4, 124.2, 123.9, 123.2, 122.3, 121.3, 120.9, 116.4, 111.4, 66.3, 62.0, 32.2

Example 83

Synthesis of 4-amino-3-(6-quinoline-8-ylpyridine-3-ylazo)naphthalene-1-sulfonic acid sodium salt

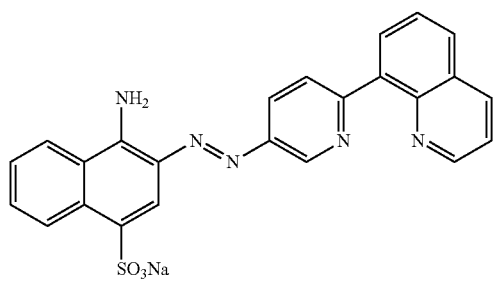

(i) 8-(5-Nitropyridine-2-yl)quinoline

The title compound was synthesized in a manner analogous to Example 7 (i), except for replacing phenylboronic acid with quinoline-8-boronic acid.

(ii) 6-Quinoline-8-ylpyridine-3-ylamine

The title compound was synthesized in a manner analogous to Example 7 (ii), except for replacing 2-phenyl-5-nitropyridine with 8-(5-nitropyridine-2-yl)quinoline obtained in (i).

(iii) 4-Amino-3-(6-quinoline-8-ylpyridine-3-ylazo)naphthalene-1-sulfonic acid sodium salt The title compound was synthesized in a manner analogous to Example 7 (iii), except for replacing 2-phenyl-5-aminopyridine with 6-quinoline-8-ylpyridine-3-ylamine obtained in (ii).

$^1$H-NMR (DMSO-d6) δ [ppm]=9.30 (1H, d, J=2.1 Hz), 8.99 (1H, dd, J=4.2, 1.8 Hz), 8.77 (1H, dd, J=8.4, 0.9 Hz), 8.46-8.50 (3H, m), 8.38 (1H, d, J=8.4 Hz), 8.36 (1H, s), 8.29 (1H, dd, J=7.5, 1.2 Hz), 8.10 (1H, dd, J=8.1, 1.5 Hz), 7.80 (2H, bs), 7.74-7.79 (1H, m), 7.59-7.63 (2H, m), 7.48-7.53 (1H, m)

$^{13}$C-NMR (DMSO-d6) δ [ppm]=156.3, 150.6, 147.1, 147.0, 145.8, 145.2, 137.4, 136.8, 132.5, 132.1, 131.1, 129.5, 129.3, 128.5, 128.4, 128.3, 127.6, 126.5, 125.9, 125.1, 124.2, 123.9, 121.6, 116.5

Example 84

Synthesis of 4-amino-3-[6-(2-methylquinoline-8-yl)pyridine-3-ylazo]naphthalene-1-sulfonic acid sodium salt

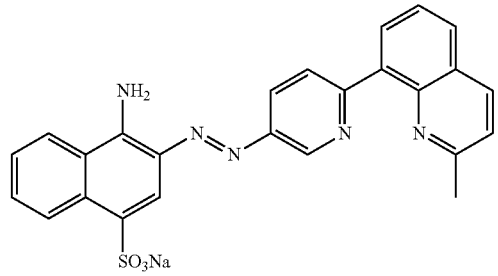

(i) 2-Methyl-8-(5-nitropyridine-2-yl)quinoline

The title compound was synthesized in a manner analogous to Example 7 (i), except for replacing phenylboronic acid with 2-methylquinoline-8-boronic acid.

(ii) 6-(2-Methylquinoline-8-yl)pyridine-3-ylamine

The title compound was synthesized in a manner analogous to Example 7 (ii), except for replacing 2-phenyl-5-nitropyridine with 2-methyl-8-(5-nitropyridine-2-yl)quinoline obtained in (i).

(iii) 4-Amino-3-[6-(2-methylquinoline-8-yl)pyridine-3-ylazo]naphthalene-1-sulfonic acid sodium salt The title compound was synthesized in a manner analogous to Example 7 (iii), except for replacing 2-phenyl-5-aminopyridine with 6-(2-methylquinoline-8-yl)pyridine-3-ylamine obtained in (ii).

¹H-NMR (DMSO-d6) δ [ppm]=9.23 (1H, s), 8.71 (1H, d, J=8.7 Hz), 8.28-8.41 (3H, m), 8.28-8.31 (2H, m), 8.22 (1H, d, J=6.9 Hz), 7.97 (1H, d, J=8.1 Hz), 7.74 (2H, bs), 7.53-7.65 (2H, m), 7.42-7.48 (2H, m), 2.62 (3H, s)

¹³C-NMR (DMSO-d6) δ [ppm]=158.9, 156.4, 147.1, 147.1, 146.3, 144.6, 136.9, 136.4, 132.4, 132.1, 131.1, 129.3, 129.2, 128.5, 125.3, 127.6, 126.7, 125.5, 125.3, 125.1, 124.2, 124.0, 122.2, 116.4, 25.3

Example 85

Synthesis of 4-amino-3-(6-dibenzothiophene-4-yl-5-methylpyridine-3-ylazo)naphthalene-1-sulfonic acid sodium salt

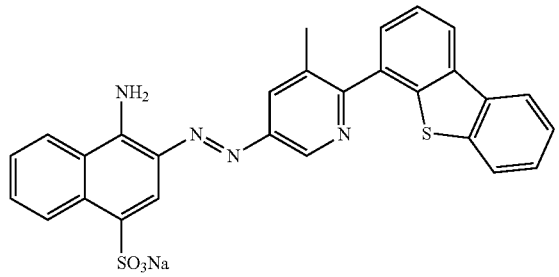

(i) 2-Dibenzothiophene-4-yl-3-methyl-5-nitropyridine

The title compound was synthesized in a manner analogous to Example 7 (i), except for replacing 2-chloro-5-nitropyridine with 2-bromo-3-methyl-5-nitropyridine, and replacing phenylboronic acid with 4-dibenzothiopheneboronic acid.

(ii) 6-Dibenzothiophene-4-yl-5-methylpyridine-3-ylamine

The title compound was synthesized in a manner analogous to Example 7 (ii), except for replacing 2-phenyl-5-nitropyridine with 2-dibenzothiophene-4-yl-3-methyl-5-nitropyridine obtained in (i).

(iii) 4-Amino-3-(6-dibenzothiophene-4-yl-5-methylpyridine-3-ylazo)naphthalene-1-sulfonic acid sodium salt The title compound was synthesized in a manner analogous to Example 31 (iii), except for replacing 6-dibenzothiophene-4-ylpyridine-3-ylamine with 6-dibenzothiophene-4-yl-5-methylpyridine-3-ylamine obtained in (ii).

¹H-NMR (DMSO-d6) δ [ppm]=9.11 (1H, d, J=2.1 Hz), 8.71 (1H, d, J=8.1 Hz), 8.35-8.44 (4H, m), 8.29 (1H, s), 7.91-7.95 (1H, m), 7.77 (2H, bs), 7.54-7.69 (3H, m), 7.44-7.48 (3H, m)

¹³C-NMR (DMSO-d6) δ [ppm]=156.4, 147.5, 147.3, 143.0, 139.5, 138.5, 135.9, 134.9, 134.3, 132.6, 132.4, 132.2, 129.5, 129.4, 128.6, 128.4, 127.5, 127.2, 125.1, 124.7, 124.2, 124.0, 122.8, 122.2, 121.8, 116.3, 19.6

Example 86

Synthesis of 4-amino-3-(6-biphenyl-2-yl-5-methyl-pyridine-3-ylazo)naphthalene-1-sulfonic acid sodium salt

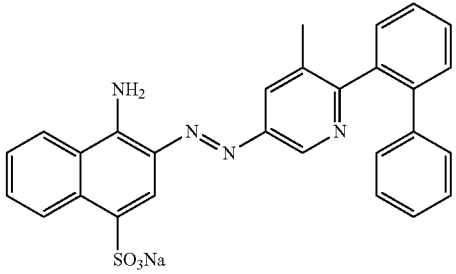

(i) 2-Biphenyl-2-yl-3-methyl-5-nitropyridine

The title compound was synthesized in a manner analogous to Example 7 (i), except for replacing 2-chloro-5-nitropyridine with 2-bromo-3-methyl-5-nitropyridine, and replacing phenylboronic acid with 2-biphenylboronic acid.

(ii) 6-Biphenyl-2-yl-5-methylpyridine-3-ylamine

The title compound was synthesized in a manner analogous to Example 7 (ii), except for replacing 2-phenyl-5-nitropyridine with 2-biphenyl-2-yl-3-methyl-5-nitropyridine obtained in (i).

(iii) 4-Amino-3-(6-biphenyl-2-yl-5-methylpyridine-3-ylazo)naphthalene-1-sulfonic acid sodium salt The title compound was synthesized in a manner analogous to Example 12 (iii), except for replacing 6-biphenyl-2-ylpyridine-3-ylamine with 6-biphenyl-2-yl-5-methylpyridine-3-ylamine obtained in (ii).

¹H-NMR (DMSO-d6) δ [ppm]=9.01 (1H, d, J=2.1 Hz), 8.74 (1H, d, J=8.4 Hz), 8.44 (1H, d, J=8.1 Hz), 8.23 (1H, s), 8.10 (1H, d, J=2.1 Hz), 7.71 (2H, bs), 7.41-7.62 (6H, m), 7.10-7.24 (5H, m), 1.84 (3H, s)

¹³C-NMR (DMSO-d6) δ [ppm]=159.5, 147.1, 146.9, 143.4, 140.6, 140.2, 139.0, 132.5, 132.1, 131.9, 130.0, 129.6, 129.1, 128.8, 128.6, 128.4, 128.3, 128.1, 127.5, 127.4, 127.0, 125.0, 124.2, 123.9, 116.4, 18.6

Example 87

Synthesis of 4-amino-3-(6-methoxy-5-phenylpyridine-3-ylazo)naphthalene-1-sulfonic acid sodium salt

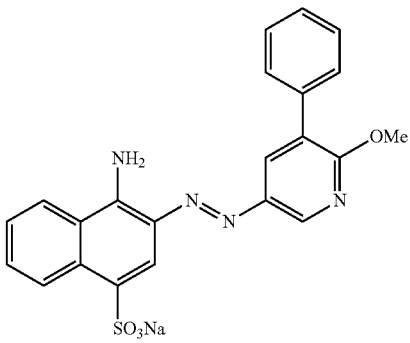

(i) 3-Iodo-2-methoxy-5-nitropyridine

To acetone (19 ml), 2-hydroxy-3-iodo-5-nitropyridine (1.0 g, 3.76 mmol), methyl iodide (0.58 g, 4.14 mmol) and potassium carbonate (1.0 g, 7.52 mmol) were added, and reacted at 60° C. for 3 hours. The mixture was cooled to room temperature and crystallized (-out) with addition of water. The precipitated crystals were filtered to give the title compound (0.88 g, 83.5%).

(ii) 2-Methoxy-5-nitro-3-phenylpyridine

The title compound was synthesized in a manner analogous to Example 7 (i), except for replacing 2-chloro-5-nitropyridine with 3-iodo-2-methoxy-5-nitropyridine synthesized in (i).

(iii) 6-Methoxy-5-phenylpyridine-3-ylamine

To methanol (50 ml), 2-methoxy-5-nitro-3-phenylpyridine (0.80 g, 3.47 mmol) obtained in (ii) and 10% palladium carbon (0.06 g) were added, and reduced at 40° C. under 0.7 MPa of hydrogen pressure. The palladium catalysts were filtered off through Celite, and the filtrate was concentrated to dryness under reduced pressure. Purification by recrystallization gave the title compound (0.60 g, 86.4%).

(iv) 4-Amino-3-(6-methoxy-5-phenylpyridine-3-ylazo)naphthalene-1-sulfonic acid sodium salt The title compound was synthesized in a manner analogous to Example 7 (iii), except for replacing 4-amino-1-naphthalenesulfonic acid with 6-methoxy-5-phenylpyridine-3-ylamine synthesized in (iii).

$^1$H-NMR (DMSO-d6) δ [ppm]=8.67 (1H, dd, J=8.4, 0.9 Hz), 8.622 (1H, d, J=2.4 Hz), 8.43 (1H, d, J=2.7 Hz), 8.32 (1H, d, J=8.1 Hz), 8.23 (1H, s), 7.69-7.72 (2H, m), 7.27-7.50 (5H, m), 7.19 (2H, bs), 3.60 (3H, s)

$^{13}$C-NMR (DMSO-d6) δ [ppm]=160.9, 145.3, 140.3, 136.6, 135.6, 132.2, 131.3, 129.6, 129.0, 128.7, 128.2, 128.0, 127.9, 127.6, 127.4, 124.6, 124.2, 123.5, 115.7, 37.8

Example 88

Synthesis of 4-amino-3-(6-chloro-5-phenylpyridine-3-ylazo)naphthalene-1-sulfonic acid sodium salt

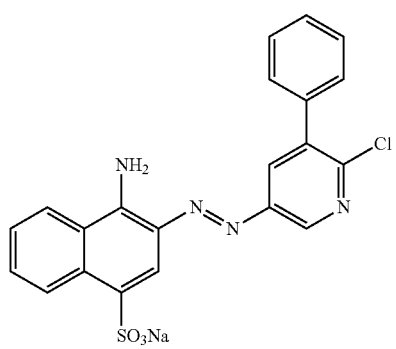

(i) 2-Chloro-3-iodo-5-nitropyridine

2-Hydroxy-3-iodo-5-nitropyridine (1.0 g, 3.76 mmol) and phosphorus oxychloride (3.5 g, 11.28 mmol) were charge, and the temperature was raised to 80° C. The reaction was carried out at 80° C. for 3 hours and the mixture was poured into ice water. The precipitated crystals were filtered to give the title compound (1.01 g, 94.4%).

(ii) 2-Chloro-5-nitro-3-phenylpyridine

The title compound was synthesized in a manner analogous to Example 7 (i), except for replacing 2-chloro-5-nitropyridine with 2-chloro-3-iodo-5-nitropyridine synthesized in (i).

(iii) 6-Chloro-5-phenylpyridine-3-ylamine

The title compound was synthesized in a manner analogous to Example 7 (ii), except for replacing 2-phenyl-5-nitropyridine with 2-chloro-5-nitro-3-phenylpyridine obtained in (ii).

(iv) 4-Amino-3-(6-chloro-5-phenylpyridine-3-ylazo)naphthalene-1-sulfonic acid sodium salt The title compound was synthesized in a manner analogous to Example 7 (iii), except for replacing 2-phenyl-5-aminopyridine with 6-chloro-5-phenylpyridine-3-ylamine obtained in (iii).

$^1$H-NMR (DMSO-d6) δ [ppm]=9.00 (1H, d, J=2.4 Hz), 8.74 (1H, d, J=8.1 Hz), 8.49 (1H, d, J=2.7 Hz), 8.45 (1H, d, J=8.4 Hz), 8.29 (1H, s), 7.81 (2H, bs), 7.45-7.63 (7H, m)

$^{13}$C-NMR (DMSO-d6) δ [ppm]=147.8, 147.6, 145.2, 137.0, 136.9, 132.6, 132.3, 129.6, 129.5, 129.4, 128.7, 128.3, 125.1, 124.2, 124.0, 116.0

Example 89

Synthesis of 4-amino-3-(5,6-diphenylpyridine-3-ylazo)naphthalene-1-sulfonic acid sodium salt

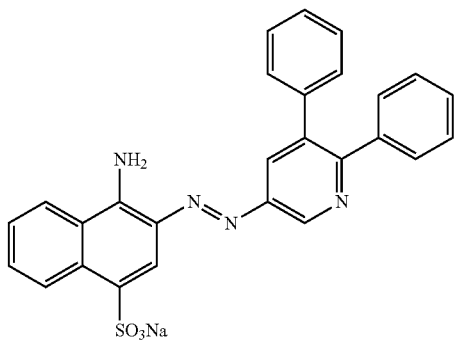

(i) 5-Nitro-2,3-diphenylpyridine

2-Chloro-3-iodo-5-nitropyridine (0.50 g, 1.76 mmol) synthesized in Example 88 (i), phenylboronic acid (0.45 g, 3.52 mmol), and bis(di-tert-butyl(4-dimethylaminophenylphosphine)dichloropalladium(II) (0.012 g, 0.02 mmol) were added to 1,2-dimethoxyethan (9 ml), degassed and purged with nitrogen three times under reduced pressure. Under nitrogen atmosphere the mixture was stirred at room temperature for 30 minutes, 1M aqueous sodium carbonate (9 ml) was poured in, and the temperature was raised to 80° C. After the reaction at 80° C. for 23 hours, the mixture was cooled to room temperature and crystallized with addition of water. The precipitated crystals were filtered to give the title compound (0.45 g, 92.5%).

(ii) 5,6-Diphenylpyridine-3-ylamine

The title compound was synthesized in a manner analogous to Example 87 (iii), except for replacing 2-methoxy-5-nitro-3-phenylpyridine with 5-nitro-2,3-diphenylpyridine synthesized in (i).

(iii) 4-Amino-3-(5,6-diphenylpyridine-3-ylazo)naphthalene-1-sulfonic acid sodium salt The title compound was synthesized in a manner analogous to Example 7 (iii), except for replacing 2-phenyl-5-aminopyridine with 5,6-diphenylpyridine-3-ylamine obtained in (ii).

$^1$H-NMR (DMSO-d6) δ [ppm]=9.23 (1H, d, J=2.4 Hz), 8.75 (1H, d, J=8.1 Hz), 8.46 (1H, d, J=8.1 Hz), 8.38 (1H, d, J=2.4 Hz), 8.32 (1H, s), 7.79 (2H, bs), 7.58-7.63 (1H, m), 7.47-7.52 (1H, m), 7.22-7.37 (10H, m)

$^{13}$C-NMR (DMSO-d6) δ [ppm]=156.2, 147.1, 147.0, 144.9, 139.7, 139.3, 136.2, 132.5, 132.1, 129.8, 129.6, 129.5, 128.5, 128.4, 128.2, 127.9, 127.7, 127.4, 125.0, 124.2, 123.9, 116.5

Example 90

Synthesis of 4-amino-3-[6-(2,6-dimethylphenyl)pyridine-3-ylazo]naphthalene-1-sulfonic acid sodium salt

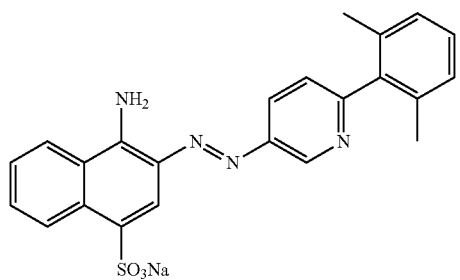

(i) 2-(2,6-Dimethylphenyl)-5-nitropyridine

2-Chloro-5-nitropyridine (1.0 g, 6.31 mmol), 2,6-dimethylphenylboronic acid (1.42 g, 9.47 mmol) and bis(di-tert-butyl(4-dimethylaminophenylphosphine)dichloropalladium (II) (0.044 g, 0.062 mmol) were added to 1,2-dimethoxyethan (32 ml), degassed and purged with nitrogen three times under reduced pressure.

Under nitrogen atmosphere the mixture was stirred at room temperature for 30 minutes, 1M aqueous sodium carbonate (12 ml) was poured in, and the temperature was raised to 80° C. After the reaction at 80° C. for 3 hours, the mixture was cooled to room temperature and extracted with addition of ethyl acetate and water. The organic layer was dried with anhydrous sodium sulfate and concentrated under reduced pressure. Purification by column chromatography gave the title compound (1.41 g, 98.1%).

(ii) 6-(2,6-Dimethylphenyl)pyridine-3-ylamine

The title compound was synthesized in a manner analogous to Example 7 (ii), except for replacing 2-phenyl-5-nitropyridine with 2-(2,6-dimethylphenyl)-5-nitropyridine obtained in (i).

(iii) 4-Amino-3-[6-(2,6-dimethylphenyl)pyridine-3-ylazo]naphthalene-1-sulfonic acid sodium salt The title compound was synthesized in a manner analogous to Example 7 (iii), except for replacing 2-phenyl-5-aminopyridine with 6-(2,6-dimethylphenyl)pyridine-3-ylamine obtained in (ii).

$^1$H-NMR (DMSO-d6) δ [ppm]=9.24 (1H, d, J=2.1 Hz), 8.76 (1H, dd, J=8.6, 0.9 Hz), 8.44-8.48 (2H, m), 8.33 (1H, s), 7.80 (2H, bs), 7.58-7.63 (1H, m), 7.47-7.53 (1H, m), 7.45 (1H, dd, J=8.4, 0.6 Hz), 7.13-7.24 (3H, m), 2.04 (6H, s)

$^{13}$C-NMR (DMSO-d6) δ [ppm]=159.3, 147.0, 146.7, 145.7, 140.2, 135.3, 132.4, 132.1, 129.2, 128.5, 128.3, 127.8, 127.4, 127.2, 125.0, 124.2, 123.9, 116.6, 20.0

Example 91

Synthesis of 4-amino-3-[6-(3-formyl-2-isopropoxy-5-methylphenyl)pyridine-3-ylazo]naphthalene-1-sulfonic acid sodium salt

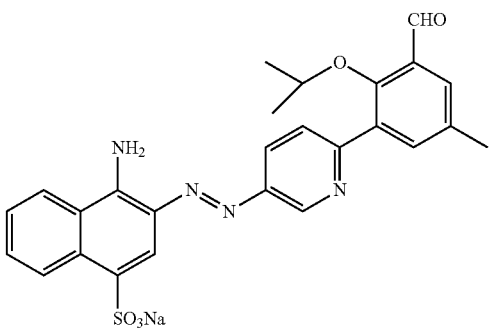

(i) 2-Isopropoxy-5-methyl-3-(5-nitropyridine-2-yl)benzaldehyde

The title compound was synthesized in a manner analogous to Example 89 (i), except for replacing 2-chloro-3-iodo-5-nitropyridine with 2-chloro-5-nitropyridine, and replacing phenylboronic acid with 3-formyl-2-isopropoxy-5-methylphenylboronic acid.

(ii) 3-(5-Aminopyridine-2-yl)-2-isopropoxy-5-methylbenzaldehyde

The title compound was synthesized in a manner analogous to Example 7 (ii), except for replacing 2-phenyl-5-nitropyridine with 2-isopropoxy-5-methyl-3-(5-nitropyridine-2-yl)benzaldehyde obtained in (i).

(iii) 4-Amino-3-[6-(3-formyl-2-isopropoxy-5-methylphenyl)pyridine-3-ylazo]naphthalene-1-sulfonic acid sodium salt The title compound was synthesized in a manner analogous to Example 7 (iii), except for replacing 2-phenyl-5-aminopyridine with 3-(5-aminopyridine-2-yl)-2-isopropoxy-5-methylbenzaldehyde obtained in (ii).

$^1$H-NMR (DMSO-d6) δ [ppm]=10.39 (1H, s), 9.27 (1H, d, J=2.4 Hz), 8.75 (1H, d, J=8.4 Hz), 8.52 (1H, dd, J=8.4, 2.4 Hz), 8.46 (1H, d, J=8.4 Hz), 8.31 (1H, s), 8.01 (1H, d, J=8.4 Hz), 7.94 (1H, d, J=2.1 Hz), 7.81 (2H, bs), 7.64 (1H, d, J=2.4 Hz), 7.59 (1H, d, J=8.4 Hz), 7.48-7.53 (1H, m), 3.80-3.88 (1H, m), 2.35 (3H, s), 1.01-1.13 (6H, m)

$^{13}$C-NMR (DMSO-d6) δ [ppm]=190.3, 156.1, 154.8, 147.2, 146.7, 138.0, 134.4, 133.7, 132.6, 132.2, 130.4, 129.3, 128.6, 128.4, 128.3, 126.4, 125.1, 124.8, 124.2, 123.9, 116.4, 78.3, 21.4, 20.2

Example 92

Synthesis of 4-amino-3-[6-(3-formyl-2-butoxy-5-methylphenyl)pyridine-3-ylazo]naphthalene-1-sulfonic acid sodium salt

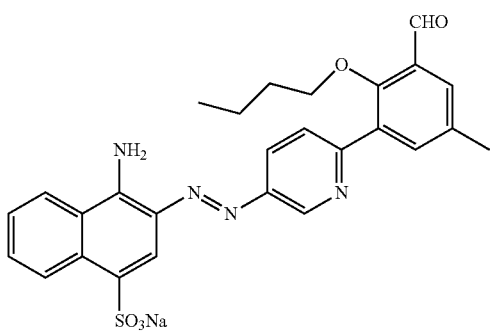

(i) 2-Butoxy-5-methyl-3-(5-nitropyridine-2-yl)benzaldehyde

The title compound was synthesized in a manner analogous to Example 89(i), except for replacing 2-chloro-3-iodo-5-nitropyridine with 2-chloro-5-nitropyridine, and replacing phenylboronic acid with 3-formyl-2-butoxy-5-methylphenylboronic acid.

(ii) 3-(5-Aminopyridine-2-yl)-2-butoxy-5-methylbenzaldehyde

The title compound was synthesized in a manner analogous to Example 7 (ii), except for replacing 2-phenyl-5-nitropyridine with 2-butoxy-5-methyl-3-(5-nitropyridine-2-yl)benzaldehyde obtained in (i).

(iii) 4-Amino-3-[6-(3-formyl-2-butoxy-5-methylphenyl)pyridine-3-ylazo]naphthalene-1-sulfonic acid sodium salt The title compound was synthesized in a manner analogous to Example 7 (iii), except for replacing 2-phenyl-5-aminopyridine with 3-(5-aminopyridine-2-yl)-2-butoxy-5-methylbenzaldehyde obtained in (ii).

$^1$H-NMR (DMSO-d6) δ [ppm]=10.4 (1H, s), 9.27 (1H, d, J=2.4 Hz), 8.75 (1H, d, J=8.1 Hz), 8.51 (1H, dd, J=8.6, 1.8 Hz), 8.46 (1H, d, J=8.1 Hz), 8.31 (1H, s,), 7.95-8.03 (2H, m), 7.81 (2H, bs), 7.58-7.64 (2H, m), 7.47-7.52 (1H, m), 3.71 (2H, t, J=6.5 Hz), 2.41 (3H, s), 1.53-1.89 (2H, m), 1.24-1.36 (2H, m), 0.78 (3H, t, J=7.2 Hz)

$^{13}$C-NMR (DMSO-d6) δ [ppm]=189.8, 157.9, 154.2, 147.3, 147.1, 146.5, 137.9, 133.9, 133.8, 132.7, 132.2, 129.4, 129.3, 128.6, 128.5, 128.4, 126.6, 125.0, 124.6, 124.2, 123.9, 116.4, 76.3, 31.3, 20.2, 18.5, 13.6

Example 93

Synthesis of 4-amino-3-phenylazonaphthalene-1-sulfonic acid sodium salt

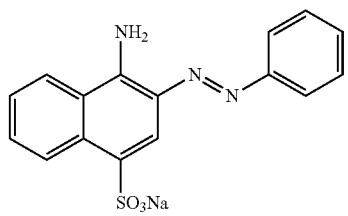

Aniline (3.00 g, 32 mmol) was suspended in water (10 ml), and added dropwise with 35% hydrochloric acid (8.39 g, 81 mmol). The mixture was cooled below 5° C., and added dropwise with an aqueous solution of sodium nitrite (2.27 g, 33 mmol). The reaction was carried out below 5° C. for about 5 minutes. After the completion of the reaction, excess sodium nitrite was decomposed with amidosulfuric acid to give diazo solution. 4-Amino-1-naphthalenesulfonic acid (7.55 g, 34 mmol) was suspended in water (25 ml), the pH of the suspension was adjusted to pH 8 to 10 with 10% aqueous sodium hydroxide with cooling on ice. The diazo solution was added dropwise to the suspension, during which 10% aqueous sodium hydroxide was added dropwise to keep the pH at 7 to 10. After the reaction at pH 7 to 10 below 10° C. for 1 hour, the temperature was raised to 40 to 50° C. with hot water, and salting-out was performed with addition of sodium chloride. After cooling to the room temperature, the precipitated crystals were filtered with suction. Purification by column chromatography gave the title compound (5.4 g, 48.0%).

$^1$H-NMR (DMSO-d6) δ [ppm]=8.76 (1H, d, J=8.1 Hz), 8.43 (1H, d, J=8.1 Hz), 8.29 (1H, s), 7.97 (2H, d, J=7.5 Hz), 7.66 (2H, s), 7.60-7.18 (5H, m)

$^{13}$C-NMR (DMSO-d6) δ [ppm]=152.8, 145.8, 132.1, 131.7, 129.4, 129.2, 128.6, 128.1, 124.9, 124.2, 123.8, 122.2, 117.7

Example 94

Synthesis of 4-amino-3-(2-fluorophenylazo)naphthalene-1-sulfonic acid sodium salt

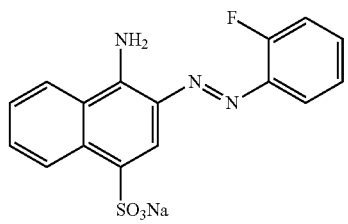

The title compound was synthesized in a manner analogous to Example 93, except for replacing aniline with 2-fluoroaniline.

$^{1}$H-NMR (DMSO-d6) δ [ppm]=8.77 (1H, d, J=8.4 Hz), 8.46 (1H, d, J=8.4 Hz), 8.32 (1H, s), 8.09 (2H, s), 8.03 (1H, dd, J=8.4 Hz, 7.5 Hz), 7.61 (1H, dd, J=7.5 Hz), 7.53-7.38 (3H, m), 7.29 (1H, dd, J=8.4 Hz, 7.5 Hz)

$^{13}$C-NMR (DMSO-d6) δ [ppm]=160.3, 156.9, 145.8, 140.6, 140.5, 132.3, 131.9, 130.9, 130.8, 129.2, 128.6, 128.2, 125.1, 124.9, 124.2, 124.0, 119.1, 117.7, 116.9, 116.7

Example 95

Synthesis of 4-amino-3-(4-trifluoromethylphenylazo)naphthalene-1-sulfonic acid sodium salt

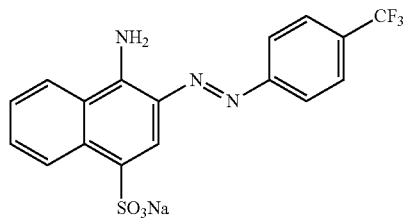

The title compound was synthesized in a manner analogous to Example 93, except for replacing aniline with 4-trifluoromethylaniline.

$^{1}$H-NMR (DMSO-d6) δ [ppm]=8.77 (1H, d, J=8.4 Hz), 8.48 (1H, d, J=8.1 Hz), 8.32 (1H, s), 8.16 (2H, d, J=8.4 Hz), 7.98 (2H, s), 7.85 (2H, d, J=8.4 Hz), 7.62 (1H, dd, J=8.4 Hz, 7.5 Hz), 7.51 (1H, dd, J=8.1 Hz, 7.5 Hz)

$^{13}$C-NMR (DMSO-d6) δ [ppm]=152.3, 130.8, 127.2, 126.3, 126.3, 126.2, 123.7, 120.1, 115.8, 115.5, 115.4, 113.5, 113.1

Example 96

Synthesis of 4-amino-3-(3-nitrophenylazo)naphthalene-1-sulfonic acid sodium salt

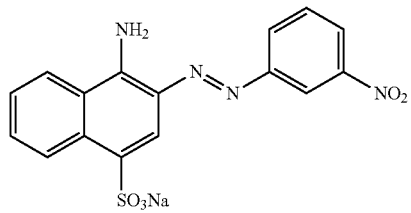

The title compound was synthesized in a manner analogous to Example 93, except for replacing aniline with 3-nitroaniline.

$^{1}$H-NMR (DMSO-d6) δ [ppm]=8.73 (1H, d, J=7.5 Hz), 8.66 (1H, dd, J=2.1 Hz, 1.8 Hz), 8.52 (1H, d, J=8.1 Hz), 8.42 (1H, d, J=8.1 Hz), 8.28 (1H, s), 8.22 (1H, dd, J=8.0 Hz, 2.1 Hz), 8.08 (2H, s), 7.79 (1H, dd, J=8.0 Hz, 7.5 Hz), 7.61 (1H, dd, J=8.1 Hz, 7.2 Hz), 7.50 (1H, dd, J=8.1 Hz, 7.2 Hz)

$^{13}$C-NMR (DMSO-d6) δ [ppm]=153.5, 148.9, 147.0, 132.5, 132.2, 130.6, 128.8, 128.7, 128.7, 128.3, 125.1, 124.2, 123.0, 117.8, 115.9

Example 97

Synthesis of 4-amino-3-[4-[(2-thienylcarbonyl)amino]phenylazo]-1-naphthalenesulfonic acid sodium salt

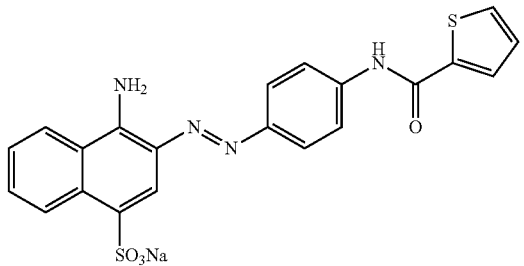

(i) N-(4-Nitrophenyl)thiophene-2-carboxyamide p-Nitroaniline (2.00 g, 14 mmol) and pyridine (2 ml) were dissolved in methylene chloride (150 ml) and cooled below 10° C. Below 10° C., 2-thiophenecarbonyl chloride (2.17 g, 15 mmol) was added dropwise, and the reaction was carried out at the same temperature for 30 minutes. The mixture was washed with water, followed by dilute aqueous hydrochloric acid, dried with anhydrous sodium sulfate, and concentrated to dryness under reduced pressure. Purification by recrystallization gave the title compound (2.63 g, 75.7%).

(ii) N-(4-Aminophenyl)thiophene-2-carboxyamide

N-(4-Nitrophenyl)thiophene-2-carboxyamide (1.00 g, 4 mmol) synthesized in (i) was reduced in ethanol:tetrahydrofuran=1:1 (20 ml) with Raney nickel (Kawaken Fine Chemicals Co., Ltd, NDT-65, 0.5 g) at room temperature under hydrogen at balloon pressure. After the completion of the reaction, Raney nickel was filtered off and the filtrate was concentrated to dryness under reduced pressure. Purification by recrystallization gave the title compound (0.75 g, 85.9%).

(iii) 4-Amino-3-[4-[(2-thienylcarbonyl)amino]phenylazo]-1-naphthalenesulfonic acid sodium salt Thiophene-2-carboxylic acid (4-aminophenyl)amide (1.64 g, 6 mmol) synthesized in (ii) was dissolved in absolute ethanol (20 ml). With cooling on ice, gaseous hydrochloric acid was bubbled in the solution to saturation. Below 5° C. isopentyl nitrite (0.82 g, 7 mmol) was added dropwise and the temperature was raised to room temperature. The reaction was carried out for 30 minutes to give a diazo solution. 4-Amino-1-naphthalenesulfonic acid (1.37 g, 6 mmol) was suspended in water (20 ml), the pH of the suspension was adjusted to pH 8 to 10 with 10% aqueous sodium hydroxide, and below 10° C. the diazo solution was added dropwise to the suspension. The reaction was carried out below 10° C. for 1 hour, the temperature was raised to room temperature and the reaction was carried out for additional 1 hour, during which the pH was kept at 7 to 10. After the completion of the reaction, the temperature was raised to 40 to 50° C., and salting-out was performed with addition of sodium chloride. After cooling to room temperature, the precipitated crystals were filtered with suction. The products were purified by column chromatography followed by recrystallization to give the title compound (0.61 g, 21.4%).

$^1$H-NMR (DMSO-d6) δ [ppm]=10.71 (1H, s), 8.74 (1H, d, J=8.4 Hz), 8.45 (1H, d, J=8.4 Hz), 8.29 (2H, m), 8.00 (4H, m), 7.87 (1H, d, J=4.8 Hz), 7.66 (2H, s), 7.60-7.45 (2H, m), 7.22 (1H, dd, J=4.8 Hz)

$^{13}$C-NMR (DMSO-d6) δ [ppm]=160.1, 148.8, 145.6, 140.2, 140.0, 132.2, 132.1, 131.5, 129.8, 128.7, 128.2, 128.1, 127.9, 124.8, 124.2, 123.8, 122.8, 120.5, 117.1

Example 98

Synthesis of 4-amino-3-(2-chlorophenylazo)naphthalene-1-sulfonic acid sodium salt

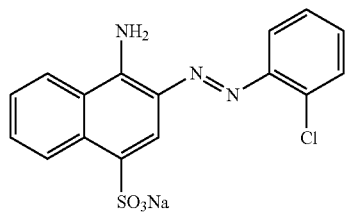

The title compound was synthesized in a manner analogous to Example 93, except for replacing aniline with 2-chloroaniline.

$^1$H-NMR (DMSO-d6) δ [ppm]=8.77 (NH$_2$), 8.76 (1H, d, J=7.5), 8.49 (1H, d, J=8.4), 8.30 (1H, s), 7.65 (1H, dd, J=7.7, 2.1), 7.67-7.61 (2H, m), 7.50-7.43 (3H, m)

$^{13}$C-NMR (DMSO-d6) δ [ppm]=148.2, 143.7, 132.5, 132.1, 131.7, 130.2, 129.4, 129.0, 128.7, 128.4, 128.2, 128.0, 125.0, 124.2, 124.1, 117.3

Example 99

Synthesis of 4-amino-3-(3-chlorophenylazo)naphthalene-1-sulfonic acid sodium salt

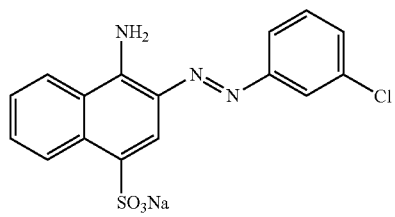

The title compound was synthesized in a manner analogous to Example 93, except for replacing aniline with 3-chloroaniline.

$^1$H-NMR (DMSO-d6) δ [ppm]=8.74 (1H, d, J=7.5), 8.50 (1H, d, J=8.1), 8.29 (1H, s), 8.09 (1H, m), 7.86 (NH$_2$), 7.63-7.41 (5H, m)

$^{13}$C-NMR (DMSO-d6) δ [ppm]=154.0, 147.1, 134.2, 132.1, 132.0, 130.9, 128.8, 128.7, 128.6, 128.2, 125.1, 124.3, 124.1, 122.9, 120.1, 117.1

Example 100

Synthesis of 4-amino-3-(4-chlorophenylazo)naphthalene-1-sulfonic acid sodium salt

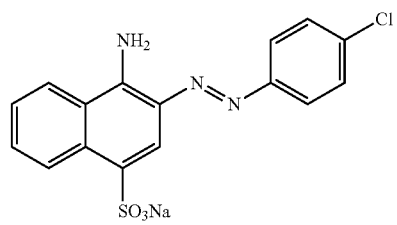

The title compound was synthesized in a manner analogous to Example 93, except for replacing aniline with 4-chloroaniline.

$^1$H-NMR (DMSO-d6) δ [ppm]=8.74 (1H, d, J=7.5), 8.46 (1H, d, J=8.1), 8.27 (1H, s), 8.00 (2H, d, J=8.7), 7.76 (2H, s), 7.61-7.54 (1H, m), 7.56 (2H, d, J=8.7), 7.50-7.46 (1H, m)

$^{13}$C-NMR (DMSO-d6) δ [ppm]=151.5, 146.3, 133.5, 132.3, 131.9, 129.2, 128.6, 128.3, 128.2, 124.9, 124.2, 123.9, 123.8, 117.3

Example 101

Synthesis of 4-amino-3-(3-fluorophenylazo)naphthalene-1-sulfonic acid sodium salt

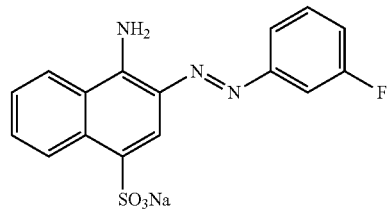

The title compound was synthesized in a manner analogous to Example 93, except for replacing aniline with 3-fluoroaniline.

$^1$H-NMR (DMSO-d6) δ [ppm]=8.74 (1H, dd, J=8.7, 1.2), 8.45 (1H, d, J=7.8), 8.27 (1H, s), 7.90-7.85 (1H, m), 7.84-7.80 (1H, m), 7.75 (NH$_2$), 7.62-7.55 (2H, m), 7.51-7.48 (1H, m), 7.27-7.23 (1H, m)

$^{13}$C-NMR (DMSO-d6) δ [ppm]=164.6, 161.4, 154.7, 154.6, 146.8, 132.4, 132.0, 130.8, 130.7, 128.6, 128.4, 128.2, 124.9, 124.2, 123.9, 120.7, 116.7, 115.9, 115.6, 106.6, 106.3

Example 102

Synthesis of 4-amino-3-(4-fluorophenylazo)naphthalene-1-sulfonic acid sodium salt

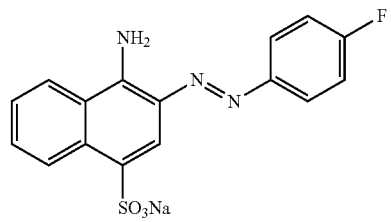

The title compound was synthesized in a manner analogous to Example 93, except for replacing aniline with 4-fluoroaniline.

$^1$H-NMR (DMSO-d6) δ [ppm]=8.74 (1H, d, J=8.1 Hz), 8.42 (1H, d, J=8.1 Hz), 8.26 (1H, s), 8.07 (1H, d, J=5.4 Hz), 8.04 (1H, d, J=5.4 Hz), 7.61 (2H, bs), 7.55-7.60 (2H, m), 7.45-7.50 (1H, m), 7.32-7.38 (1H, m)

$^{13}$C-NMR (DMSO-d6) δ [ppm]=164.2, 160.9, 149.6, 149.6, 146.0, 132.2, 131.7, 128.5, 128.1, 128.1, 124.9, 124.3, 124.2, 123.8, 117.1, 116.1, 115.9

Example 103

Synthesis of ethyl 4-(1-amino-4-sulfonaphthalene-2-ylazo)benzoate sodium salt

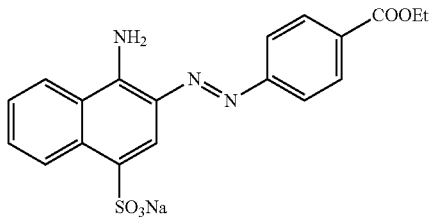

The title compound was synthesized in a manner analogous to Example 93, except for replacing aniline with ethyl 4-aminobenzoate.

$^1$H-NMR (DMSO-d6) δ [ppm]=8.73 (1H, dd, J=8.4, 1.2 Hz), 8.50 (1H, d, J=8.1 Hz), 8.29 (1H, d, J=6.9 Hz), 8.05-8.07 (4H, m), 8.02 (2H, bs), 7.52-7.63 (1H, m), 7.46-7.51 (1H, m), 4.34 (2H, q, J=7.2 Hz), 1.34 (3H, t, J=7.2 Hz)

$^{13}$C-NMR (DMSO-d6) δ [ppm]=165.4, 155.6, 146.8, 132.4, 132.1, 132.1, 130.2, 129.5, 129.0, 128.7, 128.2, 125.1, 124.2, 122.2, 117.8, 60.8, 14.2

Example 104

Synthesis of 4-(1-amino-4-sulfonaphthalene-2-ylazo)benzoic acid disodium salt

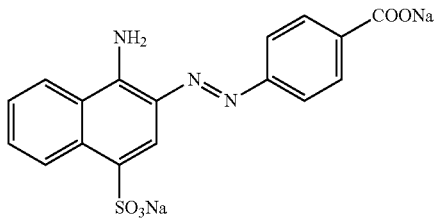

The title compound was synthesized in a manner analogous to Example 93, except for replacing aniline with 4-aminobenzoic acid.

$^1$H-NMR (DMSO-d6) δ [ppm]=8.74 (1H, dd, J=8.4, 1.2 Hz), 8.49 (1H, d, J=8.1 Hz), 8.30 (1H, d, J=7.5 Hz), 8.02-8.08 (4H, m), 7.96 (2H, bs), 7.57-7.63 (1H, m), 7.48-7.52 (1H, m)

$^{13}$C-NMR (DMSO-d6) δ [ppm]=166.9, 155.4, 146.7, 132.4, 132.0, 130.6, 130.4, 129.0, 128.6, 125.2, 125.0, 124.2, 124.1, 122.0, 117.7

Example 105

Synthesis of 4-amino-3-(2-cyanophenylazo)naphthalene-1-sulfonic acid sodium salt

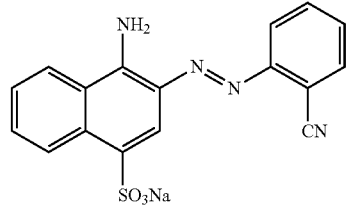

The title compound was synthesized in a manner analogous to Example 93, except for replacing aniline with 2-aminobenzonitril.

$^1$H-NMR (DMSO-d6) δ [ppm]=8.70 (1H, d, J=8.4), 8.60 (NH$_2$), 8.48 (1H, d, J=8.1), 8.24 (1H, s), 8.08 (1H, d, J=8.1), 7.92 (1H, d, J=7.5), 7.75 (1H, dd, J=7.5), 7.52-7.44 (2H, m)

$^{13}$C-NMR (DMSO-d6) δ [ppm]=154.2, 146.0, 134.2, 133.8, 132.9, 132.2, 129.2, 129.1, 128.8, 128.3, 125.3, 124.4, 124.2, 121.0, 118.2, 118.1, 108.4

Example 106

Synthesis of 4-amino-3-(3-cyanophenylazo)naphthalene-1-sulfonic acid sodium salt

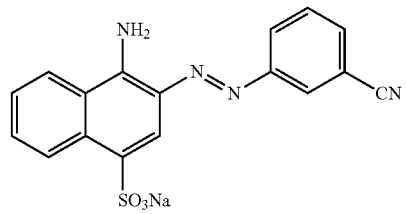

The title compound was synthesized in a manner analogous to Example 93, except for replacing aniline with 3-aminobenzonitril.

$^1$H-NMR (DMSO-d6) δ [ppm]=8.73 (1H, d, J=8.1), 8.52-8.49 (1H, m), 8.52-8.51 (1H, m), 8.29-8.26 (1H, m), 8.27 (1H, s), 7.85 (NH$_2$), 7.83 (1H, d, J=7.5), 7.71 (1H, dd, J=8.1, 7.5)

$^{13}$C-NMR (DMSO-d6) δ [ppm]=152.9, 147.7, 132.3, 132.2, 132.1, 130.6, 128.7, 128.7, 128.5, 128.3, 125.1, 124.2, 124.1, 118.7, 116.2, 112.3

Example 107

Synthesis of 4-amino-3-(4-cyanophenylazo)naphthalene-1-sulfonic acid sodium salt

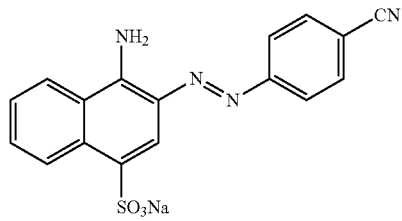

The title compound was synthesized in a manner analogous to Example 93, except for replacing aniline with 4-aminobenzonitril.

$^1$H-NMR (DMSO-d6) δ [ppm]=8.73 (1H, d, J=8.1), 8.50 (1H, d, J=8.4), 8.26 (1H, s), 8.12 (2H, d, J=8.7), 8.04 (NH$_2$), 7.95 (1H, d, J=8.7), 7.63-7.58 (1H, m), 7.51-7.47 (1H, m)

$^{13}$C-NMR (DMSO-d6) δ [ppm]=155.2, 147.7, 133.4, 132.6, 132.3, 129.1, 128.9, 128.3, 125.2, 124.2, 124.2, 122.8, 119.0, 117.1, 110.5

Example 108

Synthesis of 4-amino-3-(2-bromophenylazo)naphthalene-1-sulfonic acid sodium salt

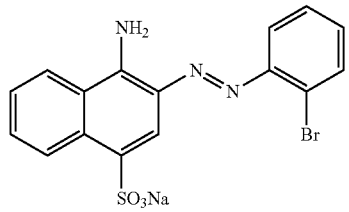

The title compound was synthesized in a manner analogous to Example 93, except for replacing aniline with 2-bromoaniline.

Example 109

Synthesis of 4-amino-3-(3-bromophenylazo)naphthalene-1-sulfonic acid sodium salt

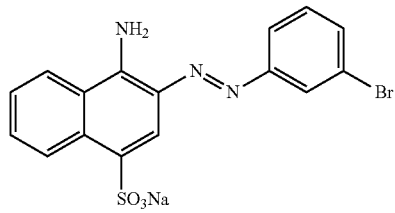

The title compound was synthesized in a manner analogous to Example 93, except for replacing aniline with 3-bromoaniline.

Example 110

Synthesis of 4-amino-3-(4-bromophenylazo)naphthalene-1-sulfonic acid sodium salt

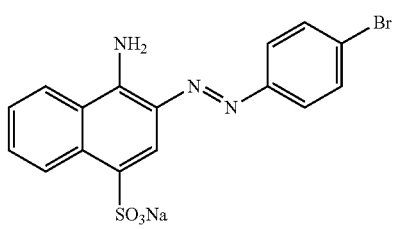

The title compound was synthesized in a manner analogous to Example 93, except for replacing aniline with 4-bromoaniline.

$^1$H-NMR (DMSO-d6) δ [ppm]=8.74 (1H, d, J=7.5), 8.44 (1H, d, J=8.1), 8.27 (1H, s), 7.94 (2H, d, J=8.7), 7.75 (NH$_2$), 7.70 (2H, d, J=8.7), 7.59 (1H, dd, J=7.5, 7.2), 7.48 (1H, dd, J=7.5, 6.9)

$^{13}$C-NMR (DMSO-d6) δ [ppm]=151.8, 146.4, 132.4, 132.1, 131.9, 128.7, 128.3, 128.2, 125.0, 124.2, 124.1, 123.9, 122.3, 117.2

Example 111

Synthesis of 4-amino-3-(2,4-dichlorophenylazo)naphthalene-1-sulfonic acid sodium salt

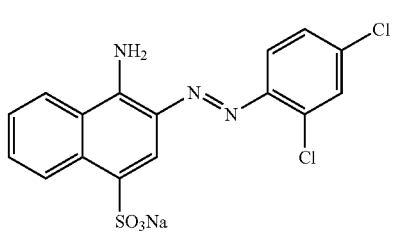

The title compound was synthesized in a manner analogous to Example 12 (iii), except for replacing 6-biphenyl-2-ylpyridine-3-ylamine with 2,4-dichloroaniline.

Example 112

Synthesis of 4-amino-3-(3,4-dichlorophenylazo)naphthalene-1-sulfonic acid sodium salt

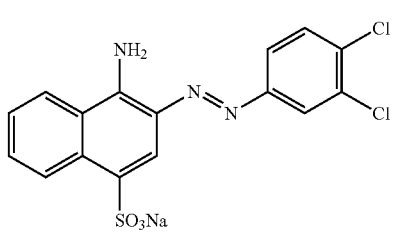

The title compound was synthesized in a manner analogous to Example 12 (iii), except for replacing 6-biphenyl-2-ylpyridine-3-ylamine with 3,4-dichloroaniline.

¹H-NMR (DMSO-d6) δ [ppm]=8.72 (1H, d, J=8.1), 8.49 (1H, d, J=8.1), 8.30 (1H, d, J=2.1), 8.25 (1H, s), 7.96 (1H, dd, J=8.5, 2.1), 7.89 (NH₂), 7.76 (1H, d, J=8.5), 7.60 (1H, dd, J=8.1, 7.2), 7.49 (1H, dd, J=7.2)

¹³C-NMR (DMSO-d6) δ [ppm]=152.3, 147.3, 132.4, 132.2, 132.1, 131.1, 130.9, 128.7, 128.6, 128.2, 125.0, 124.2, 124.1, 123.6, 122.2, 116.8

Example 113

Synthesis of 4-amino-3-(2,4-dibromophenylazo)naphthalene-1-sulfonic acid sodium salt

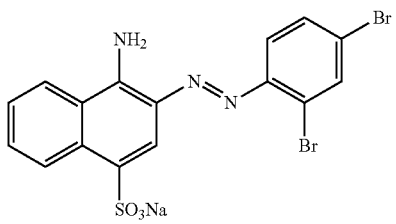

The title compound was synthesized in a manner analogous to Example 12 (iii), except for replacing 6-biphenyl-2-ylpyridine-3-ylamine with 2,4-dibromoaniline.

¹H-NMR (DMSO-d6) δ [ppm]=8.76-8.73 (NH₂, br), 8.75 (1H, d, J=8.1), 8.48 (1H, d, J=8.1), 8.28 (1H, s), 8.07 (1H, d, J=2.1), 7.89 (1H, d, J=8.7), 7.67 (1H, dd, J=8.7, 2.1), 7.63 (1H, dd, J=8.1, 7.8), 7.50 (1H, dd, J=7.5, 7.2)

¹³C-NMR (DMSO-d6) δ [ppm]=148.6, 144.1, 135.1, 132.7, 131.9, 131.7, 129.0, 128.3, 125.2, 124.2, 123.9, 123.3, 122.2, 119.0

Example 114

Synthesis of 4-amino-3-(2,4,6-tribromophenylazo)naphthalene-1-sulfonic acid sodium salt

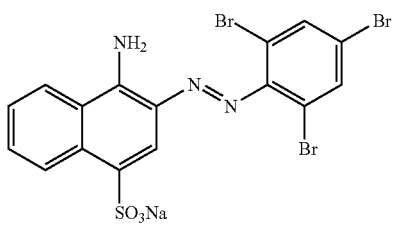

The title compound was synthesized in a manner analogous to Example 12 (iii), except for replacing 6-biphenyl-2-ylpyridine-3-ylamine with 2,4,6-tribromoaniline.

¹H-NMR (DMSO-d6) δ [ppm]=8.76 (1H, d, J=8.4), 8.45 (1H, d, J=8.1), 8.21 (1H, s), 8.21-8.05 (NH₂, br), 8.05 (2H, s), 7.64 (1H, dd, J=7.8, 7.5), 7.51 (1H, dd, J=7.5)

¹³C-NMR (DMSO-d6) δ [ppm]=149.4, 146.3, 134.9, 132.5, 132.4, 129.2, 128.4, 128.3, 125.4, 124.2, 124.1, 119.7, 119.1, 116.5

Example 115

Synthesis of 4-amino-3-(2,4,6-trichlorophenylazo)naphthalene-1-sulfonic acid sodium salt

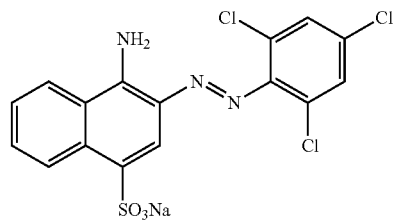

The title compound was synthesized in a manner analogous to Example 12 (iii), except for replacing 6-biphenyl-2-ylpyridine-3-ylamine with 2,4,6-trichloroaniline.

¹H-NMR (DMSO-d6) δ [ppm]=8.69 (1H, d, J=8.1), 8.38 (1H, d, J=8.4), 8.12 (1H, s), 8.01 (NH₂), 7.74 (2H, s), 7.58 (1H, dd, J=7.8, 7.2), 7.45 (1H, dd, J=7.5, 7.2)

¹³C-NMR (DMSO-d6) δ [ppm]=147.0, 146.3, 132.7, 132.4, 131.3, 129.2, 129.1, 128.9, 128.4, 127.5, 125.3, 124.1, 124.1, 118.9

Example 116

Synthesis of 4-amino-3-(2,4-difluorophenylazo)naphthalene-1-sulfonic acid sodium salt

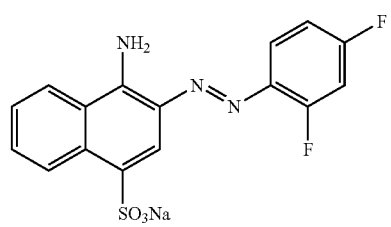

The title compound was synthesized in a manner analogous to Example 93, except for replacing aniline with 2,4-difluoroaniline.

¹H-NMR (DMSO-d6) δ [ppm]=8.73 (1H, d, J=8.1 Hz), 8.46 (1H, d, J=8.1 Hz), 8.26 (1H, s), 8.11-8.19 (1H, m), 8.00 (2H, bs), 7.57-7.62 (1H, m), 7.43-7.51 (2H, m), 7.15-7.20 (1H, m)

¹³C-NMR (DMSO-d6) δ [ppm]=164.2, 164.0, 160.9, 160.7, 160.5, 160.3, 157.1, 157.0, 146.2, 137.8, 137.7, 137.7, 137.7, 132.3, 131.9, 129.1, 128.5, 128.2, 125.1, 124.2, 124.0, 119.3, 119.2, 118.3, 112.3, 112.0, 105.4, 105.0, 104.7

Example 117

Synthesis of 4-amino-3-(2-bromo-4-chlorophenylazo)naphthalene-1-sulfonic acid sodium salt

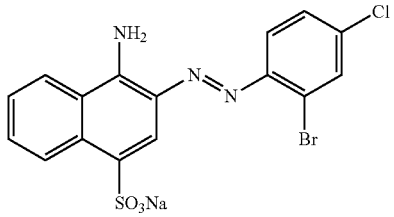

The title compound was synthesized in a manner analogous to Example 93, except for replacing aniline with 2-bromo-4-chloroaniline.

$^1$H-NMR (DMSO-d6) δ [ppm]=8.76 (NH$_2$), 8.71 (1H, d, J=8.4), 8.42 (1H, d, J=8.4), 8.23 (1H, s), 7.91 (1H, d, J=8.7), 7.90 (1H, d), 7.57 (1H, dd, J=7.8, 7.2), 7.49 (1H, dd, J=9.0, 2.1), 7.45 (1H, d, J=8.4, 7.5)

$^{13}$C-NMR (DMSO-d6) δ [ppm]=148.2, 144.1, 133.7, 132.8, 132.4, 131.9, 129.0, 128.9, 128.7, 128.3, 125.1, 124.2, 123.6, 123.1, 118.7

Example 118

Synthesis of 4-amino-3-(4-chloro-2-cyanophenylazo)naphthalene-1-sulfonic acid sodium salt

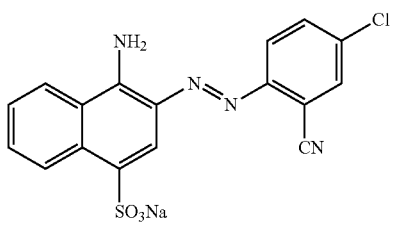

The title compound was synthesized in a manner analogous to Example 93, except for replacing aniline with 2-amino-5-chlorobenzonitril.

$^1$H-NMR (DMSO-d6) δ [ppm]=8.69 (1H, d, J=8.1), 8.64 (NH$_2$), 8.44 (1H, d, J=8.1), 8.20 (1H, s), 8.11 (1H, d, J=9.0), 8.10 (1H, d, J=2.4), 7.78 (1H, dd, J=9.0, 2.4), 7.59 (1H, dd, J=7.8, 7.2), 7.46 (1H, dd, J=7.5, 7.2)

$^{13}$C-NMR (DMSO-d6) δ [ppm]=153.1, 146.5, 134.3, 133.1, 132.9, 132.8, 132.4, 129.4, 129.0, 128.4, 125.4, 124.4, 124.1, 120.7, 119.4, 116.8, 110.1

Example 119

Synthesis of 4-amino-3-(2-chloro-4-fluorophenylazo)naphthalene-1-sulfonic acid sodium salt

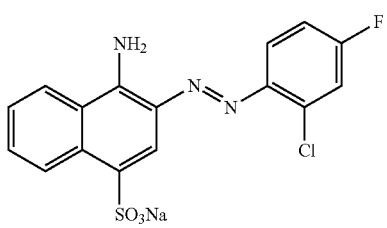

The title compound was synthesized in a manner analogous to Example 93, except for replacing aniline with 2-chloro-4-fluoroaniline.

$^1$H-NMR (DMSO-d6) δ [ppm]=8.74 (1H, dd, J=8.4, 1.2 Hz), 8.44 (1H, d, J=8.1 Hz), 8.25 (1H, s), 8.07-8.13 (3H, m), 7.58-7.68 (2H, m), 7.50-7.53 (1H, m), 7.34-7.38 (1H, m)

$^{13}$C-NMR (DMSO-d6) δ [ppm]=160.0, 156.6, 146.5, 139.6, 139.5, 134.0, 133.8, 132.5, 132.4, 132.0, 129.3, 128.7, 128.3, 125.2, 125.1, 124.2, 123.9, 119.1, 118.2, 117.5, 117.2

Example 120

Synthesis of 4-amino-3-(4-methyl-2-nitrophenylazo)naphthalene-1-sulfonic acid sodium salt

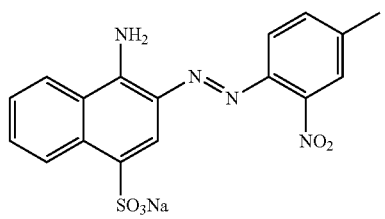

The title compound was synthesized in a manner analogous to Example 12 (iii), except for replacing 6-biphenyl-2-ylpyridine-3-ylamine with 4-methyl-2-nitroaniline.

$^1$H-NMR (DMSO-d6) δ [ppm]=8.74 (1H, dd, J=8.4, 1.2), 8.45 (1H, d, J=8.4), 8.41 (NH$_2$), 8.17 (1H, s), 8.00 (1H, d, J=6.0), 7.83 (1H, J=0.6), 7.65-7.56 (2H, m), 7.53-7.48 (1H, m), 2.44 (3H, s)

$^{13}$C-NMR (DMSO-d6) δ [ppm]=146.6, 145.5, 142.4, 139.9, 133.7, 132.6, 132.0, 129.1, 129.0, 128.3, 125.2, 124.1, 124.1, 123.9, 120.7, 118.0, 20.5

Example 121

Synthesis of 4-amino-3-(2-methoxy-4-nitrophenylazo)naphthalene-1-sulfonic acid sodium salt

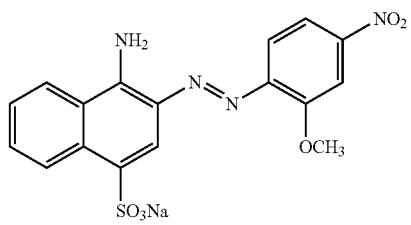

The title compound was synthesized in a manner analogous to Example 12 (iii), except for replacing 6-biphenyl-2-ylpyridine-3-ylamine with 2-methoxy-4-nitroaniline.

$^1$H-NMR (DMSO-d6) δ [ppm]=8.77-8.74 (NH$_2$, br), 8.75 (1H, J=8.1), 8.46 (1H, d, J=8.4), 8.25 (1H, s), 8.00 (1H, d, J=8.7), 7.97 (1H, s), 7.89 (1H, d, J=8.7), 7.63 (1H, d, J=7.5), 7.50 (1H, dd, J=7.5, 7.2), 4.09 (3H, s)

$^{13}$C-NMR (DMSO-d6) δ [ppm]=155.0, 147.4, 145.9, 145.4, 132.8, 132.0, 130.1, 129.1, 128.3, 125.2, 124.2, 121.6, 116.7, 116.3, 107.9, 56.6

Example 122

Synthesis of 4-amino-3-p-tolylazonaphthalene-1-sulfonic acid sodium salt

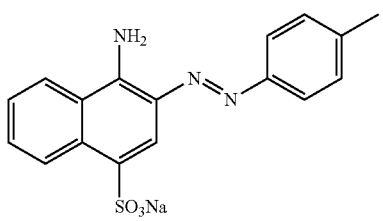

The title compound was synthesized in a manner analogous to Example 93, except for replacing aniline with p-toluidine.

$^1$H-NMR (DMSO-d6) δ [ppm]=8.75 (1H, d, J=8.4), 8.42 (1H, d, J=8.4), 8.30 (1H, s), 8.29 (NH$_2$), 7.88 (2H, d, J=8.4), 7.57 (1H, dd, J=7.8, 7.2), 7.47 (1H, dd, J=7.2), 7.33 (2H, d, J=7.8), 2.38 (3H, s)

$^{13}$C-NMR (DMSO-d6) δ [ppm]=150.9, 145.5, 139.3, 132.1, 131.6, 129.8, 128.6, 128.1, 128.0, 124.8, 124.2, 123.7, 122.2, 117.5, 21.0

Example 123

Synthesis of 4-amino-3-(4-pyridine-3-ylphenylazo)-1-naphthalenesulfonic acid sodium salt

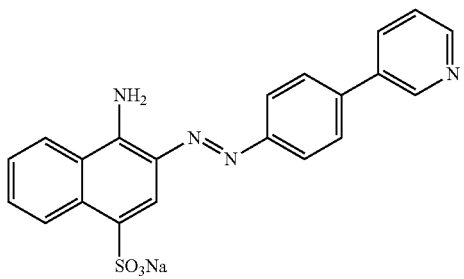

(i) 3-(4-Nitrophenyl)pyridine

To sulfuric acid (45 g) and 3-phenylpyridine (15.0 g, 97 mmol), nitric acid (6.85 g, 106 mmol) was added dropwise, and reacted for 1 hour. The reaction solution was added to water (68 ml) and neutralized with aqueous sodium hydroxide. The precipitated crystals were filtered to give the title compound (16.19 g, 83.4%).

(ii) 4-(Pyridine-3-yl)aniline

Ethanol (50 ml) and water (10 ml) was mixed and added with iron powder. The mixture was heated to 70-80° C. Ammonium chloride (0.261 g, 5 mmol) was added to the mixture, and then 3-(4-nitrophenyl)pyridine (2.0 g, 10.0 mmol) obtained in (i) was added. The reaction was carried out at 70-80° C. for 1 hour. After the completion of the reaction, the iron powder was filtered while hot through Celite, and the filtrate was concentrated under reduced pressure. The residue was dissolved in isopropyl alcohol, crystallized and filtered with addition of water to give the title compound (3.0 g, 91.0%).

(iii) 4-Amino-3-(4-pyridine-3-ylphenylazo)-1-naphthalenesulfonic acid sodium salt 4-(Pyridine-3-yl)aniline (0.75 g, 4.4 mmol) synthesized in (ii) was suspended in water (7.5 ml), and added dropwise with 35% hydrochloric acid (2.29 g, 22 mmol). The mixture was cooled below 5° C., and added dropwise with an aqueous solution of sodium nitrite (0.32 g, 4.6 mmol). The reaction was carried out below 5° C. for about 5 minutes. After the completion of the reaction, excess sodium nitrite was decomposed with amidosulfuric acid. The mixture was added with 4-amino-1-naphthalenesulfonic acid (0.96 g, 4.3 mmol) and water (19 ml), and neutralized with 10% aqueous sodium hydroxide to pH 7 to 10. The reaction was carried out below 10° C. for 1 hour, during which the pH was kept 7 to 10. After the completion of the reaction, the temperature was raised to 40 to 50° C., and salting-out was performed with addition of sodium chloride. After cooling to the room temperature, the precipitated crystals were filtered with suction. The products were purified by column chromatography followed by recrystallization to give the title compound (1.29 g, 70.4%).

$^1$H-NMR (DMSO-d6) δ [ppm]=8.99 (1H, d, J=1.8), 8.77 (1H, d, J=8.4), 8.59 (1H, dd, J=4.8, 1.2), 8.46 (1H, d, J=8.4), 8.34 (1H, s), 8.17 (1H, d, J=8.1), 8.11 (2H, d, J=8.4), 7.90 (2H, d, J=8.4), 7.78 (NH$_2$), 7.60 (dd, J=7.8, 7.2), 7.52-7.47 (2H, m)

$^{13}$C-NMR (DMSO-d6) δ [ppm]=152.5, 148.7, 147.7, 146.2, 137.7, 134.9, 134.1, 132.3, 131.8, 128.9, 128.3, 128.2, 127.7, 125.0, 124.2, 124.0, 123.9, 123.0, 117.4

Example 124

Synthesis of 2-{4-[4-(1-amino-4-sulfonaphthalene-2-ylazo)benzoylamino]benzyl}malonic acid trisodium salt

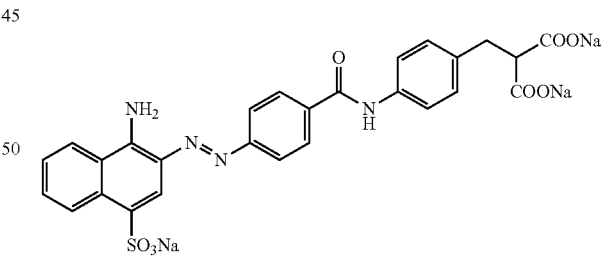

(i) 2-[4-(4-Aminobenzoylamino)benzyl]malonic acid disodium salt

To methylene chloride (20 ml), 4-nitrobenzoyl chloride (2.06 g, 11.1 mmol) and dimethyl 2-(4-aminobenzylidene) malonate (2.48 g, 10.5 mmol) were added, and reacted at room temperature for 2 hours. The mixture was reduced with Raney nickel and hydrogen. The hydrolysis was carried out in methanol with aqueous sodium hydroxide to give the title compound (2.87 g, 73.1%).

(ii) 2-{4-[4-(1-Amino-4-sulfonaphthalene-2-ylazo) benzoylamino]benzyl}malonic acid trisodium salt The title compound was synthesized in a manner analogous to Example 93, except for replacing aniline with 2-[4-(4-aminobenzoylamino)benzyl]malonic acid disodium salt obtained in (i).

$^1$H-NMR (DMSO-d6) δ [ppm]=8.72 (1H, d, J=8.4 Hz), 8.38 (1H, d, J=8.7 Hz), 8.36 (1H, s), 8.09 (2H, d, J=8.4 Hz), 8.03 (2H, d, J=8.7 Hz), 7.65-7.70 (1H, m), 7.55-7.60 (3H, m), 7.25 (2H, d, J=8.4 Hz), 3.15 (1H, t, J=7.1 Hz), 2.96 (2H, d, J=6.6 Hz)

$^{13}$C-NMR (DMSO-d6) δ [ppm]=180.4, 168.9, 158.0, 149.7, 142.0, 139.3, 138.5, 135.0, 134.5, 132.6, 132.4, 132.2, 131.2, 129.3, 127.5, 127.3, 125.6, 124.1, 122.1, 64.0, 39.7

Example 125

Synthesis of 4-amino-3-(4'-methylbiphenyl-4-ylazo) naphthalene-1-sulfonic acid sodium salt

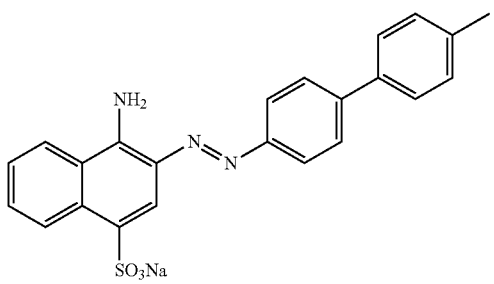

(i) 4-Methyl-4'-nitrobiphenyl

The title compound was synthesized in a manner analogous to Example 7 (i), except for replacing 2-chloro-5-nitropyridine with 4-bromonitrobenzene, and replacing phenylboronic acid with 4-methylphenylboronic acid.

(ii) 4'-Methylbiphenyl-4-ylamine

The title compound was synthesized in a manner analogous to Example 7 (ii), except for replacing 2-phenyl-5-nitropyridine with 4-methyl-4'-nitrobiphenyl obtained in (i).

(iii) 4-Amino-3-(4'-methylbiphenyl-4-ylazo)naphthalene-1-sulfonic acid sodium salt The title compound was synthesized in a manner analogous to Example 12 (iii), except for replacing 6-biphenyl-2-ylpyridine-3-ylamine with 4'-methylbiphenyl-4-ylamine obtained in (ii).

$^1$H-NMR (DMSO-d6) δ [ppm]=8.76 (1H, d, J=8.0), 8.43 (1H, d, J=8.1), 8.32 (1H, s), 8.05 (2H, d, J=8.7), 7.80 (2H, d, J=8.7), 7.71 (NH$_2$), 7.65 (2H, d, J=8.1), 7.59 (1H, m), 7.51 (1H, m), 7.29 (2H, d, J=8.1), 2.35 (3H, s)

$^{13}$C-NMR (DMSO-d6) δ [ppm]=151.9, 145.8, 140.8, 137.2, 136.5, 132.3, 131.7, 129.6, 128.9, 128.2, 128.1, 127.1, 126.5, 124.9, 124.2, 123.8, 122.8, 117.6, 20.8

Example 126

Synthesis of 4-amino-3-(3'-methylbiphenyl-4-ylazo) naphthalene-1-sulfonic acid sodium salt

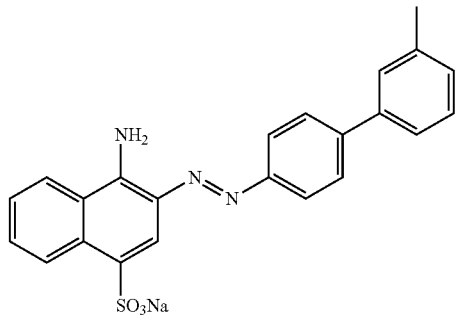

(i) 3-Methyl-4'-nitrobiphenyl

The title compound was synthesized in a manner analogous to Example 7 (i), except for replacing 2-chloro-5-nitropyridine with 4-bromonitrobenzene, and replacing phenylboronic acid with 3-methylphenylboronic acid.

(ii) 3'-Methylbiphenyl-4-ylamine

The title compound was synthesized in a manner analogous to Example 7 (ii), except for replacing 2-phenyl-5-nitropyridine with 3-methyl-4'-nitrobiphenyl obtained in (i).

(iii) 4-Amino-3-(3'-methylbiphenyl-4-ylazo)naphthalene-1-sulfonic acid sodium salt The title compound was synthesized in a manner analogous to Example 12 (iii), except for replacing 6-biphenyl-2-ylpyridine-3-ylamine with 3'-methylbiphenyl-4-ylamine obtained in (ii).

$^1$H-NMR (DMSO-d6) δ [ppm]=8.81 (1H, d, J=8.4), 8.50 (1H, d, J=8.4), 8.38 (1H, s), 8.11 (2H, d, J=8.4), 7.86 (2H, d, J=8.4), 7.79 (NH$_2$), 7.66-7.52 (4H, m), 7.41 (1H, dd, J=7.8, 7.5), 7.25 (1H, d, J=7.5)

$^{13}$C-NMR (DMSO-d6) δ [ppm]=152.0, 145.9, 141.0, 139.3, 138.2, 132.3, 131.7, 129.2, 128.9, 128.9, 128.5, 128.2, 128.2, 127.4, 127.4, 124.9, 124.2, 123.8, 122.8, 117.6, 21.2

Example 127

Synthesis of 4-amino-3-(4-isoquinoline-1-ylphenylazo)naphthalene-1-sulfonic acid sodium salt

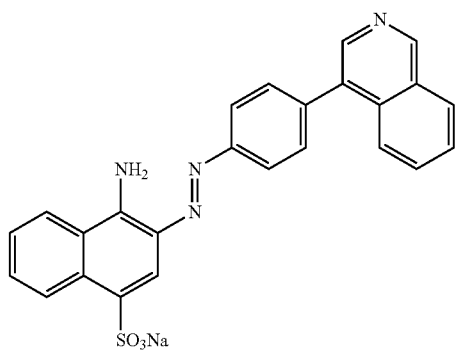

(i) 4-(4-Nitrophenyl)isoquinoline

The title compound was synthesized in a manner analogous to Example 7 (i), except for replacing 2-chloro-5-nitropyridine with 4-bromonitrobenzene, and replacing phenylboronic acid with 4-isoquinolineboronic acid.

(ii) 4-(Isoquinoline-4-yl)aniline

The title compound was synthesized in a manner analogous to Example 7 (ii), except for replacing 2-phenyl-5-nitropyridine with 4-(4-nitrophenyl)isoquinoline obtained in (i).

(iii) 4-Amino-3-(4-isoquinoline-1-ylphenylazo)naphthalene-1-sulfonic acid sodium salt The title compound was synthesized in a manner analogous to Example 93, except for replacing aniline with 4-(isoquinoline-4-yl)aniline obtained in (ii).

$^1$H-NMR (DMSO-d6) δ [ppm]=9.37 (1H, s), 8.77 (1H, d, J=8.1), 8.53 (1H, s), 8.46 (1H, d, J=8.4), 8.35 (1H, s), 8.24 (1H, d, J=8.1), 8.17 (2H, d, J=8.4), 7.95 (1H, d, J=8.4), 7.85-7.69 (4H, m), 7.70 (2H, d, J=8.4), 7.62-7.57 (1H, m), 7.52-7.49 (1H, m)

Example 128

Synthesis of 4-amino-3-(2,6-dibromo-4-pyridine-3-ylphenylazo)naphthalene-1-sulfonic acid sodium salt

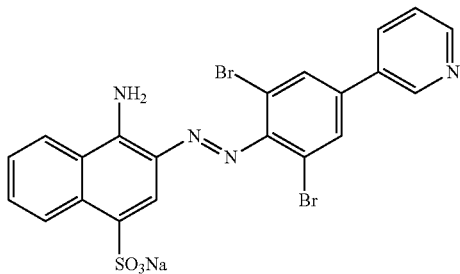

(i) 2,6-Dibromo-4-(pyridine-3-yl)aniline 3-(4'-Aminophenyl)pyridine (1.5 g, 9 mmol) was dissolved in acetonitrile (15 ml), and added dropwise with bromine (2.88 g, 18 mmol). The mixture was reacted at room temperature for 1 hour, added with water and neutralized with aqueous sodium hydroxide. The solvent was distilled off under reduced pressure. The precipitated crystals were filtered to give the title compound (2.3 g, 76.2%).

(ii) 4-Amino-3-(2,6-dibromo-4-pyridine-3-ylphenylazo)naphthalene-1-sulfonic acid sodium salt The title compound was synthesized in a manner analogous to Example 93, except for replacing aniline with 2,6-dibromo-4-(pyridine-3-yl)aniline obtained in (i).

$^1$H-NMR (DMSO-d6) δ [ppm]=9.01 (1H, d, J=1.8), 8.76 (1H, dd, J=8.7, 1.2), 8.62 (1H, dd, J=4.8, 1.8), 8.45 (1H, d, J=8.1), 8.24 (1H, s), 8.24-8.20 (1H, m), 8.18 (2H, s), 8.04 (NH2), 7.66-7.61 (m), 7.54-7.49 (2H, m)

$^{13}$C-NMR (DMSO-d6) δ [ppm]=149.4, 147.9, 146.2, 137.9, 134.6, 132.7, 132.6, 132.5, 132.4, 131.1, 129.0, 128.5, 128.4, 125.3, 124.1, 124.1, 123.9, 119.0, 116.4

Example 129

Synthesis of 4-amino-3-(4-phenylcarbamoylphenylazo)naphthalene-1-sulfonic acid sodium salt

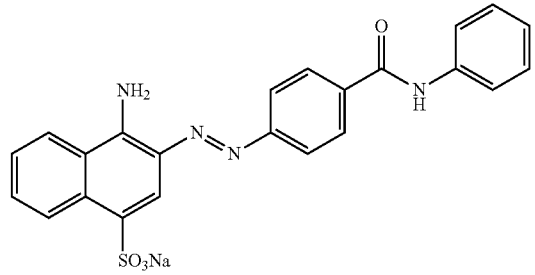

The title compound was synthesized in a manner analogous to Example 93, except for replacing aniline with 4-amino-N-phenylbenzamide.

$^1$H-NMR (DMSO-d6) δ [ppm]=10.39 (1H, s), 8.74 (1H, d, J=7.8 Hz), 8.46 (1H, d, J=8.1 Hz), 8.30 (1H, s), 8.10-8.13 (4H, m), 7.89 (2H, bs), 7.81 (2H, d, J=7.8 Hz), 7.57-7.63 (1H, m), 7.45-7.52 (1H, m), 7.33-7.38 (2H, m), 7.08-7.13 (1H, m)

$^{13}$C-NMR (DMSO-d6) δ [ppm]=165.1, 154.6, 146.7, 139.2, 134.8, 132.5, 132.0, 129.0, 128.9, 128.7, 128.3, 125.1, 124.2, 124.0, 122.0, 120.5

Example 130

Synthesis of 4-amino-3-(3-benzoylphenylazo)naphthalene-1-sulfonic acid sodium salt

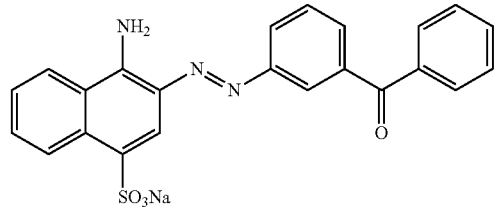

The title compound was synthesized in a manner analogous to Example 93, except for replacing aniline with 3-aminobenzophenone.

$^1$H-NMR (DMSO-d6) δ [ppm]=8.73 (1H, d, J=6.9 Hz), 8.44 (1H, d, J=8.4 Hz), 8.26-8.29 (2H, m), 8.19 (1H, s), 7.86 (2H, bs), 7.81-7.84 (2H, m), 7.68-7.77 (3H, m), 7.57-7.62 (3H, m), 7.46-7.51 (1H, m)

$^{13}$C-NMR (DMSO-d6) δ [ppm]=152.7, 146.2, 138.3, 136.9, 133.0, 132.4, 131.9, 130.0, 129.8, 129.6, 128.8, 128.5, 128.3, 125.3, 125.1, 124.2, 124.0, 123.6, 118.0

Example 131

Synthesis of 4-amino-3-(4-benzoylphenylazo)naphthalene-1-sulfonic acid sodium salt

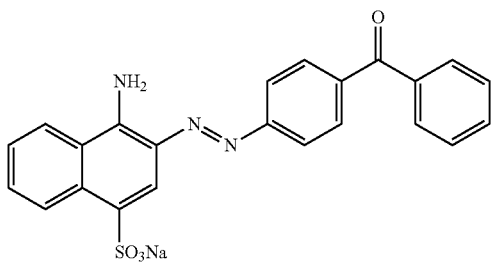

The title compound was synthesized in a manner analogous to Example 93, except for replacing aniline with 4-aminobenzophenone.

$^1$H-NMR (DMSO-d6) δ [ppm]=8.75 (1H, dd, J=8.6, 1.2 Hz), 8.48 (1H, d, J=8.4 Hz), 8.31 (1H, s), 8.12 (2H, dd, J=6.8, 1.8 Hz), 8.00 (2H, bs), 7.87 (2H, dd, J=7.8, 1.8 Hz), 7.78 (2H, dd, J=8.3, 1.2 Hz), 7.48-7.69 (5H, m)

$^{13}$C-NMR (DMSO-d6) δ [ppm]=195.2, 155.2, 147.0, 137.3, 136.6, 132.7, 132.5, 132.1, 131.0, 129.6, 129.2, 128.8, 128.7, 128.3, 125.2, 124.2, 124.1, 122.1

Example 132

Synthesis of 4-amino-3-[4-(pyridine-4-ylmethoxy)phenylazo]naphthalene-1-sulfonic acid sodium salt

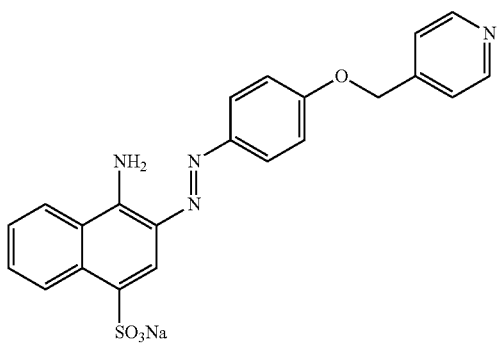

(i) 4-(Pyridine-4-ylmethoxy)aniline dihydrochloride 4-(N-Acetylamino)phenol (2.0 g, 13.2 mmol), potassium hydroxide (1.86 g, 33.1 mmol) and N,N-dimethylformamide (20 ml) were charged, added with 4-chloromethylpyridine hydrochloride (2.17 g, 13.2 mmol) and reacted at room temperature for 4 hours. Water was added to the mixture and the precipitated crystals were filtered. The resulting crystals were hydrolyzed in ethanol with hydrochloric acid to give the title compound (2.52 g, 69.9%).

(ii) 4-Amino-3-[4-(pyridine-4-ylmethoxy)phenylazo]naphthalene-1-sulfonic acid sodium salt The title compound was synthesized in a manner analogous to Example 93, except for replacing aniline with 4-(pyridine-4-ylmethoxy)aniline dihydrochloride obtained in (i).

$^1$H-NMR (DMSO-d6) δ [ppm]=8.88 (1H, dd), 8.59 (2H, dd, J=4.5, 1.8 Hz), 8.40 (1H, d, J=8.4 Hz), 8.30 (1H, s), 7.98 (2H, dd, J=7.1, 1.8 Hz), 7.26-7.72 (6H, m), 7.15-7.23 (2H, m), 5.52 (2H, s)

$^{13}$C-NMR (DMSO-d6) δ [ppm]=159.1, 149.8, 147.4, 146.0, 145.3, 132.1, 131.5, 128.6, 128.2, 127.8, 124.8, 124.2, 124.0, 123.6, 121.9, 117.1, 115.3

Example 133

Synthesis of 4-amino-3-(2-methylsulfanylphenylazo)naphthalene-1-sulfonic acid sodium salt

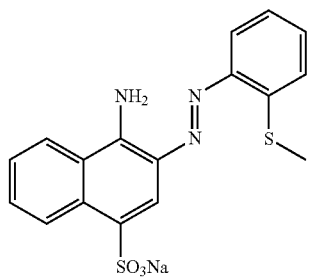

The title compound was synthesized in a manner analogous to Example 93, except for replacing aniline with 2-(methylthio)aniline.

$^1$H-NMR (DMSO-d6) δ [ppm]=8.73 (1H, d, J=8.4), 8.48 (NH$_2$), 8.40 (1H, d, J=8.4), 8.27 (1H, s), 7.80 (1H, d, J=7.8), 7.57-7.52 (1H, m), 7.47-7.42 (1H, m), 7.37-7.35 (2H, m), 7.22-7.17 (1H, m)

$^{13}$C-NMR (DMSO-d6) δ [ppm]=148.2, 142.8, 137.8, 132.5, 132.4, 131.4, 129.7, 128.8, 128.3, 128.1, 124.9, 124.6, 124.2, 123.8, 123.5, 115.9, 25.4

Example 134

Synthesis of 4-amino-3-(4-methylsulfanylphenylazo)naphthalene-1-sulfonic acid sodium salt

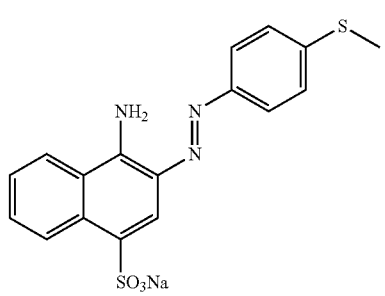

The title compound was synthesized in a manner analogous to Example 93, except for replacing aniline with 4-(methylthio)aniline.

$^1$H-NMR (DMSO-d6) δ [ppm]=8.68 (1H, d, J=8.4), 8.36 (1H, d, J=8.4), 7.89 (2H, d, J=8.7), 7.54-7.39 (4H, m), 7.32 (2H, d, J=8.7), 3.33 (3H, s)

$^{13}$C-NMR (DMSO-d6) δ [ppm]=150.0, 145.7, 140.2, 132.1, 131.5, 128.6, 128.1, 127.9, 125.9, 124.8, 124.1, 123.6, 122.7, 117.0, 14.4

Example 135

Synthesis of 4-amino-3-[4-(pyridine-3-ylmethoxy) phenylazo]naphthalene-1-sulfonic acid sodium salt

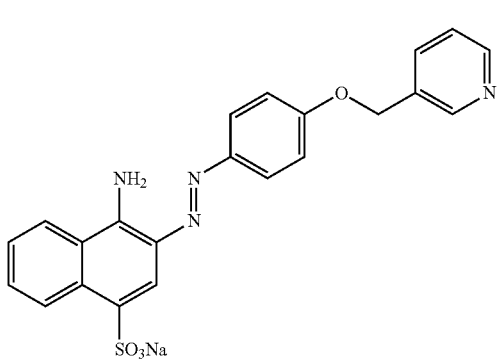

(i) 3-(4-Nitrophenoxymethyl)pyridine

4-Nitrophenol (1.50 g, 10.8 mmol) was dissolved in N,N-dimethylformamide (22.5 ml), added with potassium carbonate (5.59 g, 24.3 mmol) and 3-chloromethylpyridine hydrochloride (1.77 g, 10.8 mmol) sequentially, and reacted at room temperature for 3 hours. The products were crystallized out with addition of water, filtered, and then dried to give the title compound (2.01 g, 80.8%).

(ii) 4-(Pyridine-3-ylmethoxy)aniline

The title compound was synthesized in a manner analogous to Example 7 (ii), except for replacing 2-phenyl-5-nitropyridine with 3-(4-nitrophenoxymethyl)pyridine obtained in (i).

(iii) 4-Amino-3-[4-(pyridine-3-ylmethoxy)phenylazo]naphthalene-1-sulfonic acid sodium salt The title compound was synthesized in a manner analogous to Example 93, except for replacing aniline with 4-(pyridine-3-ylmethoxy)aniline obtained in (ii).

$^1$H-NMR (DMSO-d6) δ [ppm]=8.77 (1H, d, J=8.1), 8.72 (1H, d, J=1.5), 8.56 (1H, dd, J=4.5, 1.5), 8.43 (1H, d, J=8.1), 8.32 (1H, s), 7.99 (2H, d, J=9.0), 7.90 (1H, d, J=7.8), 7.59-7.41 (5H, m), 7.18 (2H, d, J=9.0), 5.24 (2H, s)

$^{13}$C-NMR (DMSO-d6) δ [ppm]=159.4, 149.3, 149.2, 147.4, 145.4, 135.9, 132.4, 132.0, 131.4, 128.6, 128.1, 127.8, 124.8, 124.2, 124.0, 123.7, 123.7, 117.1, 115.3, 67.3

Example 136

Synthesis of 4-amino-3-[4-(pyridine-2-ylmethoxy) phenylazo]naphthalene-1-sulfonic acid sodium salt

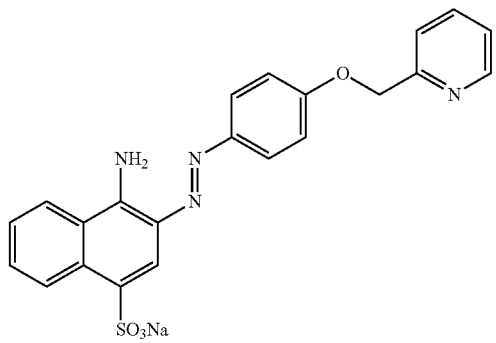

(i) 2-(4-Nitrophenoxymethyl)pyridine

The title compound was synthesized in a manner analogous to Example 135 (i), except for replacing 3-chloromethylpyridine hydrochloride with 2-chloromethylpyridine hydrochloride.

(ii) 4-(Pyridine-2-ylmethoxy)aniline

The title compound was synthesized in a manner analogous to Example 7 (ii), except for replacing 2-phenyl-5-nitropyridine with 2-(4-nitrophenoxymethyl)pyridine obtained in (i).

(iii) 4-Amino-3-[4-(pyridine-2-ylmethoxy)phenylazo]naphthalene-1-sulfonic acid sodium salt The title compound was synthesized in a manner analogous to Example 93, except for replacing aniline with 4-(pyridine-2-ylmethoxy)aniline obtained in (ii).

$^1$H-NMR (DMSO-d6) δ [ppm]=8.77 (1H, d, J=7.5), 8.60-8.58 (1H, m), 8.41 (1H, d, J=8.1), 8.31 (1H, s), 7.97 (2H, d, J=9.0), 7.84 (1H, dd, J=7.8, 1.8), 7.59-7.54 (2H, m), 7.49-7.44 (3H, m), 7.37-7.33 (1H, m), 7.17 (2H, d, J=9.0), 5.28 (2H, s)

$^{13}$C-NMR (DMSO-d6) δ [ppm]=159.3, 126.4, 149.1, 147.3, 145.1, 137.0, 132.1, 131.4, 128.6, 128.1, 127.7, 124.7, 124.2, 123.9, 123.5, 123.0, 121.8, 117.2, 115.2, 70.6

Example 137

Synthesis of 4-amino-3-[3-(pyridine-2-ylmethoxy) phenylazo]naphthalene-1-sulfonic acid sodium salt

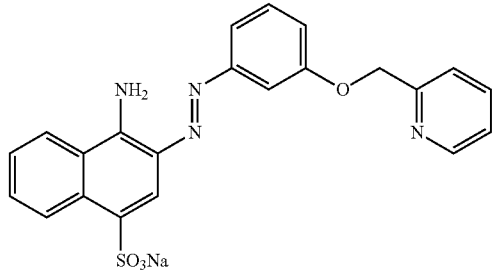

(i) 2-(3-Nitrophenoxymethyl)pyridine

The title compound was synthesized in a manner analogous to Example 135(i), except for replacing 4-nitrophenol with 3-nitrophenol, and replacing 3-chloromethylpyridine hydrochloride with 2-chloromethylpyridine hydrochloride.

(ii) 3-(Pyridine-2-ylmethoxy)aniline

The title compound was synthesized in a manner analogous to Example 7 (ii), except for replacing 2-phenyl-5-nitropyridine with 2-(3-nitrophenoxymethyl)pyridine obtained in (i).

(iii) 4-Amino-3-[3-(pyridine-2-ylmethoxy)phenylazo]naphthalene-1-sulfonic acid sodium salt The title compound was synthesized in a manner analogous to Example 93, except for replacing aniline with 3-(pyridine-2-ylmethoxy)aniline obtained in (ii).

$^1$H-NMR (DMSO-d6) δ [ppm]=8.79 (1H, d, J=8.1), 8.61 (1H, d, J=4.2 Hz), 8.47 (1H, d, J=8.1), 8.35 (1H, s), 7.82-7.87 (1H, m), 7.721 (1H, bs), 7.65-7.72 (1H, m), 7.58-7.65 (3H, m), 7.43-7.52 (2H, m), 7.32-7.36 (1H, m), 7.10 (1H, dd, J=8.1, 1.5 Hz), 5.32 (1H, s)

$^{13}$C-NMR (DMSO-d6) δ [ppm]=159.1, 156.7, 154.1, 149.2, 146.1, 137.1, 132.1, 131.8, 130.1, 128.6, 128.3, 128.2, 125.0, 124.2, 123.9, 123.1, 121.9, 117.5, 116.8, 116.5, 106.3, 70.6

Example 138

Synthesis of 4-amino-3-[3-(pyridine-3-ylmethoxy)phenylazo]naphthalene-1-sulfonic acid sodium salt

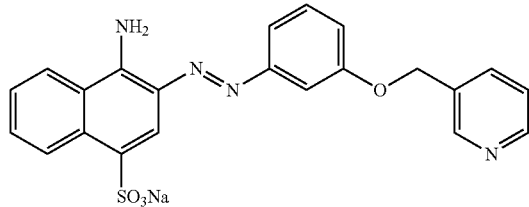

(i) 3-(3-Nitrophenoxymethyl)pyridine

The title compound was synthesized in a manner analogous to Example 135 (i), except for replacing 4-nitrophenol with 3-nitrophenol.

(ii) 3-(Pyridine-3-ylmethoxy)aniline

The title compound was synthesized in a manner analogous to Example 7 (ii), except for replacing 2-phenyl-5-nitropyridine with 3-(3-nitrophenoxymethyl)pyridine obtained in (i).

(iii) 4-Amino-3-[3-(pyridine-3-ylmethoxy)phenylazo]naphthalene-1-sulfonic acid sodium salt The title compound was synthesized in a manner analogous to Example 93, except for replacing aniline with 3-(pyridine-3-ylmethoxy)aniline obtained in (ii).

$^1$H-NMR (DMSO-d6) δ [ppm]=8.76 (1H, s), 8.73 (1H, s), 8.55 (1H, d, J=4.2 Hz), 8.47 (1H, d, J=8.1 Hz), 8.30 (1H, s), 7.93 (1H, d, J=7.8 Hz), 7.73 (2H, bs), 7.65 (1H, s), 7.56-7.61 (2H, m), 7.42-7.51 (3H, m), 7.09 (1H, dd, J=8.1, 1.5 Hz), 5.30 (2H, s)

$^{13}$C-NMR (DMSO-d6) δ [ppm]=159.0, 154.1, 149.2, 146.1, 135.8, 132.6, 132.2, 131.8, 130.1, 128.6, 128.2, 124.9, 124.2, 123.9, 123.7, 117.4, 116.8, 116.6, 106.2, 67.2

Example 139

Synthesis of 4-amino-3-[3-(pyridine-4-ylmethoxy)phenylazo]naphthalene-1-sulfonic acid sodium salt

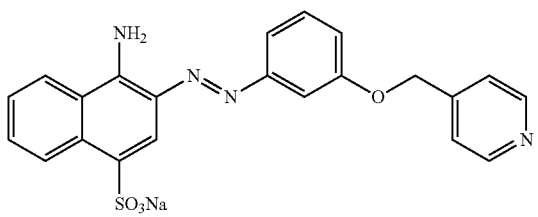

(i) 4-(3-Nitrophenoxymethyl)pyridine

The title compound was synthesized in a manner analogous to Example 135 (i), except for replacing 4-nitrophenol with 3-nitrophenol, and replacing 3-chloromethylpyridine hydrochloride with 4-chloromethylpyridine hydrochloride.

(ii) 3-(Pyridine-4-ylmethoxy)aniline

The title compound was synthesized in a manner analogous to Example 7 (ii), except for replacing 2-phenyl-5-nitropyridine with 4-(3-nitrophenoxymethyl)pyridine obtained in (i).

(iii) 4-Amino-3-[3-(pyridine-4-ylmethoxy)phenylazo]naphthalene-1-sulfonic acid sodium salt The title compound was synthesized in a manner analogous to Example 93, except for replacing aniline with 3-(pyridine-4-ylmethoxy)aniline obtained in (ii).

$^1$H-NMR (DMSO-d6) δ [ppm]=8.77 (1H, d, J=8.4 Hz), 8.60 (2H, d, J=5.7 Hz), 8.46 (1H, d, J=8.1 Hz), 8.32 (1H, s), 7.73 (2H, bs), 7.57-7.63 (3H, m), 7.43-7.51 (4H, m), 7.09 (1H, dd, J=8.0, 1.5 Hz), 5.33 (2H, s)

$^{13}$C-NMR (DMSO-d6) δ [ppm]=158.8, 154.1, 149.8, 146.2, 146.1, 132.2, 131.8, 130.1, 128.6, 128.3, 128.2, 125.0, 124.2, 123.9, 121.9, 117.5, 116.7, 116.5, 106.5, 67.7

Example 140

Synthesis of 4-amino-3-[2-(pyridine-2-ylmethoxy)phenylazo]naphthalene-1-sulfonic acid sodium salt

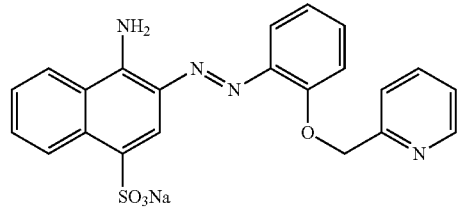

(i) 2-(2-Nitrophenoxymethyl)pyridine

The title compound was synthesized in a manner analogous to Example 135 (i), except for replacing 4-nitrophenol with 2-nitrophenol, and replacing 3-chloromethylpyridine hydrochloride with 2-chloromethylpyridine hydrochloride.

(ii) 2-(Pyridine-2-ylmethoxy)aniline

The title compound was synthesized in a manner analogous to Example 7 (ii), except for replacing 2-phenyl-5-nitropyridine with 2-(2-nitrophenoxymethyl)pyridine obtained in (i).

(iii) 4-Amino-3-[2-(pyridine-2-ylmethoxy)phenylazo]naphthalene-1-sulfonic acid sodium salt The title compound was synthesized in a manner analogous to Example 93, except for replacing aniline with 2-(pyridine-2-ylmethoxy)aniline obtained in (ii).

$^1$H-NMR (DMSO-d6) δ [ppm]=8.81 (1H, d, J=8.1 Hz), 8.59 (1H, d, J=4.2 Hz), 8.49 (1H, s), 8.46 (1H, s), 8.37 (2H, bs), 7.94-7.99 (1H, m), 7.88 (1H, dd, J=8.0, 1.5 Hz), 7.75 (1H, d, J=7.8 Hz), 7.58-7.63 (1H, m), 7.47-7.52 (1H, m), 7.30-7.42 (3H, m), 7.05-7.10 (1H, m), 5.42 (2H, s)

$^{13}$C-NMR (DMSO-d6) δ [ppm]=156.9, 154.5, 149.0, 143.3, 141.9, 137.5, 132.1, 131.3, 130.7, 129.3, 128.1, 124.8, 124.3, 123.9, 122.8, 122.4, 121.3, 121.2, 116.2, 114.6, 70.9

Example 141

Synthesis of 4-amino-3-[2-(pyridine-4-ylmethoxy)phenylazo]naphthalene-1-sulfonic acid sodium salt

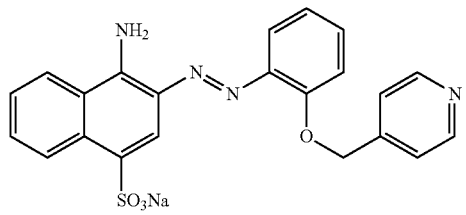

(i) 4-(2-Nitrophenoxymethyl)pyridine

The title compound was synthesized in a manner analogous to Example 135 (i), except for replacing 4-nitrophenol with 2-nitrophenol, and replacing 3-chloromethylpyridine hydrochloride with 4-chloromethylpyridine hydrochloride.

(ii) 2-(Pyridine-4-ylmethoxy)aniline

The title compound was synthesized in a manner analogous to Example 7 (ii), except for replacing 2-phenyl-5-nitropyridine with 4-(2-nitrophenoxymethyl)pyridine obtained in (i).

(iii) 4-Amino-3-[2-(pyridine-4-ylmethoxy)phenylazo]naphthalene-1-sulfonic acid sodium salt The title compound was synthesized in a manner analogous to Example 93, except for replacing aniline with 2-(pyridine-4-ylmethoxy)aniline obtained in (ii).

$^1$H-NMR (DMSO-d6) δ [ppm]=8.80 (1H, d, J=8.4 Hz), 8.64 (2H, d, J=5.7 Hz), 8.47 (1H, d, J=8.4 Hz), 8.44 (1H, s), 8.38 (2H, bs), 7.88 (1H, d, J=7.8 Hz), 7.61 (1H, d, J=7.2 Hz), 7.56 (2H, d, J=5.7 Hz), 7.47-7.52 (1H, m), 7.37-7.42 (1H, m), 7.28 (1H, d, J=8.1 Hz), 7.06-7.11 (1H, m), 5.42 (2H, s)

$^{13}$C-NMR (DMSO-d6) δ [ppm]=154.3, 149.9, 146.3, 143.2, 141.9, 132.3, 131.3, 130.7, 129.3, 128.1, 128.0, 124.7, 124.3, 123.9, 122.4, 121.3, 116.1, 114.6, 68.3

Example 142

Synthesis of 4-amino-3-[2-(pyridine-3-ylmethoxy)phenylazo]naphthalene-1-sulfonic acid sodium salt

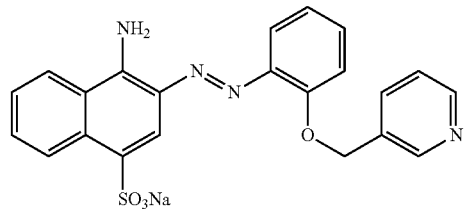

(i) 3-(2-Nitrophenoxymethyl)pyridine

The title compound was synthesized in a manner analogous to Example 135 (i), except for replacing 4-nitrophenol with 2-nitrophenol.

(ii) 2-(Pyridine-3-ylmethoxy)aniline

The title compound was synthesized in a manner analogous to Example 7 (ii), except for replacing 2-phenyl-5-nitropyridine with 3-(2-nitrophenoxymethyl)pyridine obtained in (i).

(iii) 4-Amino-3-[2-(pyridine-3-ylmethoxy)phenylazo]naphthalene-1-sulfonic acid sodium salt The title compound was synthesized in a manner analogous to Example 93, except for replacing aniline with 2-(pyridine-3-ylmethoxy)aniline obtained in (ii).

$^1$H-NMR (DMSO-d6) δ [ppm]=8.79 (1H, dd, J=8.4, 0.9 Hz), 8.72 (1H, d, J=1.8 Hz), 8.54 (1H, dd, J=4.8, 1.8 Hz), 8.48 (1H, s), 8.45 (2H, bs), 8.40 (1H, s), 7.98-8.02 (1H, m), 7.83 (1H, dd, J=7.8, 1.5 Hz), 7.57-7.62 (1H, m), 7.46-7.52 (2H, m), 7.33-7.40 (2H, m), 7.05-7.11 (1H, m), 5.41 (2H, s)

$^{13}$C-NMR (DMSO-d6) δ [ppm]=154.4, 149.0, 148.5, 142.9, 142.2, 135.3, 132.8, 132.1, 131.2, 130.6, 129.2, 128.0, 124.7, 124.3, 123.9, 123.1, 121.5, 116.1, 115.2, 68.0

Example 143

Synthesis of 4-amino-3-[4-(2-cyano-2-phenylvinyl)phenylazo]naphthalene-1-sulfonic acid sodium salt

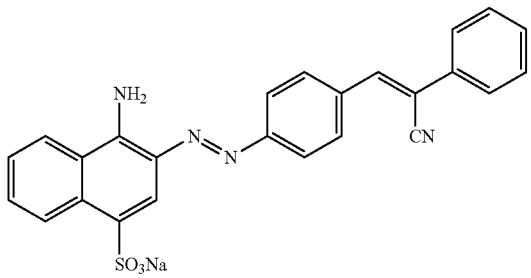

(i) 3-(4-Nitrophenyl)-2-phenylacrylonitrile

To ethanol (10.0 ml), 4-nitrobenzaldehyde (2.0 g, 13.2 mmol) and phenylacetonitrile (1.6 g, 13.2 mmol) were added, and added dropwise with a solution of 20% sodium ethoxide in ethanol. The reaction solution was cooled and the precipitated solids were filtered and washed with water and ethanol to give the title compound (2.92 g, 88.4%).

(ii) 3-(4-Aminophenyl)-2-phenylacrylonitril

The title compound was synthesized in a manner analogous to Example 7 (ii), except for replacing 2-phenyl-5-nitropyridine with 3-(4-nitrophenyl)-2-phenylacrylonitril obtained in (i).

(iii) 4-Amino-3-[4-(2-cyano-2-phenylvinyl)phenylazo]naphthalene-1-sulfonic acid sodium salt The title compound was synthesized in a manner analogous to Example 93, except for replacing aniline with 3-(4-aminophenyl)-2-phenylacrylonitril obtained in (ii).

$^1$H-NMR (DMSO-d6) δ [ppm]=8.76 (1H, d, J=8.1 Hz), 8.45 (1H, d, J=8.1 Hz), 8.31 (1H, s), 8.11-8.13 (5H, m), 7.79-7.84 (4H, m), 7.43-7.63 (5H, m)

$^{13}$C-NMR (DMSO-d6) δ [ppm]=153.7, 147.0, 142.1, 134.1, 133.9, 132.6, 132.1, 130.3, 129.3, 129.2, 129.2, 128.5, 128.3, 125.8, 125.0, 124.2, 123.9, 122.7, 118.1, 116.9, 109.9

Example 144

Synthesis of 4-amino-3-(2,4'-difluoro-2'-methyl-diphenyl-4-ylazo)naphthalene-1-sulfonic acid sodium salt

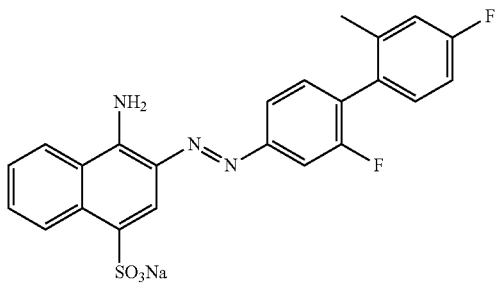

(i) 2,4'-Difluoro-2'-methyldiphenyl-4-ylamine

Benzyl (4-bromo-3-fluorophenyl)carbamate (1.5 g, 5.36 mmol), 4-fluoro-2-methylphenylboronic acid (0.83 g, 5.42 mmol), and bis(di-tert-butyl(4-dimethylaminophenylphosphine)dichloropalladium(II) (0.038 g, 0.05 mmol) were added to 1,2-dimethoxyethan (14 ml), degassed and purged with nitrogen three times under reduced pressure. Under nitrogen atmosphere the mixture was stirred at room temperature for 30 minutes, 1M aqueous sodium carbonate (14 ml) was poured into the mixture, and the temperature was raised to 80° C. After the reaction at 80° C. for 1 hour, the mixture was cooled to room temperature and extracted with addition of ethyl acetate and water. The organic layer was dried with anhydrous sodium sulfate, and concentrated under reduced pressure. The concentrates were dissolved in methanol, added with palladium carbon, deprotected with hydrogen at balloon pressure at room temperature, concentrated under reduced pressure, and neutralized. The precipitated crystals were filtered to give the title compound (0.94 g, 79.9%).

(ii) 4-Amino-3-(2,4'-difluoro-2'-methyl-diphenyl-4-ylazo)naphthalene-1-sulfonic acid sodium salt The title compound was synthesized in a manner analogous to Example 93, except for replacing aniline with 2,4'-difluoro-2'-methyldiphenyl-4-ylamine obtained in (i).

$^1$H-NMR (DMSO-d6) δ [ppm]=8.76 (1H, d, J=8.7 Hz), 8.46 (1H, dd, J=8.4, 2.4 Hz), 8.30 (1H, d, J=5.7 Hz), 8.00 (1H, dd, J=11.6, 1.8 Hz), 7.90 (1H, dd, J=8.1, 1.8 Hz), 7.78 (2H, bs), 7.57-7.62 (1H, m), 7.42-7.52 (2H, m), 7.29-7.34 (1H, m), 7.20-7.24 (1H, m), 7.09-7.16 (1H, m), 2.20 (3H, s)

Example 145

Synthesis of 4-amino-3-(quinoline-3-ylazo)naphthalene-1-sulfonic acid sodium salt

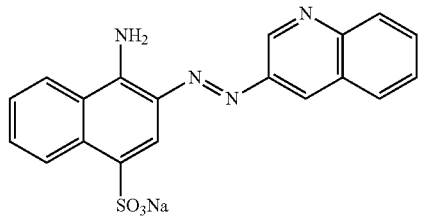

The title compound was synthesized in a manner analogous to Example 93, except for replacing aniline with 3-aminoquinoline.

$^1$H-NMR (DMSO-d6) δ [ppm]=9.59 (1H, d, J=2.4 Hz), 8.86 (1H, d, J=2.4 Hz), 8.77 (1H, d, J=8.6 Hz), 8.49 (1H, d, J=8.1 Hz), 8.37 (1H, s), 8.14 (1H, d, J=7.2 Hz), 8.08 (1H, d, J=8.4 Hz), 7.87 (2H, s), 7.79 (1H, dd, J=7.6 Hz, 7.2 Hz), 7.69-7.59 (2H, m), 7.51 (1H, dd, J=8.1 Hz, 7.7 Hz)

$^{13}$C-NMR (DMSO-d6) δ [ppm]=147.6, 147.1, 146.4, 145.4, 132.5, 132.1, 130.0, 129.3, 128.9, 128.6, 128.3, 128.1, 127.4, 127.3, 125.1, 124.2, 124.0, 116.6

Example 146

Synthesis of methyl 3-(1-amino-4-sulfonaphthalene-2-ylazo)thiophene-2-carboxylate sodium salt

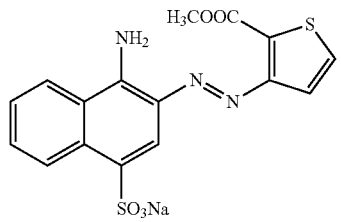

The title compound was synthesized in a manner analogous to Example 93, except for replacing aniline with methyl 3-amino-2-thiophenecarboxylate.

$^1$H-NMR (DMSO-d6) δ [ppm]=9.86 (2H, s), 8.73 (1H, d, J=8.1 Hz), 8.58 (1H, d, J=7.8 Hz), 8.24 (1H, s), 7.94 (1H, d, J=5.4 Hz), 7.67 (1H, d, J=5.4 Hz), 7.66-7.47 (2H, m)

$^{13}$C-NMR (DMSO-d6) δ [ppm]=161.8, 157.2, 141.2, 132.7, 132.3, 131.4, 128.8, 128.7, 128.5, 128.0, 125.0, 124.5, 124.4, 124.0, 117.5, 52.4

Example 147

Synthesis of 4-amino-3-(quinoline-6-ylazo)naphthalene-1-sulfonic acid sodium salt

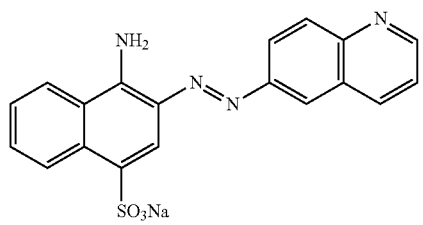

The title compound was synthesized in a manner analogous to Example 93, except for replacing aniline with 6-aminoquinoline.

$^1$H-NMR (DMSO-d6) δ [ppm]=8.91 (1H, dd, J=4.2 Hz, 1.2 Hz), 8.74 (1H, d, J=8.4 Hz), 8.56-8.47 (4H, m), 8.36 (1H, s), 8.03 (1H, d, J=9.0 Hz), 7.83 (2H, s), 7.62-7.57 (2H, m), 7.50 (1H, dd, J=7.5 Hz)

$^{13}$C-NMR (DMSO-d6) δ [ppm]=150.9, 150.4, 148.2, 146.5, 136.9, 132.3, 131.9, 130.0, 128.9, 128.5, 128.4, 128.2, 125.0, 124.3, 124.2, 124.0, 122.1, 121.9

Example 148

Synthesis of 4-amino-3-[6-(2-butoxy-3-ethoxy-5-formylphenyl)pyridine-3-ylazo]naphthalene-1-sulfonic acid sodium salt

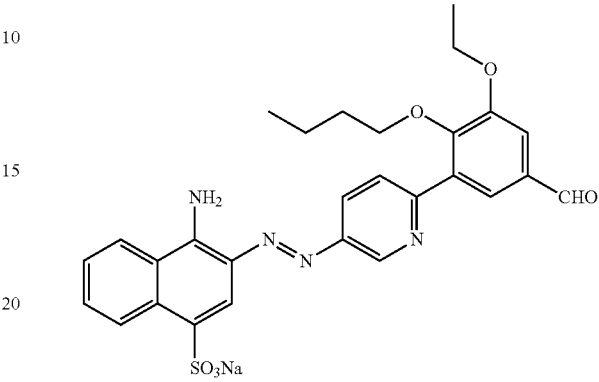

(i) 3-Ethoxy-4-hydroxy-5-iodobenzaldehyde

Ethylvanillin (2.0 g, 12 mmol) and sodium iodide (1.8 g, 12 mmol) were dissolved in acetic acid (8 ml), and added dropwise with a solution of N-chlorosuccinimide (1.6 g, 12 mmol) in N,N-dimethylacetamide (10 ml) at room temperature. After the reaction at room temperature for 1 hour, water (40 ml) was added to the mixture, and the precipitated crystals were filtered to give the title compound (3.3 g, yield 94%).

(ii) 4-Butoxy-3-ethoxy-5-iodobenzaldehyde

A solution of 3-ethoxy-4-hydroxy-5-iodobenzaldehyde (3.2 g, 11 mmol) obtained in (i), 1-bromobutane (2.3 g, 17 mmol) and potassium carbonate (3.8 g, 28 mmol) in N,N-dimethylacetamide (23 ml) was reacted at 60° C. for 4 hours. After cooling, the mixture was added with water and extracted with dichloromethane. The organic layer was concentrated under reduced pressure to give the title compound (4.2 g, 109% yield) as yellow oil.

(iii) 2-Butoxy-1-ethoxy-5-(diethoxymethyl)-3-iodobenzene

A solution of 4-butoxy-3-ethoxy-5-iodobenzaldehyde (3.8 g, 11 mmol) obtained in (ii), triethyl orthoformate (4.9 g, 33 mmol), and ammonium chloride (0.1 g, 2 mmol) in ethanol (39 ml) was reacted under reflux for 4 hours. After cooling, ethanol was removed by concentration under reduced pressure, and the concentrated residues were extracted with water/dichloromethane. The organic layer was concentrated under reduced pressure to give the title compound (4.2 g, 89%) as yellow oil.

(iv) 2-Butoxy-3-ethoxy-5-formylphenylboronic acid

A solution of 2-butoxy-1-ethoxy-5-(diethoxymethyl)-3-iodobenzene (4.2 g, 10 mmol) obtained in (iii) in anhydrous tetrahydrofuran (42 ml) was cooled to −10° C., and added dropwise with a solution of isopropyl magnesium chloride (9.9 ml, 10 mmol) in tetrahydrofuran. After reaction at −10°

C. for 30 minutes, trimethyl borate (3.1 g, 30 mmol) was poured into the mixture at −10° C. After reaction at −10° C. for 2 hours, an aqueous solution of 2% hydrogen chloride (90 ml) and sodium chloride (10 g) were added, and the mixture was partitioned. The organic layer was concentrated to dryness, and recrystallized from acetone/water to give the title compound as white powder (1.6 g, 61% yield).

(v) 4-Butoxy-3-ethoxy-5-(5-nitropyridine-2-yl)benzaldehyde

A solution of 2-chloro-5-nitropyridine (1.0 g, 6 mmol), 2-butoxy-3-ethoxy-5-formylphenylboronic acid (1.6 g, 6 mmol) obtained in (iv), and bis(di-tert-butyl(4-dimethylaminophenyl)phosphine)dichloropalladium(II) (A-Phos) (0.04 g, 0.06 mmol) in dimethylether (15 ml) was added with aqueous sodium carbonate (1 mol/L, 15 ml) and refluxed under an inert gas atmosphere for 2 hours with heating. After cooling, water was added to the mixture and the precipitated crystals were filtered to give the title compound as brown solids (2.1 g, 99% yield).

(vi) 3-(5-Aminopyridine-2-yl)-4-butoxy-5-ethoxybenzaldehyde

Iron powder (100 mesh, 0.8 g, 15 mmol) and ammonium chloride (0.2 g, 3 mmol) were added to ethanol (31 ml), followed by 4-butoxy-3-ethoxy-5-(5-nitropyridine-2-yl)benzaldehyde (2.1 g, 6 mmol) obtained in (v), and reacted at 75° C. for 1 hour. The brown insoluble materials were filtered with heating, and washed thoroughly with ethanol. The filtrate was concentrated under reduced pressure, added with water, and the precipitated crystals were filtered to give the title compound as yellow solids (1.7 g, 93% yield).

(vii) 4-Amino-3-[6-(2-butoxy-3-ethoxy-5-formylphenyl)pyridine-3-ylazo]naphthalene-1-sulfonic acid sodium salt 3-(5-Aminopyridine-2-yl)-4-butoxy-5-ethoxybenzaldehyde (1.7 g, 6 mmol) obtained in (vi) was dissolved in 99% acetic acid, and added with 35% hydrochloric acid to form hydrochloride. With cooling on ice, an aqueous solution of sodium nitrite was added dropwise to the mixture at 0 to 5° C., and the reaction was carried out for about 15 minutes. The reaction was carried out for additional 5 minutes with addition of amidosulfuric acid to give diazo solution.

4-Amino-1-naphthalenesulfonic acid (1.2 g, 6 mmol) was suspended in water, and the pH of the suspension was adjusted to pH 8 to 9 with 10% aqueous sodium hydroxide. The diazo solution was added dropwise to the suspension at 5 to 10° C., during which 10% aqueous sodium hydroxide was added dropwise to keep the pH at 7 to 10. After the completion of the addition, the reaction was carried out at 5-10° C. for 1 hour, and then the temperature raised to room temperature. After adding saturated aqueous sodium chloride, the precipitated crystals were filtered with suction. Purification through an alumina column gave the title compound (17% yield).

$^1$H-NMR (DMSO-d6) δ [ppm]=9.99 (1H, s), 9.27 (1H, dd), 8.75 (1H, dd), 8.51 (1H, dd), 8.46 (1H, d), 8.30 (1H, s), 8.52-8.44 (2H, m), 7.79 (2H, bs), 7.63-7.47 (3H, m), 4.19 (2H, t), 4.01 (2H, t), 1.58 (2H, q), 1.45-1.29 (6H, m), 0.82 (3H, t)

$^{13}$C-NMR (DMSO-d6) δ [ppm]=192.1, 154.1, 152.7, 151.4, 147.2, 146.2, 133.7, 132.7, 132.2, 132.0, 129.3, 128.5, 128.4, 126.4, 126.3, 126.2, 125.2, 125.0, 124.2, 123.9, 116.3, 111.9, 72.9, 64.3, 31.6, 18.5, 14.6, 13.5

Example 149

Synthesis of 4-amino-3-[6-(2-ethoxy-3-formyl-5-methylphenyl)pyridine-3-ylazo]naphthalene-1-sulfonic acid sodium salt

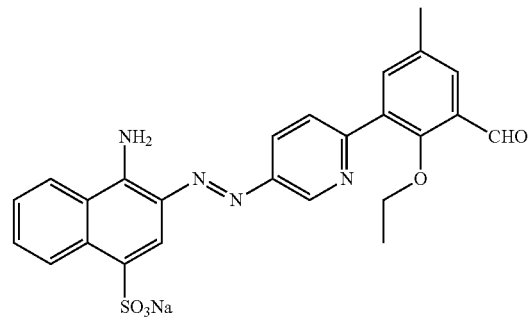

(i) 5-Methyl-3-iodosalicylaldehyde

The title compound was synthesized in a manner analogous to Example 148 (i), except for replacing ethylvanillin with 5-methylsalicylaldehyde.

(ii) 2-Ethoxy-3-iodo-5-methylbenzaldehyde

A solution of 5-methyl-3-iodosalicylaldehyde (4.0 g, 15 mmol) obtained in (i), 1-bromoethan (2.8 g, 23 mmol) and potassium carbonate (5.3 g, 38 mmol) in N,N-dimethylacetamide (28 ml) was reacted at 60° C. for 4 hours. After cooling, the solution was added with water and extracted with dichloromethane. The organic layer was concentrated under reduced pressure to give the title compound as yellow oil (3.8 g, 87% yield).

(iii) 1-Diethoxymethyl-2-ethoxy-3-iodo-5-methylbenzene

The title compound was synthesized in a manner analogous to Example 148 (iii), except for replacing 4-butoxy-3-ethoxy-5-iodobenzaldehyde with 2-ethoxy-3-iodo-5-methylbenzaldehyde obtained in (ii).

(iv) 2-Ethoxy-3-formyl-5-methylphenylboronic acid

The title compound was synthesized in a manner analogous to Example 148 (iv), except for replacing 2-butoxy-1-ethoxy-5-(diethoxymethyl)-3-iodobenzene with 1-diethoxymethyl-2-ethoxy-3-iodo-5-methylbenzene obtained in (iii).

(v) 2-Ethoxy-5-methyl-3-(5-nitropyridine-2-yl)benzaldehyde

The title compound was synthesized in a manner analogous to Example 148 (v), except for replacing 2-butoxy-3- ethoxy-5-formylphenylboronic acid with 2-ethoxy-3-formyl-5-methylphenylboronic acid obtained in (iv).

(vi) 3-(5-Aminopyridine-2-yl)-2-ethoxy-5-methylbenzaldehyde

A solution of 2-ethoxy-5-methyl-3-(5-nitropyridine-2-yl)benzaldehyde (1.5 g, 5 mmol) obtained in (v) and 5% Pd(en)cat (0.2 g) in methanol (30 ml) was reacted under hydrogen atmosphere (0.7 MPa) at 40° C. for 2 hours. The catalysts were filtered, and the filtrate was concentrated under reduced pressure and added with water. The precipitated crystals were filtered to give the title compound as yellow solids (1.3 g, 96% yield).

(vii) 4-Amino-3-[6-(2-ethoxy-3-formyl-5-methyl-phenyl)pyridine-3-ylazo]naphthalene-1-sulfonic acid sodium salt The title compound was synthesized in a manner analogous to Example 148 (vii), except for replacing 3-(5-aminopyridine-2-yl)-4-butoxy-5-ethoxybenzaldehyde with 3-(5-aminopyridine-2-yl)-2-ethoxy-5-methylbenzaldehyde obtained in (vi).
$^1$H-NMR (DMSO-d6) δ [ppm]=10.4 (1H, s), 9.27 (1H, d), 8.75 (1H, dd), 8.52 (1H, dd), 8.47 (1H, d), 8.31 (1H, s), 8.03 (1H, d), 7.99 (1H, d), 7.83 (2H, bs), 7.65-7.47 (3H, m), 8.77 (2H, q), 2.41 (3H, s), 1.19 (3H, t)
$^{13}$C-NMR (DMSO-d6) δ [ppm]=190.1, 157.7, 154.2, 147.3, 146.6, 137.9, 134.0, 133.7, 132.6, 132.5, 132.2, 129.6, 129.3, 128.6, 128.3, 126.6, 125.1, 124.5, 124.2, 124.0, 116.4, 72.3, 20.2, 15.0

Biological Example 1

Mouse VCP cDNA was added with a DNA sequence corresponding to histidine tag at the amino-terminal, subcloned into a baculovirus vector pVL1392 (BD Bioscience), and expressed in Sf-9 insect cells. The protein was purified with a nickel column (GE Healthcare). The concentration of the protein was adjusted to 0.25-0.5 μg/ml and the protein was stored in a solution containing 50 mM TrisCl pH 8.0, 5 mM EDTA, 10% glycerol, and 15 mM DTT.

The ATPase activity was determined as follows. 500 ng of the purified VCP was mixed with 100 μM [γ-32P]ATP (18.5 GBq/mmol) and the test substance in 20 μL of ATPase buffer (20 mM HEPES (pH7.4), 50 mM KCl, 5 mM MgCl$_2$, 15 mM DTT), and incubated at 37° C. for 10 minutes.

The enzyme reaction was stopped with addition of 200 μL of an ice-cold solution containing 7% TCA and 1 mM K$_2$HPO$_4$. 50μ of a solution containing 3.75% ammonium molybdate and 0.02M tungstate silicic/3 NH$_2$SO$_4$ was added, followed by 300 μL of n-butylacetic acid, and then the liberated phosphate was extracted into the organic layer. The reaction tube was centrifuged for 5 minutes at 20,000 g to separate the aqueous layer and the organic layer, 200 μL of the organic layer was taken, and the beta ray radiated from the liberated phosphate was quantified with liquid scintillation counter.

By measuring the ATPase activity in the presence of the test substance at various concentrations, ATPase inhibitory activity of the test substance was measured. IC$_{50}$ of the each test substance was calculated by applying the measured values to the equation below using GraphPad Prism (GraphPad Software).

$$Y=\text{Bottom}+(\text{Top}-\text{Bottom})/(1+10^{\wedge}((\log IC_{50}-X)))$$

X: Logarithm of the concentration of the test substance
Y: ATPase activity in the presence of test substance
Bottom: Value when the activity was inhibited to the maximum
Top: ATPase activity in the absence of the test substance IC$_{50}$ values (nM) of the compounds of Examples are shown in the table below.

TABLE 4

| Example | IC50 |
|---|---|
| 1 | 1,582 |
| 2 | 571 |
| 3 | 281 |
| 4 | 407 |
| 5 | 495 |
| 6 | 518 |
| 7 | 229 |
| 8 | 430 |
| 9 | 188 |
| 10 | 149 |
| 11 | 426 |
| 12 | 116 |
| 13 | 26,630 |
| 14 | 178 |
| 15 | 189 |
| 16 | 136 |
| 17 | 143 |
| 18 | 163 |
| 19 | 178 |
| 20 | 170 |
| 21 | 445 |
| 22 | 197 |
| 23 | 324 |
| 24 | 540 |
| 25 | 300 |
| 26 | 304 |
| 27 | 145 |
| 28 | 416 |
| 29 | 287 |
| 30 | 1,137 |
| 31 | 1,032 |
| 32 | 428 |
| 33 | 301 |
| 34 | 274 |
| 35 | 632 |
| 36 | 279 |
| 37 | 726 |
| 38 | 234 |
| 39 | 754 |
| 40 | 328 |
| 41 | 210 |
| 42 | 769 |
| 43 | 1,037 |
| 44 | 584 |
| 45 | 524 |
| 46 | 2,750 |
| 47 | 589 |
| 48 | 127 |
| 49 | 330 |
| 50 | 468 |
| 51 | 3,068 |
| 52 | 1,390 |
| 53 | 1,151 |
| 54 | 1,058 |
| 55 | 139 |
| 56 | 246 |
| 57 | 1,390 |
| 58 | 320 |
| 59 | 380 |
| 60 | 250 |

TABLE 4-continued

| Example | IC50 |
|---|---|
| 61 | 843 |
| 62 | 856 |
| 63 | 807 |
| 64 | 324 |
| 65 | 378 |
| 66 | 232 |
| 67 | 130 |
| 68 | 201 |
| 69 | 90 |
| 70 | 712 |
| 71 | 257 |
| 72 | 796 |
| 73 | 499 |
| 74 | 3,998 |
| 75 | 924 |
| 76 | 1,412 |
| 77 | 366 |
| 78 | 402 |
| 79 | 798 |
| 80 | 329 |
| 81 | 207 |
| 82 | 289 |
| 83 | 350 |
| 84 | 567 |
| 85 | 1,051 |
| 86 | 552 |
| 87 | 469 |
| 88 | 348 |
| 89 | 501 |
| 90 | 112 |
| 91 | 212 |
| 92 | 161 |
| 93 | 762 |
| 94 | 1,111 |
| 95 | 393 |
| 96 | 1,627 |
| 97 | 804 |
| 98 | 591 |
| 99 | 1,393 |
| 100 | 408 |
| 101 | 1,759 |
| 102 | 904 |
| 103 | 887 |
| 104 | 2,065 |
| 105 | 238 |
| 106 | 2,259 |
| 107 | 540 |

TABLE 4-continued

| Example | IC50 |
|---|---|
| 108 | 288 |
| 109 | 856 |
| 110 | 226 |
| 111 | 244 |
| 112 | 526 |
| 113 | 266 |
| 114 | 99 |
| 115 | 297 |
| 116 | 1,226 |
| 117 | 230 |
| 118 | 105 |
| 119 | 737 |
| 120 | 162 |
| 121 | 2,558 |
| 122 | 849 |
| 123 | 274 |
| 124 | 4,006 |
| 125 | 417 |
| 126 | 343 |
| 127 | 295 |
| 128 | 128 |
| 129 | 1,900 |
| 130 | 260 |
| 131 | 242 |
| 132 | 135 |
| 133 | 518 |
| 134 | 327 |
| 135 | 716 |
| 136 | 601 |
| 137 | 610 |
| 138 | 516 |
| 139 | 600 |
| 140 | 596 |
| 141 | 747 |
| 142 | 243 |
| 143 | 1,220 |
| 144 | 199 |
| 145 | 295 |
| 146 | 1,290 |
| 147 | 502 |
| 148 | 1,564 |
| 149 | 182 |

The compounds of the following comparative examples were prepared in the same manner as in Example 7 or Example 93 using the appropriate starting materials or commercially obtained.

TABLE 5

| Comparative Example | structure | NMR spectrum |
|---|---|---|
| 1 | 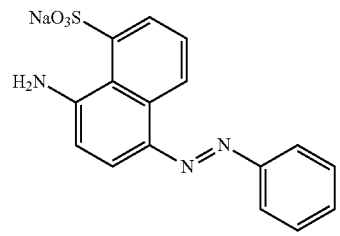 | $^1$H-NMR (DMSO-d6) δ [ppm] = 9.03 (1H, dd, J = 8.6 Hz, 1.2 Hz), 8.26 (2H, s), 8.15 (1H, dd, J = 8.6 Hz, 1.2 Hz), 7.88 (1H, d, J = 9.0 Hz), 7.78 (2H, d, J = 7.5 Hz), 7.54-7.45 (2H, m), 7.37 (1H, dd, J = 7.4 Hz), 6.76 (1H, d, J = 9.0 Hz) $^{13}$C-NMR (DMSO-d6) δ [ppm] = 153.3, 151.7, 143.9, 136.1, 136.0, 129.2, 128.6, 125.5, 125.4, 124.8, 121.8, 116.8, 114.8, 110.6 |

TABLE 5-continued

| Comparative Example | structure | NMR spectrum |
|---|---|---|
| 2 | 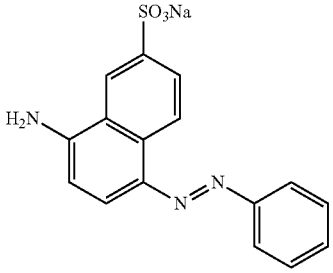 | ¹H-NMR (DMSO-d6) δ [ppm] = 8.82 (1H, d, J = 8.7 Hz), 8.44 (1H, d, J = 1.5 Hz), 7.89-7.82 (4H, m), 7.53 (2H, dd, J = 7.8 Hz, 7.2 Hz), 7.41 (1H, dd, J = 7.2 Hz), 7.00 (2H, s), 6.71 (1H, d, 8.4 Hz) ¹³C-NMR (DMSO-d6) δ [ppm] = 153.1, 151.1, 144.2, 136.6, 133.2, 129.3, 129.1, 125.4, 122.2, 121.9, 120.1, 119.4, 115.3, 107.8 |
| 3 | 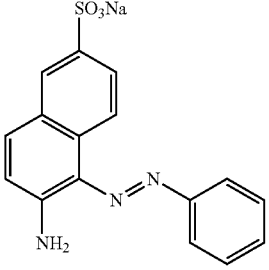 | ¹H-NMR (DMSO-d6) δ [ppm] = 8.66 (1H, d, J = 8.7 Hz), 7.94 (1H, d, J = 1.8 Hz), 7.92 (2H, d, J = 7.2 Hz), 7.81 (1H, d, J = 9.0 Hz), 7.74 (1H, dd, J = 8.7 Hz, 1.8 Hz), 7.54 (2H, dd, J = 7.4 Hz, 7.2 Hz), 7.18 (1H, d, J = 9.0 Hz) ¹³C-NMR (DMSO-d6) δ [ppm] = 153.2, 142.6, 140.6, 134.2, 134.2, 129.3, 128.9, 125.4, 125.3, 125.2, 124.9, 121.5, 120.4 |
| 4 | 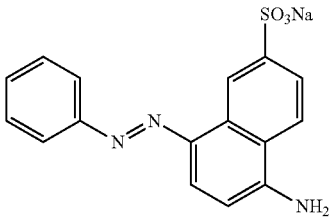 | ¹H-NMR (DMSO-d6) δ [ppm] = 9.11 (1H, d, J = 1.8 Hz), 8.15 (1H, d, J = 8.7 Hz), 7.89 (1H, d, J = 9.0 Hz), 7.85 (2H, d, J = 7.5 Hz), 7.66 (1H, dd, J = 9.0 Hz, 1.8 Hz), 7.54 (2H, dd, J = 7.5 Hz, 7.2 Hz), 7.41 (1H, dd, J = 7.5 Hz, 7.2 Hz), 6.93 (2H, s), 6.77 (1H, d, J = 8.7 Hz) ¹³C-NMR (DMSO-d6) δ [ppm] = 153.1, 150.2, 146.7, 146.6, 137.3, 132.7, 129.3, 122.4, 122.1, 121.8, 120.7, 119.4, 115.3, 107.9 |
| 5 | 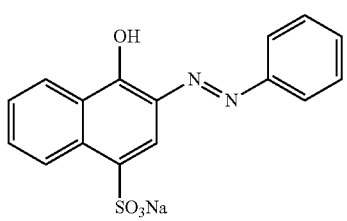 | ¹H-NMR (DMSO-d6) δ [ppm] = 14.74 (1H, s), 8.63 (1H, d, J = 8.4 Hz), 8.34 (1H, d, J = 7.8 Hz), 7.85 (2H, d, J = 6.9 Hz), 7.83 (1H, s), 7.71 (1H, dd, J = 7.8 Hz), 7.57-7.50 (3H, m), 7.36 (1H, dd, J = 7.4 Hz) ¹³C-NMR (DMSO-d6) δ [ppm] = 169.2, 145.1, 136.7, 132.9, 131.2, 131.0, 129.7, 129.0, 128.2, 128.0, 126.3, 125.5, 123.2, 119.0 |

| Comparative Example | structure | NMR spectrum |
|---|---|---|
| 6 | 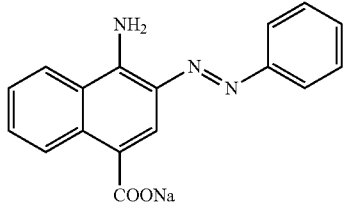 | ¹H-NMR (DMSO-d6) δ [ppm] = 8.43 (1H, d, J = 8.4 Hz), 8.41 (1H, dd, J = 8.1 Hz, 1.5 Hz), 8.05 (1H, s), 7.99 (2H, d, J = 7.2 Hz), 7.92 (2H, br), 7.62 (1H, dd, J = 8.4 Hz, 0.9 Hz), 7.57-7.50 (3H, m), 7.44 (1H, dd, J = 7.2 Hz) ¹³C-NMR (DMSO-d6) δ [ppm] = 170.6, 152.6, 146.1, 132.7, 129.7, 129.3, 129.0, 128.8, 126.5, 125.3, 124.2, 124.0, 122.3, 121.6, 119.4 |
| 7 | 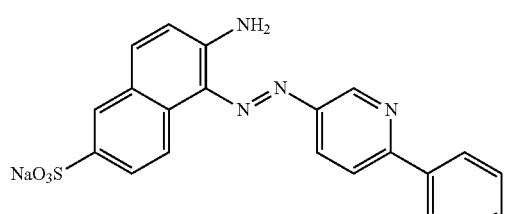 | ¹H-NMR (DMSO-d6) δ [ppm] = 9.18 (1H, d, J = 2.1 Hz), 8.65 (1H, d, J = 9.0 Hz), 8.29 (1H, dd, J = 8.7, 2.4 Hz), 8.06-8.14 (3H, m), 7.95 (1H, d, J = 1.5 Hz), 7.80 (1H, d, J = 9.3 Hz), 7.73 (1H, dd, J = 9.0, 1.5 Hz), 7.4-7.49 (3H, m), 7.13 (1H, d, J = 9.0 Hz) ¹³C-NMR (DMSO-d6) δ [ppm] = 155.4, 147.8, 145.7, 143.0, 141.2, 138.2, 135.0, 134.0, 129.3, 128.9, 126.7, 126.6, 126.1, 125.7, 125.4, 125.0, 120.8, 120.6, 120.4 |
| 8 | 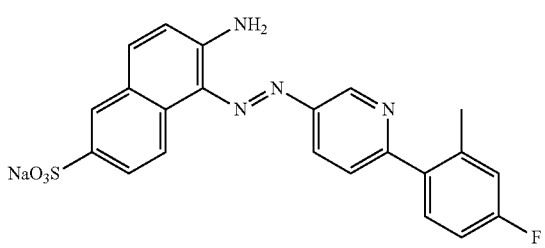 | ¹H-NMR (DMSO-d6) δ [ppm] = 9.21 (1H, d, J = 2.1 Hz), 8.68 (1H, d, J = 8.7 Hz), 8.32 (1H, dd, J = 8.4, 2.4 Hz), 8.00 (1H, d, J = 1.8 Hz), 7.84 (1H, d, J = 9.0 Hz), 7.76 (1H, dd, J = 8.4, 0.6 Hz), 7.67 (1H, dd, J = 8.4, 0.6 Hz), 7.51-7.56 (1H, m), 7.11-7.21 (3H, m), 2.41 (3H, s) ¹³C-NMR (DMSO-d6) δ [ppm] = 163.5, 160.2, 157.6, 147.2, 145.1, 143.0, 141.1, 138.1, 138.6, 136.1, 136.1, 135.0, 134.0, 131.7, 131.6, 126.1, 126.0, 125.7, 125.4, 125.0, 124.7, 120.5, 120.3, 117.3, 117.0, 112.8, 112.6, 20.4 |

TABLE 5-continued

| Comparative Example | structure | NMR spectrum |
|---|---|---|
| 9 | 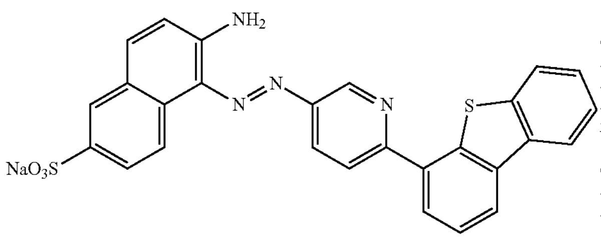 | $^1$H-NMR (DMSO-d6) δ [ppm] = 9.34 (1H, d, J = 1.2 Hz), 8.68 (1H, d, J = 9.0 Hz), 8.45 (1H, d, J = 7.8 Hz), 8.34-8.41 (3H, m), 8.31 (1H, d, J = 7.8 Hz), 8.01-8.05 (1H, m), 7.96 (1H, d, J = 1.8 Hz), 7.82 (1H, d, J = 9.3 Hz), 7.75 (1H, dd, J = 8.7, 1.8 Hz), 7.62-7.68 (1H, m), 7.44-7.52 (2H, m), 7.15 (1H, d, J = 9.0 Hz) $^{13}$C-NMR (DMSO-d6) δ [ppm] =154.1, 147.5, 143.7, 143.2, 141.6, 141.3, 136.9, 136.5, 135.2, 134.2, 134.0, 132.1, 127.1, 126.3, 125.8, 125.5, 125.4, 125.1, 125.0, 124.5, 122.9, 122.5, 121.8, 121.5, 120.6, 120.3 |
| 10 | 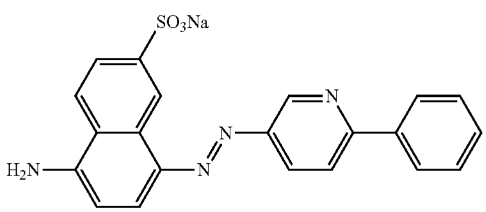 | $^1$H-NMR (DMSO-d6) δ [ppm] = 9.10 (1H, d, J = 1.2 Hz), 9.97 (1H, d, J = 1.8 Hz), 8.11-8.18 (5H, m), 7.94 (1H, d, J = 8.4 Hz), 7.66 (1H, dd, J = 8.7, 1.5 Hz), 7.40-7.50 (3H, m), 7.11 (2H, bs), 6.77 (1H, d, J = 8.7 Hz) $^{13}$C-NMR (DMSO-d6) δ [ppm] = 155.8, 151.1, 147.6, 147.0, 146.1, 138.1, 137.7, 133.0, 129.4, 128.9, 126.7, 126.6, 122.5, 122.3, 120.9, 120.6, 119.3, 116.0, 108.2 |
| 11 | 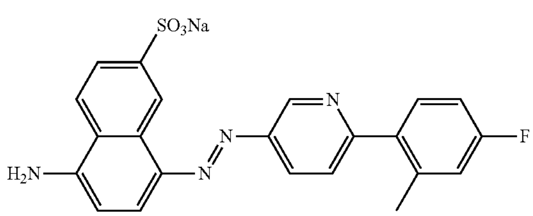 | $^1$H-NMR (DMSO-d6) δ [ppm] = 9.14 (1H, d, J = 1.5 Hz), 9.10 (1H, d, J = 2.7 Hz), 8.18-8.23 (2H, m), 7.98 (1H, d, J = 8.7 Hz), 7.68-7.74 (2H, m), 7.55 (1H, dd, J = 8.4, 6.3 Hz), 7.22 (2H, bs), 7.12-7.18 (2H, m), 6.82 (1H, d, J = 9.0 Hz) $^{13}$C-NMR (DMSO-d6) δ [ppm] = 163.6, 160.3, 158.0, 151.2, 147.0, 146.9, 145.3, 138.9, 138.7, 137.7, 136.1, 136.0, 133.0, 131.9, 131.7, 126.3, 124.8, 122.6, 122.3, 120.6, 119.3, 117.4, 117.1, 116.0, 112.9, 112.6, 108.2, 25.5 |

TABLE 5-continued
| Comparative Example | structure | NMR spectrum |
|---|---|---|
| 12 | 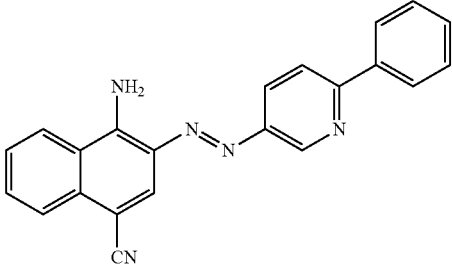 [SMILES: N#Cc1cc(/N=N/c2ccc(-c3ccccc3)nc2)c(N)c2ccccc12] | $^1$H-NMR (DMSO-d6) δ [ppm] = 8.23 (1H, d, J = 2.4 Hz), 8.60 (1H, d, J = 8.4 Hz), 8.43-8.47 (3H, m), 8.24 (1H, s), 8.16 (2H, dd, J = 8.1, 1.5 Hz), 8.07 (1H, d, J = 8.7 Hz), 7.89-7.92 (1H, m), 7.75-7.80 (1H, m), 7.61-7.66 (1H, m), 7.45-7.53 (3H, m) $^{13}$C-NMR (DMSO-d6) δ [ppm] = 156.7, 149.1, 146.8, 146.7, 137.9, 133.2, 131.1, 129.7, 129.6, 128.9, 127.9, 126.8, 126.7, 125.4, 125.0, 125.0, 123.3, 120.6, 118.6, 95.2 |
| 13 | 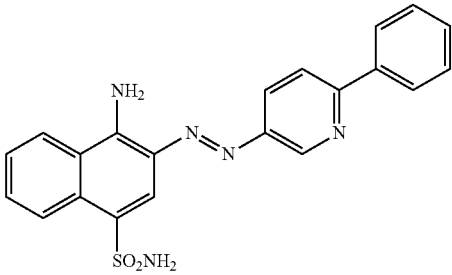 [SMILES: Nc1c(/N=N/c2ccc(-c3ccccc3)nc2)cc(S(N)(=O)=O)c2ccccc12] | $^1$H-NMR (DMSO-d6) δ [ppm] = 8.27 (1H, d, J = 2.4 Hz), 8.31 (1H, d, J = 8.7 Hz), 8.51-8.56 (3H, m), 8.19-8.22 (4H, m), 8.14 (1H, d, J = 8.7 Hz), 7.73-7.78 (1H, m), 7.62-7.66 (1H, m), 7.45-7.56 (5H, m) $^{13}$C-NMR (DMSO-d6) δ [ppm] = 156.5, 149.0, 147.0, 146.6, 138.0, 130.1, 130.0, 129.6, 129.0, 128.3, 127.9, 126.8, 126.7, 126.1, 126.0, 124.8, 124.3, 120.7, 119.3 |
| 14 | 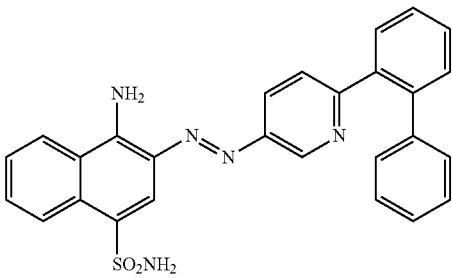 [SMILES: Nc1c(/N=N/c2ccc(-c3ccccc3-c3ccccc3)nc2)cc(S(N)(=O)=O)c2ccccc12] | $^1$H-NMR (DMSO-d6) δ [ppm] = 9.18 (1H, d, J = 2.4 Hz), 8.59 (1H, d, J = 8.4 Hz), 8.52 (1H, d, J = 7.8 Hz), 8.47 (1H, s), 8.22 (1H, dd, J = 8.6, 2.4 Hz), 8.12 (2H, bs), 7.72-8.12 (2H, m), 7.62-7.71 (1H, m), 7.43-7.60 (5H, m), 7.25-7.31 (3H, m), 7.14-7.17 (2H, m), 7.06 (1H, d, J = 8.4 Hz) $^{13}$C-NMR (DMSO-d6) δ [ppm] = 159.4, 149.1, 146.6, 146.2, 140.9, 140.4, 138.6, 130.6, 130.6, 130.1, 130.0, 129.4, 129.0, 128.4, 128.2, 127.7, 127.0, 126.6, 126.1, 126.0, 125.5, 124.8, 124.2, 119.0 |

TABLE 5-continued

| Comparative Example | structure | NMR spectrum |
|---|---|---|
| 15 | 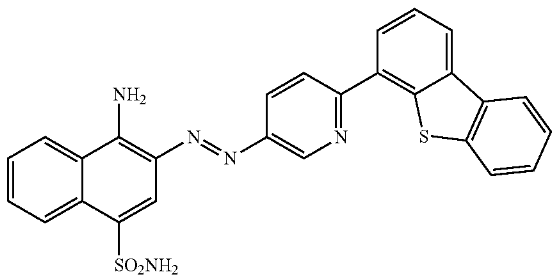 | $^1$H-NMR (DMSO-d6) δ [ppm] = 9.44 (1H, d, J = 2.1 Hz), 8.64 (2H, dd, J = 8.4, 2.4 Hz), 8.51-8.56 (3H, m), 8.41-8.48 (3H, m), 8.27 (2H, bs), 8.06-8.09 (1H, m), 7.62-7.79 (3H, m), 7.49-7.55 (3H, m), 7.46 (1H, s) $^{13}$C-NMR (DMSO-d6) δ [ppm] = 155.2, 149.2, 146.7, 144.7, 141.5, 136.9, 136.6, 134.1, 131.9, 130.1, 130.0, 128.4, 128.4, 127.2, 127.2, 126.7, 126.1, 126.0, 125.7, 125.1, 124.8, 124.5, 123.2, 122.5, 121.9, 121.4, 119.2 |
| 16 | 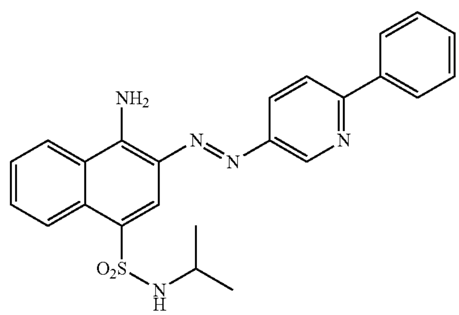 [SMILES: CC(C)NS(=O)(=O)c1cc(/N=N/c2ccc(-c3ccccc3)nc2)c(N)c2ccccc12] | $^1$H-NMR (DMSO-d6) δ [ppm] = 9.29 (1H, d, J = 2.4 Hz), 8.62 (1H, d, = 8.4 Hz), 8.56 (1H, d, J = 2.4 Hz), 8.53 (1H, d, J = 3.0 Hz), 8.51 (1H, s), 8.25 (2H, bs), 8.20-8.22 (2H, m), 8.15 (1H, d, J = 8.7 Hz), 7.61-7.77 (3H, m), 7.44-7.56 (3H, m), 3.15-3.26 (1H, m), 0.89 (6H, d, J = 6.6 Hz) $^{13}$C-NMR (DMSO-d6) δ [ppm] = 156.5, 149.4, 147.0, 146.7, 138.0, 130.2, 130.0, 129.6, 128.9, 128.4, 128.0, 126.8, 126.1, 125.7, 124.8, 124.3, 123.2, 121.0, 120.7, 45.1, 23.3 |
| 17 | 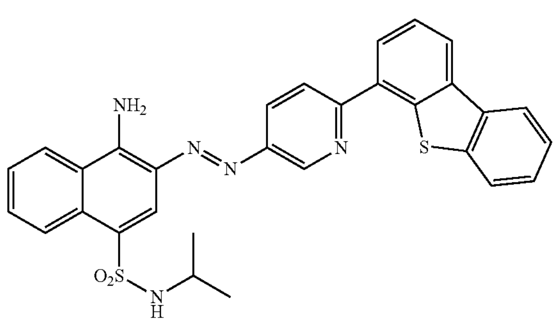 [SMILES: CC(C)NS(=O)(=O)c1cc(/N=N/c2ccc(-c3cccc4c3sc3ccccc34)nc2)c(N)c2ccccc12] | $^1$H-NMR (DMSO-d6) δ [ppm] = 9.45 (1H, d, J = 2.4 Hz), 8.66 (1H, d, J = 2.4 Hz), 8.63 (1H, d, J = 2.4 Hz), 8.41-8.55 (6H, m), 8.32 (2H, bs), 8.06-8.09 (1H, m), 7.62-7.79 (4H, m), 7.48-7.57 (2H, m), 3.19-3.26 (1H, m), 0.91 (6H, d, J = 6.6 Hz) $^{13}$C-NMR (DMSO-d6) δ [ppm] = 155.3, 149.5, 146.7, 144.7, 141.5, 136.9, 136.6, 134.1, 131.9, 130.2, 130.1, 128.5, 128.5, 127.2, 126.2, 125.7, 125.1, 124.9, 124.5, 124.3, 123.3, 123.2, 122.5, 121.9, 121.4, 121.1, 45.1, 23.3 |

TABLE 5-continued

| Comparative Example | structure | NMR spectrum |
|---|---|---|
| 18 | (naphthalene with NH₂, N=N-pyridine-phenyl, and CH₂CH₂COONa substituent) | ¹H-NMR (DMSO-d6) δ [ppm] = 9.20 (1H, d, J = 2.1 Hz), 8.48 (1H, d, J = 8.1 Hz), 8.41 (1H, dd, J = 8.6, 2.4 Hz), 8.16-8.19 (2H, m), 8.08 (1H, d, J = 8.4 Hz), 7.97 (1H, d, J = 8.1 Hz), 7.68 (1H, s), 7.60-7.64 (3H, m), 7.42-7.54 (4H, m), 3.06-3.11 (2H, m), 2.24-2.30 (2H, m) ¹³C-NMR (DMSO-d6) δ [ppm] = 176.4, 155.6, 147.4, 146.2, 145.1, 138.1, 134.7, 131.1, 129.3, 128.9, 128.9, 127.4, 127.2, 126.6, 125.0, 124.8, 124.6, 124.6, 120.6, 116.6, 79.2, 29.5 |
| 19 | (naphthalene with NH₂, N=N-pyridine-phenyl, and O₂S-NH-CH₂-COOEt substituent) | ¹H-NMR (DMSO-d6) δ [ppm] = 9.24 (1H, d, J = 2.4 Hz), 8.56 (1H, d, J = 8.4 Hz), 8.47 (2H, dd, J = 8.7, 2.4 Hz), 8.41 (1H, s), 8.25-8.31 (3H, m), 8.14-8.17 (2H, m), 8.09 (1H, d, J = 8.7 Hz), 7.68-7.73 (1H, m), 7.56-7.61 (1H, m), 7.39-7.50 (3H, m), 3.72 (2H, q, J = 7.2 Hz), 3.61 (2H, d, J = 6.3 Hz), 0.85 (3H, t, J = 7.2 Hz) ¹³C-NMR (DMSO-d6) δ [ppm] = 169.0, 156.5, 149.3, 146.9, 146.5, 137.9, 130.2, 130.0, 129.5, 128.9, 128.3, 128.0, 126.8, 126.1, 125.8, 124.7, 124.2, 122.4, 121.7, 120.7, 60.4, 13.7 |
| 20 | (4-amino-naphthalene-1-sulfonic acid) | commercially obtained |
| 21 | (4-amino-benzenesulfonic acid) | commercially obtained |
| 22 | (benzene with two NH₂, N=N-phenyl, and SO₃Na substituents) | ¹H-NMR (DMSO-d6) δ [ppm] = 7.85 (1H, s), 7.72 (2H, d, J = 7.8 Hz), 7.44 (2H, dd, J = 7.8, 7.2), 7.29 (1H, dd, J = 7.2 Hz), 6.96 (2H, s), 6.28 (2H, s), 6.91 (1H, s) ¹³C-NMR (DMSO-d6) δ [ppm] = 153.0, 149.7, 147.4, 129.0, 128.0, 127.9, 126.8, 122.2, 121.1, 97.4 |

TABLE 5-continued

| Comparative Example | structure | NMR spectrum |
|---|---|---|
| 23 | 8-amino-7-(phenyldiazenyl)quinoline-5-sulfonate sodium | $^1$H-NMR (DMSO-d6) δ [ppm] = 9.30 (1H, dd, J = 8.7 Hz, 1.5 Hz), 8.91 (1H, dd, J = 4.2 Hz, 1.5 Hz), 8.53 (1H, s), 8.04-7.96 (3H, m), 7.74 (2H, m), 7.61-7.50 (3H, m) $^{13}$C-NMR (DMSO-d6) δ [ppm] = 152.8, 148.6, 143.0, 137.6, 136.2, 132.0, 130.4, 129.4, 126.8, 123.1, 122.4, 114.6, 110.4 |
| 24 | 5-amino-6-(phenyldiazenyl)quinoline-8-sulfonate sodium | $^1$H-NMR (DMSO-d6) δ [ppm] = 9.04 (1H, s), 8.98 (1H, dd, J = 4.2 Hz, 1.5 Hz), 8.86 (1H, dd, J = 8.4 Hz, 1.5 Hz), 7.92 (1H, s), 7.90 (2H, d, J = 8.7 Hz), 7.69 (1H, d, J = 8.7 Hz), 7.60-7.46 (4H, m) $^{13}$C-NMR (DMSO-d6) δ [ppm] = 153.0, 150.7, 145.1, 143.8, 140.2, 131.6, 130.1, 129.3, 122.4, 120.1, 118.3, 116.7, 110.7 |
| 25 | 8-aminoquinoline-5-sulfonate sodium | $^1$H-NMR (DMSO-d6) δ [ppm] = 9.29 (1H, d, J = 8.1 Hz), 9.11 (1H, dd, J = 5.3, 1.2 Hz), 7.75-7.87 (3H, m), 7.26 (1H, d, J = 8.4 Hz), 6.94 (1H, d, J = 8.1 Hz) $^{13}$C-NMR (DMSO-d6) δ [ppm] = 149.1, 138.9, 137.3, 136.8, 128.7, 127.5, 126.9, 122.5, 115.6 |
| 26 | 4-amino-3-phenylnaphthalene-1-sulfonic acid | $^1$H-NMR (DMSO-d6) δ [ppm] = 8.83-8.80 (1H, m), 8.17-8.14 (1H, m), 7.75 (1H, s), 7.57-7.42 (6H, m) |
| 27 | 8-amino-7-(quinolin-3-yldiazenyl)quinoline-5-sulfonate sodium | $^1$H-NMR (DMSO-d6) δ [ppm] = 9.52 (1H, d, J = 2.1 Hz), 9.41 (1H, dd, J = 8.7 Hz, 1.8 Hz), 8.92 (1H, dd, J = 4.7 Hz, 1.8 Hz), 8.70 (1H, d, J = 2.1 Hz), 8.64 (1H, s), 8.21-8.08 (3H, m), 7.85-7.66 (4H, m) $^{13}$C-NMR (DMSO-d6) δ [ppm] = 148.7, 148.0, 145.6, 145.2, 143.8, 137.9, 136.1, 132.2, 130.6, 129.6, 128.9, 128.6, 127.9, 127.5, 127.0, 123.4, 115.2, 110.4 |

TABLE 5-continued

| Comparative Example | structure | NMR spectrum |
|---|---|---|
| 28 | 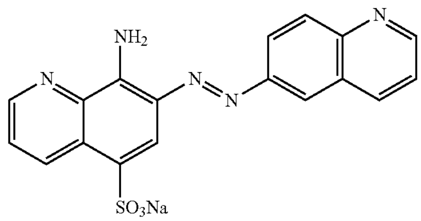 | $^1$H-NMR (DMSO-d6) δ [ppm] = 9.39 (1H, dd, J = 8.7 Hz, 1.5 Hz), 8.96-8.94 (1H, m), 8.93-8.91 (1H, m), 8.61 (1H, d, J = 2.1 Hz), 8.60-8.57 (1H, m), 8.58 (1H, s), 8.42 (1H, dd, J = 9.0 Hz, 2.1 Hz), 8.15-8.10 (2H, m), 7.80-7.74 (1H, m), 7.76 (1H, d, J = 9.0 Hz) $^{13}$C-NMR (DMSO-d6) δ [ppm] = 151.5, 150.2, 148.7, 148.6, 143.4, 137.7, 137.2, 136.2, 132.1, 130.3, 128.4, 126.9, 125.8, 123.3, 122.3, 121.1, 114.9, 110.4 |
| 29 | 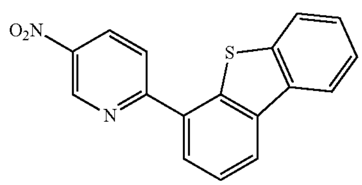 [SMILES: O=[N+]([O-])c1ccc(-c2cccc3c2sc2ccccc23)nc1] | $^1$H-NMR (CDCl3) δ [ppm] = 9.67 (1H, dd, J = 2.7, 0.6 Hz), 8.59 (1H, dd, J = 8.7, 2.7 Hz), 8.35 (1H, dd, J = 7.8, 0.9 Hz), 8.23-8.20 (1H, m), 8.16 (1H, dd, J = 8.7, 0.6 Hz), 8.10 (1H, dd, J = 7.8, 0.9 Hz), 7.96-7.92 (1H, m), 7.64 (1H, dd, J = 7.8 Hz), 7.54-7.49 (2H, m) |
| 30 | 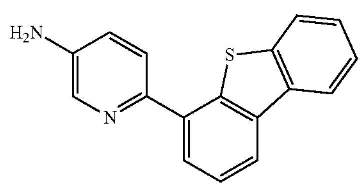 | $^1$H-NMR (CDCl3) δ [ppm] = 8.34 (1H, dd, J = 2.7, 0.6 Hz), 8.20-8.16 (2H, m), 7.92-7.87 (2H, m), 7.79 (1H, d, J = 8.4 Hz), 7.55 (1H, dd, J = 7.8 Hz), 7.47-7.44 (2H, m), 7.14 (1H, dd, J = 8.4, 2.7 Hz), 3.84 (2H, bs) |
| 31 | 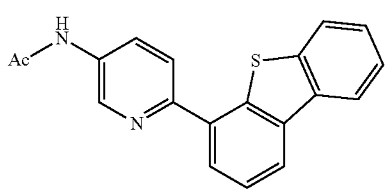 [SMILES: CC(=O)Nc1ccc(-c2cccc3c2sc2ccccc23)nc1] | data not shown |
| 32 | 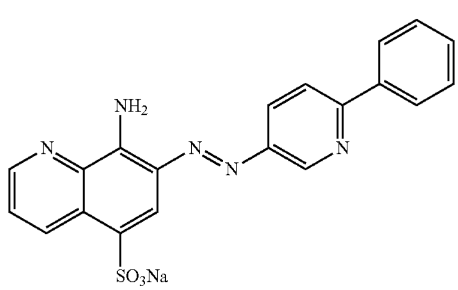 | $^1$H-NMR (DMSO-d6) δ [ppm] = 9.35 (1H, dd, J = 8.6, 1.5 Hz), 9.25 (1H, d, J = 2.1 Hz), 8.92 (1H, dd, J = 4.2, 1.5 Hz), 8.60 (1H, s), 8.39 (1H, dd, J = 8.7, 2.4 Hz), 8.16-8.22 (3H, m), 8.10 (1H, d, J = 8.7 Hz), 7.73-7.78 (2H, m), 7.48-7.56 (3H, m) $^{13}$C-NMR (DMSO-d6) δ [ppm] = 156.9, 148.7, 147.2, 146.6, 143.7, 137.9, 137.9, 136.1, 132.1, 129.6, 128.9, 127.6, 127.0, 126.8, 123.4, 120.8, 115.2, 110.3 |

TABLE 5-continued

| Comparative Example | structure | NMR spectrum |
|---|---|---|
| 33 | 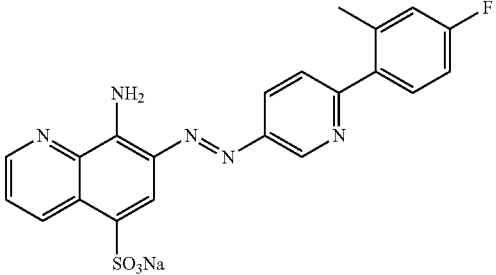 | $^1$H-NMR (DMSO-d6) δ [ppm] = 9.35 (1H, dd, J = 8.6, 1.5 Hz), 9.23 (1H, d, J = 2.1 Hz), 8.92 (1H, dd, J = 4.2, 1.5 Hz), 8.60 (1H, s), 8.38 (1H, dd, J = 8.6, 2.1 Hz), 8.10 (1H, d, J = 8.7 Hz), 7.71-7.78 (3H, m), 7.56 (1H, dd, J = 9.0, 6.0 Hz), 7.12-7.23 (2H, m), 2.42 (3H, s) $^{13}$C-NMR (DMSO-d6) δ [ppm] = 163.6, 160.4, 159.2, 148.7, 146.6, 145.7, 143.7, 138.9, 138.8, 137.8, 136.1, 135.9, 135.9, 132.1, 131.9, 131.8, 127.2, 127.0, 124.8, 123.4, 117.4, 117.1, 115.2, 113.0, 112.6, 110.3, 20.4 |

The IC$_{50}$ values (nM) of these compounds were determined in the same manner as the compounds of the Examples. The results are shown in the following table.

TABLE 6

| Comparative Example | IC50 |
|---|---|
| 1 | >10,000 |
| 2 | >10,000 |
| 3 | 104,300 |
| 4 | >10,000 |
| 5 | >10,000 |
| 6 | >10,000 |
| 7 | 62,640 |
| 8 | 25,530 |
| 9 | >10,000 |
| 10 | 21,800 |
| 11 | 34,595 |
| 12 | >10,000 |
| 13 | >10,000 |
| 14 | >10,000 |
| 15 | >10,000 |
| 16 | >10,000 |
| 17 | >10,000 |
| 18 | >100,000 |
| 19 | >10,000 |
| 20 | >10,000 |
| 21 | >10,000 |
| 22 | >10,000 |
| 23 | >10,000 |
| 24 | >10,000 |
| 25 | >10,000 |
| 26 | >10,000 |
| 27 | >10,000 |
| 28 | >10,000 |
| 29 | >100,000 |
| 30 | >100,000 |
| 31 | >100,000 |
| 32 | >10,000 |
| 33 | 60,467 |

The invention claimed is:

1. A compound of formula (I)

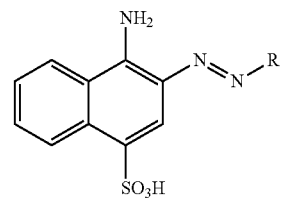

wherein
R is 3-pyridyl, wherein
3-pyridyl is optionally substituted by 1 to 3 substituent selected from the group consisting of halo, alkyl, alkenyl which is optionally substituted by phenyl, alkoxy which is optionally substituted by pyridyl, tetrahydrofuranyl, halo or alkoxy, phenyl, naphthalenyl, pyridyl, thiophenyl, oxazolyl, dibenzofuranyl, benzothiophenyl, dibenzothiophenyl which is optionally substituted by pyridylmethoxy, chloropyridinecarbonylaminopropoxy or hydroxypropoxy, dioxodibenzothiophenyl, thianthrenyl, and quinolinyl which is optionally substituted by methyl;
wherein phenyl substituting 3-pyridyl is optionally substituted by 1 to 3 substituent selected from the group consisting of halo, alkyl which is optionally substituted by morpholinyl or up to 3 halo, alkoxy which is optionally substituted by hydroxy, carboxyl, butoxycarbonylamino, chloropyridinecarbonylamino or dioxodihydroisoindolyl, phenyl which is optionally substituted by halo or alkyl, alkylthio, acetyl, phenoxy, methoxycarbonylethylcarbonyl, cyano, phenylcarbonyl, hydroxy and formyl,
or a pharmaceutically acceptable salt or solvate thereof.

2. The compound or the pharmaceutically acceptable salt or solvate thereof according to claim 1, wherein
R is 3-pyridyl, wherein
3-pyridyl is optionally substituted by 1 to 3 substituent selected from the group consisting of chloro, methyl, phenylvinyl, methoxy, ethoxy, pyridylmethoxy, trifluoroethoxy, methoxyethoxy, tetrahydrofuranylmethoxy, phenyl, naphthalenyl, pyridyl, thiophenyl, oxazolyl, dibenzofuranyl, benzothiophenyl, dibenzothiophenyl which is optionally substituted by pyridylmethoxy, chloropyridinecarbonylaminopropoxy or hydroxypropoxy, dioxodibenzothiophenyl, thianthrenyl, quinolinyl which is optionally substituted by methyl;
  wherein phenyl substituting 3-pyridyl is optionally substituted by 1 to 3 substituent selected from the group consisting of fluoro, chloro, methyl, ethyl, morpholinylmethyl, trifluoromethyl, butyl, methoxy, ethoxy, propoxy, isopropoxy, hydroxypropoxy, carboxylpropoxy, butoxycarbonylaminopropoxy, chloropyridinecarbonylaminopropoxy, dioxodihydroisoindolylpropoxy, butoxy, isobutoxy, hexyloxy, hydroxyhexyloxy, methylthio, phenyl, chlorophenyl, dimethylphenyl, acetyl, phenoxy, methoxycarbonylethylcarbonyl, cyano, phenylcarbonyl, hydroxy and formyl.

3. A pharmaceutical composition comprising
the compound or pharmaceutically acceptable salt or solvate thereof according to claim 1, and
a pharmaceutically acceptable carrier.

4. The pharmaceutical composition according to claim 3 comprising a therapeutically effective amount of the compound for treating a VCP (Valosin-Containing Protein)-mediated disease selected from the group consisting of IBMPFD (Inclusion Body Myopathy with Paget disease of bone and Front-temporal Dementia), neurodegenerative disease, inflammatory disease, cystic fibrosis, autoimmune disease, viral infection, tumor disease, dyslipidemia, depression, anxiety and schizophrenia.

5. The compound or the pharmaceutically acceptable salt or solvate thereof according to claim 1, wherein the compound is 4-amino-3-(6-phenylpyridine-3-ylazo)naphthalene-1-sulfonic acid.

6. The compound or the pharmaceutically acceptable salt or solvate thereof according to claim 1, wherein the compound is 4-amino-3-(6-biphenyl-2-ylpyridine-3-ylazo)naphthalene-1-sulfonic acid.

7. The compound or the pharmaceutically acceptable salt or solvate thereof according to claim 1, wherein the compound is 4-amino-3-[6-(4-fluoro-2-methylphenyl)pyridine-3-ylazo]naphthalene-1-sulfonic acid.

8. The compound or the pharmaceutically acceptable salt or solvate thereof according to claim 1, wherein the compound is 4-amino-3-[6-(3-formyl-2-butoxy-5-methylphenyl)pyridine-3-ylazo]naphthalene-1-sulfonic acid.

9. The compound or the pharmaceutically acceptable salt or solvate thereof according to claim 1, wherein the compound is 4-amino-3-(6-dibenzothiophene-4-ylpyridine-3-ylazo)naphthalene-1-sulfonic acid.

10. A compound selected from the group consisting of
4-amino-3-(pyridine-3-ylazo)naphthalene-1-sulfonic acid;
4-amino-3-(6-methoxypyridine-3-ylazo)naphthalene-1-sulfonic acid;
3-(2-pyridinomethoxy-5-pyridinoazo)-4-amino-1-naphthalenesulfonic acid;
4-amino-3-[6-(tetrahydrofuran-2-ylmethoxy)pyridine-3-ylazo]-1-naphthalenesulfonic acid;
4-amino-3-[6-(2,2,2-trifluoroethoxy)pyridine-3-ylazo]naphthalene-1-sulfonic acid;
4-amino-3-[6-(2-methoxyethoxy)pyridine-3-ylazo]naphthalene-1-sulfonic acid;
4-amino-3-(6-phenylpyridine-3-ylazo)naphthalene-1-sulfonic acid;
4-amino-3-(6-p-tolylpyridine-3-ylazo)naphthalene-1-sulfonic acid;
4-amino-3-(6-m-tolylpyridine-3-ylazo)naphthalene-1-sulfonic acid;
4-amino-3-(6-o-tolylpyridine-3-ylazo)naphthalene-1-sulfonic acid;
4-amino-3-[6-(3-morpholine-4-ylmethylphenyl)pyridine-3-ylazo]naphthalene-1-sulfonic acid;
4-amino-3-(6-biphenyl-2-ylpyridine-3-ylazo)naphthalene-1-sulfonic acid;
4-amino-3-(4-ethoxypyridine-3-ylazo)naphthalene-1-sulfonic acid;
3-[6-(2-acetylphenyl)pyridine-3-ylazo]-4-aminonaphthalene-1-sulfonic acid;
3-[6-(3-acetylphenyl)pyridine-3-ylazo]-4-aminonaphthalene-1-sulfonic acid;
3-[6-(4-acetylphenyl)pyridine-3-ylazo]-4-aminonaphthalenesulfonic acid;
4-amino-3-(6-thiophene-2-ylpyridine-3-ylazo)naphthalene-1-sulfonic acid;
4-amino-3-(6-thiophene-3-ylpyridine-3-ylazo)naphthalene-1-sulfonic acid;
4-amino-3-[6-(2,4-dichlorophenyl)pyridine-3-ylazo]naphthalene-1-sulfonic acid;
4-amino-3-[6-(2-trifluoromethylphenyl)pyridine-3-ylazo]naphthalene-1-sulfonic acid;
4-amino-3-[6-(4-trifluoromethylphenyl)pyridine-3-ylazo]naphthalene-1-sulfonic acid;
4-amino-3-[6-(2-chlorophenyl)pyridine-3-ylazo]naphthalene-1-sulfonic acid;
4-amino-3-[6-(3-chlorophenyl)pyridine-3-ylazo]naphthalene-1-sulfonic acid;
4-amino-3-[6-(4-chlorophenyl)pyridine-3-ylazo]naphthalene-1-sulfonic acid;
4-amino-3-[6-(2-methoxyphenyl)pyridine-3-ylazo]naphthalene-1-sulfonic acid;
4-amino-3-[6-(4-methoxyphenyl)pyridine-3-ylazo]naphthalene-1-sulfonic acid;
4-amino-3-[6-(2-isopropoxyphenyl)pyridine-3-ylazo]naphthalene-1-sulfonic acid;
4-amino-3-[6-(4-isopropoxyphenyl)pyridine-3-ylazo]naphthalene-1-sulfonic acid;
4-amino-3-[6-(2-phenoxyphenyl)pyridine-3-ylazo]naphthalene-1-sulfonic acid;
4-amino-3-(6-styrylpyridine-3-ylazo)naphthalenesulfonic acid;
4-amino-3-(6-dibenzothiophene-4-ylpyridine-3-ylazo)naphthalene-1-sulfonic acid;
4-amino-3-[6-(3-methoxyphenyl)pyridine-3-ylazo]naphthalene-1-sulfonic acid;
4-amino-3-[6-(2,3-dimethylphenyl)pyridine-3-ylazo]naphthalene-1-sulfonic acid;
4-amino-3-[6-(2,5-dimethylphenyl)pyridine-3-ylazo]naphthalene-1-sulfonic acid;
4-amino-3-[6-(3,5-dimethylphenyl)pyridine-3-ylazo]naphthalene-1-sulfonic acid;
4-amino-3-(6-oxazole-2-ylpyridine-3-ylazo)naphthalene-1-sulfonic acid;
4-amino-3-[6-(3-trifluoromethylphenyl)pyridine-3-ylazo]naphthalene-1-sulfonic acid;
4-amino-3-(6-naphthalene-1-ylpyridine-3-ylazo)naphthalene-1-sulfonic acid;
4-amino-3-(6-dibenzofuran-4-ylpyridine-3-ylazo)naphthalene-1-sulfonic acid;

methyl 4-{4-[5-(1-amino-4-sulfonaphthalene-2-ylazo) pyridine-2-yl]phenyl}-4-oxobutyrate;
4-amino-3-(6-benzo[b]thiophene-3-ylpyridine-3-ylazo) naphthalene-1-sulfonic acid;
4-amino-3-(6-biphenyl-3-ylpyridine-3-ylazo)naphthalene-1-sulfonic acid;
4-amino-3-[6-(3-cyanophenyl)pyridine-3-ylazo]naphthalene-1-sulfonic acid;
4-amino-3-[6-(4-cyanophenyl)pyridine-3-ylazo]naphthalene-1-sulfonic acid;
4-amino-3-[6-(3,5-bistrifluoromethylphenyl)pyridine-3-ylazo]naphthalenesulfonic acid;
4-amino-3-[6-(4-benzoylphenyl)pyridine-3-ylazo]naphthalene-1-sulfonic acid;
4-amino-3-[6-(2-propoxyphenyl)pyridine-3-ylazo]naphthalene-1-sulfonic acid;
4-amino-3-[6-(4-fluoro-2-methylphenyl)pyridine-3-ylazo]naphthalene-1-sulfonic acid;
4-amino-3-(2-phenylpyridine-3-ylazo)naphthalene-1-sulfonic acid;
4-amino-3-([2,3']bipyridinyl 3-ylazo)naphthalene-1-sulfonic acid;
4-amino-3-([2,3']bipyridinyl-5-ylazo)naphthalene-1-sulfonic acid;
4-amino-3-(4-methyl-[2,3']bipyridinyl-5-ylazo)naphthalene-1-sulfonic acid;
4-amino-3-([3,2';6',3'']terpyridine-3'-ylazo)naphthalene-1-sulfonic acid;
4-amino-3-[6-(5-fluoro-2-propoxyphenyl)pyridine-3-ylazo]naphthalene-1-sulfonic acid;
4-amino-3-[6-(2-fluoro-6-propoxyphenyl)pyridine-3-ylazo]naphthalene-1-sulfonic acid;
4-amino-3-[6-(4-fluoro-2-propoxyphenyl)pyridine-3-ylazo]naphthalene-1-sulfonic acid;
4-amino-3-[6-(5-fluoro-2-methylphenyl)pyridine-3-ylazo]naphthalene-1-sulfonic acid;
4-amino-3-[6-(2-fluoro-5-methylphenyl)pyridine-3-ylazo]naphthalene-1-sulfonic acid;
4-amino-3-[6-(2-butoxyphenyl)pyridine-3-ylazo]naphthalene-1-sulfonic acid;
4-amino-3-[6-(2-hexyloxyphenyl)pyridine-3-ylazo]naphthalene-1-sulfonic acid;
4-amino-3-[6-(4-butylphenyl)pyridine-3-ylazo]naphthalene-1-sulfonic acid;
4-amino-3-[6-(2-hydroxyphenyl)pyridine-3-ylazo]naphthalene-1-sulfonic acid;
4-amino-3-{6-[2-(6-hydroxyhexyloxy)phenyl]pyridine-3-ylazo}naphthalene-1-sulfonic acid;
4-{2-[5-(1-amino-4-sulfonaphthalene-2-ylazo)pyridine-2-yl]phenoxy}butyric acid;
4-amino-3-{6-[2-(3-hydroxypropoxy)phenyl]pyridine-3-ylazo}naphthalene-1-sulfonic acid;
4-amino-3-[6-(2-isobutoxyphenyl)pyridine-3-ylazo] naphthalene-1-sulfonic acid;
4-amino-3-{6-[2-(3-tert-butoxycarbonylaminopropoxy) phenyl]pyridine-3-ylazo}naphthalene-1-sulfonic acid;
4-amino-3-[6-(2-{3-[(2-chloropyridine-3-carbonyl) amino]propoxy}phenyl)pyridine-3-ylazo]naphthalene-1-sulfonic acid;
4-amino-3-[6-(5-chloro-2-hydroxyphenyl)pyridine-3-ylazo]naphthalene-1-sulfonic acid;
4-amino-3-[6-(4-methylbiphenyl-2-yl)pyridine-3-ylazo] naphthalene-1-sulfonic acid;
4-amino-3-[6-(4'-chloro-4-methylbiphenyl-2-yl)pyridine-3-ylazo]naphthalene-1-sulfonic acid;
4-amino-3-[6-(5,5-dioxo-5H-5λ⁶-dibenzothiophene-4-yl) pyridine-3-ylazo]naphthalene-1-sulfonic acid;
4-amino-3-[6-(4,3',5'-trimethylbiphenyl-2-yl)pyridine-3-ylazo]naphthalene-1-sulfonic acid;
4-amino-3-[6-(3'-chloro-4-methylbiphenyl-2-yl)pyridine-3-ylazo]naphthalene-1-sulfonic acid;
4-amino-3-(6-thianthrene-1-ylpyridine-3-ylazo)naphthalene-1-sulfonic acid;
4-amino-3-[6-(2-{3-[(2-chloropyridine-4-carbonyl) amino]propoxy}phenyl)pyridine-3-ylazo]naphthalene-1-sulfonic acid;
4-amino-3-(6-{2-[3-(1,3-dioxo-1,3-dihydroisoindole-2-yl)propoxy]phenyl}pyridine-3-ylazo)naphthalene-1-sulfonic acid;
4-amino-3-[6-(4-fluoro-2-methylphenyl)-5-methylpyridine-3-ylazo]naphthalene-1-sulfonic acid;
4-amino-3-{6-[3-(pyridine-3-ylmethoxy)dibenzothiophene-4-yl]pyridine-3-ylazo}naphthalene-1-sulfonic acid;
4-amino-3-[6-(3-{3-[(2-chloropyridine-3-carbonyl) amino]propoxy}dibenzothiophene-4-yl)pyridine-3-ylazo]naphthalene-1-sulfonic acid;
4-amino-3-{6-[3-(3-hydroxypropoxy)dibenzothiophene-4-yl]pyridine-3-ylazo}naphthalene-1-sulfonic acid;
4-amino-3-(6-quinoline-8-ylpyridine-3-ylazo)naphthalene-1-sulfonic acid;
4-amino-3-[6-(2-methylquinoline-8-yl)pyridine-3-ylazo] naphthalene-1-sulfonic acid;
4-amino-3-(6-dibenzothiophene-4-yl-5-methylpyridine-3-ylazo)naphthalene-1-sulfonic acid;
4-amino-3-(6-biphenyl-2-yl-5-methylpyridine-3-ylazo) naphthalene-1-sulfonic acid;
4-amino-3-(6-methoxy-5-phenylpyridine-3-ylazo)naphthalene-1-sulfonic acid;
4-amino-3-(6-chloro-5-phenylpyridine-3-ylazo)naphthalene-1-sulfonic acid;
4-amino-3-(5,6-diphenylpyridine-3-ylazo)naphthalene-1-sulfonic acid;
4-amino-3-[6-(2,6-dimethylphenyl)pyridine-3-ylazo] naphthalene-1-sulfonic acid;
4-amino-3-[6-(3-formyl-2-isopropoxy-5-methylphenyl) pyridine-3-ylazo]naphthalene-1-sulfonic acid;
4-amino-3-[6-(3-formyl-2-butoxy-5-methylphenyl)pyridine-3-ylazo]naphthalene-1-sulfonic acid;
4-amino-3-[6-(2-butoxy-3-ethoxy-5-formylphenyl)pyridine-3-ylazo]naphthalene-1-sulfonic acid;
4-amino-3-[6-(2-ethoxy-3-formyl-5-methylphenyl)pyridine-3-ylazo]naphthalene-1-sulfonic acid;
or a pharmaceutically acceptable salt or solvate thereof.

11. A method of treating a VCP-mediated disease selected from the group consisting of IBMPFD, neurodegenerative disease, inflammatory disease, cystic fibrosis, autoimmune disease, viral infection, tumor disease, dyslipidemia, depression, anxiety and schizophrenia, the method comprising administering to a subject in need thereof a therapeutically effective amount of the compound or pharmaceutically acceptable salt or solvate thereof according to claim 1.

12. A method of treating a VCP-mediated disease selected from the group consisting of IBMPFD, neurodegenerative disease, inflammatory disease, cystic fibrosis, autoimmune disease, viral infection, tumor disease, dyslipidemia, depression, anxiety and schizophrenia, the method comprising administering to a subject in need thereof a therapeutically effective amount of the pharmaceutical composition according to claim 3.

13. A method of treating a VCP-mediated disease selected from the group consisting of IBMPFD, inflammatory disease, cystic fibrosis, autoimmune disease, tumor disease, dyslipidemia, depression, anxiety and schizophrenia, the method comprising
administering to a subject in need thereof a therapeutically effective amount of a compound of formula (I)

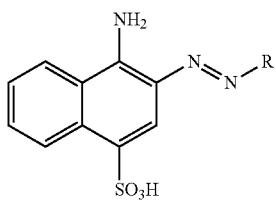

(I)

wherein:
R is phenyl, 3-pyridyl, quinolinyl or thiophenyl, wherein
phenyl is optionally substituted by 1 to 3 substituent selected from the group consisting of halo, nitro, cyano, alkyl which is optionally substituted by 1 to 3 halo, alkoxy which is optionally substituted by pyridyl, alkenyl which is optionally substituted by cyano and phenyl, methylsulfanyl, thienylcarbonylamino, dicarboxylethylphenylaminocarbonyl, phenylaminocarbonyl, phenylcarbonyl, —C(O)O-alkyl, carboxyl, pyridyl, phenyl which is optionally substituted by 1 or 2 substituent selected from the group consisting of alkyl and halo, and isoquinolinyl;
3-pyridyl is optionally substituted by 1 to 3 substituent selected from the group consisting of halo, alkyl, alkenyl which is optionally substituted by phenyl, alkoxy which is optionally substituted by pyridyl, tetrahydrofuranyl, halo or alkoxy, phenyl, naphthalenyl, pyridyl, thiophenyl, oxazolyl, dibenzofuranyl, benzothiophenyl, dibenzothiophenyl which is optionally substituted by pyridylmethoxy, chloropyridinecarbonylaminopropoxy or hydroxypropoxy, dioxodibenzothiophenyl, thianthrenyl, and quinolinyl which is optionally substituted by methyl;
wherein phenyl substituting 3-pyridyl is optionally substituted by 1 to 3 substituent selected from the group consisting of halo, alkyl which is optionally substituted by morpholinyl or up to 3 halo, alkoxy which is optionally substituted by hydroxy, carboxyl, butoxycarbonylamino, chloropyridinecarbonylamino or dioxodihydroisoindolyl, phenyl which is optionally substituted by halo or alkyl, alkylthio, acetyl, phenoxy, methoxycarbonylethylcarbonyl, cyano, phenylcarbonyl, hydroxy and formyl,
thiophenyl is optionally substituted by methoxycarbonyl,
or a pharmaceutically acceptable salt or solvate.

14. The method of treating a VCP-mediated disease according to claim 13, comprising administering to the subject in need thereof a therapeutically effective amount of a pharmaceutical composition comprising the compound or the pharmaceutically acceptable salt or solvate, and a pharmaceutically acceptable carrier.

* * * * *